United States Patent
Zhai et al.

(10) Patent No.: US 11,981,666 B2
(45) Date of Patent: May 14, 2024

(54) GLP-1 RECEPTOR AGONIST AND COMPOSITION AND USE THEREOF

(71) Applicant: HANGZHOU ZHONGMEIHUADONG PHARMACEUTICAL CO., LTD., Zhejiang (CN)

(72) Inventors: Wenqiang Zhai, Zhejiang (CN); Zhimin Zhang, Zhejiang (CN); Zhe Wang, Zhejiang (CN); Hao Pan, Zhejiang (CN); Liubin Guo, Zhejiang (CN); Qian Wang, Zhejiang (CN)

(73) Assignee: HANGZHOU ZHONGMEIHUADONG PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 18/367,517

(22) Filed: Sep. 13, 2023

(65) Prior Publication Data
US 2024/0116906 A1  Apr. 11, 2024

Related U.S. Application Data

(63) Continuation of application No. PCT/CN2022/100685, filed on Jun. 23, 2022.

(30) Foreign Application Priority Data

Jun. 24, 2021  (CN) .......................... 202110702643.0

(51) Int. Cl.
*C07D 405/14* (2006.01)

(52) U.S. Cl.
CPC .................................. *C07D 405/14* (2013.01)

(58) Field of Classification Search
CPC ...................................................... C07D 405/14
USPC .......................................................... 514/333
See application file for complete search history.

(56) References Cited

FOREIGN PATENT DOCUMENTS

| WO | 2020103815 | 5/2020 |
|----|------------|--------|
| WO | 2020207474 | 10/2020 |
| WO | 2021081207 | 4/2021 |
| WO | 2021160127 | 8/2021 |
| WO | 2022109182 | 5/2022 |

*Primary Examiner* — Kahsay Habte
(74) *Attorney, Agent, or Firm* — Robin L. Teskin; Baker, Donelson, Bearman, Caldwell & Berkowitz PC

(57) ABSTRACT

Provided are a GLP-1 receptor agonist compound and a composition and use thereof. The compound can be used for treating or preventing GLP-1 receptor-mediated diseases or disorders and related diseases or disorders.

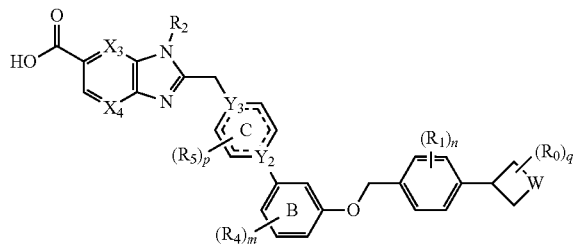

12 Claims, No Drawings

GLP-1 RECEPTOR AGONIST AND COMPOSITION AND USE THEREOF

CROSS-REFERENCE TO RELATED APPLICATIONS

This application is a continuation application of Int'l Chinese Appl. No. PCT/CN2022/100685, filed Jun. 23, 2022, which claims priority to Int'l Chinese Appl. No. 202110702643.0 filed Jun. 24, 2021, each and all of which are incorporated herein by reference in their entireties.

FIELD OF THE INVENTION

The present disclosure relates to GLP-1 receptor agonists and compositions and uses thereof, and the compounds can be used for the treatment or prevention of GLP-1 receptor-mediated diseases or disorders and related diseases or disorders.

BACKGROUND OF THE INVENTION

Diabetes is a chronic comprehensive disease mainly characterized by glucose metabolism disorder due to absolute or relative deficiency of insulin or decreased sensitivity of target cells to insulin, and can be divided into type I diabetes and type II diabetes. Type II diabetes is an endocrine disease mainly characterized by chronic increase in blood sugar level due to insulin resistance and/or inadequate insulin secretion. Patients with type II diabetes account for more than 90% of diabetic patients.

At present, drugs used to treat type II diabetes mainly include the following kinds of drugs: insulin secretagogues, metformins, α-glycosidase inhibitors, insulin sensitizers, sodium-glucose cotransporter 2 inhibitors, dipeptidyl peptidase 4 (DPP-4) inhibitors, GLP-1 receptor agonists, insulins and analogues thereof, among which, insulins and GLP-1 receptor agonists are ones of the most effective drugs for treating diabetes. Insulin formulations are still the most widely used diabetes drugs all over the world, and about 30-40% of patients with type II diabetes finally need insulins. GLP-1 formulations mainly include exenatide, liraglutide, somalutide, etc., and are suitable for patients with type II diabetes whose blood sugar cannot be fully controlled by the combination of metformin and sulfonylurea, and so on. However, current insulin formulations and GLP-1 formulations are substantially polypeptides and injectable formulations. There are still many limitations in administration even for oral somarutide. Thus, it is still necessary to further develop small molecule GLP-1 receptor agonists.

GLP-1 stimulates insulin secretion in a glucose dependent manner, and inhibits glucagon secretion in a glucose dependent manner, so there is no risk of hypoglycemia. GLP-1 can increase the production of insulin by β cells and improve the response of β cells to glucose. GLP-1 may delay gastric emptying and reduce food intake, and therefore can lead to weight loss. In addition, GLP-1 also has the unique effect of cardiovascular benefits. GLP-1 receptor agonists are used in the transitional stage between oral hypoglycemic drugs and insulins in clinical practice, can be used in combination with other drugs.

Other conditions associated with type II diabetes include diabetic nephropathy, diabetic complications of the eye (diabetic retinopathy, diabetes-related uveitis, diabetic cataract), diabetic foot, diabetic cardiovascular complications, diabetic cerebrovascular disease, diabetic neuropathy, obesity, and hypertension.

GLP-1 receptor agonists, as very potential drugs, are marketed mostly in forms for administration by injection at present. Oral small molecule GLP-1 receptor agonists can improve patient compliance, representing the development trend of GLP-1 receptor agonists in the future. The development of small molecule GLP-1 receptor agonists can be found in WO2009111700A2, WO2010114824A1, WO2017078352A1, KR1020180101671A, WO2018056453A1, and WO2018109607A1.

There remains a need to develop small molecule GLP-1 receptor agonists with improved properties in one or more of GLP-1 receptor agonistic activity, intestinal absorption, safety, and pharmacokinetics.

Contents of the Disclosure

SUMMARY

In one aspect, the present disclosure provides the compounds of Formula I and Formula II as described in the "Detailed Description" section below:

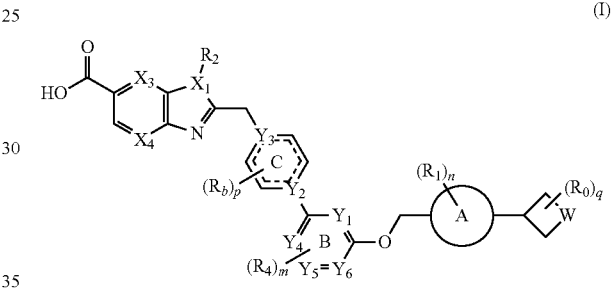

(I)

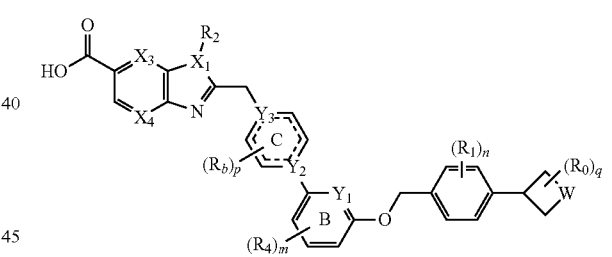

(II)

or pharmaceutically acceptable salts or stereoisomers thereof.

The compounds of the present disclosure are GLP-1 receptor agonists. Preferred compounds of the present disclosure (e.g., compounds of Formula II) have excellent GLP-1 receptor agonistic activity, good intestinal absorption, and/or good safety and pharmacokinetic properties (e.g., metabolic stability, plasma binding, $C_{max}$, half-life, and oral bioavailability). For example, some of the compounds of Formula II have improved GLP-1 receptor agonistic activity (e.g., lower $EC_{50}$) compared to some prior art compounds, and/or higher in vivo and/or in vitro safety and/or improved pharmacokinetic properties (e.g., metabolic stability, $C_{max}$, half-life, and/or oral bioavailability) compared to some prior art compounds.

In one aspect, the present disclosure provides a pharmaceutical composition comprising the compound of Formula I or Formula II, or a pharmaceutically acceptable salt or stereoisomer thereof, and a pharmaceutically acceptable carrier, excipient, or diluent.

In one aspect, the present disclosure provides use of the compound of Formula I or Formula II, or a pharmaceutically acceptable salt or stereoisomer thereof, in the manufacture of a medicament for the treatment of GLP-1 receptor-mediated diseases or disorders and related diseases or disorders.

In one aspect, the present disclosure provides a method for the prevention and/or treatment of a GLP-1 receptor mediated disease or disorder and a related disease or disorder in a subject, comprising administering to the subject a therapeutically effective amount of the compound of Formula I or Formula II, or a pharmaceutically acceptable salt or stereoisomer thereof.

In some embodiments, the GLP-1 receptor-mediated disease or disorder and a related disease or disorder is selected from a group consisting of diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia.

DETAILED DESCRIPTION

In one aspect, the present disclosure provides a compound of Formula I:

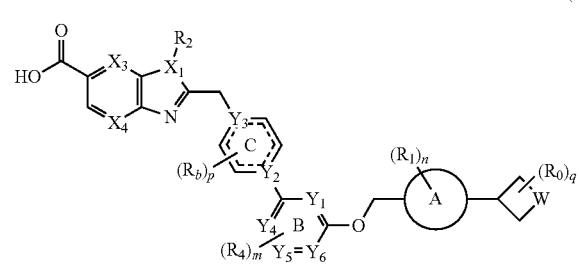

(I)

or a pharmaceutically acceptable salt or stereoisomer thereof,
wherein:
⋯ represents a single or double bond;
W is selected from O, N or NH;
$X_1$, $X_3$, and $X_4$ are independently selected from N and C;
$Y_1$ is selected from CH and N;
$Y_2$ is selected from CH, N, and C;
$Y_3$ is selected from CH, N, and C;
$Y_4$, $Y_5$, and $Y_6$ are independently selected from CH and N, and $Y_4$, $Y_5$, and $Y_6$ are not simultaneously N;
ring A is selected from a group consisting of benzene ring, thiophene, pyridine, and piperidine;
$R_1$ is independently selected from a group consisting of hydrogen, oxo, halogen, cyano, $C_{1-6}$ alkyl, $C_{1-6}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-6}$ alkyl, $C_{1-6}$ alkoxy, $C_{3-6}$ cycloalkyl may optionally be independently substituted 1 to 3 times by halogen, cyano, $C_{1-3}$ alkyl, $C_{1-3}$ alkoxy, $C_{3-6}$ cycloalkyl, or $C_{3-6}$ heterocyclyl;
$R_2$ is selected from a group consisting of $R_z$, —O—$R_z$, —S—$R_z$, $C_{1-3}$ alkyl, —$C_{1-3}$ alkylene-$R_z$, —$C_{0-3}$ alkylene-amino-$R_z$, —$C_{0-3}$ alkylene-carbonyl-$R_z$, —$C_{0-3}$ alkylene-amido-$R_z$, —$C_{0-3}$ alkylene-sulfonyl-$R_z$, —$C_{0-3}$ alkylene-phosphoryl-$R_z$, and —$C_{0-3}$ alkylene-sulfonamido-$R_z$, wherein the alkyl, amino, amido, sulfonyl, sulfonamido, and phosphoryl for $R_2$ may be optionally substituted 1-3 times by halogen or one time by $R_w$, if valence permits;

$R_4$ is independently selected from a group consisting of hydrogen, halogen, $C_{1-3}$ alkyl, $C_{1-3}$ haloalkyl, $C_{1-3}$ alkoxy, cyano, hydroxy, amino, amido, sulfonyl, and sulfonamido;
$R_5$ is independently selected from a group consisting of hydrogen, halogen, hydroxy, CN, $C_{1-3}$ alkyl, $C_{1-3}$ alkoxy, and $C_{3-6}$ cycloalkyl, wherein the alkyl, alkoxy, and cycloalkyl for $R_5$ may be optionally substituted 1-3 times by halogen, hydroxy, —N$R_z$, CN, $C_{1-3}$ alkyl, $C_{1-3}$ alkoxy, $C_{3-6}$ cycloalkyl, if valence permits;
$R_0$ is independently selected from a group consisting of hydrogen, halogen, hydroxy, oxo, CN, $C_{1-3}$ alkyl, $C_{1-3}$ alkoxy, $C_{3-6}$ cycloalkyl, 3- to 6-membered heterocyclyl, phenyl, and 5- to 6-membered heteroaryl, wherein the alkyl, alkoxy, cycloalkyl, heterocyclyl, phenyl, and heteroaryl for $R_0$ may be optionally substituted 1-3 times by halogen, CN, $NH_2$, $C_{1-3}$ alkyl, $C_{1-3}$ alkoxy, $C_{3-6}$ cycloalkyl, if valence permits;
n is 0, 1, 2, 3, or 4;
m is 0, 1, or 2;
p is 0, 1, 2, or 3;
q is 0, 1, 2, 3, or 4;
when p is greater than or equal to 2, any two $R_5$ may be further cyclized with ring C to form a 6 to 10-membered spiro ring or bridged ring, and the spiro ring and the bridged ring formed may be optionally substituted 1-3 times by $C_{1-3}$ alkyl, $C_{1-3}$ alkoxy, $C_{1-3}$ haloalkyl, halogen, cyano, or $C_{1-3}$ alkoxy;
when m is not 0 and p is not 0, any $R_4$ and any $R_5$ may be further cyclized into a 5- to 8-membered ring, and the formed ring may be optionally substituted 1-3 times by $C_{1-3}$ alkyl, $C_{1-3}$ alkoxy, $C_{1-3}$ haloalkyl, halogen, cyano, oxo or $C_{1-3}$ alkoxy, if valence permits;
$R_w$ is independently selected from a group consisting of CN, —$CH_2CN$, $C_{1-3}$ alkyl, OH, $C_{1-3}$ alkoxy, amido, sulfonyl, sulfonamido, $NH_2$, and —NH—$C_{1-3}$ alkyl, wherein the alkyl for $R_w$ may be optionally substituted 1-3 times by $C_{1-3}$ alkyl, $C_{1-3}$ haloalkyl, halogen, cyano, oxo, or $C_{1-3}$ alkoxy, if valence permits;
$R_z$ is independently selected from a group consisting of hydrogen, $C_{1-3}$ alkyl, $C_{1-3}$ alkoxy, $C_{3-6}$ cycloalkyl, 3- to 6-membered heterocyclyl, aryl, and 5- to 6-membered heteroaryl, wherein $R_z$ may be optionally substituted 1-3 times by $C_{1-3}$ alkyl, $C_{1-3}$ haloalkyl, cyano-$C_{1-3}$ alkyl, halogen, cyano, oxo, $C_{1-3}$ alkoxy, or 3- to 6-membered heterocyclyl, if valence permits.

In the Formula I, the letters "B" and "C" in the rings are the designations of the corresponding rings. In other words, the ring with $Y_2$ and $Y_3$ as shown may be referred to as ring C; the ring with $Y_1$ as shown may be referred to as ring B; and so on.

In some embodiments, $X_1$ is N.

In some embodiments, $X_3$ is CH, and $X_4$ is N. In some embodiments, $X_3$ is N, and $X_4$ is CH. In some embodiments, $X_3$ and $X_4$ are each N. In some preferred embodiments, $X_3$ and $X_4$ are each CH.

In some embodiments, $R_1$ is independently selected from a group consisting of hydrogen, oxo, halogen, cyano, $C_{1-3}$ alkyl, $C_{1-3}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-3}$ alkyl, $C_{1-3}$ alkoxy and $C_{3-6}$ cycloalkyl may optionally be independently substituted 1-3 times by halogen, cyano, $C_{1-3}$ alkyl, $C_{1-3}$ alkoxy, $C_{3-6}$ cycloalkyl, or $C_{3-6}$ heterocyclyl.

In some embodiments, $R_2$ is selected from —$CH_2$—$R_z$.

In some embodiments, W is O.

In some embodiments, $R_z$ is preferably selected from $C_{3-6}$ cycloalkyl, and 3- to 6-membered heterocycloalkyl having 1 or 2 heteroatoms independently selected from N, O, and S, wherein $R_z$ may be optionally substituted 1-3 times by $C_{1-3}$ alkyl, $C_{1-3}$ haloalkyl, cyano-$C_{1-3}$ alkyl, halogen, cyano, oxo, $C_{1-3}$ alkoxy, or 3- to 6-membered heterocyclyl.

In some embodiments, the compound of Formula I has a structure of Formula I-2 or Formula I-2':

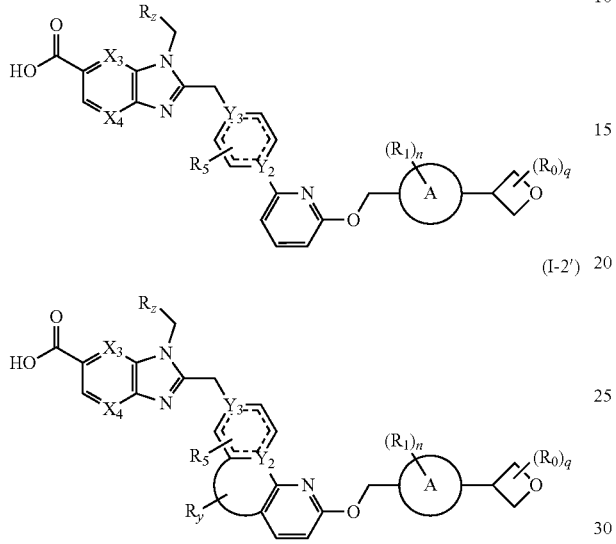

or a pharmaceutically acceptable salt or stereoisomer thereof, wherein

┈┈ represents a single or double bond;
$X_3$ and $X_4$ are independently selected from CH and N;
$Y_2$ is selected from CH, N and C;
$Y_3$ is selected from CH and N;
ring A is selected from a group consisting of

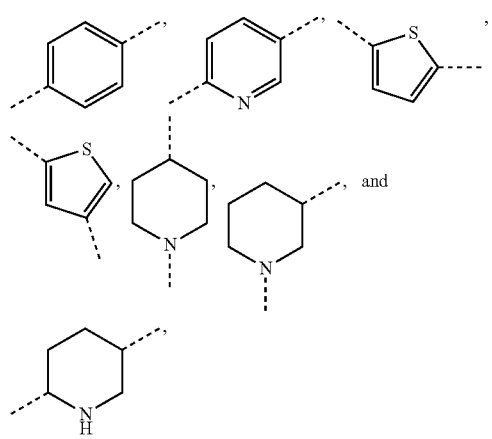

and may be further substituted n times by $R_1$;

$R_1$ is independently selected from a group consisting of hydrogen, oxo, halogen, cyano, $C_{1-6}$ alkyl, $C_{1-6}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-6}$ alkyl, $C_{1-6}$ alkoxy, and $C_{3-6}$ cycloalkyl may optionally be independently substituted 1-3 times by halogen, cyano, $C_{1-3}$ alkyl, $C_{1-3}$ alkoxy, $C_{3-6}$ cycloalkyl, or $C_{3-6}$ heterocyclyl;

$R_z$ is selected from a group consisting of methyl, ethyl, isopropyl, cyclopropyl, cyclobutyl, methoxy, ethoxy

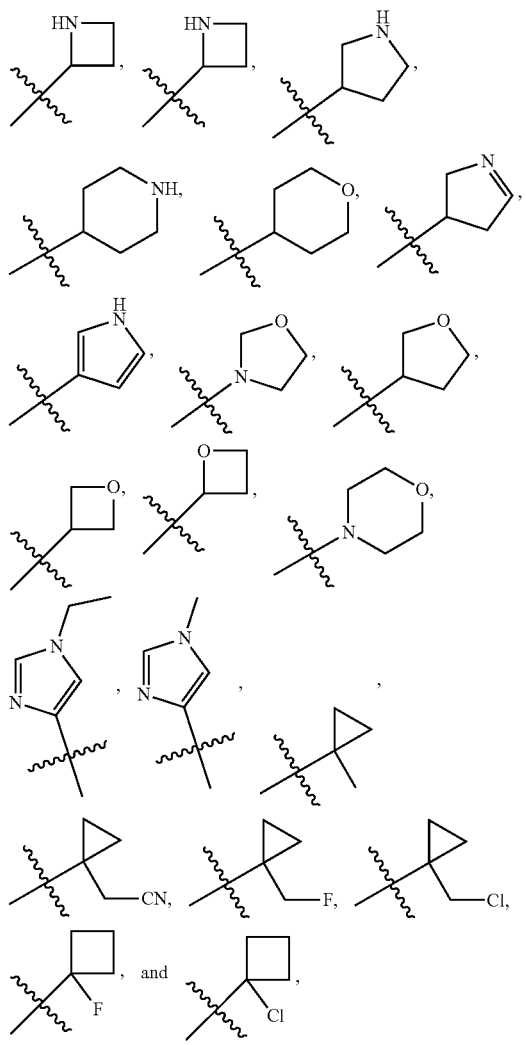

wherein $R_z$ may be optionally substituted 1-3 times by halogen, cyano, $C_{1-3}$ alkyl, $C_{1-3}$ alkoxy, $C_{3-6}$ cycloalkyl, or 3- to 6-membered heterocyclyl, if valence permits;

$R_5$ is independently selected from a group consisting of hydrogen, halogen, hydroxy, CN, $C_{1-3}$ alkyl, $C_{1-3}$ alkoxy, and $C_{3-6}$ cycloalkyl, wherein the alkyl, alkoxy, and cycloalkyl for $R_5$ may be optionally substituted 1-3 times by halogen, hydroxy, —$NR_z$, CN, $C_{1-3}$ alkyl, $C_{1-3}$ alkoxy, or $C_{3-6}$ cycloalkyl, if valence permits;

n is an integer selected from 0, 1, or 2; and $R_y$ is independently selected from a group consisting of hydrogen, halogen, oxo, $C_{1-3}$ alkoxy, cyano, hydroxyl, amino, carboxyl, amido, sulfonyl, sulfonamido, $C_{1-3}$ alkyl, $C_{3-6}$ cycloalkyl, 3- to 6-membered heterocyclyl, and phenyl, wherein the alkyl, alkoxy, cycloalkyl, and heterocyclyl for $R_y$ may be optionally substituted 1-3 times by halogen, if valence permits.

In some embodiments, $R_z$ is selected from a group consisting of methyl, ethyl, isopropyl, cyclopropyl, cyclobutyl, methoxy, ethoxy,

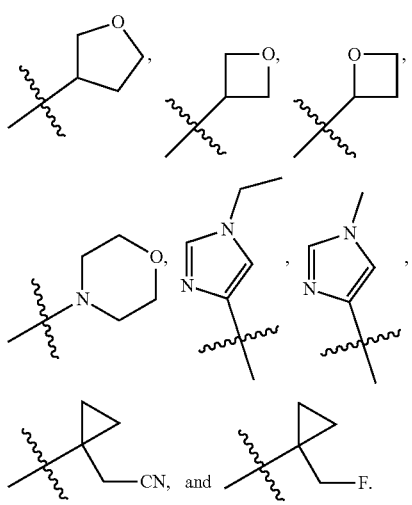

In some embodiments, $R_z$ is selected from a group consisting of cyclopropyl, cyclobutyl,

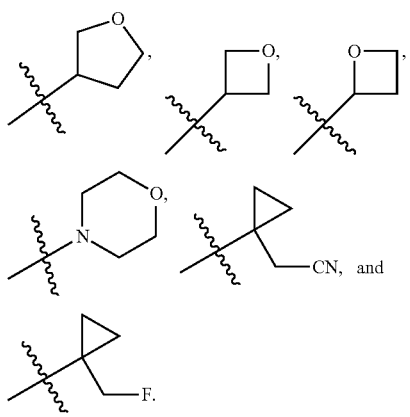

In other embodiments, $R_z$ is selected from $C_{3-6}$ cycloalkyl and 3- to 6-membered heterocyclyl, wherein $R_z$ may be optionally substituted 1-3 times by $C_{1-3}$ alkyl, $C_{1-3}$ haloalkyl, cyano-$C_{1-3}$ alkyl, halogen, cyano, oxo, $C_{1-3}$ alkoxy, or 3- to 6-membered heterocyclyl, if valence permits.

In some preferred embodiments, $R_z$ is selected from $C_{3-6}$ cycloalkyl and 3- to 6-membered heterocycloalkyl, wherein $R_z$ is optionally substituted one time by $C_{1-3}$ alkyl, $C_{1-3}$ haloalkyl, cyano-$C_{1-3}$ alkyl, halogen or cyano, preferably by $C_{1-3}$ haloalkyl (preferably halomethyl), cyano-$C_{1-3}$ alkyl (preferably cyanomethyl) or halogen, if valence permits. In some embodiments, the halo or halogen is F or Cl. In some such embodiments, $R_z$ is preferably selected from the group consisting of

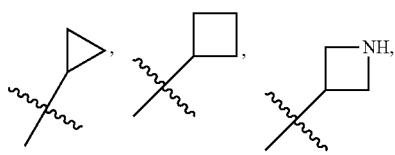

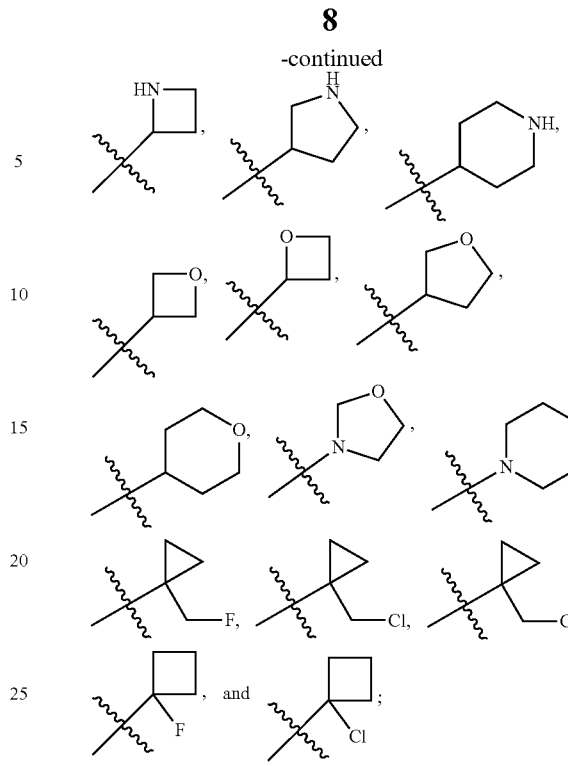

more preferably selected from the group consisting of

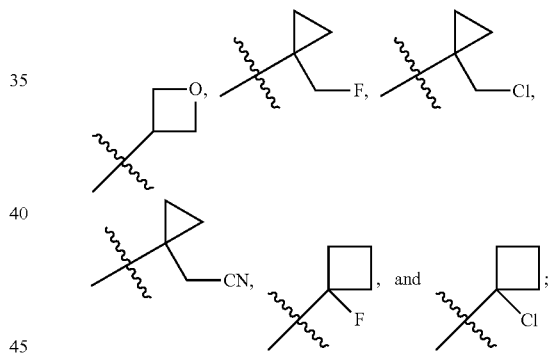

even more preferably selected from a group consisting of

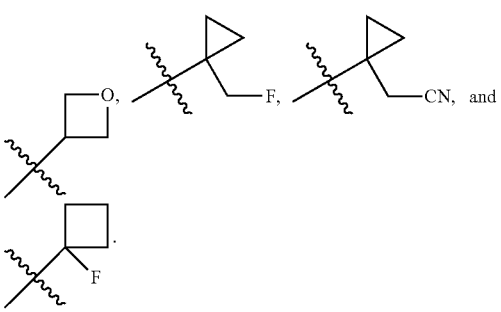

In some embodiments, $R_1$ is independently selected from a group consisting of hydrogen, oxo, halogen, cyano, $C_{1-3}$ alkyl, $C_{1-3}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-3}$ alkyl, $C_{1-3}$ alkoxy, and $gC_{3-6}$ cycloalkyl may optionally be independently substituted 1-3 times by halogen, cyano, $C_{1-3}$ alkyl, $C_{1-3}$ alkoxy, $C_{3-6}$ cycloalkyl, or $C_{3-6}$ heterocyclyl.

In some embodiments, $R_2$ or

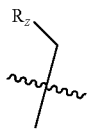

is selected from the group consisting of

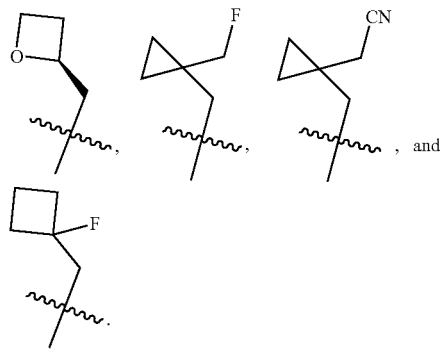

In some other embodiments, any adjacent $R_4$ and $R_5$ may be further cyclized into a 5- to 8-membered ring; the 5- to 8-membered ring includes a $C_{5-6}$ carbocyclic ring, a 5- to 8-member heterocyclic ring, a phenyl ring, and a 5- to 8-membered heteroaromatic ring, and the formed ring may be optionally substituted 1-3 times by alkyl, haloalkyl, halogen, cyano, alkoxy, if valency permits.

In some embodiments, when m is not 0 and p is not 0, any adjacent $R_4$ and $R_5$ may be further cyclized into a 5- to 8-membered ring, which is preferably selected from a group consisting of

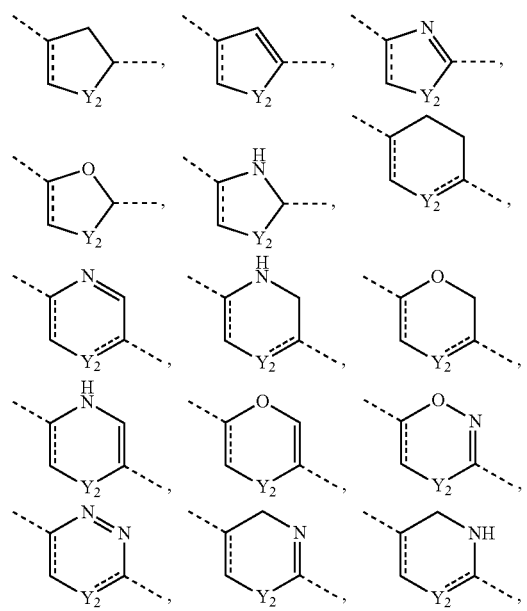

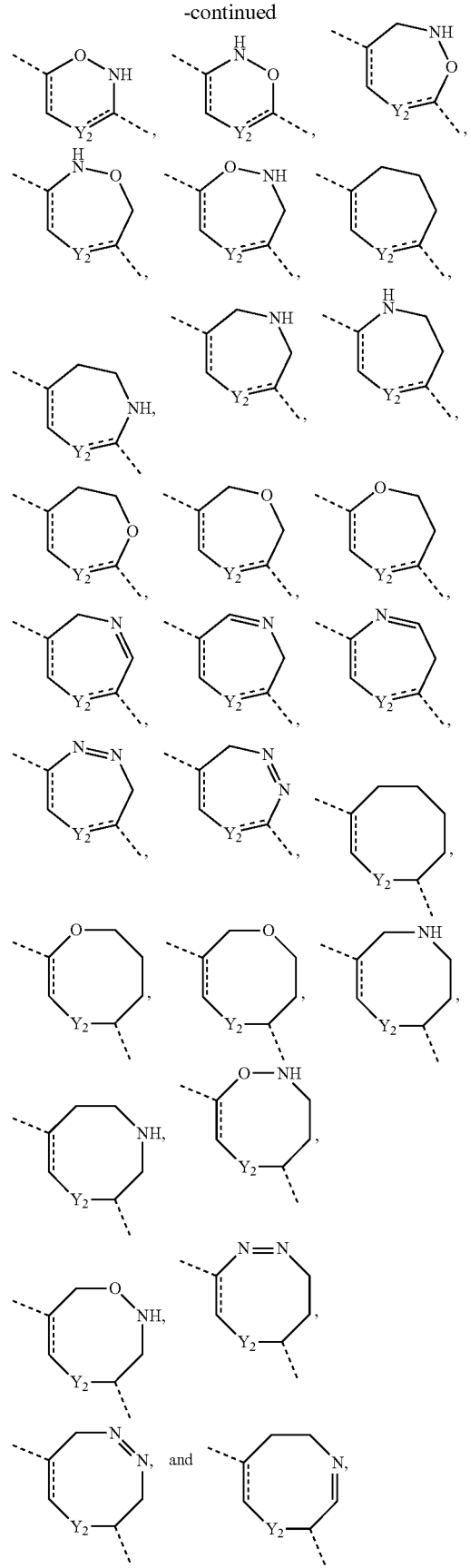

wherein the 5- to 8-membered ring may be optionally substituted 1-3 times by $C_{1-3}$ alkyl, $C_{1-3}$ alkoxy, $C_{1-3}$ haloalkyl, halogen, cyano, oxo, $C_{1-3}$ alkoxy, if valence permits.

In some embodiments, when m is not 0 and p is not 0, any adjacent $R_4$ and $R_5$ may be further cyclized into a 5- to 8-membered ring, which is preferably

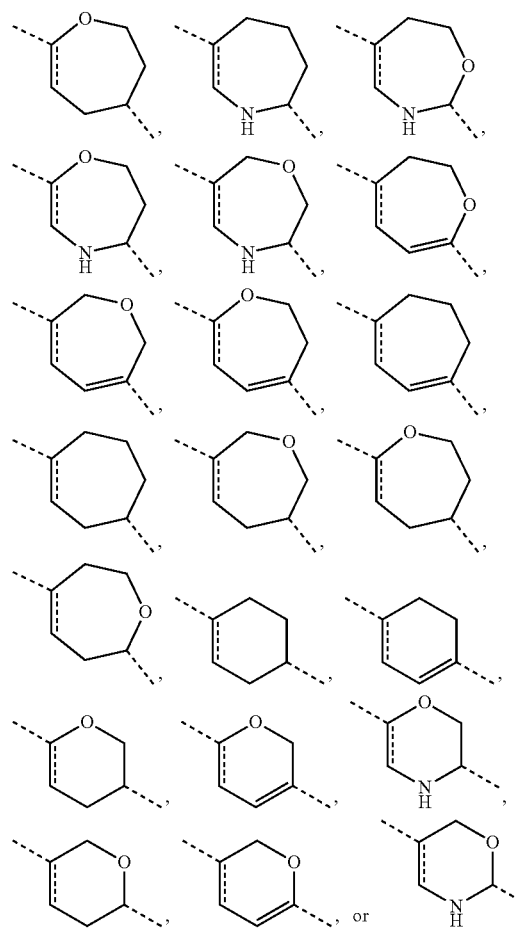

wherein the 5- to 8-membered ring may be optionally substituted 1-3 times by $C_{1-3}$ alkyl, $C_{1-3}$ haloalkyl, halogen, cyano, oxo, or $C_{1-3}$ alkoxy, if valence permits.

In some embodiments, when m is not 0 and p is not 0, any adjacent $R_4$ and $R_5$ may be further cyclized into a 5- to 8-membered ring, which may be selected from a group consisting of

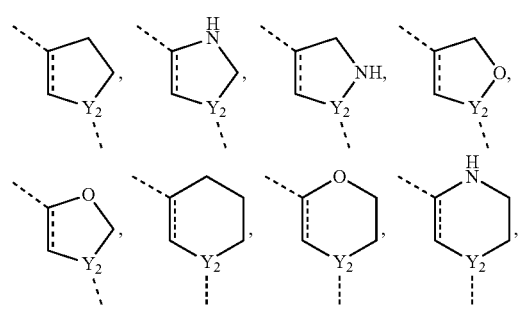

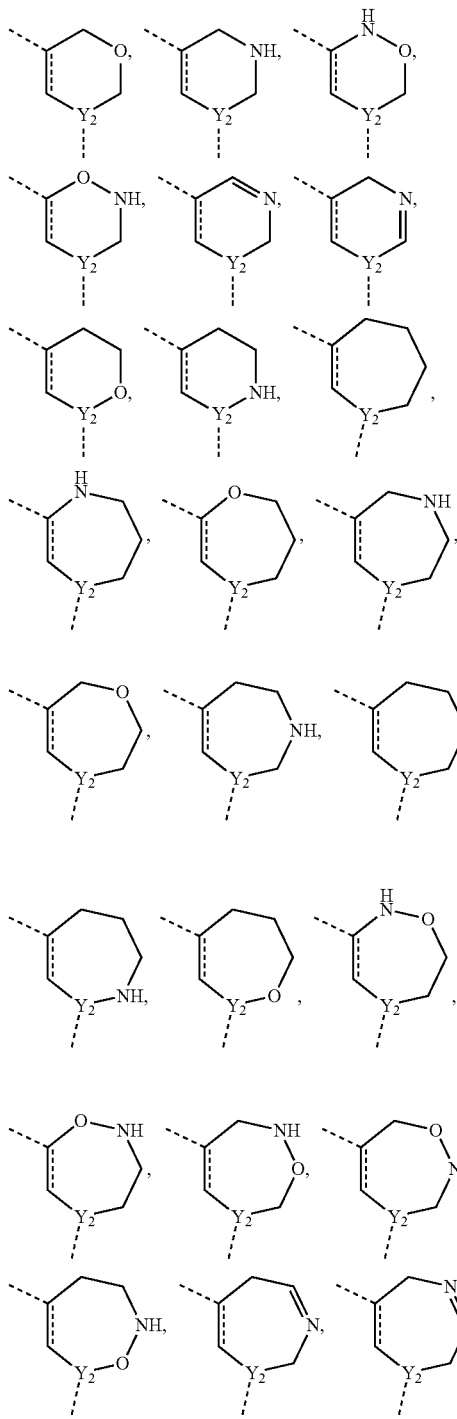

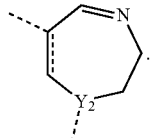

wherein the 5- to 8-membered ring may be optionally substituted 1-3 times by $C_{1-3}$ alkyl, $C_{1-3}$ haloalkyl, halogen, cyano, oxo, or $C_{1-3}$ alkoxy, if valence permits.

In some embodiments, the 5- to 8-membered ring
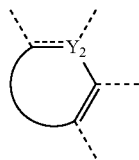
is selected from the group consisting of:
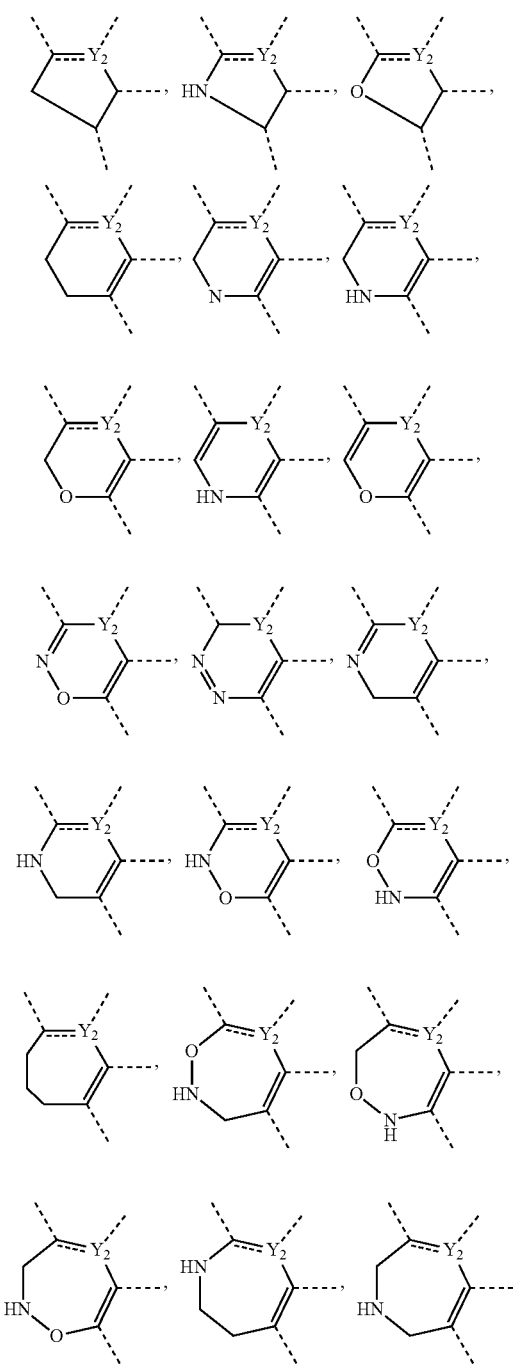
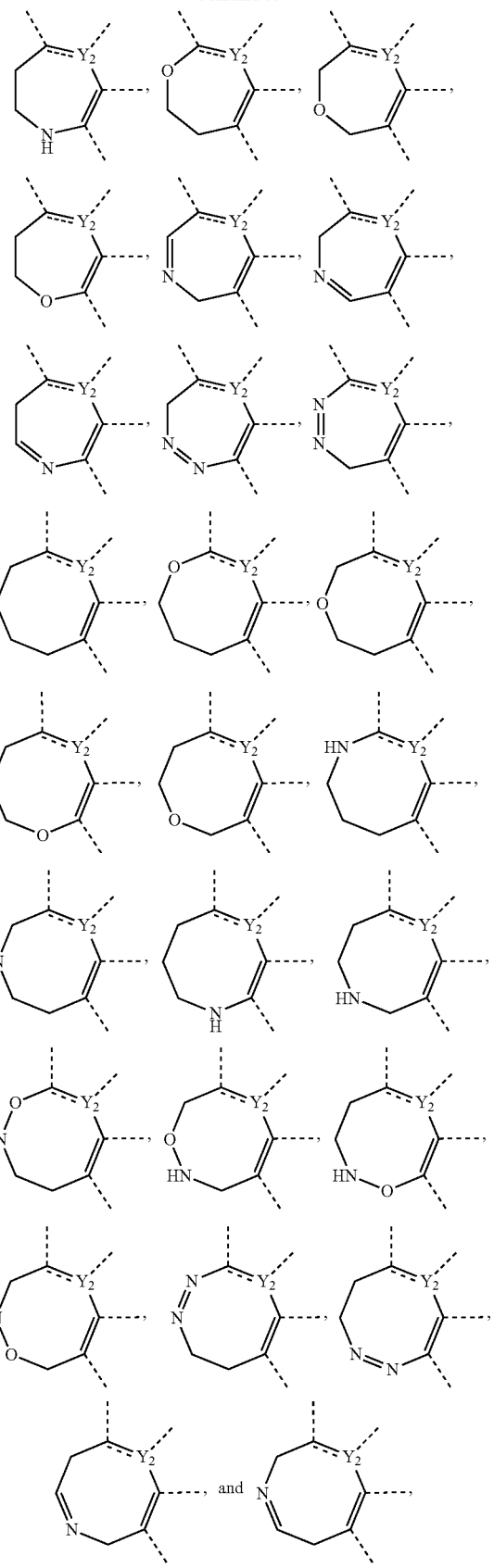

preferably selected from a group consisting

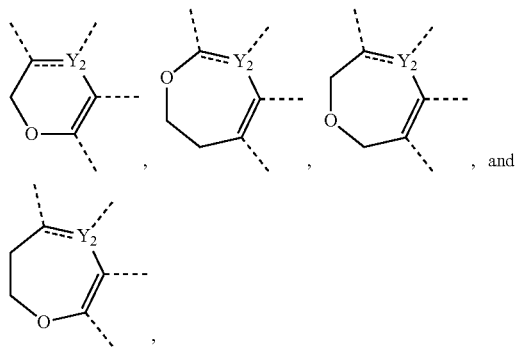

and more preferably

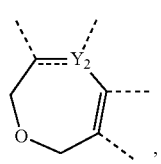

wherein the 5- to 8-membered ring may be optionally substituted 1-3 times by $C_{1-3}$ alkyl, $C_{1-3}$ haloalkyl, halogen, cyano, oxo, or $C_{1-3}$ alkoxy, if valence permits.

In some of the embodiments described above, the compound of Formula I described in the present disclosure has the following structure:

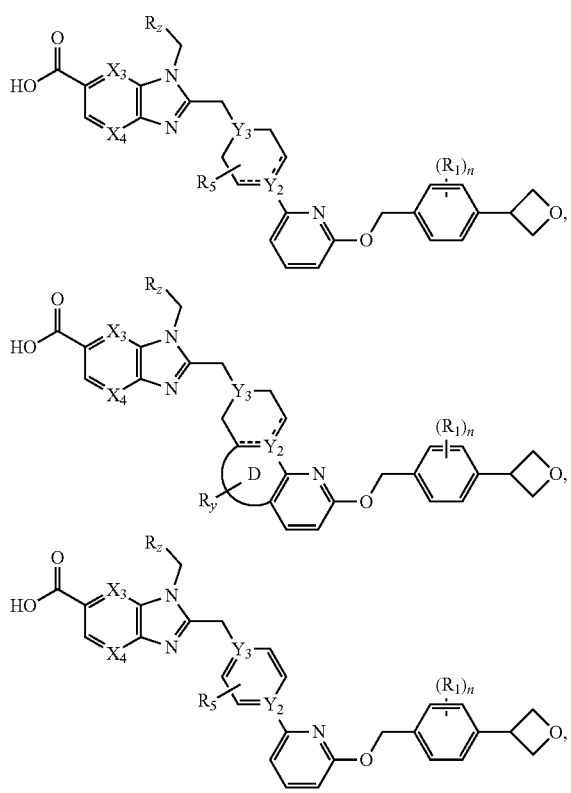

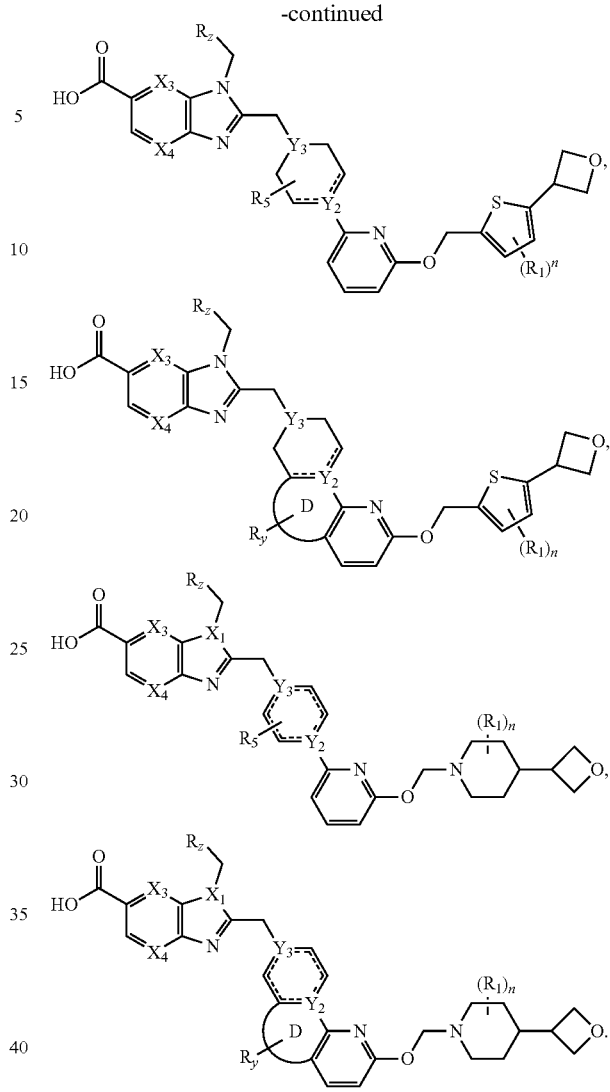

Ring D is a 5- to 8-membered ring as described above.

In some embodiments, $R_1$ is selected from a group consisting of —F, —Cl, —CN, —OCH$_3$, —OCH$_2$CH$_3$, —O—cyclopropyl, —CH$_3$, —CH$_2$CH$_3$, —CH$_2$CH$_2$CH$_3$, —(CH)$_2$CH$_3$, —COCH$_3$, —CONH$_2$, —CF$_3$, —CHF$_2$, —CH$_2$F, —CH$_2$CH$_2$F, —CO-cyclopropyl, —COCH$_2$F, —COCHF$_2$, —CO—CH(CH$_3$)$_2$, and —CO—CH$_2$CH$_3$.

In some other embodiments, $R_1$ is independently selected from halogen and —$C_{1-3}$ alkoxy, preferably selected from a group consisting of F, Cl, methoxy, ethoxy, n-propoxy, or isopropoxy, and more preferably selected from a group consisting of F, Cl, and methoxy.

In some embodiments, $R_4$ is independently selected from a group consisting of hydrogen, halogen, $C_{1-3}$ alkyl, $C_{1-3}$ haloalkyl, $C_{1-3}$ alkoxy, cyano, hydroxyl, and amino, and more preferably hydrogen.

In some embodiments, $R_5$ is selected from a group consisting of F, Cl, CH$_3$, —OCH$_3$, NH$_2$, OH, —CH$_2$CH$_3$, —CH$_2$OH, —NHCH$_3$, —COCH$_3$, —SO$_2$CH$_3$, —OCH$_2$CH$_3$, CF$_3$, —CHF$_2$, —CH$_2$F, isopropyl, cyclopropyl, and fluorocyclopropyl.

In some other embodiments, $R_5$ is independently selected from hydrogen and halogen, and preferably selected from a group consisting of hydrogen, F, and Cl.

In some embodiments, $Y_2$ is C or CH.

In some embodiments, $Y_3$ is C or N.

In another aspect, the present disclosure provides some preferred compounds of Formula I, which have the structure of Formula II:

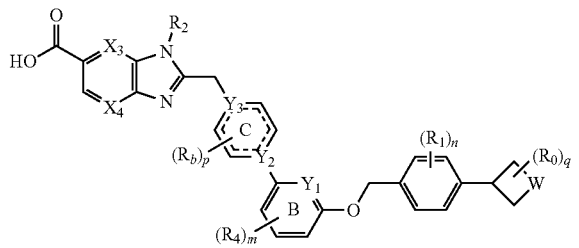

(II)

or pharmaceutically acceptable salts or stereoisomers thereof, wherein:

⚌ represents a single or double bond;

W is selected from O, N, and NH;

$X_3$ and $X_4$ are independently selected from CH, N, and C;

$Y_1$ is selected from CH or N;

$Y_2$ is selected from CH, N, or C;

$Y_3$ is selected from CH, N, or C;

$R_1$ is independently selected from a group consisting of hydrogen, halogen, $C_{1-6}$ alkyl, $C_{1-6}$ haloalkyl, $C_{1-6}$ alkoxy, and $C_{1-6}$ haloalkoxy;

$R_2$ is $R_z$—$C_{1-3}$ alkylene-;

$R_4$ is independently selected from a group consisting of hydrogen, halogen, $C_{1-3}$ alkyl, $C_{1-3}$ haloalkyl, $C_{1-3}$ alkoxy, cyano, hydroxy, amino, amido, sulfonyl, and sulfonamido, preferably selected from a group consisting of hydrogen, halogen, $C_{1-3}$ alkyl, $C_{1-3}$ haloalkyl, $C_{1-3}$ alkoxy, cyano, hydroxy, and amino, and more preferably hydrogen;

$R_5$ is independently selected from a group consisting of hydrogen, halogen, hydroxy, CN, $C_{1-3}$ alkyl, $C_{1-3}$ alkoxy, and $C_{3-6}$ cycloalkyl; preferably, $R_5$ is independently selected from hydrogen and halogen;

$R_0$ is independently selected from a group consisting of hydrogen, hydroxyl, and halogen;

n is 0, 1, 2, 3, or 4;

m is 0, 1, or 2;

p is 0, 1, 2, or 3;

q is 0, 1, 2, 3, or 4;

when m is not 0 and p is not 0, any $R_4$ and any $R_5$, together with the ring atoms of ring B and ring C therebetween, may form a 5- to 8-membered ring, wherein the 5- to 8-membered ring may be optionally substituted 1-3 times by $C_{1-3}$ alkyl, $C_{1-3}$ alkoxy, $C_{1-3}$ haloalkyl, halogen, cyano, oxo, or $C_{1-3}$ alkoxy, if valence permits;

$R_z$ is selected from $C_{3-6}$ cycloalkyl and 3- to 6-membered heterocycloalkyl, wherein $R_z$ may be optionally substituted 1-3 times by $C_{1-3}$ alkyl, $C_{1-3}$ haloalkyl, cyano-$C_{1-3}$ alkyl, halogen, cyano, oxo, $C_{1-3}$ alkoxy, or 3- to 6-membered heterocyclyl, if valence permits.

In the Formula II, the letters "B" and "C" are designations for the corresponding rings. In other words, the ring with $Y_2$ and $Y_3$ as shown may be referred to as ring C; the ring with $Y_1$ as shown may be referred to as ring B; and so on.

In some preferred embodiments, $R_1$ is independently selected from a group consisting of hydrogen, halogen, $C_{1-6}$ alkyl, and $C_{1-6}$ alkoxy.

In some preferred embodiments, $R_0$ is independently selected from hydrogen and halogen.

In some preferred embodiments, $R_z$ is selected from $C_{3-6}$ cycloalkyl and 3- to 6-membered heterocycloalkyl having 1 or 2 heteroatoms independently selected from N, O and S, wherein $R_z$ may be optionally substituted 1-3 times by $C_{1-3}$ alkyl, $C_{1-3}$ haloalkyl, cyano-$C_{1-3}$ alkyl, halogen, cyano, oxo, $C_{1-3}$ alkoxy, or 3- to 6-membered heterocyclyl, if valence permits.

In some embodiments, $X_3$ is CH, and $X_4$ is N. In some embodiments, $X_3$ is N, and $X_4$ is CH. In some embodiments, $X_3$ and $X_4$ are each N. In some preferred embodiments, $X_3$ and $X_4$ are each CH.

In some of the embodiments described above, n is 1.

In some of such embodiments, is

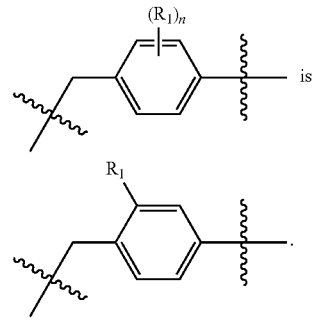

In some of the embodiments described above, $R_2$ is selected from —$CH_2$—$R_z$.

In some of the embodiments described above, W is O.

In some of the embodiments described above, q is 1.

In some of such embodiments,

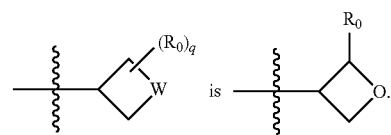

In some of the embodiments described above, the compound has a structure of Formula II-1:

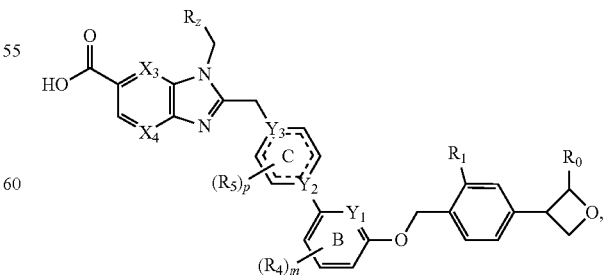

(II-1)

wherein $X_3$, $X_4$, $Y_1$, $Y_2$, $Y_3$, $R_z$, $R_0$, $R_1$, $R_4$, $R_5$, m and p are as defined for the compound of Formula II above;

preferably having a structure of formula II-2:

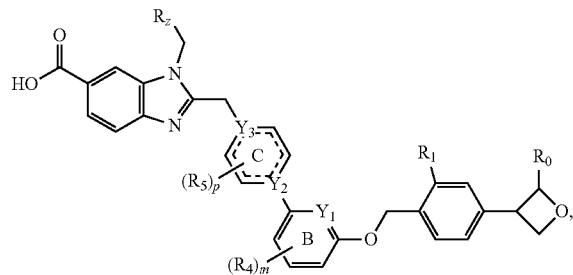

wherein $Y_1$, $Y_2$, $Y_3$, $R_z$, $R_0$, $R_1$, $R_4$, $R_5$, m and p are as defined for the compound of Formula II above.

In some of the embodiments described above, $R_1$ is independently selected from a group consisting of hydrogen, halogen, $C_{1-3}$ alkyl, and $C_{1-3}$ alkoxy, preferably independently selected from halogen and $C_{1-3}$ alkoxy, preferably selected from a group consisting of F, Cl, $CH_3O—$, $CH_3CH_2—O—$, $CH_3CH_2CH_2—O—$, or $(CH_3)_2CH—O—$, and more preferably selected from a group consisting of F, Cl, and $CH_3O—$.

In some of the embodiments described above,

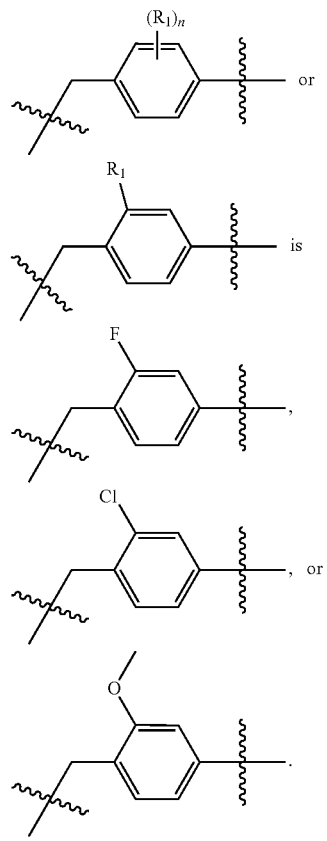

In some of the embodiments described above, $R_z$ is selected from $C_{3-6}$ cycloalkyl and 3- to 6-membered heterocycloalkyl having 1 or 2 heteroatoms independently selected from N, O, and S, wherein $R_z$ may be optionally substituted one time by $C_{1-3}$ alkyl, $C_{1-3}$ haloalkyl, cyano-$C_{1-3}$ alkyl, halogen or cyano, preferably by $C_{1-3}$ haloalkyl (preferably halomethyl), cyano-$C_{1-3}$ alkyl (preferably cyanomethyl) or halogen, if valence permits. In some embodiments, the halo or halogen is F or Cl.

In some preferred embodiments $R_z$ is selected from the group consisting of

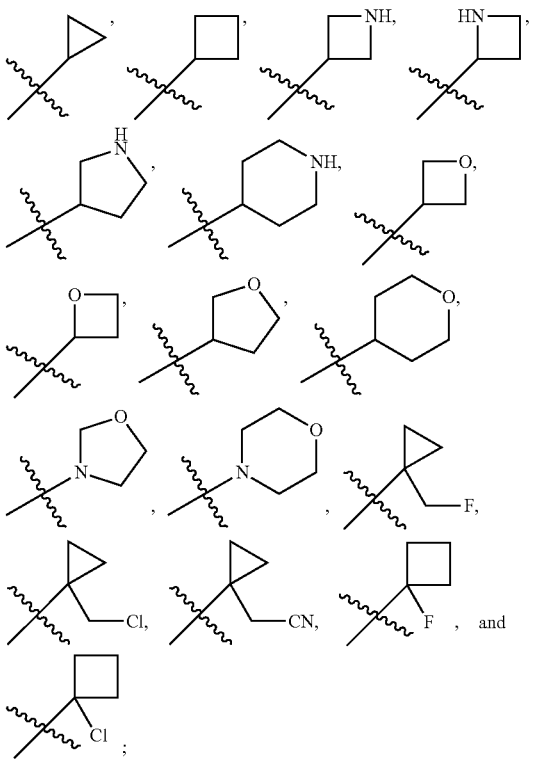

preferably selected from the group consisting of

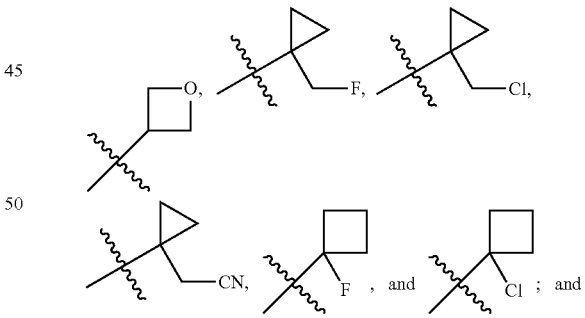

more preferably selected from a group consisting of

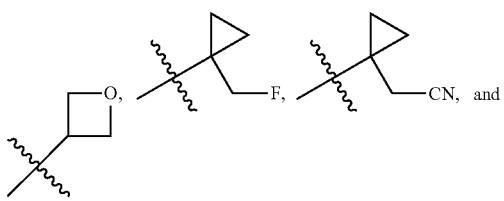

-continued

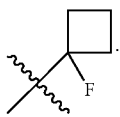

In some of the embodiments described above, $R_2$ or

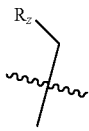

is preferably selected from the group consisting of

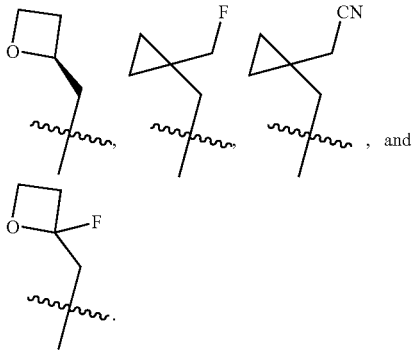
, and
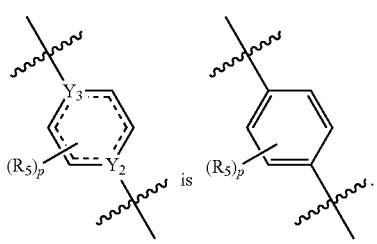

In some of the embodiments described above, $Y_2$ is C or CH.

In some of the embodiments described above, $Y_3$ is C or N.

In some embodiments, the present disclosure provides some preferred compounds of Formula II, wherein:
$Y_2$ is CH, $Y_3$ is N, p is 0, and

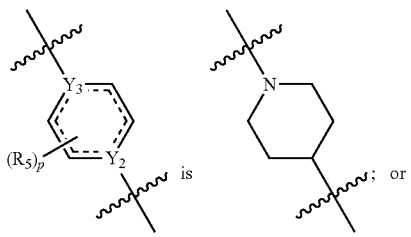

$Y_2$ is C, $Y_3$ is C, p is an integer of 1, 2 or 3, and

In some embodiments of the preferred compounds of Formula II, $Y_2$ is CH, $Y_3$ is N, p is 0, and

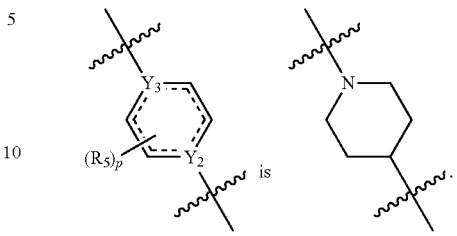 is

In some embodiments, the compound has a structure of Formula II-3:

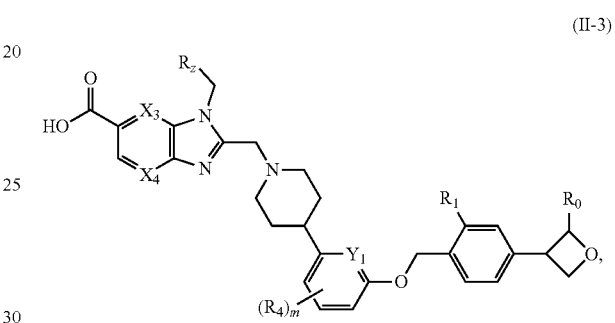

(II-3)

wherein $X_3$, $X_4$, $Y_1$, $R_z$, $R_0$, $R_1$, $R_4$, and m are as defined for the compound of Formula II above; preferably having a structure of Formula II-4:

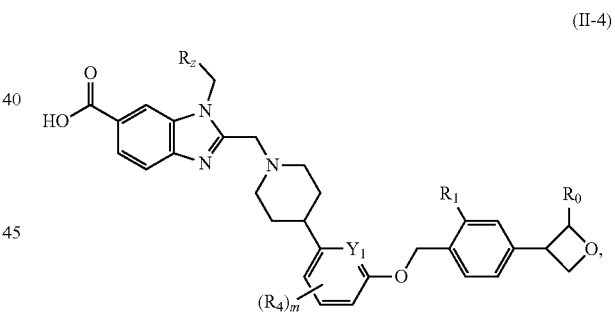

(II-4)

wherein $Y_1$, $R_z$, $R_0$, $R_1$, $R_4$, and m are as defined for the compound of Formula II above.

In some preferred embodiments, $R_z$ is selected from unsubstituted 3- to 6-membered heterocycloalkyl (preferably 3- to 4-membered heterocycloalkyl) having one O heteroatom, and preferably

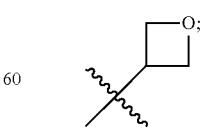

m is 0;
$R_1$ is F, Cl, $CH_3O$—, $CH_3CH_2$—O—, $CH_3CH_2CH_2$—O—, or $(CH_3)_2CH$—O—, preferably F, Cl, or $CH_3O$—; and
$R_0$ is hydrogen, F or Cl, and preferably hydrogen or F.

More preferably,

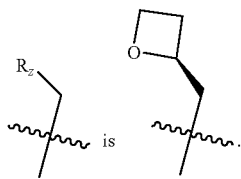

is 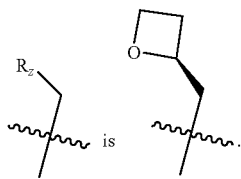.

In other preferred embodiments, $R_z$ is $C_{3-6}$ cycloalkyl (preferably $C_{3-4}$ cycloalkyl) optionally substituted by one substituent selected from a group consisting of $C_{1-3}$ haloalkyl (preferably halomethyl, more preferably —$CFH_2$ or —$CClH_2$), cyano-$C_{1-3}$ alkyl (preferably cyanomethyl) and halogen (preferably F or Cl), preferably

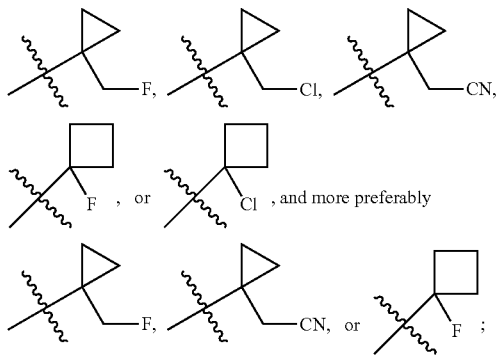

m is 0;
$R_1$ is F, Cl, $CH_3O$—, $CH_3CH_2$—O—, $CH_3CH_2CH_2$—O—, or $(CH_3)_2CH$—O—, preferably F or Cl; and
$R_0$ is hydrogen, F, or Cl, preferably hydrogen.

In other embodiments of the preferred compounds of Formula II, $Y_2$ is C, $Y_3$ is C, p is 1, and

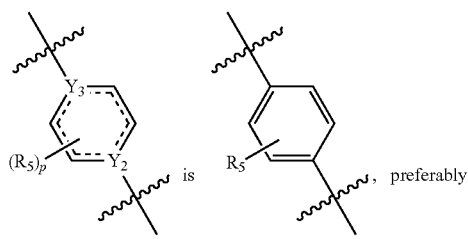

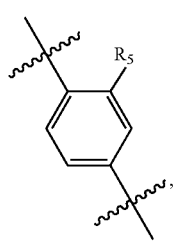

wherein $R_5$ is at the ortho position of $Y_3$.

In some embodiments, the compound has a structure of Formula II-5:

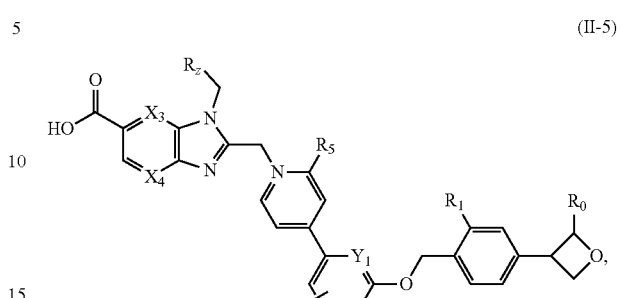

(II-5)

wherein $X_3$, $X_4$, $Y_1$, $R_z$, $R_0$, $R_1$, $R_4$, $R_5$, and m are as defined for the compound of Formula II above; preferably having a structure of Formula II-6:

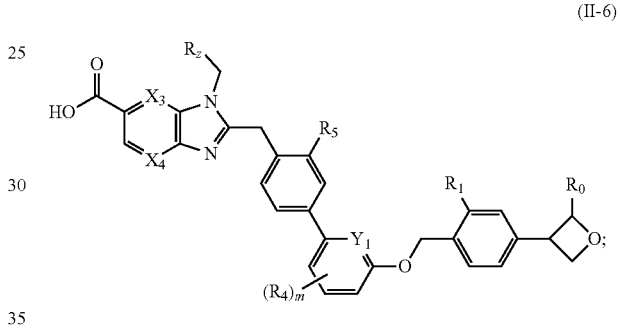

(II-6)

wherein $Y_1$, $R_z$, $R_0$, $R_1$, $R_4$, $R_5$, and m are as defined for the compound of Formula II above.

In some preferred embodiments, $R_5$ is hydrogen or halogen, preferably F or Cl, and more preferably F. In some preferred embodiments, $R_0$ is hydrogen, F, or Cl, and preferably hydrogen. In some preferred embodiments, $Y_1$ is N. In some preferred embodiments, $R_4$ is hydrogen.

In some embodiments, the present disclosure provides other preferred compounds of Formula II, wherein:

m is not 0 and p is not 0, and any $R_4$ and any $R_5$, together with the ring atoms of ring B and ring C therebetween, form a 5- to 8-membered ring, wherein the 5- to 8-membered ring has 0, 1, or 2 ring heteroatom(s) independently selected from N, O, and S, and the ring heteroatom(s) is not the ring atom(s) of ring B or ring C, and wherein the 5- to 8-membered ring may be optionally substituted 1-3 times by $C_{1-3}$ alkyl, $C_{1-3}$ alkoxy, $C_{1-3}$ haloalkyl, halogen, cyano, oxo, $C_{1-3}$ alkoxy, if valence permits.

In some preferred embodiments, m is 1 and p is 1, $R_4$ and $R_5$, together with the ring atoms of ring B and ring C therebetween, form a 5- to 8-membered ring, wherein the 5- to 8-membered ring has 0, 1, or 2 ring heteroatoms independently selected from N, O, and S, and the ring heteroatoms are not the ring atom(s) of ring B or ring C, and wherein the 5- to 8-membered ring may be optionally substituted 1-3 times by $C_{1-3}$ alkyl, $C_{1-3}$ alkoxy, $C_{1-3}$ haloalkyl, halogen, cyano, oxo, $C_{1-3}$ alkoxy, if valence permits.

In some of such embodiments, the compound has a structure of Formula II-7:

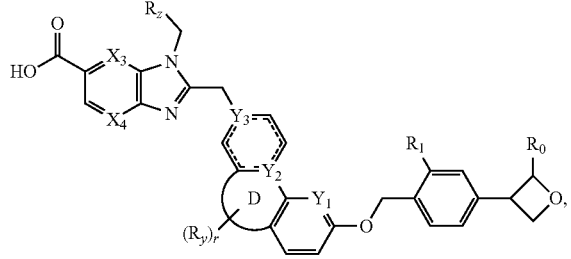

(II-7)

wherein:

ring D

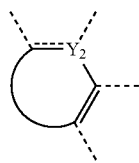

is a 5- to 8-membered ring as defined above;

===== represents a single or double bond;

$Y_1$, $Y_2$, and $Y_3$ are each as defined for the compound of Formula II above;

$R_y$ is selected from a group consisting of hydrogen, $C_{1-3}$ alkyl, $C_{1-3}$ alkoxy, $C_{1-3}$ haloalkyl, halogen, cyano, oxo, and $C_{1-3}$ alkoxy; and r is 1, 2, or 3. Preferably, r is 1.

Preferably, the compound has a structure of Formula II-8:

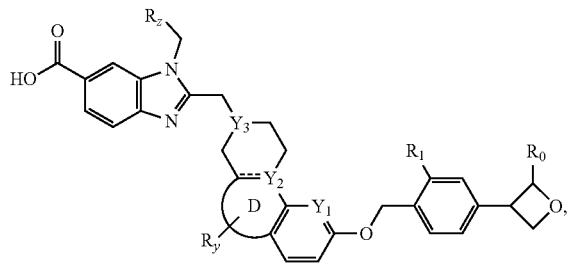

(II-8)

Preferably, $R_y$ is hydrogen.

In some of the embodiments described above, ring D

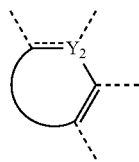

is selected from the group consisting

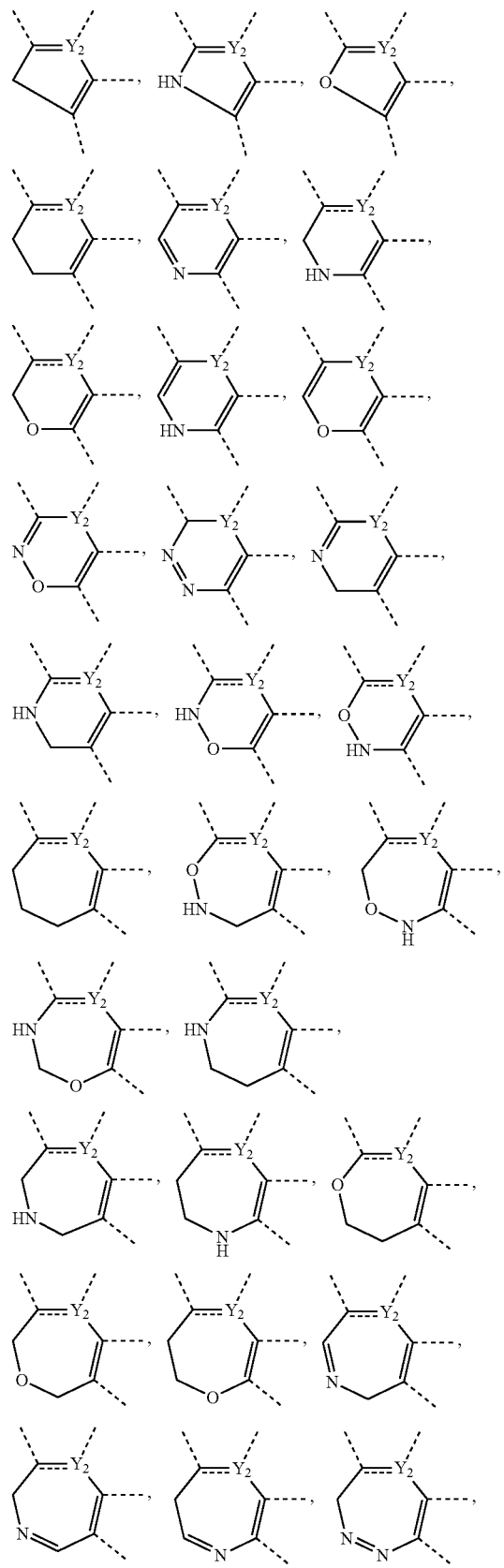

-continued
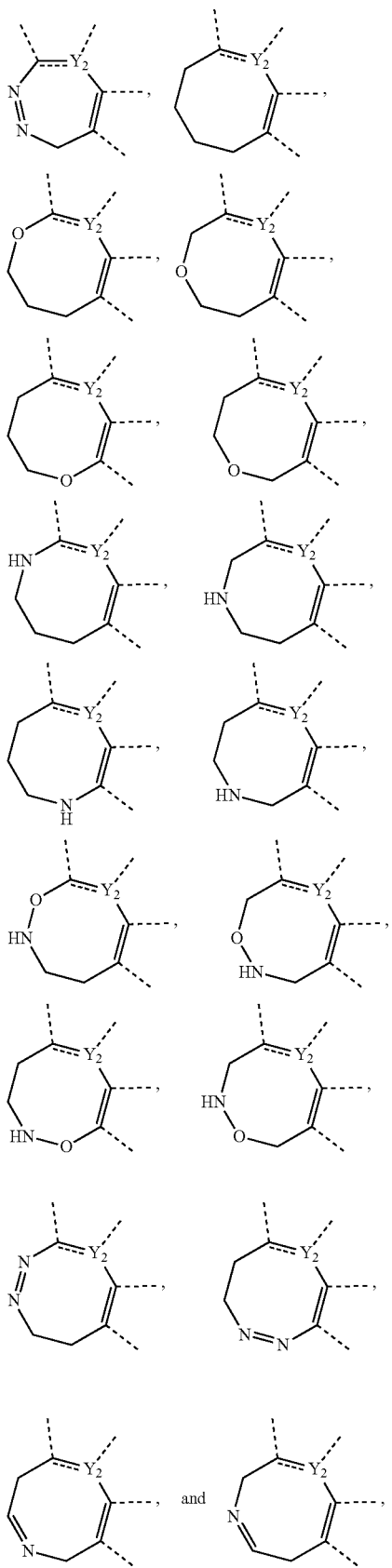
preferably selected from a group consisting of
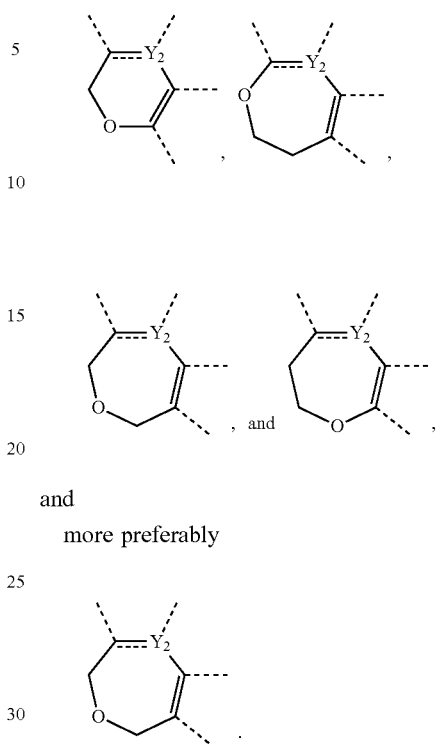
and more preferably
and
In some preferred embodiments, the compound has a structure of Formula II-9:
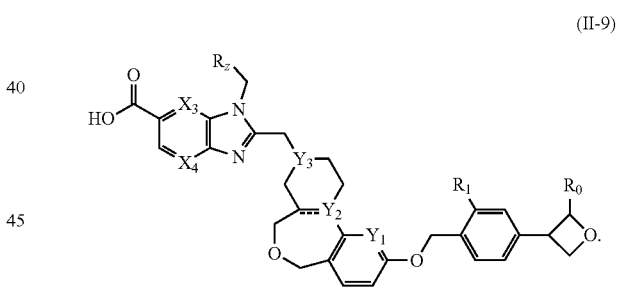
(II-9)
In some of the embodiments described above, $Y_3$ is N. In some of the embodiments described above, $Y_1$ is N.
In some of such embodiments,
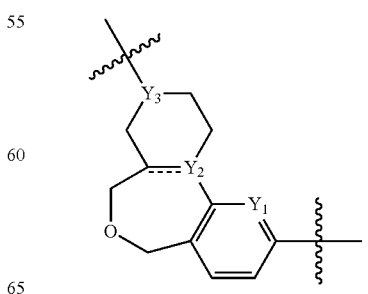

is selected from

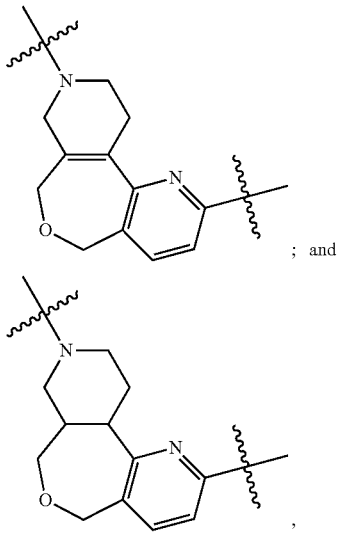
; and including

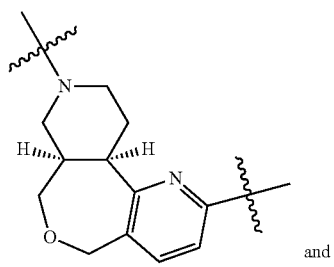
and

-continued

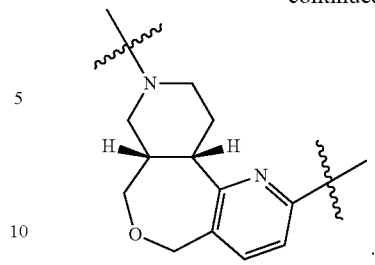

In some of the embodiments described above, $R_z$ is selected from unsubstituted 3- to 6-membered heterocycloalkyl (preferably 3- to 4-membered heterocycloalkyl) having one O heteroatom, preferably

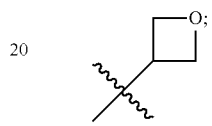

$R_1$ is F, Cl, $CH_3O$—, $CH_3CH_2$—O—, $CH_3CH_2CH_2$—O—, or $(CH_3)_2CH$—O—, preferably F or Cl; and
$R_0$ is hydrogen, F, or Cl, preferably hydrogen.
More preferably,

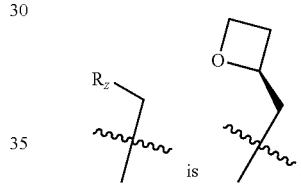

In some embodiments, the present disclosure provides a compounds as described above, which is:

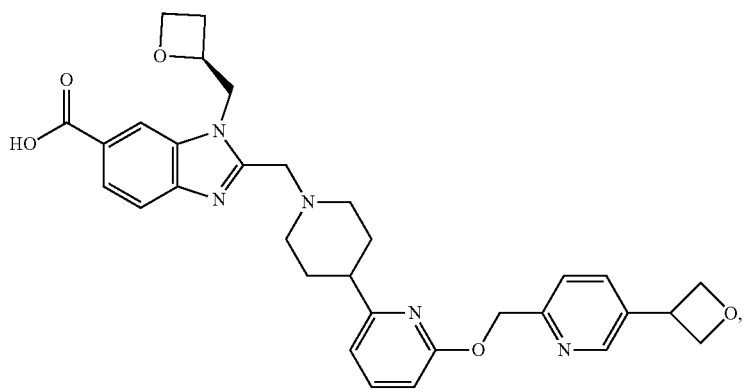

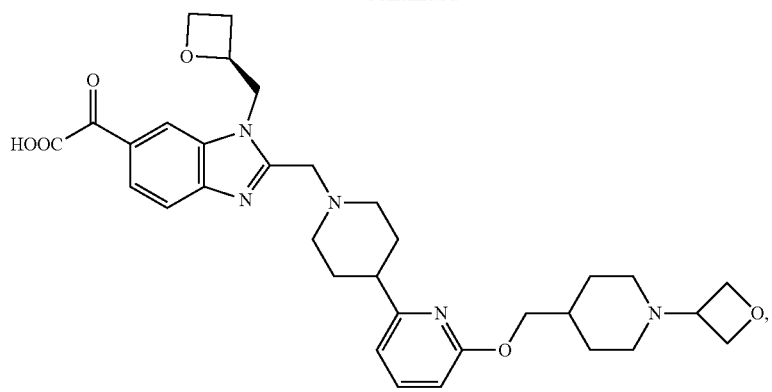
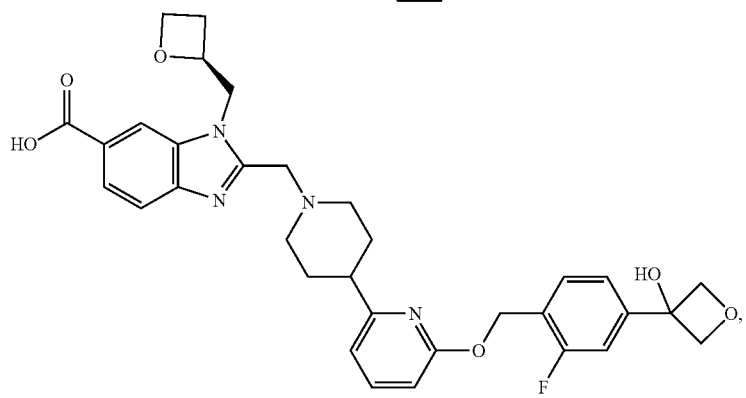
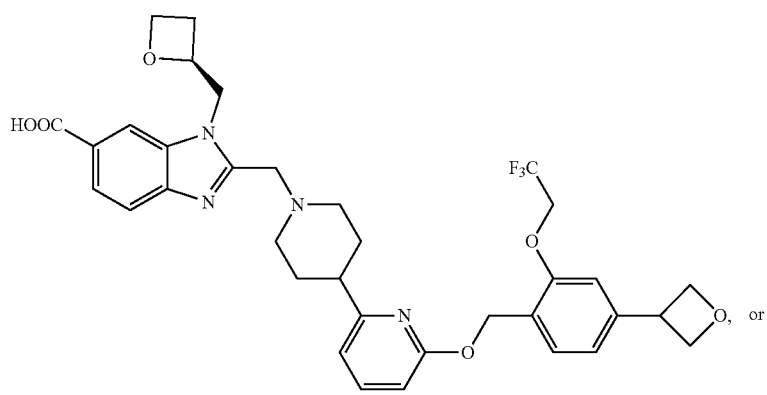
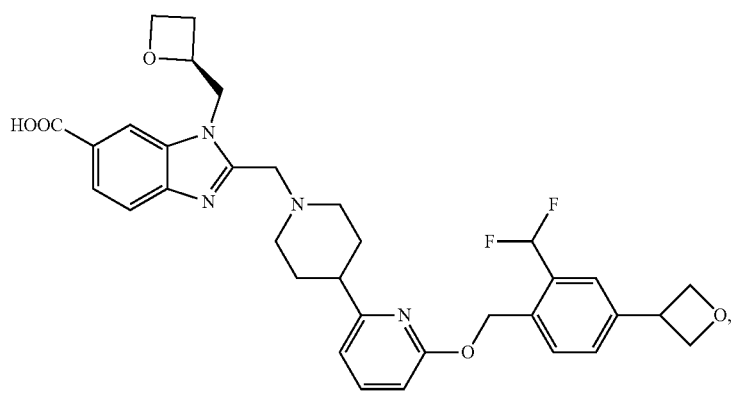

-continued
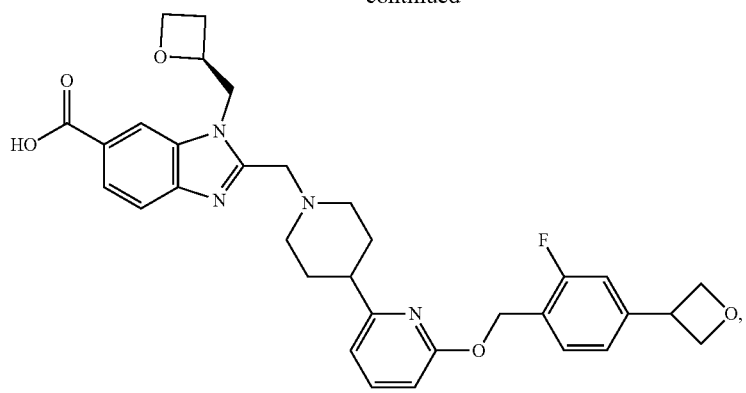
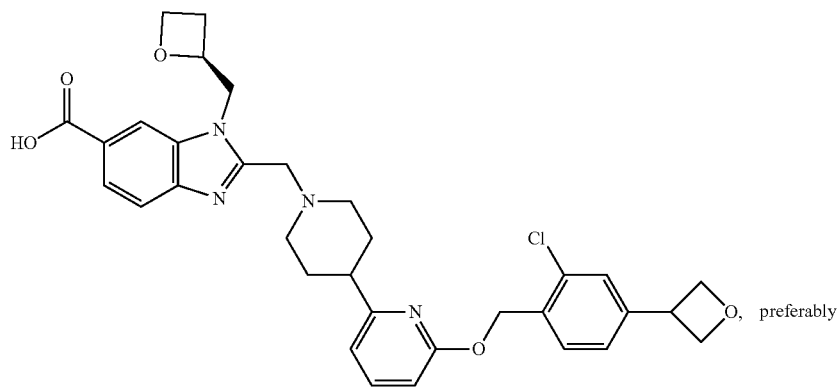, preferably
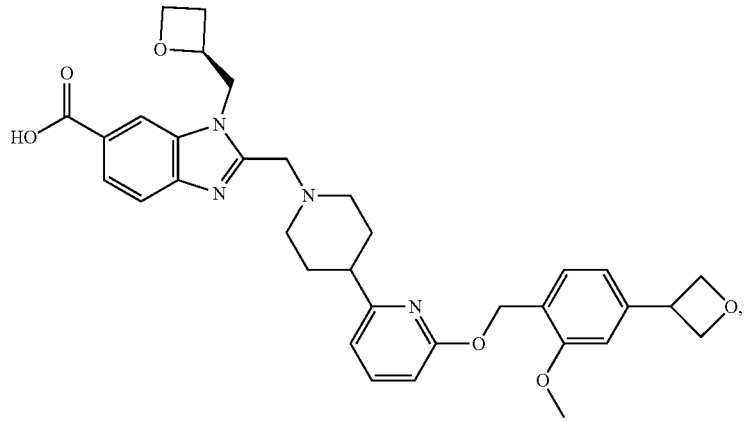
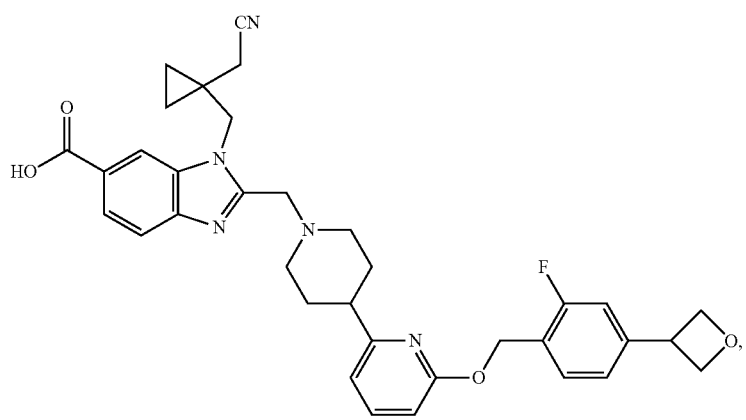,

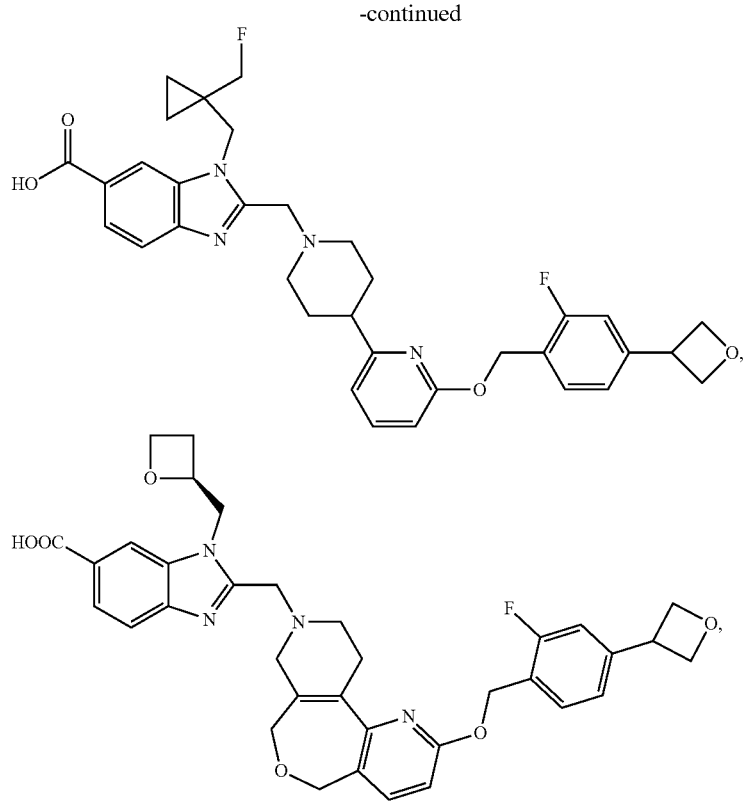
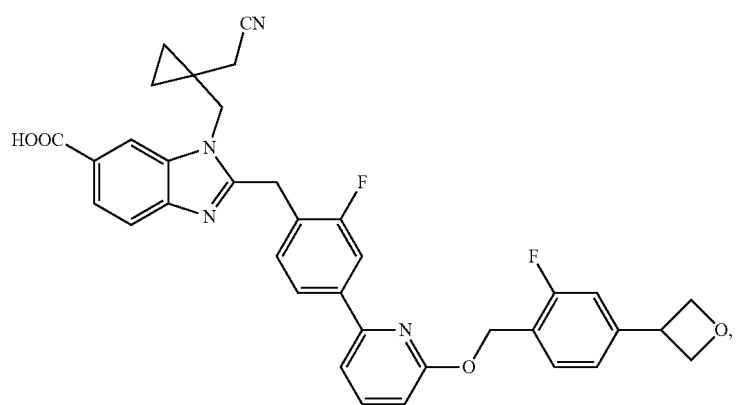
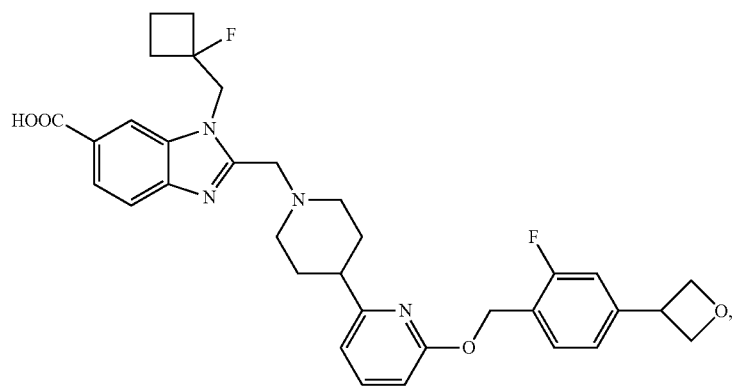

-continued
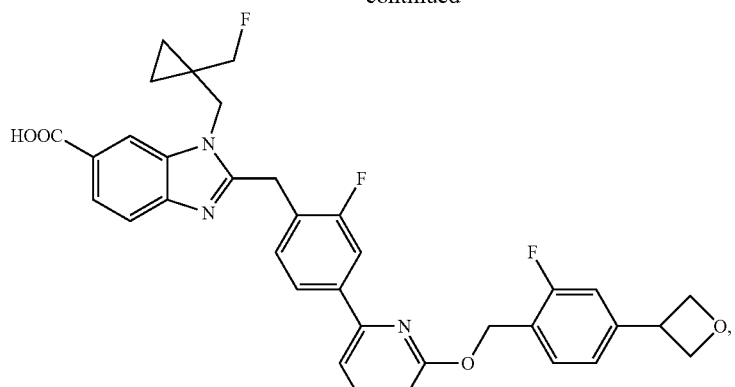,
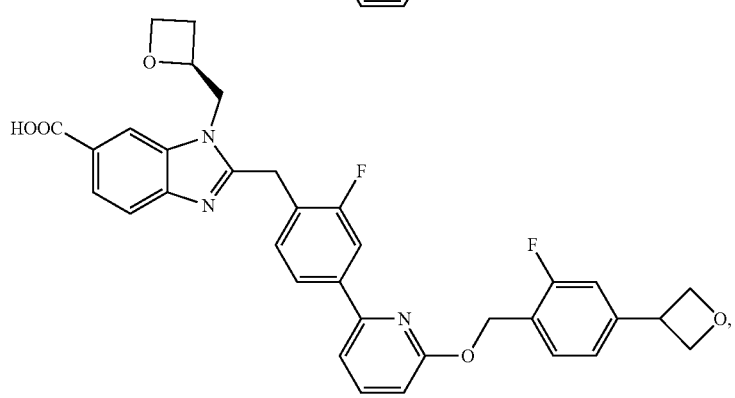,
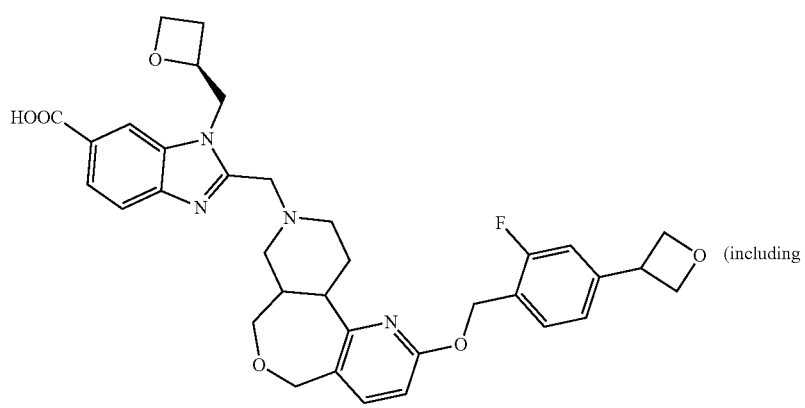 (including
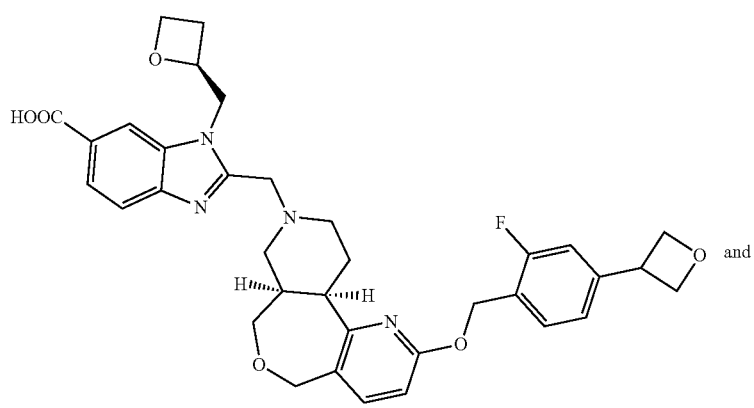 and

-continued
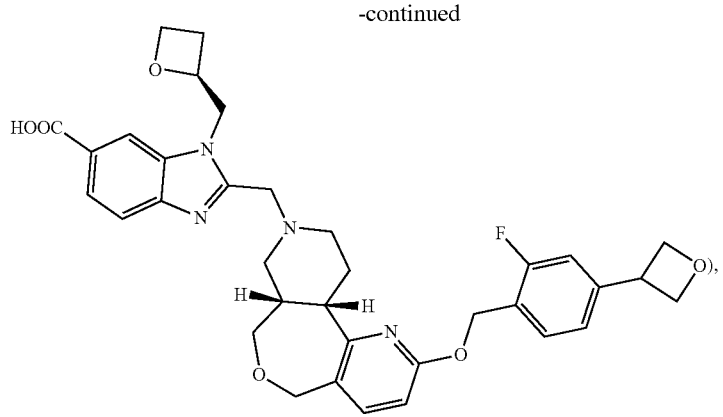
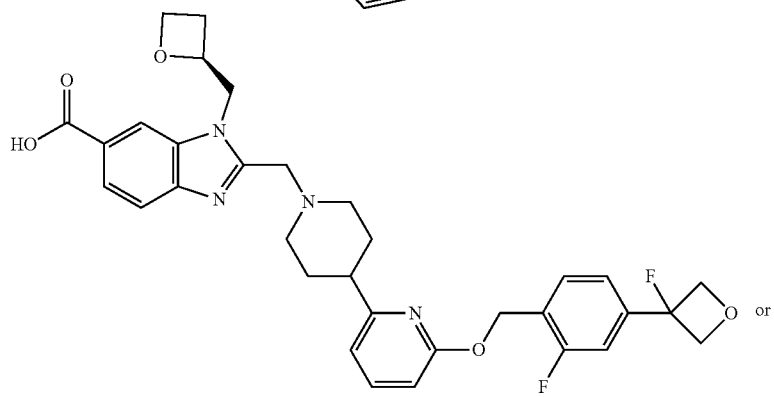
or
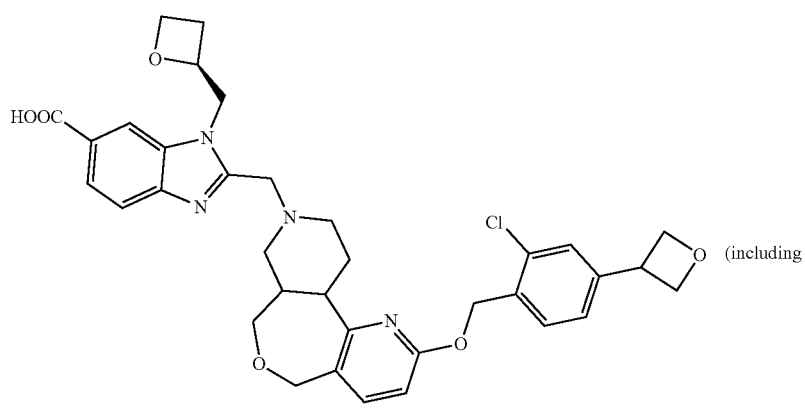
(including
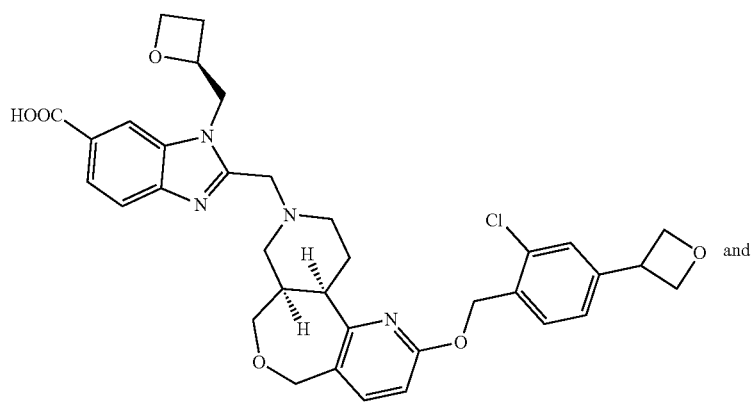
and

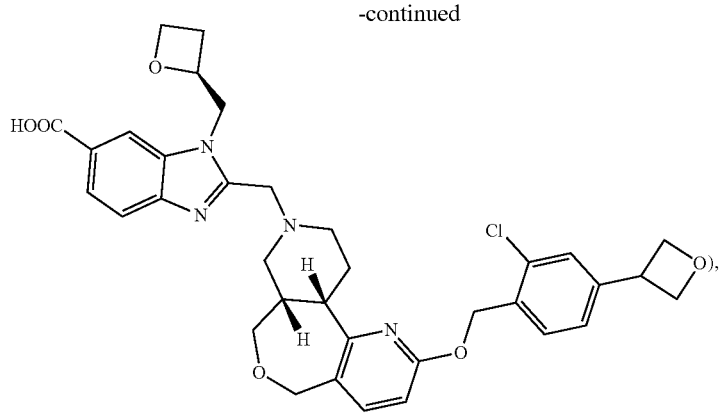
or a pharmaceutically acceptable salt or stereoisomer thereof.
The present disclosure further provides the following compounds:
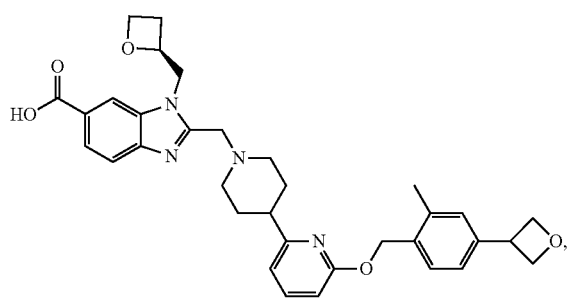
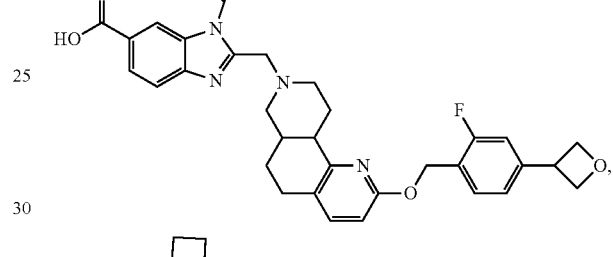
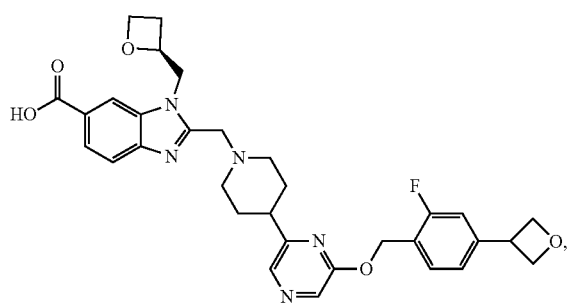
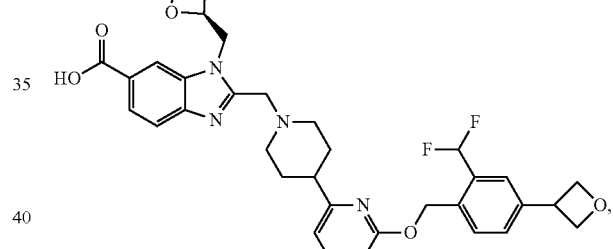
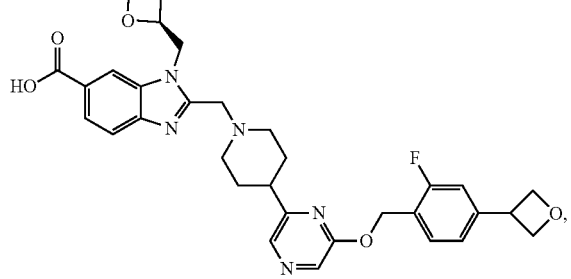
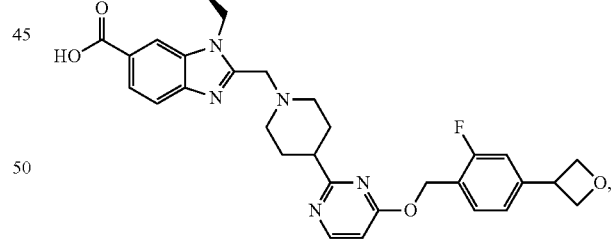
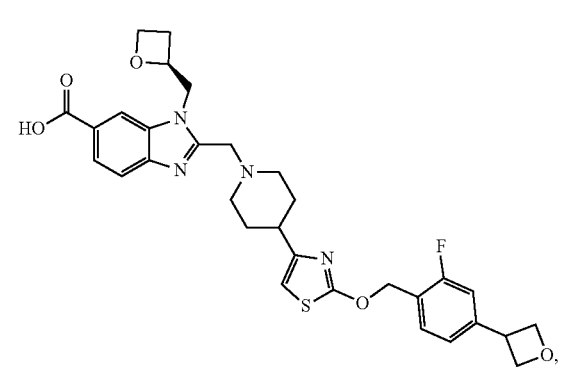
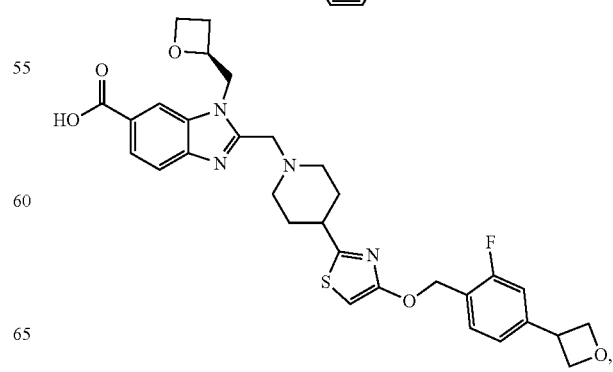

43
-continued

44
-continued

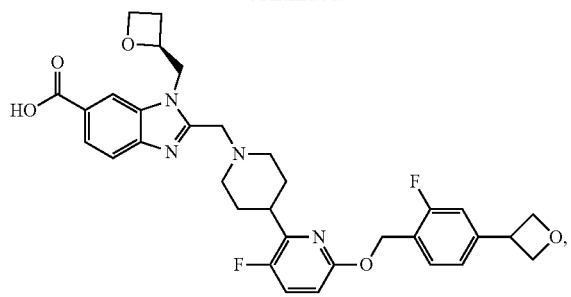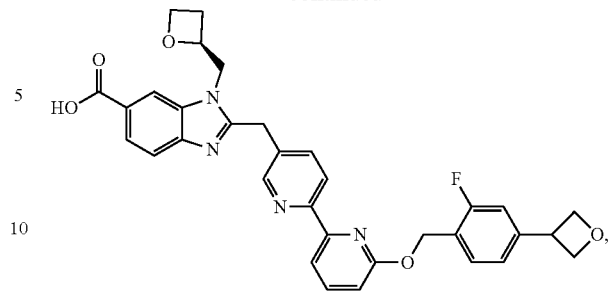

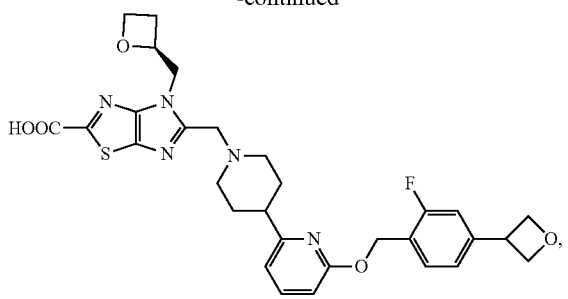

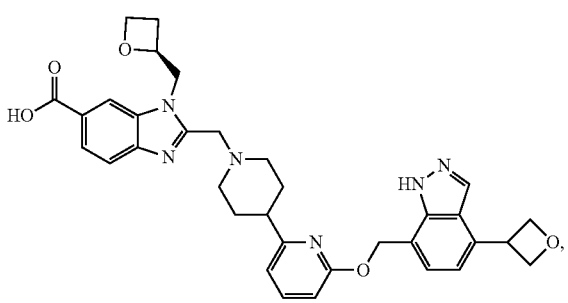

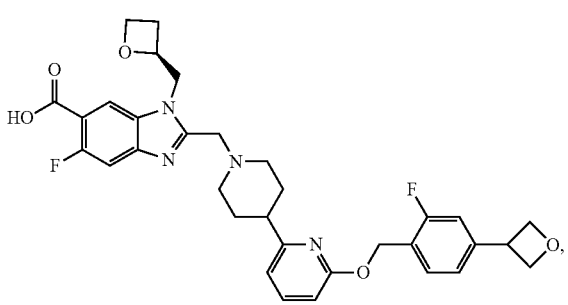

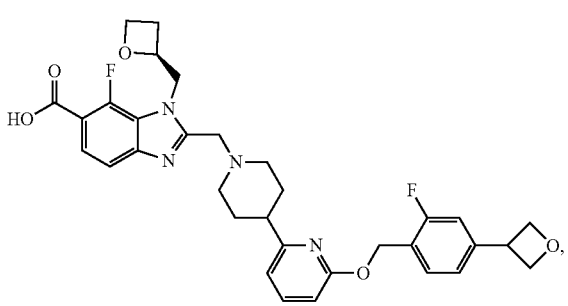

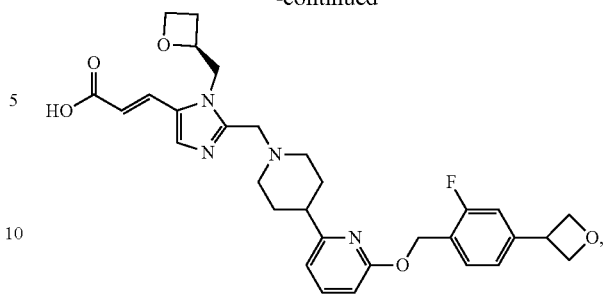

or pharmaceutically acceptable salts or stereoisomers thereof.

The compounds provided by the present disclosure are GLP-1 receptor agonists, and some of the preferred compounds of Formula I, particularly the compounds of Formula II, and pharmaceutically acceptable salts thereof, have excellent GLP-1 receptor agonistic activity. These GLP-1 receptor agonistic compounds are capable of treating and/or preventing GLP-1 receptor mediated diseases or disorders and related diseases or disorders.

The compounds of Formula I or Formula II and pharmaceutically acceptable salts and stereoisomers thereof provided in the present disclosure can be used alone or in combination with at least one other therapeutic agent in the treatment.

The present disclosure further provides a pharmaceutical composition comprising the compound of Formula I or Formula II, or a pharmaceutically acceptable salt or stereoisomer thereof, as described above, as well as one, two or more additional therapeutically active ingredients.

The present disclosure also provides a pharmaceutical composition comprising the compound of Formula I or Formula II, or a pharmaceutically acceptable salt or stereoisomer thereof, as described above, as well as a pharmaceutically acceptable carrier, excipient, or diluent.

The present disclosure also provides a pharmaceutical formulation comprising the compound of Formula I or Formula II, or a pharmaceutically acceptable salt or stereoisomer thereof, as described above, as well as one or more pharmaceutically acceptable carriers, excipients, or diluents.

The pharmaceutically acceptable carriers, excipients, and/or diluents that can be used in the pharmaceutical composition or pharmaceutical formulation of the present disclosure can be any conventional carriers, excipients, and/or diluents in the field of pharmaceutical formulation.

The pharmaceutically acceptable salt described herein includes an acid addition salt and a base salt.

The pharmaceutically acceptable salt described herein may be present in non-solvated and solvated forms.

The present disclosure further provides use of the compound of Formula I or Formula II, and a pharmaceutically acceptable salt or stereoisomer thereof, as described above, in the manufacture of a medicament for the treatment and/or prevention of a metabolism related disease or disorder. The metabolism related disease or disorder includes GLP-1 receptor-mediated diseases or disorders and related diseases or disorders.

The present disclosure further provides a method for treating a disease or disorder, comprising administering to a patient in need thereof a therapeutically effective amount of the compound of Formula I or Formula II, and a pharmaceutically acceptable salt or stereoisomer thereof, as described above, wherein the disease or disorder is a GLP-1 receptor-mediated disease or disorder, or a related disease or disorder.

In some embodiments, the GLP-1 receptor-mediated disease or disorder is diabetes. In some embodiments, the diabetes includes, but is not limited to, type I diabetes (T1D) and/or type II diabetes (T2DM), idiopathic T1D, early-onset T2DM, latent autoimmune diabetes, juvenile atypical diabetes, gestational diabetes. In some embodiments, the GLP-1 receptor-mediated disease or disorder is hyperglycemia, insulin resistance, glucose intolerance. In some embodiments, the related disease or disorder of a GLP-1 receptor-mediated disease or disorder includes diabetic nephropathy, diabetic ocular complications (diabetic retinopathy, uveitis related to diabetes, diabetic cataract), diabetic foot, diabetic cardiovascular complications, diabetic cerebrovascular disease, diabetic neuropathy, obesity, hypertension.

In some embodiments, the GLP-1 receptor-mediated disease or disorder and related diseases or disorders include, but are not limited to, diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia. Said diabetes includes, but is not limited to, T1D and/or T2DM, idiopathic T1D, early-onset T2DM, latent autoimmune diabetes, juvenile atypical diabetes, gestational diabetes.

The present disclosure further provides use of the compounds of Formula I and Formula II, or pharmaceutically acceptable salts or stereoisomers thereof in the preparation of GLP-1 receptor agonist related drugs.

In some embodiments, the GLP-1 receptor agonist related drugs are for the treatment of type II diabetes, type I diabetes, and obesity.

Definitions

The compounds in the present disclosure are named according to the chemical structural formula. Where the name of a compound is inconsistent with the chemical structural formula of the same compound, the chemical structural formula shall prevail.

In the present disclosure, unless defined otherwise, all scientific and technical terms used herein have the same meaning as those commonly understood by a person skilled in the art. Nevertheless, definitions of some terms are provided below for a better understanding of the present disclosure. Where the definitions and interpretations of the terms provided herein differ from those commonly understood by a person skilled in the art, the definitions and interpretations of the terms provided herein shall prevail.

The compound and pharmaceutically acceptable salt thereof provided in the present disclosure may be present in a chiral form, i.e., in S-configuration or R-configuration. The compound and pharmaceutically acceptable salt thereof provided in the present disclosure may be present in an achiral form. When the structure of a compound described in the present disclosure is exemplified by one configuration, it is intended that the other configuration or the achiral form thereof is disclosed as well.

The compound described in the present disclosure comprises a stereoisomer of the compound. The stereoisomer described in the present disclosure means that when the compound as shown by Formula I or formula II has a asymmetric carbon atom, enantiomers will exist; when the compound has a carbon-carbon double bond or cyclic structure, cis-trans isomers will exist; when a ketone or oxime is present in the compound, tautomers will exist. In some embodiments, stereoisomers described in the present disclosure include, but are not limited to, enantiomers, diastereomers, racemic isomers, cis-trans isomers, tautomers, geometric isomers, epimers, and mixtures thereof.

The compound of the present disclosure may exist in specific geometric or stereoisomer forms. All of such compounds are contemplated in the present disclosure, including cis and trans isomers, (−)- and (+)-enantiomers, (R)- and (S)-enantiomers, diastereomers, (D)-isomers, (L)-isomers, and the racemic mixtures and other mixtures thereof, such as enantiomer- or diastereomer-enriched mixtures, all of these mixture falling within the scope of the present disclosure. Additional asymmetric carbon atoms may be present in substituents such as alkyl. All these isomers and mixtures thereof are included within the scope of the present disclosure.

Unless otherwise stated, the terms "enantiomers" or "optically active isomers" refer to stereoisomers that are mirror images of one another.

Unless otherwise stated, the terms "cis-trans isomers" or "geometrical isomers" occur due to the inability to freely rotate of a double bond or a single bond of ring-forming carbon atoms.

Unless otherwise stated, the term "diastereomers" refer to stereoisomers that have two or more chiral centers and are not mirror images of one another.

Unless otherwise stated, "(+)" denotes right-handed, "(−)" denotes left-handed, and "(±)" denotes racemic.

Unless otherwise stated, the wedged solid bond ($\blacktriangleleft$) and wedged dashed bond ($\triangleleft^{\cdots}$) are used to denote the absolute configuration of a stereocenter, the straight solid bond ($\blacktriangleleft$) and straight dashed bond ($\triangleleft^{\cdots}$) are used to indicate that the stereocenter is an absolute configuration, but it is not sur6 whether it is a wedged solid bond ($\blacktriangleleft$) or a wedged dashed bond ($\triangleleft^{\cdots}$). .

Optically active (R)- and (S)-isomers and D and L isomers can be prepared by chiral synthesis or chiral reagents or other conventional techniques. If one enantiomer of a compound of the present disclosure is desired, it can be prepared by asymmetric synthesis or the derivatization with a chiral auxiliary reagent, in which the obtained diastereomeric mixture is separated and the auxiliary group is cleaved to provide the pure desired enantiomer. Alternatively, when a basic functional group (e.g., amino) or an acidic functional group (e.g., carboxyl) in a molecule, the molecule can be reacted with a suitable optically active acid or base to form salts of the diastereomers, which can then be subjected to diastereomeric resolution by conventional techniques known to those skilled in the art, followed by recovery of pure enantiomers. In addition, enantiomers and diastereomers are usually separated by chromatography using a chiral fixed phase and optionally combined with chemical derivatization (e.g., producing a carbamate from an amine).

The term "pharmaceutically acceptable" in the present disclosure means that those compounds, materials, compositions and/or dosage forms, within the limits of sound medical judgment, are suitable for use in contact with human and animal tissues without excessive toxicity, irritation, allergic reactions, or other issues or complications, and are commensurate with a reasonable benefit/risk ratio.

The term "pharmaceutically acceptable salt" in the present disclosure refers to a salt of the compound of the invention, which is prepared from the compound with a specific substituent of the present disclosure and a relatively non-toxic acid or base. Where the compounds of the present disclosure contain relatively acidic functional groups, base addition salts can be obtained by contacting such compounds with a sufficient amount of a base in a pure solution or in a suitable inert solvent. Where the compounds of the present disclosure contain relatively basic functional groups, acid addition salts can be obtained by contacting such compounds with a sufficient amount of an acid in a pure solution or in a suitable inert solvent. Examples of pharmaceutically acceptable acid addition salts include salts of inorganic acids, and also salts of amino acids (such as arginine), as well as salts of organic acids such as glucuronic acid. Some specific compounds of the present disclosure contain both basic and acidic functional groups, and are allowed to be converted to any base or acid addition salt.

The pharmaceutically acceptable salts of the present disclosure can be synthesized by conventional chemical methods from parent compounds containing acid or base groups. Typically, such salts are prepared by reacting these compounds in a form of free acids or bases with a stoichiometric amount of an appropriate base or acid in water or an organic solvent or a mixture of both.

The term "optional" or "optionally" in the present disclosure means that a subsequently described event or condition may, but not necessarily, occur and that the description includes cases in which the event or condition occurs and cases in which the event or condition does not occur.

The term "substituted" as used herein means that any one or more hydrogen atoms on a particular atom are substituted by a substituent which may include heavy hydrogen and variants of hydrogen, as long as the valence state of the particular atom is normal and the substituted compound is stable. When the substituent is oxo (i.e., =O), it means that two hydrogen atoms are substituted. Oxo substitution does not occur on aromatic groups. The term "optionally substituted" refers to being substituted or unsubstituted. Unless otherwise specified, the kind and number of the substituent may be arbitrary on a chemically achievable basis.

The term "optionally substituted" in the present disclosure refers to both "substituted" and "unsubstituted".

When any variable (e.g., R) occurs more than once in the constitution or structure of a compound, it is defined independently of one another in each case. Therefore, for example, if a group is substituted by 0-2 R, said group may be optionally substituted by at most two R, and R in each case has independent options. Furthermore, combinations of substituents and/or variants thereof are permitted only if such combinations will result in stable compounds.

When the number of a linking group is 0, such as —(CRR)$_0$—, it means that the linking group is a single bond.

When the number of a substituent is 0, it means that the substituent does not exist, for example, -A-(R)$_0$ indicates that the structure is actually -A.

When a substituent is vacant, it means that the substituent does not exist, for example, when X is vacant in A-X, it means that this structure is actually A.

When one of the variables is selected from a single bond, it means that the two groups to which it is linked are directly connected, for example, when L in A-L-Z represents a single bond, it means that this structure is actually A-Z.

When the bond of a substituent may be cross-linked to two or more atoms in a ring, such substituent may be bonded to any atom in the ring. For example, the structural unit

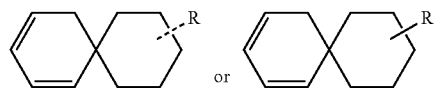

means that the substituent R may substitute any position on the cyclohexyl or cyclohexadiene. When it is not specified by which atom in a recited substituent it is attached to the substituted group, the substituent may be bonded by any of its atoms. For example, the pyridyl group as a substituent may be attached to the substituted group by any of the carbon atoms in the pyridine ring.

Where the linking orientation of a recited linking group is not indicated, the linking orientation thereof is arbitrary. For example, where the linking group L in

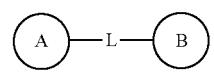

is -M-W—, the -M-W— can either connect ring A and ring B in the same orientation as the reading order from left to right to form

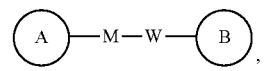, or connect ring A and ring B in the opposite orientation to the reading order from left to right to form

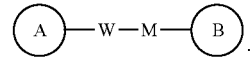.

Combinations of the linking groups, substituents and/or variants thereof are permitted only if such combinations may result in stable compounds.

Unless otherwise specified, when a group has one or more linkable sites, any one or more sites of the group may be linked to other groups by a chemical bond. When the site to which the chemical bond is linked is not specified and there exist H atoms at a linkable site, the number of the H atoms at the linkable site when linked to the chemical bond will decrease correspondingly with the number of the linking chemical bond to become a group with a corresponding valence number. The chemical bond between the site and other groups may be represented by a straight solid bond (╱), a straight dashed bond (╱), or a wavy line (⌇). For example, the straight solid bond in —OCH$_3$ indicates connection to other groups through the oxygen atom in the group; the straight dashed bonds in the group

indicate connection to other groups through both ends of the nitrogen atom in the group; the wavy lines in

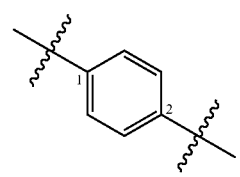 [SMILES: *c1ccc(*)cc1]

indicate connection to other groups through carbon atoms at positions 1 and 2 in the phenyl group;

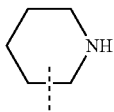

indicates that any linkable site on the piperidine group can be connected to other groups through one chemical bond, at least including the four connection manners:

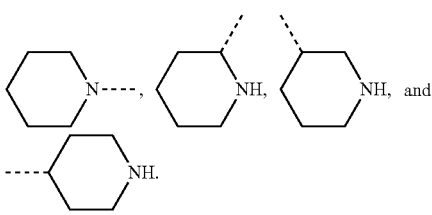

Even if an H atom is shown on —N—,

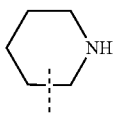

still includes the

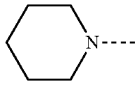

group in such a connection manner which causes a corresponding reduction by one of H on this site when connected with one chemical bond, resulting in a corresponding monovalent piperidinyl.

Unless otherwise specified, the number of atoms in a ring is usually defined as the number of the members of the ring. For example, a "5- to 7-membered ring" refers to a "ring" of 5 to 7 atoms in a cyclic arrangement.

The terms "halo", "halogen" and "halogen atom" in the present disclosure means a fluorine atom, a chlorine atom, a bromine atom, an iodine atom, and the like. Preferably, the halogen atoms as substituents on the aryl groups in the present disclosure are fluorine and chlorine atoms. Preferably, the halogen atoms as substituents on the alkyl groups in the present disclosure are fluorine and chlorine atoms. $C_{1-6}$ alkyl groups with a halogen atom as a substituent include, but are not limited to, fluoromethyl, difluoromethyl, trifluoromethyl, chloromethyl, pentafluoroethyl, 2-fluoroethyl, 2,2,2-trifluoroethyl, 2-chloroethyl, heptafluoropropyl, 3,3,3-trifluoropropyl, 2,3-dichloropropyl, 1-fluoro-3-bromopropyl, 4-bromobutyl, 3,3,3,4,4-pentafluorobutyl, 4,4-dichlorobutyl, 5-iodopentyl, 5,5-difluoropentyl, 6-chlorohexyl, and 6,6,6-trifluorohexyl.

The term "$C_{1-6}$ alkyl" in the present disclosure is a straight or branched alkyl group having 1 to 6 carbons, including but not limited to, methyl, ethyl, n-propyl, isopropyl, n-butyl, isobutyl, sec-butyl, tert-butyl, 1-methylpropyl, n-amyl, iso-amyl, 2-methylbutyl, 1,1-dimethylpropyl, 1-ethylpropyl, n-hexyl, 4-methylpentyl, and 2-ethylbutyl. The term "$C_{1-3}$ alkyl" is a straight or branched alkyl group having 1 to 3 carbons, including but not limited to, methyl, ethyl, n-propyl and isopropyl.

The term "$C_{1-6}$ alkoxy" in the present disclosure means a $C_{1-6}$ alkyl-O— group, including but not limited to methoxy, ethoxy, n-propoxy, isopropoxy, n-butoxy, isobutoxy, sec-butoxy, tert-butoxy, 1-methylpropoxy, n-amyloxy, isoamyloxy, 2-methylbutoxy, 1,1-dimethylpropoxy, 1-ethylpropoxy, n-hexyloxy, 4-methylamyloxy, and 2-ethylbutoxy. The term "$C_{1-3}$ alkoxy" means a $C_{1-3}$ alkyl-O— group, including but not limited to methoxy, ethoxy, n-propoxy and isopropoxy.

The term "aryl" in the present disclosure refers to a 6- to 14-membered all-carbon monocyclic or fused polycyclic (i.e., rings sharing a pair of adjacent carbon atoms) group having a conjugated n-electron system, preferably a 6- to 10-membered ring, such as phenyl and naphthyl, more preferably phenyl. The aryl ring may be fused to heteroaryl, heterocyclyl or cycloalkyl rings, including benzo 3- to 8-membered cycloalkyl and benzo 3- to 8-membered heterocyclyl, wherein the heterocyclyl is a heterocyclic group containing 1 to 3 ring heteroatoms independently selected from N, O and S; or further including a ternary nitrogen-containing fused ring containing a benzene ring.

The term "heteroaryl" or "heteroaryl ring" in the present disclosure refers to a heteroaromatic system with 5 to 14 ring atoms, which has 1 to 4 ring heteroatoms independently selected from N, O and S. The heteroaryl group is preferably 5- to 10-membered, more preferably 5- or 6-membered, such as imidazolyl, furyl, thienyl, thiazolyl, pyrazolyl, oxazolyl, pyrrolyl, triazolyl, tetrazolyl, pyridyl, pyrimidine, thiadiazole, pyrazinyl, preferably triazolyl, thienyl, imidazolyl, pyrazolyl, oxazolyl, pyrimidine or thiazolyl. The heteroaryl ring may be fused to an aryl, heterocyclyl or cycloalkyl ring, wherein the ring attached to the parent structure is a heteroaryl ring, including but not limited to

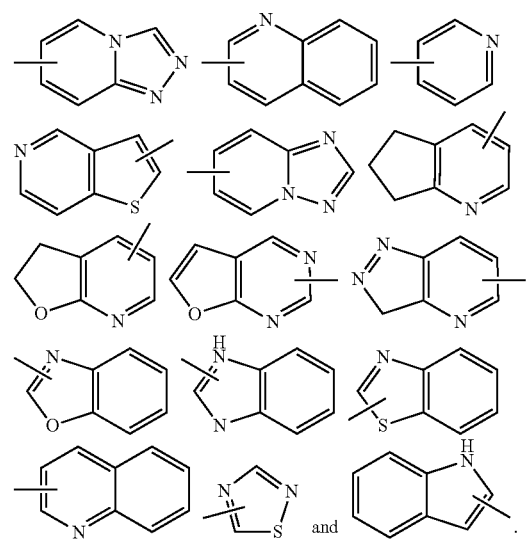

The heteroaryl group may be optionally substituted or unsubstituted. When substituted, the substituent may be preferably one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxyl, heterocyclylalkoxyl, cycloalkylthio, heterocyclylalkylthio, carboxyl, or carboxylic ester groups.

Unless otherwise specified, the terms "5- to 6-membered heteroaromatic ring" and "5- to 6-membered heteroaryl" in the present disclosure can be used interchangeably. The term "5-6-membered heteroaryl" means a monocyclic group having a conjugated n-electron system which consists of 5 to 6 ring atoms, of which 1, 2, 3 or 4 ring atoms are heteroatoms independently selected from O, S and N and the remainder are carbon atoms, wherein the nitrogen atom is optionally quaternized, and nitrogen and sulfur heteroatoms may be optionally oxidized (i.e., NO and S(O)p, p being 1 or 2). The 5- to 6-membered heteroaryl may be connected to the rest of the molecule through a heteroatom or carbon atom. The 5- to 6-membered heteroaryl comprises 5-membered and 6-membered heteroaryl groups. Examples of the 5- to 6-membered heteroaryl group include, but are not limited to, pyrrolyl (including N-pyrrolyl, 2-pyrrolyl, 3-pyrrolyl, etc.), pyrazolyl (including 2-pyrazolyl, and 3-pyrazolyl), imidazolyl (including N-imidazolyl, 2-imidazolyl, 4-imidazolyl, and 5-imidazolyl), oxazolyl (including 2-oxazolyl, 4-oxazolyl, and 5-oxazolyl), triazolyl (1H-1,2,3-triazolyl, 2H-1,2,3-triazolyl, 1H-1,2,4-triazolyl, and 4H-1,2,4-triazolyl), tetrazolyl, isoxazolyl (3-isoxazolyl, 4-isoxazolyl, and 5-isoxazolyl), thiazolyl (including 2-thiazolyl, 4-thiazolyl, and 5-thiazolyl), furyl (including 2-furyl, and 3-furyl), thienyl (including 2-thienyl, and 3-thienyl), pyridyl (including 2-pyridyl, 3-pyridyl, and 4-pyridyl), pyrazinyl or pyrimidinyl (including 2-pyrimidinyl and 4-pyrimidinyl).

The term "haloalkyl" in the present disclosure refers to an alkyl group substituted with one or more halogens.

The term "3- to 8-membered heterocyclyl" in the present disclosure means a non-aromatic cyclic group with 3 to 8 ring atoms, which has one or more ring heteroatoms independently selected from N, O and S, and may be fully saturated (i.e., 3- to 8-membered heterocycloalkyl) or partially unsaturated. The heterocyclyl ring can be a 3- to 8-membered monocyclic ring, bicyclic ring or spiro ring, including but not limited to, oxetanyl, azetidinyl, piperazinyl, piperidinyl, morpholinyl, thiomorpholinyl, pyrrolidinyl, tetrahydropyranyl, tetrahydrofuryl, oxazolidinyl, thiazolidinyl, imidazolidinyl, pyrazolidinyl, thianyl, oxanyl, oxathianyl, dihydroindolyl, dihydroisoindolyl, tetrahydrodihydroindolyl, quinuclidinyl, azepinyl, and the like. The heterocyclyl has, in some embodiments, 3 to 6 ring atoms (i.e., 3- to 6-membered heterocyclyl), or in some other embodiments, 5 to 8 ring atoms (i.e., 5- to 8-membered heterocyclyl). The 3- to 6-membered heterocycloalkyl refers to a fully saturated 3- to 6-membered heterocyclyl which may have 1 or 2 heteroatoms independently selected from N, O and S. Examples include, but are not limited to, oxetanyl, azetidinyl, piperazinyl, piperidinyl, morpholinyl, thiomorpholinyl, pyrrolidinyl, tetrahydropyranyl, tetrahydrofuranyl, oxazolidine, thiazolidine, imidazolidine, pyrazolidine, thianyl, oxanyl, and oxathianyl.

The heterocyclic ring may be fused to an aryl, heteroaryl or cycloalkyl ring, where the ring attached to the parent structure is the heterocyclyl group. Non-limiting examples include

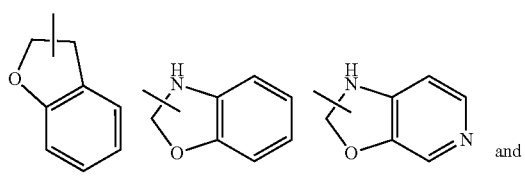

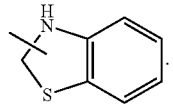

The term "$C_{3-8}$ cycloalkyl" in the present disclosure means a monovalent group obtained by removing any single hydrogen atom from a cyclic saturated aliphatic hydrocarbon having 3 to 8 carbons, i.e., a cycloalkyl group having 3 to 8 carbons. Examples include, but are not limited to cyclopropyl, cyclobutyl, cyclopentyl, cyclohexyl, cycloheptyl, and cyclooctyl. When two groups together form a $C_{3-8}$ cycloalkyl ring, the resultant group may be divalent, such as cyclopropane-1,1-diyl, cyclobutane-1,1-diyl, cyclopentane-1,1-diyl, cyclohexane-1,1-diyl, cycloheptane-1,1-diyl, and cyclooctane-1,1-diyl. In some embodiments, the cycloalkyl group has 3 to 6 ring atoms (i.e., $C_{3-6}$ cycloalkyl).

The term "bridged ring" in the present disclosure refers to a 5- to 20-membered all-carbon polycyclic group, wherein any two rings in the system shares a pair of non-adjacent carbon atoms. The bridged ring may contain one or more double bonds, but there is no ring having a completely conjugated n-electron system. The bridged ring is preferably 6- to 14-membered, e.g., 6- to 10-membered, more preferably 7- to 10-membered. Depending on the number of ring components, the bridged ring can be divided into bicyclic, tricyclic, tetracyclic or polycyclic bridged ring groups, preferably a bicyclic, tricyclic or tetracyclic bridged ring group, more preferably a bicyclic or tricyclic bridged ring group. The bridged ring includes but is not limited to:

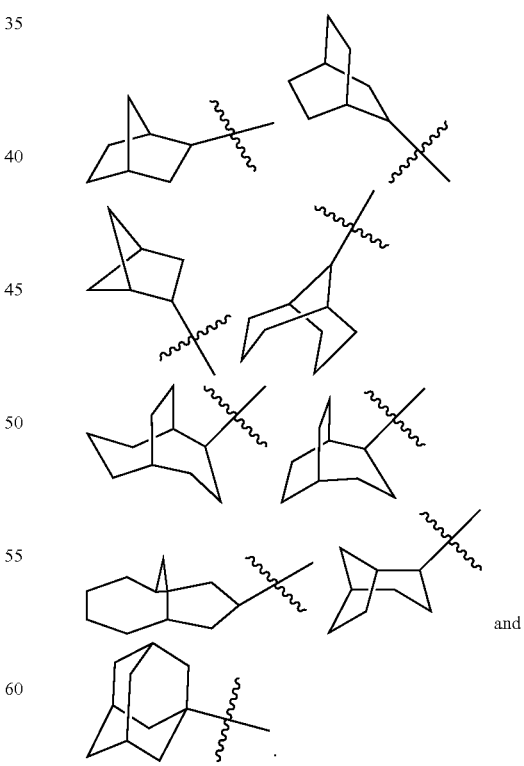

and

The carbon atoms in the bridged ring may optionally be replaced with a heteroatom selected from O, S, and N, i.e., a "bridged heterocycle" is also included herein.

The term "bridged heterocycle" in the present disclosure refers to a 5- to 14-membered polycyclic heterocyclic group, wherein any two rings in the system shares a pair of non-adjacent carbon atoms, wherein the bridged heterocycle may contain one or more double bonds, but there is no ring having a completely conjugated π-electron system, and wherein one or more of the ring atoms are heteroatoms selected from N, O or S(O)$_m$ (wherein m is an integer of 0 to 2), and the remaining ring atoms are carbon. The bridged heterocycle is preferably 6- to 14-membered, e.g., 6- to 10-membered, more preferably 7- to 10-membered. Depending on the number of ring components, the bridged heterocycle can be divided into bicyclic, tricyclic, tetracyclic or polycyclic bridged heterocycle groups, preferably a bicyclic, tricyclic or tetracyclic bridged heterocycle, more preferably a bicyclic or tricyclic bridged heterocycle. The bridged heterocycle includes but is not limited to

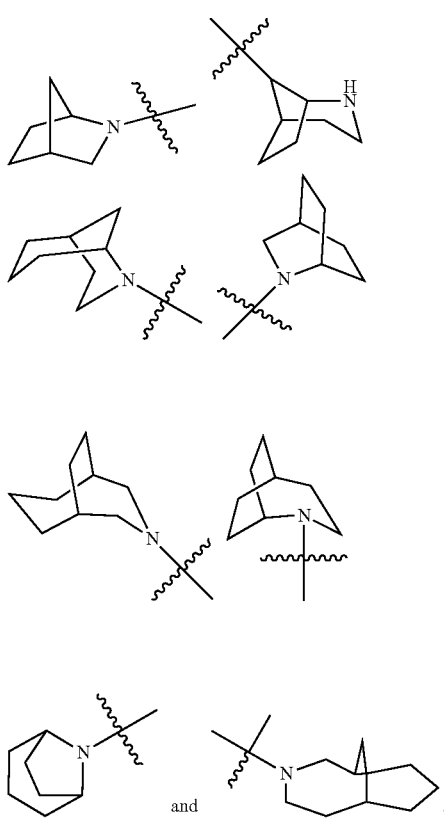

The term "spiro ring" in the present disclosure refers to a 5- to 20-membered polycyclic group, wherein the monocyclic rings in the system shares one carbon atom (called as spiro atom). The spiro ring may contain one or more double bonds, but there is no ring having a completely conjugated π-electron system. The spiro ring is preferably 6- to 14-membered, e.g., 6- to 10-membered, more preferably 7- to 10-membered. Depending on the number of spiro atoms shared between the rings, the spirocycloalkyl groups are divided into monospirocycloalkyl, dispirocycloalkyl or polyspirocycloalkyl, preferably monospirocycloalkyl and dispirocycloalkyl, more preferably 4-membered/4-membered, 4-membered/5-membered, 4-membered/6-membered, 5-membered/5-membered or 5-membered/6-membered monospirocycloalkyl, including but not limited to

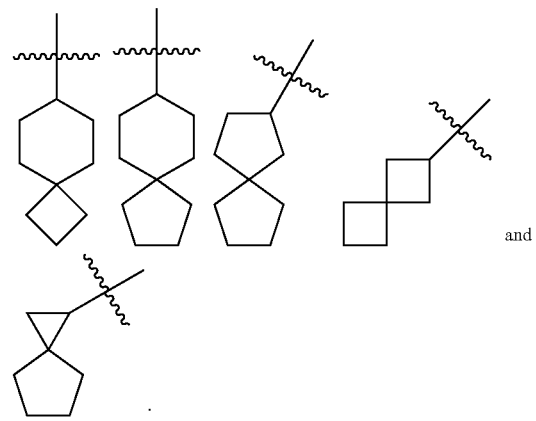

The carbon atoms in the spiro ring may be optionally replaced by a heteroatom selected from O, S, and N, i.e., a "spiro heterocycle" is also included herein.

The term "spiro heterocycle" in the present disclosure refers to a 5- to 20-membered polycyclic heterocyclic group, wherein the monocyclic rings in the system shares one carbon atom (called as spiro atom), wherein one or more of the ring atoms are heteroatoms selected from N, O or S(O)$_m$ (wherein m is an integer of 0 to 2) and the remaining ring atoms are carbon. The spiro heterocycle may contain one or more double bonds, but there is no ring having a completely conjugated π-electron system. The spiro heterocycle is preferably 6- to 14-membered, e.g., 6- to 10-membered, more preferably 7- to 10-membered. Depending on the number of spiro atoms shared between the rings, the spiroheterocyclyl groups are divided into monospiroheterocyclyl, dispiroheterocyclyl or polyspiroheterocyclyl, preferably monospiroheterocyclyl and dispiroheterocyclyl, more preferably 4-membered/4-membered, 4-membered/5-membered, 4-membered/6-membered, 5-membered/5-membered or 5-membered/6-membered monospiroheterocyclyl, including but not limited to

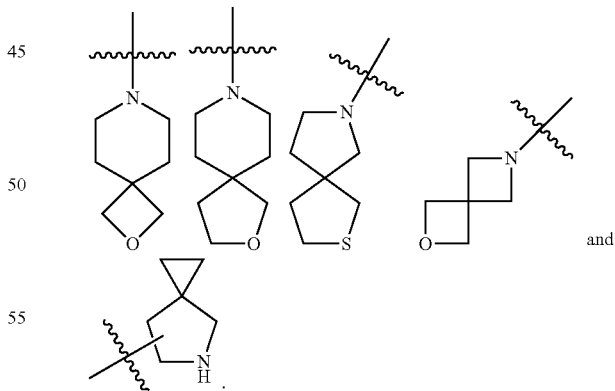

The compounds of the present disclosure can be prepared by a variety of synthetic methods well known to those skilled in the art, including the following specific embodiments, embodiments formed by their combination with other chemical synthetic methods, and the equivalent alternatives well known to those skilled in the art. Preferred embodiments include, but are not limited to, the examples of the present disclosure.

The compounds described in the present disclosure are named according to the chemical structural formula. Where the name of a compound is inconsistent with the chemical structural formula of the same compound, the chemical structural formula shall prevail.

The present disclosure further provides the following embodiments:

Embodiment 1: A compound of Formula I

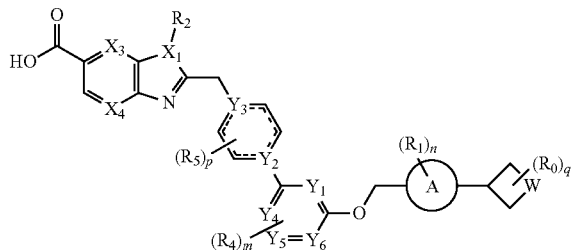

(I)

and a pharmaceutically acceptable salt thereof, wherein
----- represents a single or double bond;
W is selected from O, N, or NH;
$X_1$, $X_3$, and $X_4$ are independently selected from CH, N, or C;
$Y_1$ is selected from CH or N;
$Y_2$ is selected from CH, N, or C;
$Y_3$ is selected from CH, N, or C;
$Y_4$, $Y_5$, and $Y_6$ are independently selected from CH or N, and $Y_4$, $Y_5$, and $Y_6$ are not simultaneously N;
ring A is selected from a group consisting of benzene ring, thiophene, or pyridine;
$R_1$ is independently selected from a group consisting of hydrogen, oxo, halogen, cyano, $C_{1-3}$ alkyl, $C_{1-3}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-3}$ alkyl, $C_{1-3}$ alkoxy, and $C_{3-6}$ cycloalkyl may optionally be independently substituted 1 to 3 times by halogen, cyano, $C_{1-3}$ alkyl, $C_{1-3}$ alkoxy, $C_{3-6}$ cycloalkyl, or $C_{3-6}$ heterocyclyl;
$R_2$ is selected from a group consisting of $R_z$, —O—$R_z$, —S—$R_z$, $C_{1-3}$ alkyl, —$C_{1-3}$ alkylene-$R_z$, —$C_{0-3}$ alkylene-amino-$R_z$, —$C_{0-3}$ alkylene-carbonyl-$R_z$, —$C_{0-3}$ alkylene-amido-$R_z$, —$C_{0-3}$ alkylene-sulfonyl-$R_z$, —$C_{0-3}$ alkylene-phosphoryl-$R_z$, and —$C_{0-3}$ alkylene-sulfonamido-$R_z$, wherein the alkyl, amino, amido, sulfonyl, sulfonamido, and phosphoryl in $R_2$ may be optionally substituted 1 to 3 times by halogen or one time by $R_W$, if valency permits;
$R_4$ is independently selected from a group consisting of hydrogen, halogen, $C_{1-3}$ alkyl, $C_{1-3}$ haloalkyl, $C_{1-3}$ alkoxy, cyano, hydroxy, amino, amido, sulfonyl, and sulfonamido;
$R_5$ is independently selected from a group consisting of hydrogen, halogen, hydroxyl, CN, $C_{1-3}$ alkyl, $C_{1-3}$ alkoxy, and $C_{3-6}$ cycloalkyl, wherein the alkyl, alkoxy, and cycloalkyl in $R_5$ may be optionally substituted 1 to 3 times by halogen, hydroxyl, —$NR_z$, CN, $C_{1-3}$ alkyl, $C_{1-3}$ alkoxy, $C_{3-6}$ cycloalkyl, if valency permits;
$R_0$ is independently selected from a group consisting of hydrogen, halogen, hydroxy, oxo, CN, $C_{1-3}$ alkyl, $C_{1-3}$ alkoxy, $C_{3-6}$ cycloalkyl, 3- to 6-membered heterocyclyl, phenyl, and 5- to 6-membered heteroaryl, wherein the alkyl, alkoxy, cycloalkyl, heterocyclyl, phenyl, and heteroaryl in $R_0$ may be optionally substituted 1 to 3 times by halogen, CN, $NH_2$, $C_{1-3}$ alkyl, $C_{1-3}$ alkoxy, $C_{3-6}$ cycloalkyl, if valency permits;

n is an integer selected from 0, 1, 2, 3, or 4;
m is an integer selected from 0, 1, or 2;
p is an integer selected from 0, 1, 2, or 3;
q is an integer selected from 0, 1, 2, 3, or 4;
when p is greater than or equal to 2, any two $R_5$ may be further cyclized with ring C to form a 6- to 10-membered spiro ring or bridged ring, wherein the spiro ring and the bridged ring formed may be optionally substituted 1 to 3 times by $C_{1-3}$ alkyl, $C_{1-3}$ alkoxy, $C_{1-3}$ haloalkyl, halogen, cyano, $C_{1-3}$ alkoxy, if valency permits;
when m is not 0 and p is not 0, any $R_4$ and any $R_5$ may be further cyclized into a 5- to 8-membered ring, wherein the formed ring may be optionally substituted 1 to 3 times by $C_{1-3}$ alkyl, $C_{1-3}$ alkoxy, $C_{1-3}$ haloalkyl, halogen, cyano, oxo, $C_{1-3}$ alkoxy, if valence permits;
$R_w$ is independently selected from a group consisting of CN, —$CH_2CN$, $C_{1-3}$ alkyl, OH, $C_{1-3}$ alkoxy, amido, sulfonyl, sulfonamido, $NH_2$, and —NH—$C_{1-3}$ alkyl, wherein the alkyl in $R_w$ may be optionally substituted 1 to 3 times by $C_{1-3}$ alkyl, $C_{1-3}$ haloalkyl, halogen, cyano, oxo, $C_{1-3}$ alkoxy, if valence permits; and
$R_z$ is independently selected from a group consisting of hydrogen, $C_{1-3}$ alkyl, $C_{1-3}$ alkoxy, $C_{3-6}$ cycloalkyl, 3- to 6-membered heterocyclyl, aryl, and 5- to 6-membered heteroaryl, wherein $R_z$ may be optionally substituted 1 to 3 times by $C_{1-3}$ alkyl, $C_{1-3}$ haloalkyl, cyano-$C_{1-3}$ alkyl, halogen, cyano, oxo, $C_{1-3}$ alkoxy, 3- to 6-membered heterocyclyl, if valence permits.

Embodiment 2: The compound according to Embodiment 1, which is a compound of Formula I-2 or Formula I-2',

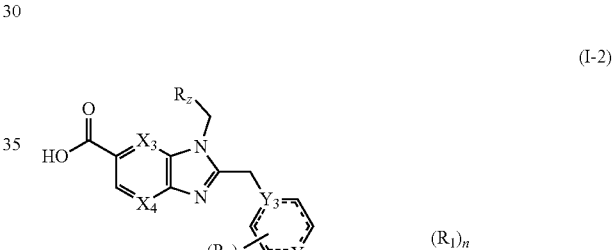

(I-2)

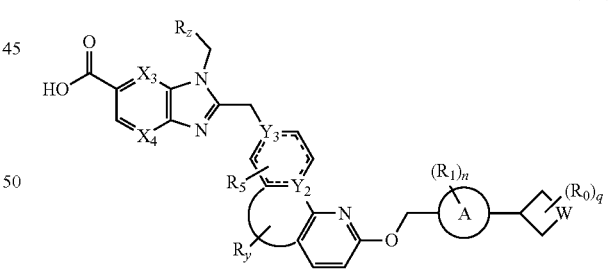

(I-2')

and a pharmaceutically acceptable salt thereof, wherein
----- represents a single or double bond;
$X_3$ and $X_4$ are independently selected from CH or N;
$Y_2$ is selected from a group consisting of CH, N or C;
$Y_3$ is selected from CH or N;
ring A is selected from a group consisting of

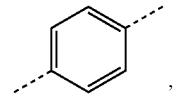

,

-continued

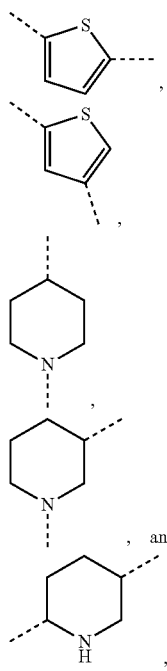

and may be further substituted n times by $R_1$;

$R_1$ is independently selected from a group consisting of hydrogen, oxo, halogen, cyano, $C_{1-3}$ alkyl, $C_{1-3}$ alkoxy, $C_{3-6}$ cycloalkyl, $C_{3-6}$ heterocyclyl, —CO—$C_{1-3}$ alkyl, —CO—$C_{3-6}$ cycloalkyl, and —CO—NH—$C_{1-3}$ alkyl, wherein the $C_{1-3}$ alkyl, $C_{1-3}$ alkoxy, and $C_{3-6}$ cycloalkyl may optionally be independently substituted 1 to 3 times by halogen, cyano, $C_{1-3}$ alkoxy, $C_{3-6}$ cycloalkyl, or $C_{3-6}$ heterocyclyl;

$R_z$ is selected from a group consisting of methyl, ethyl, isopropyl, cyclopropyl, cyclobutyl, methoxy, ethoxy

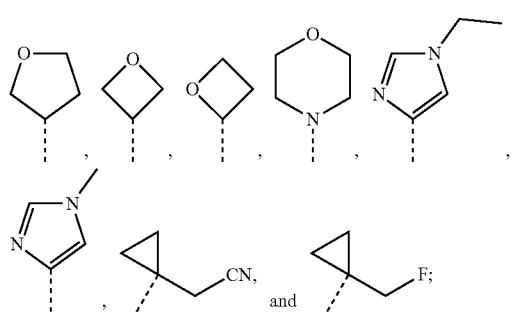

$R_5$ is independently selected from a group consisting of hydrogen, halogen, hydroxyl, CN, $C_{1-3}$ alkyl, $C_{1-3}$ alkoxy, and $C_{1-3}$ cycloalkyl, wherein the alkyl, alkoxy, and cycloalkyl in $R_5$ may be optionally substituted 1 to 3 times by halogen, hydroxyl, —$NR_z$, CN, $C_{1-3}$ alkyl, $C_{1-3}$ alkoxy, $C_{1-3}$ cycloalkyl, if valency permits;

n is an integer selected from 0, 1, or 2;

$R_y$ is independently selected from a group consisting of hydrogen, halogen, oxo, $C_{1-3}$ alkoxy, cyano, hydroxyl, amino, carboxyl, amido, sulfonyl, sulfonamido, $C_{1-3}$ alkyl, $C_{3-6}$ cycloalkyl, 3- to 6-membered heterocyclyl, and phenyl, wherein the alkyl, alkoxy, cycloalkyl, and heterocyclyl in $R_y$ may be optionally substituted 1 to 3 times by halogen, if valence permits.

Embodiment 3: The compound according to Embodiment 1, wherein when o is not 0 and p is not 0, any adjacent $R_4$ and $R_5$ may be further cyclized into a 5- to 8-membered ring; the 5- to 8-membered ring comprises a $C_{5-6}$ carbocyclic ring, 5- to 8-membered heterocyclic ring, benzene ring, and 5- to 8-member heteroaromatic ring, and the formed ring may be optionally substituted 1 to 3 times by alkyl, haloalkyl, halogen, cyano, alkoxy, if valence permits.

Embodiment 4: The compound according to Embodiment 1, wherein the compound of Formula I has the following subformula:

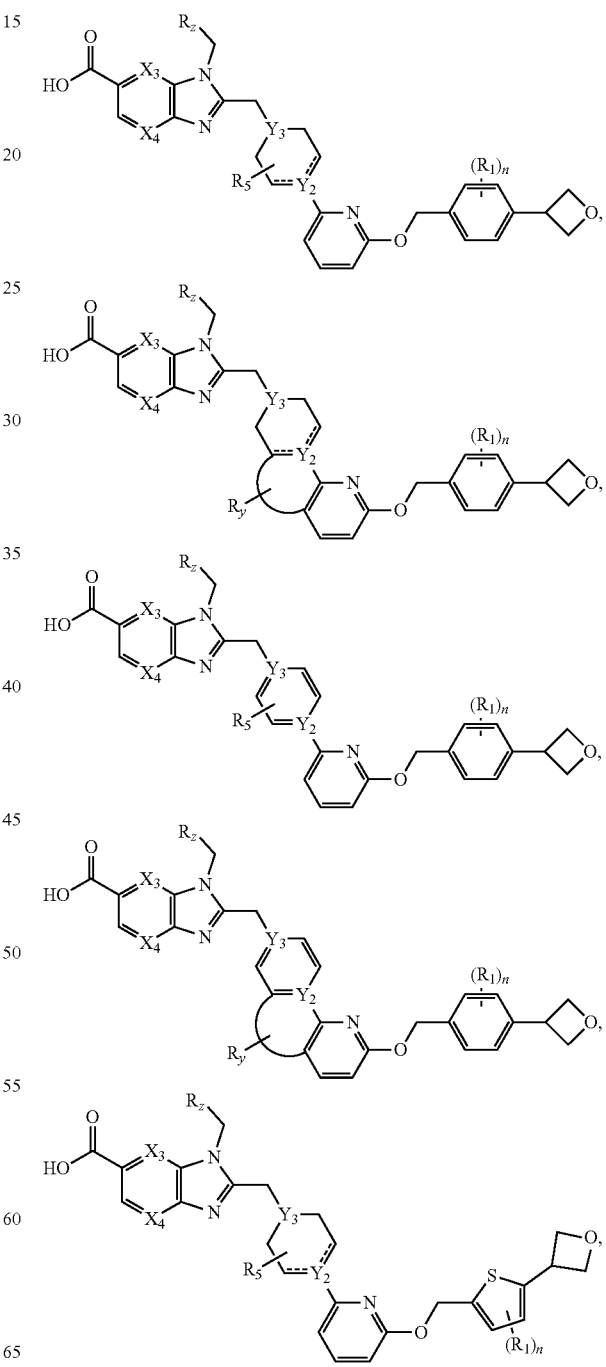

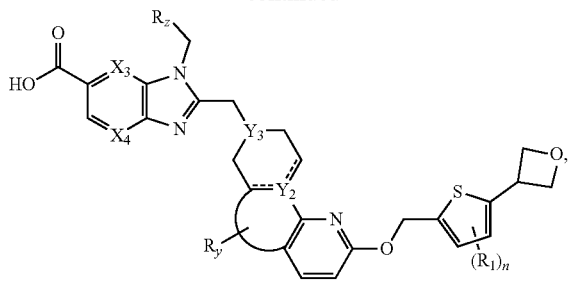

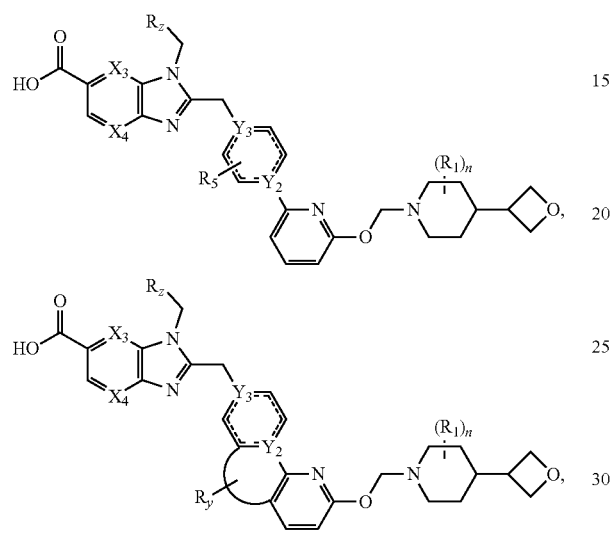

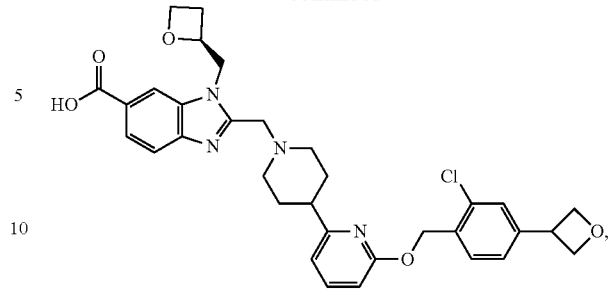

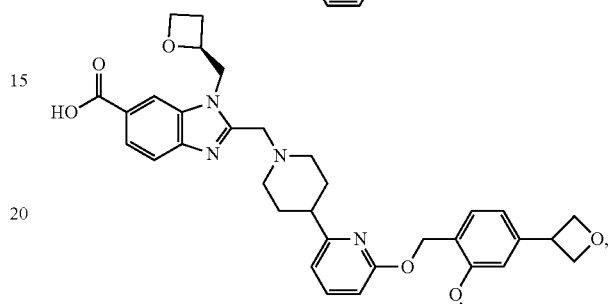

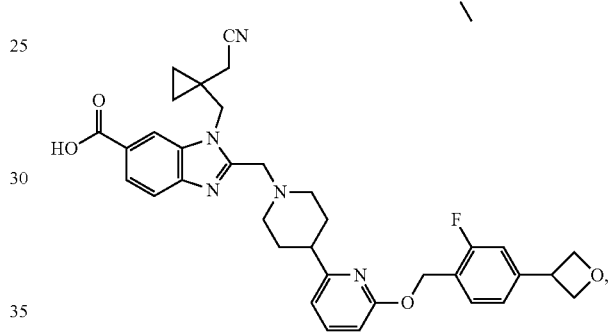

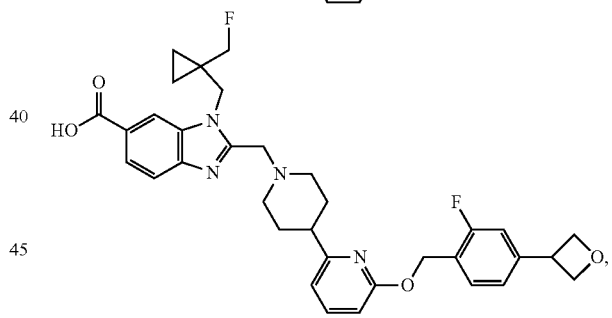

Embodiment 5: The compound according to Embodiment 1, wherein n is selected from 1, 2, or 3; and/or, p is selected from 0, 1, or 2.

Embodiment 6: The compound according to Embodiment 1, wherein $R_1$ may be further independently selected from a group consisting of F, Cl, CN, —OCH$_3$, —OCH$_2$CH$_3$, —O-cyclopropyl, CH$_3$, —CH$_2$CH$_3$, —CH$_2$CH$_2$CH$_3$, —(CH)$_2$CH$_3$, —COCH$_3$, —CONH$_2$, CF$_3$, —CHF$_2$, —CH$_2$F, —CH$_2$CH$_2$F, —CO-cyclopropyl, —COCH$_2$F, —COCHF$_2$, —CO—CH(CH$_3$)$_2$, and —CO—CH$_2$CH$_3$.

Embodiment 7: The compound according to Embodiment 1, wherein $R_5$ may be further selected from a group consisting of F, Cl, CH$_3$, —OCH$_3$, NH$_2$, OH, —CH$_2$CH$_3$, —CH$_2$OH, —NHCH$_3$, —COCH$_3$, —SO$_2$CH$_3$, —OCH$_2$CH$_3$, CF$_3$, —CHF$_2$, —CH$_2$F, isopropyl, cyclopropyl, and fluorocyclopropyl.

Embodiment 8: The compound according to Embodiment 1, which may be:

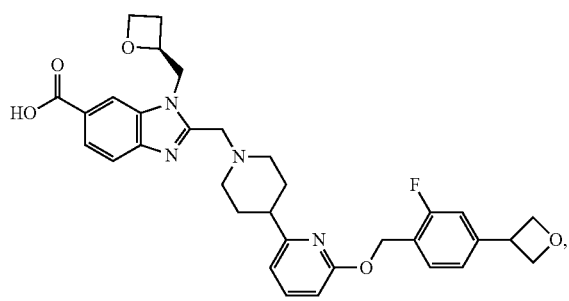

and a pharmaceutically acceptable salt thereof.

Embodiment 9: A pharmaceutical composition comprising the compound according to any one of Embodiments 1 to 8 and a pharmaceutically acceptable salt thereof, as well as a pharmaceutically acceptable carrier.

Embodiment 10: Use of the compound according to any one of Embodiments 1 to 8, or a pharmaceutically acceptable salt thereof, in the manufacture of a medicament for the treatment of a GLP-1 receptor-mediated disease or a related disease.

Embodiment 11: A method for preventing and/or treating a GLP-1 receptor-mediated disease and a related disease, comprising administering to a subject a therapeutically effective amount of the compound according to any one of Embodiments 1-8, or a pharmaceutically acceptable salt thereof, wherein the GLP-1 receptor-mediated diseases and the related diseases include, but are not limited to, diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia.

Beneficial Effects

The compounds of the present disclosure are GLP-1 receptor agonists. Preferred compounds of the present disclosure (e.g., compounds of Formula II) have excellent GLP-1 receptor agonistic activity, good intestinal absorption, and/or excellent safety and/or pharmacokinetic properties (e.g., metabolic stability, plasma binding, $C_{max}$, half-life, and oral bioavailability). For example, some of the compounds of Formula II above have improved GLP-1 receptor agonistic activity (e.g., lower $EC_{50}$) compared to some prior art compounds, and/or higher in vivo and/or in vitro safety and/or improved pharmacokinetic properties (e.g., metabolic stability, $C_{max}$, half-life, and/or oral bioavailability) compared to some prior art compounds.

EXAMPLES

The present disclosure is described in further detail below with reference to specific examples, which are not intended to limit the scope of the invention. The experimental methods where no specific conditions are indicated in the examples of the present disclosure usually adopt conventional conditions or the conditions suggested by the manufacturer; reagents without specifying sources may be commercially available conventional reagents.

Identification and Characterization of Compounds

The 1H NMR spectra in the present disclosure are determined using a Bruker instrument (400 MHz), and chemical shifts are reported in ppm. Tetramethylsilane (0.00 ppm) was used as internal standard. 1H NMR was expressed as follows: s=singlet, d=doublet, t=triplet, m=multiplet, br=broad, dd=doublet of doublet, dt=doublet of triplet. The coupling constant, if provided, is expressed in Hz.

The mass spectra of the present disclosure are determined by an LC/MS instrument, and ionization may be carried out by ESI or APCI.

Preparation Example

The intermediate reaction materials used in the preparation processes were prepared according to the preparation method described in WO2018109607A1.

SFC Method

System: Waters SFC 150

Column: Dr. maish Reprosil Chiral-MIC (DAICELCHIRALPAK®IC)

Column size: 250*25 mm 10 m

Mobile phase A is supercritical $CO_2$, and mobile phase B is MeOH (±0.1% 7.0 mol/l ammonia in MeOH), A:B=50:50

Wavelength: 214 nm

Flow rate: 120 ml/min

Column temperature: normal temperature

Back pressure: 100 bar

Injection volume: 4 mL

Cycle time: 10 min

Sample preparation method: dissolving the sample in about 20 mL of MeOH.

PREPARATION EXAMPLE OF INTERMEDIATES

Preparation of (S)-methyl 2-(chloromethyl)-1-(oxetan-2-ylmethyl)-1H-benzo[d]imidazole-6-carboxylate (Int-2)

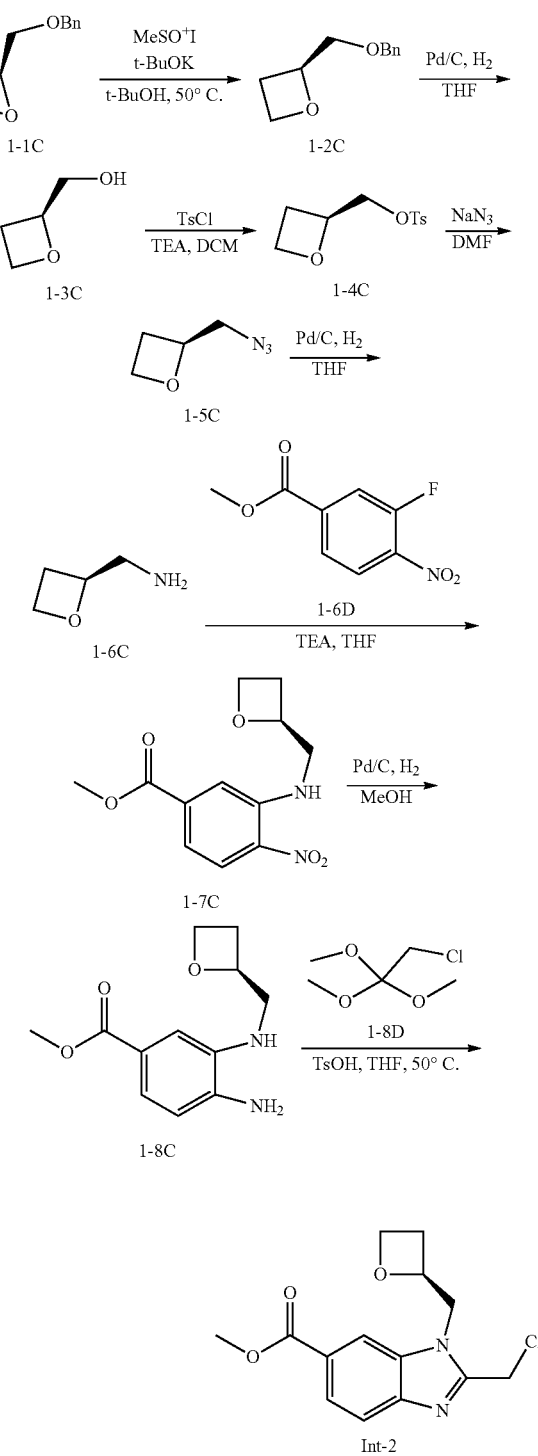

(1) Preparation of Compound 1-2C

Me$_3$S$^+$O$^+$I$^-$ (335 g, 1520 mmol, 2.5 eq) was added in portions to a stirred solution of t-BuOK (170 g, 1520 mmol, 2.5 eq) in t-BuOH (500 mL) at 60° C. under an argon atmosphere. After 30 minutes, (S)-2-((benzyloxy)methyl) oxirane (1-1C) (100 g, 610 mmol, 1.00 eq) was added dropwise to the above mixture. The resulting mixture was stirred at 60° C. for an additional 13 hours. The mixture was cooled to room temperature and then filtered. The filter cake was washed with EtOAc (3×200 mL). The combined organic layers were washed with brine (200 mL), dried over Na$_2$SO$_4$, and concentrated under reduced pressure to give a residue. The residue was purified by silica gel column chromatography, eluted with PE/EtOAc (10:1) to give (S)-2-((benzyloxy)methyl)oxetane (1-2C) (50.0 g, 46% yield).

$^1$H NMR (400 MHz, CDCl$_3$) δ=7.39-7.26 (m, 5H), 5.04-4.90 (m, 1H), 4.73-4.50 (m, 4H), 3.64 (qd, J=11.0, 4.3 Hz, 2H), 2.72-2.45 (m, 2H).

(2) Preparation of Compound 1-3C

A solution of compound 1-2C (50 g, 280.9 mmol, 1.0 eq) and Pd/C (20 g, wet) in THF (200 mL) was stirred at 50° C. under H$_2$ (4 MPa) for 16 h. The mixture was cooled to room temperature and then filtered. The filter cake was washed with THF (100 mL). The filtrate was concentrated under reduced pressure to give (S)-oxetan-2-ylmethanol (1-3C) (28 g, crude), which was used directly in the next step.

(3) Preparation of Compound 1-4C

To a solution of compound 1-3C (28 g, 317.8 mmol, 1 eq) in THF (200 mL) was added TsCl (66.6 g, 349.6 mmol, 1.1 eq) and TEA (48.2 g, 476.7 mmol, 1.5 eq) at 25° C. The mixture was stirred at room temperature for 2 h. The mixture was diluted with H$_2$O (100 mL) and extracted with DCM (100 mL×3). The combined organic layers were dried over Na$_2$SO$_4$, filtered, and concentrated to give a residue. The residue was purified by column chromatography on silica gel, eluted with (EA/PE=0-10%) to give (S)-oxetan-2-ylmethyl-4-methylbenzenesulfonate (1-4C) (56 g, 72.7% yield).

$^1$H NMR (400 MHz, CDCl$_3$) δ=7.85-7.79 (m, 2H), 7.35 (dd, J=8.6, 0.6 Hz, 2H), 5.00-4.83 (m, 1H), 4.68-4.38 (m, 2H), 4.16 (d, J=4.0 Hz, 2H), 2.78-2.64 (m, 1H), 2.58 (d, J=9.0 Hz, 1H), 2.45 (s, 3H).

(4) Preparation of Compound 1-5C

To a solution of compound 1-4C (56 g, 231 mmol, 1 eq) in DMF (200 mL) was added NaN$_3$ (22.5 g, 346.7 mmol, 1.5 eq). The mixture was stirred at 60° C. for 12 h. The mixture was diluted with H$_2$O (100 mL), and extracted with EtOAc (100 mL×3). The combined organic layers were dried over Na$_2$SO$_4$, filtered, and concentrated to give (S)-2-(azidomethyl)oxetane (1-5C) (20 g, crude), which was used directly in the next step.

(5) Preparation of Compound 1-6C

A solution of compound 1-5C (20 g, crude) and Pd/C (8 G) in THF (100 mL) was stirred at 25° C. under H$_2$ (15 psi) for 16 h. The resulting mixture was filtered. The filter cake was washed with THF (3×100 mL). The filtrate was concentrated directly to give (S)-oxetan-2-ylmethylamine (1-6C) (3.8 g, crude).

$^1$H NMR (400 MHz, DMSO) δ=4.60 (dq, J=6.5, 5.2 Hz, 1H), 4.52-4.43 (m, 1H), 4.40-4.30 (m, 1H), 2.67 (t, J=5.5 Hz, 2H), 2.57-2.51 (m, 1H), 2.38 (ddt, J=10.8, 9.0, 7.0 Hz, 2H).

(6) Preparation of Compound 1-7C

To a solution of compound 1-6C (3.8 g, 43.6 mmol, 1 eq) in THF (80 mL) was added methyl 3-fluoro-4-nitrobenzoate (1-6D) (8.69 g, 43.6 mmol, 1.0 eq) and TEA (8.83 g, 87.2 mmol, 2 eq) at 25° C. The mixture was stirred at 40° C. for 6 h. The mixture was concentrated to give a residue. The residue was purified by silica gel column chromatography, eluted with (EtOAc/petroleum ether=0-80%) to give (S)-methyl 4-nitro-3-((oxetan-2-ylmethyl)amino)benzoate (1-7C) (6.2 g, 53.4% yield).

$^1$H NMR (400 MHz, CDCl$_3$) δ=8.36 (s, 1H), 8.23 (d, J=8.9 Hz, 1H), 7.63 (d, J=1.4 Hz, 1H), 7.26 (dd, J=8.8, 1.7 Hz, 1H), 5.16 (tt, J=7.4, 4.5 Hz, 1H), 4.81-4.55 (m, 2H), 3.94 (s, 3H), 3.71-3.55 (m, 2H), 2.84-2.72 (m, 1H), 2.70-2.52 (m, 1H).

(7) Preparation of Compound 1-8C

A solution of compound 1-7C (6.2 g, 23.3 mmol, 1.0 eq) and Pd/C (1.0 g, wet) in MeOH (100 mL) was stirred at 25° C. under H$_2$ (1atm) for 12 h. The mixture was filtered. The filter cake was washed with MeOH (3×20 mL). The filtrate was concentrated directly to give (S)-methyl 4-amino-3-((oxetan-2-ylmethyl)amino) benzoate (1-8C) (5.2 g, 94.5% yield).

LCMS: r.t.=1.201 min, [M+1]$^+$=237.1, purity: 89.7%.

(8) Preparation of Compound Int-2

To a solution of compound 1-8C (1.0 g, 4.23 mmol, 1 eq) in THF (20 mL) was added 2-chloro-1,1,1-trimethoxyethane (1-8D) (0.98 g, 6.35 mmol, 1.5 eq) and TsOH·H$_2$O (0.08 g, 0.423 mmol, 0.1 eq). The mixture was stirred at 50° C. for 8 h. The mixture was diluted with saturated sodium bicarbonate solution NaHCO$_3$ (20 mL), and extracted with EtOAc (10 mL×3). The combined organic layers were dried over Na$_2$SO$_4$, filtered, and concentrated to give a residue. The residue was purified by column chromatography on silica gel, eluted with (EtOAc/petroleum ether=0-80%) to give (S)-methyl 2-(chloromethyl)-1-(oxetan-2-ylmethyl)-1H-benzo[d]imidazole-6-carboxylate (Int-2) (1.1 g, 88% yield).

$^1$H NMR (400 MHz, CDCl$_3$) δ 8.12 (d, J=0.9 Hz, 1H), 8.01 (dd, J=8.5, 1.5 Hz, 1H), 7.79 (d, J=8.5 Hz, 1H), 5.21 (ddd, J=9.6, 7.3, 2.7 Hz, 1H), 5.03 (s, 2H), 4.69-4.45 (m, 3H), 4.34 (d, J=9.2 Hz, 1H), 3.96 (s, 3H), 2.76 (dtd, J=11.5, 8.1, 6.0 Hz, 1H), 2.42 (ddt, J=11.5, 9.2, 7.3 Hz, 1H).

Example 1: (S)-2-((4-(6-((2-fluoro-4-(oxetan-3-yl)benzyl)oxy)pyridin-2-yl)piperidin-1-yl)methyl)-1-(oxetan-2-ylmethyl)-1H-benzo[d]imidazole-6-carboxylic acid (compound 1)
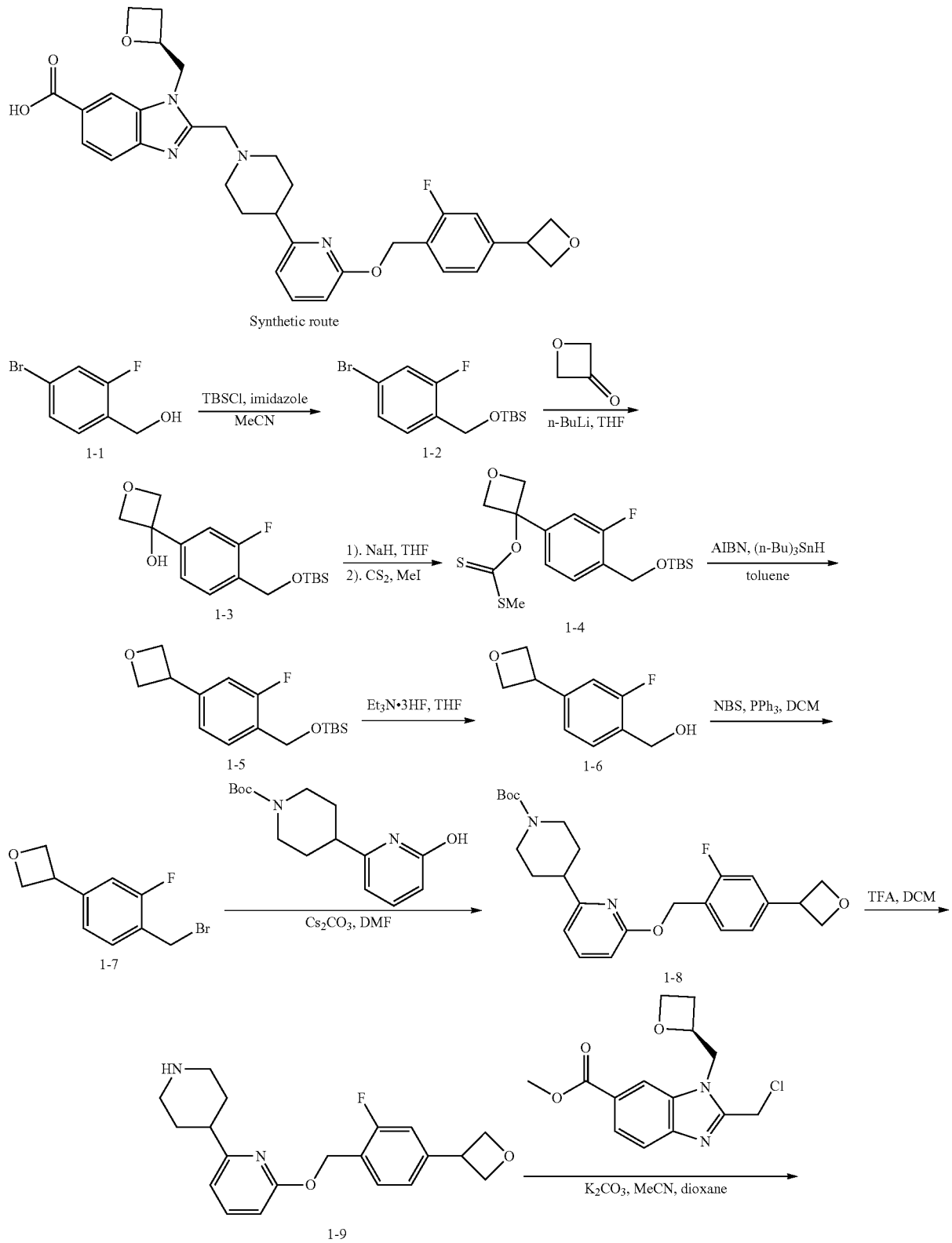
Synthetic route

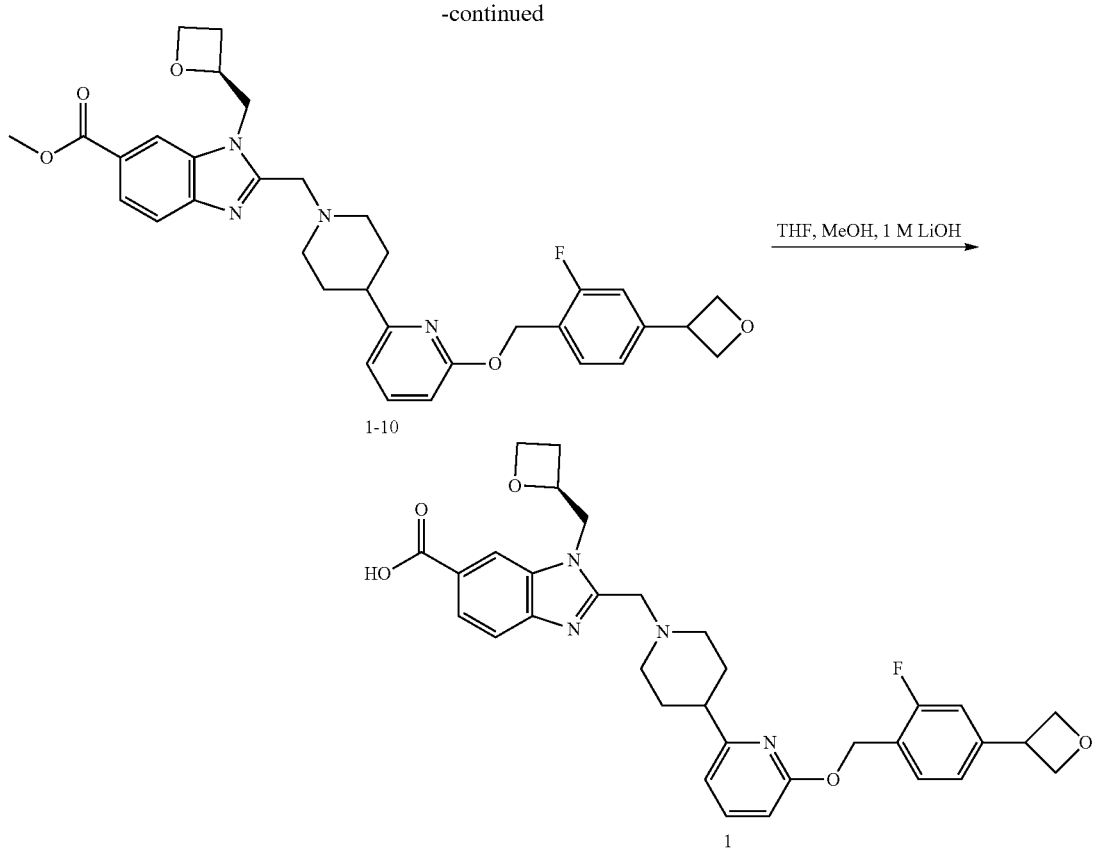

Preparation Method

Compound 1-2: To a solution of 1-1 (20.0 g, 98.0 mmol) in MeCN (500 mL) was added imidazole (10.0 g, 147.0 mmol) followed by addition of TBSCl (16.3 g, 107.8 mmol). The mixture was stirred at room temperature for 5 h. $H_2O$ (500 mL) was added. The reaction solution was extracted with EtOAc (3×500 mL). The combined organic phases were washed with brine (500 mL), dried ($Na_2SO_4$), filtered, and concentrated, and subjected to flash chromatography ($SiO_2$, hexane) to give 31 g of compound 1-2. Yield: 99.6%. $^1$H NMR (400 MHz, DMSO-d6) δ 7.35 (m, 3H), 4.62 (s, 2H), 0.81 (s, 9H), 0.00 (s, 6H).

Compound 1-3: To a solution of 1-2 (20.0 g, 62.8 mmol) in anhydrous THF (200 mL) was added dropwise N-BuLi (2.5 M in THF, 27.6 mL, 69.1 mmol) at −78° C. under $N_2$. The mixture was stirred at this temperature for 0.5 h, and then added with oxetane-3-one (4.5 g, 62.8 mmol). The mixture was then stirred at room temperature under $N_2$ atmosphere for 2.5 h. The reaction solution was quenched with water (100 mL), and extracted with EtOAc (3×100 mL). The combined organic phases were washed with brine (100 mL), dried ($Na_2SO_4$), filtered, and concentrated, and subjected to flash chromatography ($SiO_2$, 25% EtOAc-hexane) to give 14 g of compound 1-3. Yield: 71.0%. $^1$H NMR (400 MHz, DMSO-d6) δ 7.42-7.33 (m, 2H), 7.26-7.18 (m, 1H), 6.36 (s, 1H), 4.69-4.53 (m, 6H), 0.81 (s, 9H), −0.00 (s, 6H).

Compound 1-4: To a solution of 1-3 (14.0 g, 44.8 mmol) in anhydrous THF (200 mL) was added NaH (3.6 g, 89.7 mmol) at 0° C. The mixture was stirred at room temperature for 2 h, and then added with $CS_2$ (3.6 g, 89.7 mmol) and MeI (6.4 g, 44.8 mmol) at 0° C. under $N_2$. The mixture was then stirred at 0° C. in $N_2$ for 0.5 h. The reaction solution was quenched with saturated $NH_4Cl$ solution (100 mL), and extracted with EtOAc (3×200 mL). The combined organic phases were washed with brine (200 mL), dried ($Na_2SO_4$), filtered, and concentrated to give 14 g of compound 1-4. The product was used directly in the next step without further purification.

Compound 1-5: To a solution of 1-4 (14.0 g, 44.8 mmol) in toluene (200 mL) was added (n-Bu)$_3$SnH (26.2 g, 89.7 mmol) followed by addition of AIBN (736 mg, 4.4 mmol). The mixture was stirred at 125° C. under $N_2$ atmosphere for 0.5 h. The reaction solution was concentrated, and purified by flash chromatography ($SiO_2$, 20% EtOAc-hexane) to give 8 g of compound 1-5. Two-step yield: 60.6%. $^1$H NMR (400 MHz, DMSO-d6) δ 7.41 (t, J=8.0 Hz, 1H), 7.23-7.16 (m, 2H), 4.91 (dd, J=8.3, 5.9 Hz, 2H), 4.72 (s, 2H), 4.59 (t, J=6.3 Hz, 2H), 4.30-4.18 (m, 1H), 0.88 (s, 9H), 0.07 (s, 6H).

Compound 1-6: To a solution of 1-5 (8.0 g, 43.0 mmol) in THF (200 mL) was added $Et_3N·HF_3$ (13.9 g, 86.0 mmol). The reaction solution was stirred at room temperature under $N_2$ atmosphere for 16 h. The reaction solution was concentrated, and purified by flash chromatography ($SiO_2$, EtOAc-hexane) to give 5 g of compound 1-6. Yield: 99.9%. $^1$H NMR (400 MHz, DMSO-d6) δ 7.44 (t, J=7.8 Hz, 1H), 7.20 (t, J=9.1 Hz, 2H), 5.22 (t, J=5.7 Hz, 1H), 4.92 (dd, J=8.0, 6.1 Hz, 2H), 4.59 (t, J=6.3 Hz, 2H), 4.52 (d, J=5.6 Hz, 2H), 4.30-4.18 (m, 1H).

Compound 1-7: To a solution of 1-6 (4.8 g, 26.3 mmol) in DCM (100 mL) was added NBS (5.2 g, 29.0 mmol) followed by addition of PPh$_3$ (7.7 g, 29.0 mmol) at 0° C. The mixture was stirred at room temperature under $N_2$ atmosphere for 5 h. $H_2O$ (100 mL) was added. The reaction solution was extracted with DCM (3×100 mL). The combined organic phases were washed with brine (100 mL), dried (Na₂SO₄), filtered, and concentrated, and purified by flash chromatography (SiO₂, EtOAc-hexane) to give 2 g of compound 1-7. Yield: 30.7%. ¹H NMR (400 MHz, DMSO-d6) δ 7.53 (t, J=8.0 Hz, 1H), 7.33-7.20 (m, 2H), 4.92 (dd, J=8.3, 6.0 Hz, 2H), 4.70 (s, 2H), 4.60 (t, J=6.3 Hz, 2H), 4.34-4.20 (m, 1H).

Compound 1-8: Compound 1-7 (600 mg, 2.45 mmol) and tert-butyl 4-(6-hydroxypyridin-2-yl)piperidine-1-carboxylate (684 mg, 2.45 mmol) were added to the solvent DMF (50 mL). Then Cs₂CO₃ (2.4 g, 7.37 mmol) was added. The reaction solution was stirred at room temperature for 16 h. H₂O (50 mL) was added. The reaction solution was extracted with EtOAc (3×50 mL). The combined organic phases were washed with brine (50 mL), dried (Na₂SO₄), filtered, and concentrated, and purified by flash chromatography (SiO₂, EtOAc-hexane) to give 500 mg of compound 1-8. Yield: 45.9%. ¹H NMR (400 MHz, CDCl₃) δ 7.60 (t, J=7.7 Hz, 1H), 7.46 (t, J=7.6 Hz, 1H), 7.17 (s, 1H), 7.13 (d, J=11.4 Hz, 1H), 6.75 (d, J=7.3 Hz, 1H), 6.68 (d, J=8.1 Hz, 1H), 5.43 (d, J=7.5 Hz, 3H), 5.33 (s, 1H), 4.45 (s, 2H), 4.14 (d, J=14.0 Hz, 2H), 3.03 (t, J=12.8 Hz, 1H), 2.80 (t, J=12.9 Hz, 2H), 1.85 (d, J=12.5 Hz, 2H), 1.57-1.61 (m 3H), 1.42 (s, 9H)./LC-MS (ESI) m/z: 443.2 [M⁺H]⁺.

Compound 1-9: To a solution of 1-8 (210 mg, 0.49 mmol) in DCM (10 mL) was added TFA (10 mL). The reaction solution was stirred at room temperature for 3 h. The reaction solution was concentrated to give 250 mg of compound 1-9. LC-MS: MC20-1128-086C (ESI) m/z: 343.1 [M⁺H]⁺.

Compound 1-10: Compound 1-9 (200 mg, 0.58 mmol) and (S)-methyl 2-(chloromethyl)-1-(oxetan-2-ylmethyl)-1H-benzo[d]imidazole-6-carboxylate (172 mg, 0.58 mmol) were added to the solvents dioxane (20 mL) and MeCN (12 mL), followed by K₂CO₃ (162 mg, 1.16 mmol). The reaction solution was stirred at 65° C. for 3 h. H₂O (20 mL) was added. The reaction solution was extracted with EtOAc (3×20 mL). The combined organic phases were washed with brine (20 mL), dried (Na₂SO₄), filtered, and concentrated, and purified by flash chromatography (SiO₂, EtOAc-hexane) to give 60 mg of compound 1-10. Yield: 22.0%. ¹H NMR (400 MHz, DMSO-d6) δ 8.30 (d, J=1.1 Hz, 1H), 7.82 (dd, J=8.5, 1.6 Hz, 1H), 7.70-7.59 (m, 2H), 7.53 (t, J=7.8 Hz, 1H), 7.27 (d, J=11.3 Hz, 1H), 7.21 (d, J=9.5 Hz, 1H), 6.86 (d, J=7.4 Hz, 1H), 6.65 (d, J=8.0 Hz, 1H), 5.38 (s, 2H), 5.35-5.30 (m, 1H), 5.12 (qd, J=7.0, 2.5 Hz, 1H), 4.90 (dd, J=8.3, 6.0 Hz, 2H), 4.80-4.84 (m 1H), 4.65-4.71 (m, 1H), 4.58 (t, J=6.4 Hz, 2H), 4.47 (dt, J=8.3, 6.5 Hz, 1H), 4.37 (dt, J=9.1, 5.9 Hz, 1H), 4.21-4.28 (m, 1H), 3.94-4.02 (m, 1H), 3.87 (s, 3H), 3.78 (d, J=13.6 Hz, 1H), 3.01 (d, J=9.4 Hz, 1H), 2.85 (d, J=13.5 Hz, 1H), 2.73-2.59 (m, 2H), 2.27 (d, J=10.0 Hz, 1H), 2.17 (d, J=11.6 Hz, 1H), 1.76 (m, 4H)./LC-MS (ESI) m/z: 601.4 [M⁺H]⁺.

Compound 1: To a solution of 1-10 (60 mg, 0.1 mmol) in MeOH (1 mL) and THF (5 mL) was added 1 M LiOH (2 mL). The reaction solution was stirred at room temperature for 3 h. The reaction solution was concentrated, and purified by preparative HPLC to give 10.95 mg of compound 1. Yield: 18.6%. ¹H NMR (400 MHz, DMSO-d6) δ 8.20 (s, 1H), 7.79 (dd, J₁=4.0 Hz, J₂=8.0 Hz, 1H), 7.62 (t, J=8.0 Hz, 1H), 7.54 (t, J=8.0 Hz, 1H), 7.45 (d, J=8.0 Hz, 1H), 7.27 (d, J=12.0 Hz, 1H), 7.21 (d, J=8.0 Hz, 1H), 6.87 (d, J=8.0 Hz, 1H), 6.65 (d, J=8.0 Hz, 1H), 5.38 (s, 2H), 5.12 (m, 1H), 4.90 (dd, J=8.0 Hz, 2H), 4.77 (dd, J₁=4.0 Hz, J₂=16.0 Hz, 1H), 4.64 (d, J=4.0 Hz, 1H), 4.58 (m, 2H), 4.50-4.44 (m, 1H), 4.38 (m, 1H), 4.29-4.19 (m, 1H), 3.94 (d, J=12.0 Hz, 1H), 3.77 (d, J=12.0 Hz, 1H), 3.00 (d, J=12.0 Hz, 1H), 2.86 (d, J=12.0 Hz, 1H), 2.71 (m, 1H), 2.64-2.56 (m, 1H), 2.47-2.42 (m, 1H), 2.21 (m, 2H), 1.73 (m, 4H).

Example 2: (S)-2-((4-(6-((2-chloro-4-(oxetan-3-yl)benzyl)oxy)pyridin-2-yl)piperidin-1-yl)methyl)-1-(oxetan-2-ylmethyl)-1H-benzo[d]imidazole-6-carboxylic acid (compound 2)

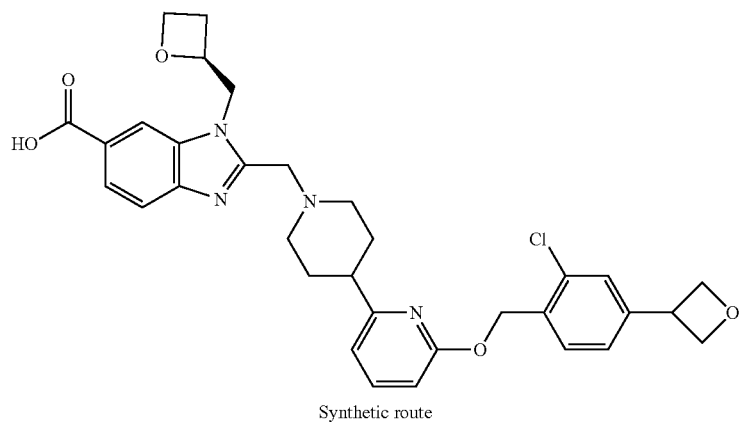

Synthetic route

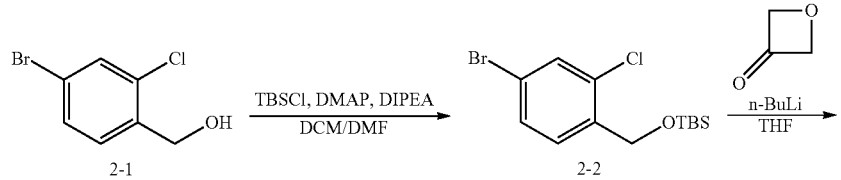

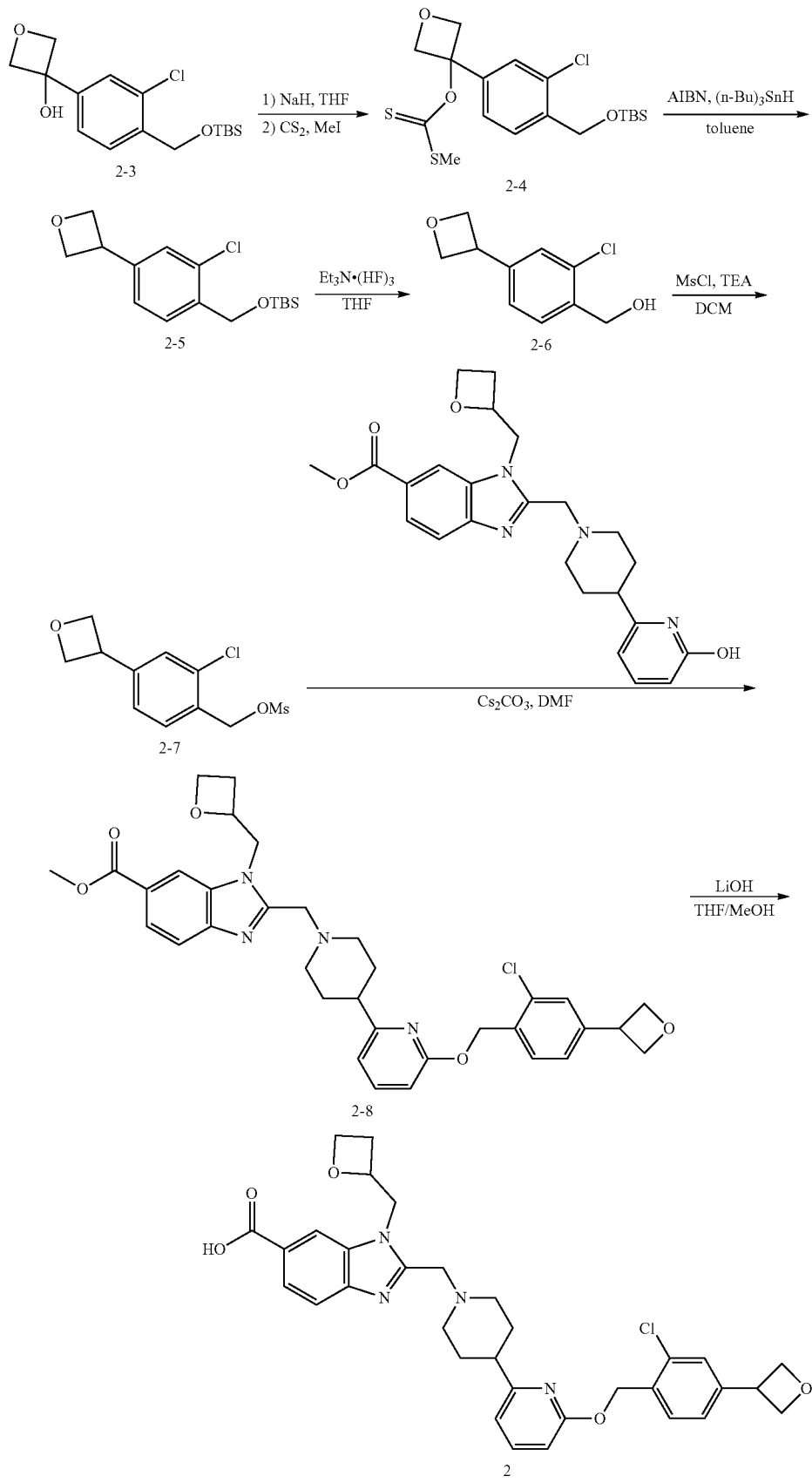

Preparation Method

Compound 2-2: To a solution of 2-1 (1.2 g, 5.42 mmol), DMAP (13 mg, 0.11 mmol), and DIPEA (1.1 g, 8.13 mmol) in DCM/DMF (5:1, 36 mL) was added in portions TBSCl (1.1 g, 7.59 mmol) with stirring at 0° C. Then the mixture was moved to room temperature and stirred overnight. After the reaction was complete, the reaction mixture was subjected to reduced pressure to remove the solvents, and then extracted three times with EA. The combined organic layers were washed with water and brine, dried over anhydrous $Na_2SO_4$, filtered and concentrated. The resulting residue was purified by flash column chromatography (silica gel, eluted with 0-5% EA in PE) to give 2-2 (1.8 g, 99% yield). $^1$H NMR (400 MHz, DMSO) δ 7.67 (d, J=1.8 Hz, 1H), 7.58 (dd, J=8.3, 1.9 Hz, 1H), 7.44 (d, J=8.3 Hz, 1H), 4.69 (s, 2H), 0.90 (s, 9H), 0.09 (s, 6H).

Compound 2-3: To a solution of 2-2 (6.0 g, 17.87 mmol) in anhydrous THF (60 mL) was added dropwise n-BuLi (8.0 mL, 2.5 M in hexane) with stirring at −78° C. The mixture was stirred at the same temperature for 30 min. Oxetan-3-one (1.3 g, 17.87 mmol) was then added. The mixture was moved to room temperature, and stirred for another 2.5 h. After the reaction was complete, the mixture was quenched with water, and then extracted three times with EA. The combined organic layers were washed with water and brine, dried over anhydrous $Na_2SO_4$, filtered, and concentrated. The resulting residue was purified by flash column chromatography (silica gel, eluted with 0-30% EA in PE) to give 2-3 (4.4 g, 74% yield). $^1$H NMR (400 MHz, DMSO) δ 7.55-7.62 (m, 3H), 6.48 (s, 1H), 4.76 (d, J=5.5 Hz, 4H), 4.66 (d, J=6.8 Hz, 2H), 0.92 (s, 9H), 0.11 (s, 6H).

Compound 2-4: To a solution of 2-3 (1.0 g, 3.04 mmol) in anhydrous THF (10 mL) was added in portions NaH (146 mg, 6.08 mmol) with stirring at 0° C. The mixture was removed to room temperature and stirred for 2 h, then cooled to 0° C. $CS_2$ (231 mg, 3.04 mmol) and MeI (431 mg, 3.04 mmol) were added. The mixture was stirred at 0° C. for another 0.5 h. After the reaction was complete, the reaction mixture was quenched with saturated $NH_4Cl$, and then extracted three times with EA. The combined organic layers were washed with water and brine, dried over anhydrous $Na_2SO_4$, filtered, and concentrated to give 2-4 (1.37 g, crude), which was used in the next step without further purification.

Compound 2-5: To a solution of 2-4 (1.37 g, 3.27 mmol) in dry toluene (15 mL) was added AIBN (54 mg, 0.33 mmol), and n-Bu3SnH (1.90 g, 6.54 mmol). The mixture was stirred at 125° C. for 0.5 h. After the reaction was complete, the reaction mixture was placed. KF (20 mL) was added. The mixture was stirred at room temperature for 2 h, and then extracted three times with EA. The combined organic layers were washed with water and brine, dried over anhydrous $Na_2SO_4$, filtered, and concentrated. The resulting residue was purified by flash column chromatography (silica gel, eluted with 0-30% EA in PE) to give 2-5 (700 mg, 69% yield). $^1$H NMR (400 MHz, DMSO) δ 7.67 (d, J=1.8 Hz, 1H), 7.58 (dd, J=8.3, 1.9 Hz, 1H), 7.44 (d, J=8.3 Hz, 1H), 4.69 (s, 2H), 0.90 (s, 9H), 0.09 (s, 6H).

Compound 2-6: To a solution of 2-5 (366 mg, 1.17 mmol) in dry THF (5.0 mL) was added $Et_3N·HF_3$ (377 mg, 2.34 mmol). The mixture was stirred at room temperature for 16 h. After the reaction was completed, the solvent was removed under reduced pressure. The resulting residue was purified by Prep-TLC (PE:EA=3:1) to give 2-6 (170 mg, 73% yield). $^1$H NMR (400 MHz, DMSO) δ 7.53 (d, J=7.8 Hz, 1H), 7.47-7.32 (m, 2H), 5.37 (t, J=5.6 Hz, 1H), 4.92 (dd, J=8.3, 6.0 Hz, 2H), 4.59 (t, J=6.3 Hz, 2H), 4.55 (d, J=5.6 Hz, 2H), 4.30-4.19 (m, 1H).

Compound 2-7: To a solution of 2-6 (170 mg, 0.86 mmol), and TEA (870 mg, 8.60 mmol) in anhydrous THF (10 mL) was added dropwise MsCl (197 mg, 1.72 mmol) with stirring at 0° C. The mixture was move to room temperature and stirred for 2 h. After the reaction was complete, the reaction mixture was extracted three times with DCM. The combined organic layers were washed with water and brine, dried over anhydrous $Na_2SO_4$, filtered and concentrated to give 2-7 (140 mg, crude), which was used directly in the next step.

Compound 2-8: To a solution of 2-7 (140 mg, 0.5 mmol), methyl 2-((4-(3-hydroxyphenyl)piperidin-1-yl) methyl)-1-(oxetan-2-ylmethyl)-1H-benzo[d]imidazole-6-carboxylate (100 mg) in anhydrous DMF (10 mL) was added $Cs_2CO_3$ (326 mg, 1.0 mmol). The mixture was stirred at 50° C. for 16 h. After the reaction was complete, the reaction mixture was extracted three times with EA. The combined organic layers were washed with water and brine, dried over anhydrous $Na_2SO_4$, filtered, and concentrated. The resulting residue was purified by Prep-TLC (PE/EA=1:1) to give 2-8 (97 mg). $^1$H NMR (400 MHz, DMSO) δ 8.30 (d, J=1.1 Hz, 1H), 7.82 (dd, J=8.5, 1.5 Hz, 1H), 7.71-7.59 (m, 2H), 7.56 (d, J=7.9 Hz, 1H), 7.51 (d, J=1.6 Hz, 1H), 7.38 (dd, J=7.9, 1.6 Hz, 1H), 6.87 (d, J=7.2 Hz, 1H), 6.69 (d, J=8.1 Hz, 1H), 5.42 (s, 2H), 5.11 (dt, J=6.8, 4.6 Hz, 1H), 4.90 (dd, J=8.3, 6.0 Hz, 2H), 4.77-4.85 (m, 1H), 4.62-4.69 (m, 1H), 4.61-4.54 (m, 2H), 4.43-4.50 (m, 1H), 4.37 (dt, J=9.0, 5.9 Hz, 1H), 4.29-4.19 (m, 1H), 4.03 (q, J=7.1 Hz, 1H), 3.92-3.99 (m, 1H), 3.87 (s, 3H), 3.74-3.81 (m 1H), 2.99 (d, J=10.5 Hz, 1H), 2.84 (d, J=11.0 Hz, 1H), 2.76-2.66 (m, 1H), 2.65-2.55 (m, 1H), 2.48-2.39 (m, 1H), 2.31-2.12 (m, 2H), 1.85-1.61 (m, 4H). LCMS: (ESI) m/z: 618.1 [M+H]+.

Compound 2: To a solution of 2-8 (80 mg, 0.13 mmol) in THF/MeOH (1:1, 4.0 mL) was added LiOH (2 mL, 2 M aqueous solution). The mixture was stirred at room temperature for 2 h. After the reaction was complete, the solvents were removed under reduced pressure. The resulting residue was purified by Prep-HPLC To give compound 2 (40 mg, 51% yield). $^1$H NMR (400 MHz, DMSO) δ 8.25 (s, 1H), 7.81 (d, J=8.0 Hz, 1H), 7.63 (t, J=8.0 Hz, 2H), 7.56 (d, J=8.0 Hz, 1H), 7.50 (s, 1H), 7.38 (d, J=8.0 Hz, 1H), 6.87 (d, J=8.0 Hz, 1H), 6.69 (d, J=8.0 Hz, 1H), 5.42 (s, 2H), 5.16-5.07 (m, 1H), 4.90 (dd, J=8.0 Hz, 2H), 4.79 (dd, $J_1$=6.0 Hz, $J_2$=14.0 Hz, 1H), 4.65 (d, J=12.0 Hz, 1H), 4.57 (t, J=10.0 Hz, 2H), 4.47 (dd, $J_1$=8.0 Hz, $J_2$=16.0 Hz, 1H), 4.38 (m, 1H), 4.29-4.19 (m, 1H), 3.95 (d, J=12.0 Hz, 1H), 3.77 (d, J=16.0 Hz, 1H), 2.99 (d, J=12.0 Hz, 2H), 2.84 (d, J=8.0 Hz, 1H), 2.71 (m, 1H), 2.65-2.55 (m, 1H), 2.44 (m, 1H), 2.29-2.11 (m, 2H), 1.85-1.61 (m, 4H)./LCMS: (ESI) m/z: 603.4 [M+H]+.

Example 3: (S)-2-((4-(6-((2-methoxy-4-(oxetan-3-yl)benzyl)oxy)pyridin-2-yl)piperidin-1-yl) methyl)-1-(oxetan-2-ylmethyl)-1H-benzo[d]imidazole-6-carboxylic acid (compound 3)
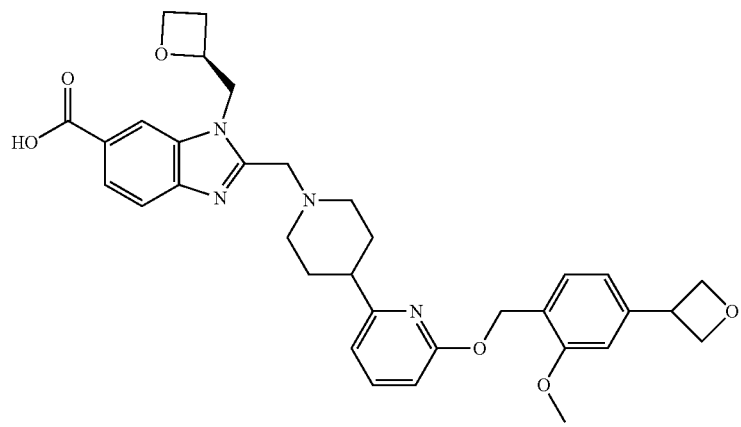
Synthetic route
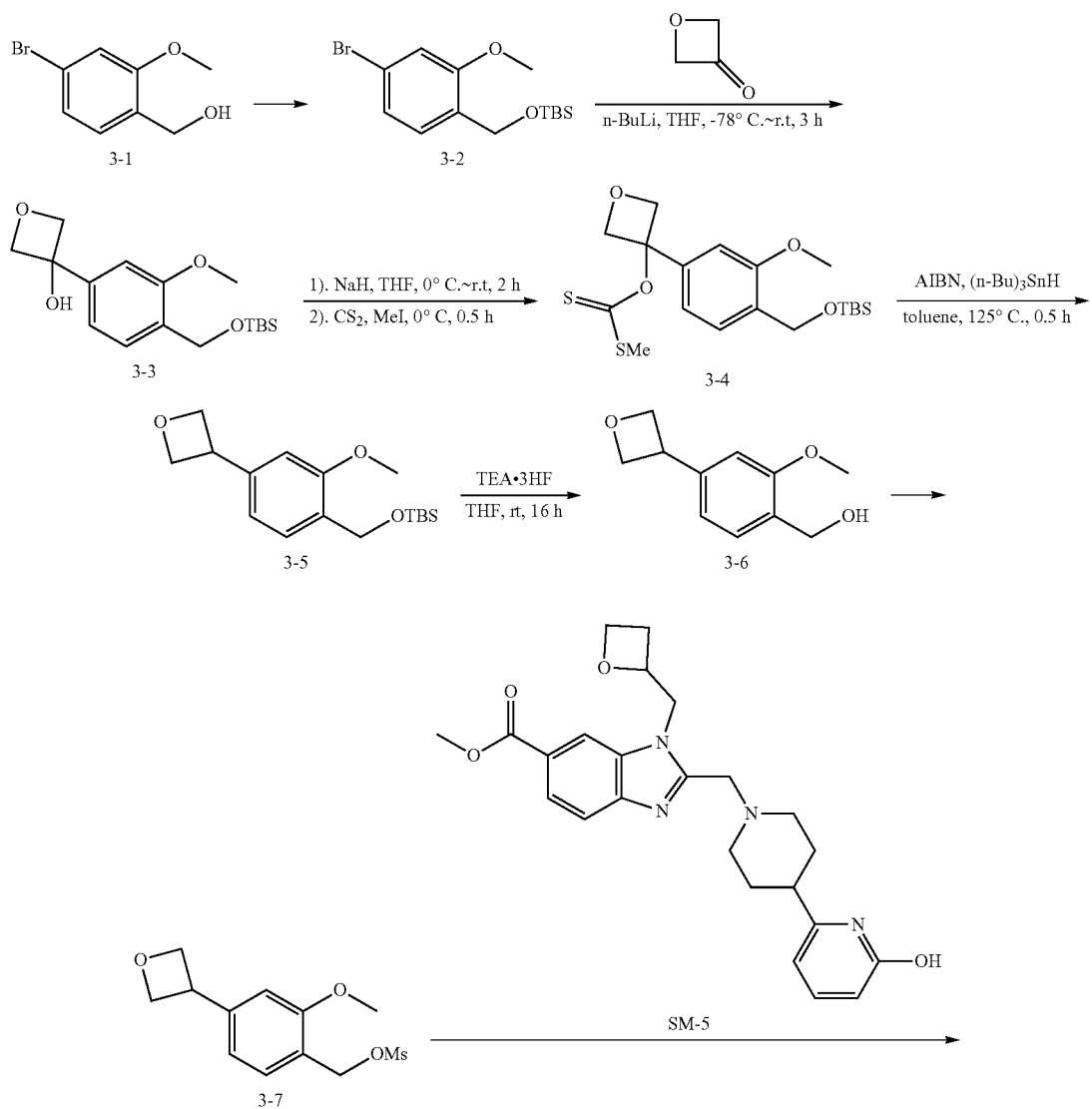

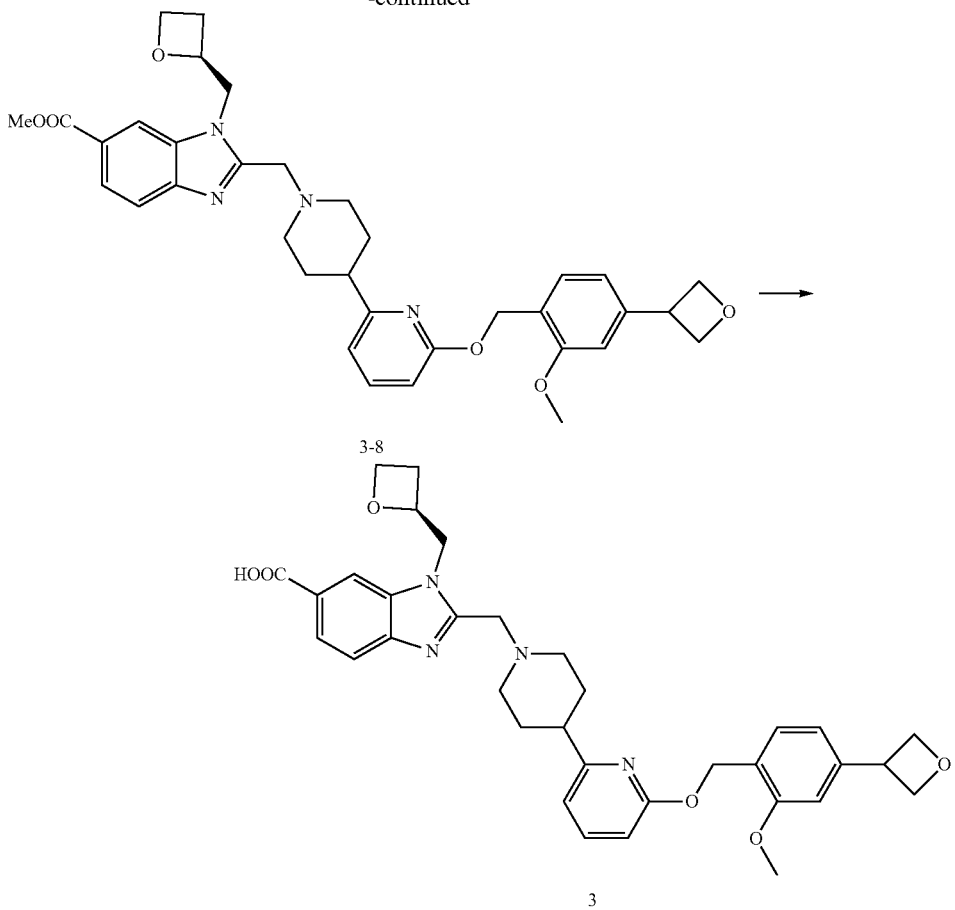

Preparation Method

Compound 3-2: To a solution of (4-bromo-2-methoxyphenyl)methanol (2.0 g, 9.21 mmol) in anhydrous DCM (75 mL) and anhydrous DMF (15 mL) was added DMAP (23 mg, 0.18 mmol) and DIPEA (2.4 mL, 13.8 mmol). Then, the mixture was cooled at 0° C., and added with TBSCl (1.9 g, 12.8 mmol). The mixture was stirred at room temperature for 16 h. The reaction solution was concentrated, and subjected to flash chromatography (SiO$_2$, hexane) to give 2.87 g of compound 3-2. $^1$H NMR (400 MHz, DMSO) δ 7.20 (d, J=8.3 Hz, 1H), 7.10-7.05 (m, 2H), 4.55 (s, 2H), 3.73 (s, 3H), 0.83 (s, 9H), 0.00 (s, 6H).

Compound 3-3: To a solution of 3-2 (2.87 g, 8.66 mmol) in anhydrous THF (30 mL) was added dropwise N-BuLi (2.5 M in THF, 3.8 mL, 9.52 mmol) at −78° C. under N$_2$. The mixture was stirred at this temperature for 0.5 h, and then added with oxetane-3-one (0.5 mL, 8.66 mmol). The mixture was then stirred at room temperature under N$_2$ atmosphere for 2.5 h. The reaction solution was quenched with water (30 mL), and extracted with EtOAc (3×30 mL). The combined organic phases were washed with brine (30 mL), dried (Na$_2$SO$_4$), filtered, and concentrated, and subjected to flash chromatography (SiO$_2$, 25% EtOAc-hexane) to give 1.93 g of compound 3-3. $^1$H NMR (400 MHz, DMSO) δ 7.27 (d, J=7.8 Hz, 1H), 7.11 (dd, J=7.8, 1.2 Hz, 1H), 7.05 (s, 1H), 6.22 (s, 1H), 4.67 (d, J=6.3 Hz, 2H), 4.64-4.58 (m, 4H), 3.72 (s, 3H), 0.83 (s, 9H), 0.51 (s, 6H).

Compound 3-4: To a solution of 3-3 (1.93 g, 5.94 mmol) in anhydrous THF (20 mL) was added NaH (476 mg, 11.89 mmol) at 0° C. The mixture was stirred at room temperature for 2 h, and then added with CS$_2$ (0.36 mL, 5.94 mmol) and MeI (0.37 mL, 5.94 mmol) at 0° C. under N$_2$. The mixture was then stirred at 0° C. in N$_2$ for 0.5 h. The reaction solution was quenched with saturated NH$_4$Cl solution (20 mL), and extracted with EtOAc (3×20 mL). The combined organic phases were washed with brine (20 mL), dried (Na$_2$SO$_4$), filtered, and concentrated to give 2.5 g of compound 3-4. The product was used directly in the next step without further purification.

Compound 3-5: To a solution of 3-4 (2.5 g, 6.03 mmol) in toluene (25 mL) was added (n-Bu)$_3$SnH (3.24 mL, 12.0 mmol) and AIBN (99 mg, 0.6 mmol). The mixture was stirred at 125° C. under N$_2$ atmosphere for 0.5 h. After addition of KF (1.4 g), the mixture was stirred at room temperature for 16 h. The reaction solution was concentrated, and subjected to flash chromatography (SiO$_2$, 20% EtOAc-hexane) to give 1.36 g of compound 3-5. $^1$H NMR (400 MHz, DMSO) δ 7.24 (d, J=8.1 Hz, 1H), 6.90 (d, J=6.6 Hz, 2H), 4.85 (dd, J=8.4, 5.8 Hz, 2H), 4.57 (dd, J=6.9, 6.0 Hz, 4H), 4.21-4.10 (m, 1H), 3.73 (s, 3H), 0.83 (s, 9H), −0.00 (s, 6H).

Compound 3-6: To a stirred solution of 3-5 (1.36 g, 4.4 mmol, 1.0 equiv) in THF (15 mL) was added Et$_3$N·HF (2.13 g, 13.2 mmol, 3 equiv). The resulting mixture was stirred at room temperature for 16 h. The solvent was then removed under reduced pressure. The reaction was quenched with H$_2$O (10 mL). After extraction with (CHCl$_3$:IPA (1:3)), the organic layer was washed with brine, dried over anhydrous Na₂SO₄, and concentrated in vacuo to give a residue. The crude product was purified by HPLC (gradient: 10% MeCN/90% H$_2$O, H$_2$O-100% MeCN) to give 734 mg of compound 3-6. $^1$H NMR (400 MHz, DMSO) δ 7.40 (d, J=7.5 Hz, 1H), 7.01 (d, J=7.8 Hz, 2H), 5.05-4.93 (m, 3H), 4.72-4.64 (m, 2H), 4.53 (d, J=5.2 Hz, 2H), 4.32-4.21 (m, 1H), 3.85 (s, 3H).

Compound 3-7: To a solution of 3-6 (20 mg, 0.12 mmol) in anhydrous DCM (2 mL) was added MsCl (17 mg, 0.14 mmol) and TEA (0.16 mL, 1.21 mmol). The reaction mixture was stirred at 0° C. for 30 min, and then quenched with water. After extraction with DCM, the organic layer was washed with brine, dried over anhydrous Na$_2$SO$_4$, and concentrated in vacuo to give 70 mg of crude compound 3-7.

Compound 3-8: A mixture of 3-7 (70 mg, 0.25 mmol), methyl 2-((4-(6-hydroxypyridin-2-yl) piperidin-1-yl) methyl)-1-(oxetan-2-ylmethyl)-1H-benzo[d]imidazole-6-carboxylate (56 mg, 0.12 mmol) and Cs$_2$CO$_3$ (92 mg, 0.28 mmol) in DMF (5 mL) was stirred at 50° C. overnight. The reaction was quenched with H$_2$O (10 mL). After extraction with EA (10 mL×3), the organic layer was washed with brine, and dried over anhydrous Na$_2$SO$_4$, and concentrated in vacuo to give a residue. The residue was purified by flash column chromatography (silica gel, eluted with 0-5% MeOH/DCM) to give 10 mg of compound 3-8.

Compound 3: A solution of 3-8 (80 mg, 0.13 mmol), and LiOH (0.5 mL) in THF (0.5 mL) was stirred at room temperature for 2 h. The solvent was then removed under reduced pressure to give a crude product, which was purified by HPLC (gradient: 10% MeCN/90% H$_2$O, 0.1% NH$_3$H$_2$O 100% MeCN) to give 12.85 mg of compound 3. $^1$H NMR (400 MHz, DMSO) δ 8.22 (s, 1H), 7.81 (d, J=8.0 Hz, 1H), 7.64-7.54 (m, 2H), 7.39 (d, J=8.0 Hz, 1H), 7.04 (s, 1H), 6.96 (d, J=8.0 Hz, 1H), 6.85 (d, J=4.0 Hz, 1H), 6.64 (d, J=8.0 Hz, 1H), 5.30 (s, 2H), 5.12 (m, 1H), 4.92 (dd, J=8.0 Hz, 2H), 4.77 (dd, J$_1$=6.0 Hz, J$_2$=14.0 Hz, 1H), 4.69-4.59 (m, 3H), 4.46 (dd, J=6.0 Hz, J$_2$=14.0 Hz, 1H), 4.38 (m, 1H), 4.25 (m, 1H), 3.94 (d, J=12.0 Hz, 1H), 3.84 (s, 3H), 3.78 (s, 1H), 3.01 (d, J=12.0 Hz, 1H), 2.86 (d, J=12.0 Hz, 1H), 2.71 (m, 1H), 2.59 (m, 1H), 2.49-2.41 (m, 1H), 2.29-2.13 (m, 2H), 1.75 (m, 4H)./LC-MS: (ESI) m/z: 599.4 [M+H]$^+$.

Example 4: 1-((1-(cyanomethyl)cyclopropyl) methyl)-2-((4-(6-((2-fluoro-4-(oxetan-3-yl)benzyl) oxy)pyridin-2-yl)piperidin-1-yl)methyl)-1H-benzo [d]imidazole-6-carboxylic acid (compound 4)

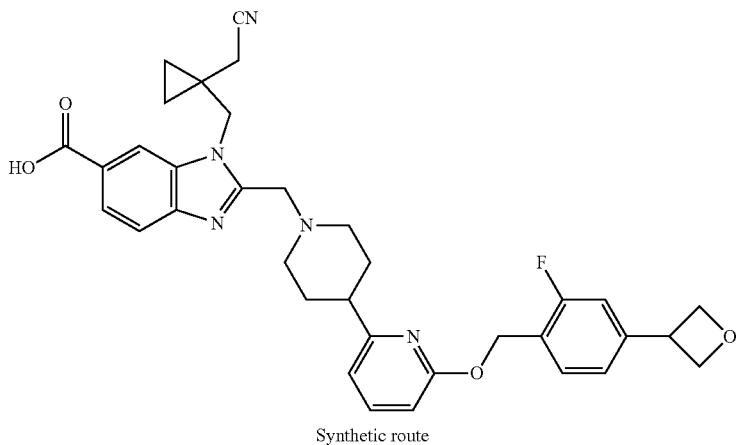

Synthetic route

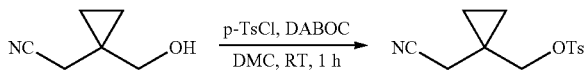

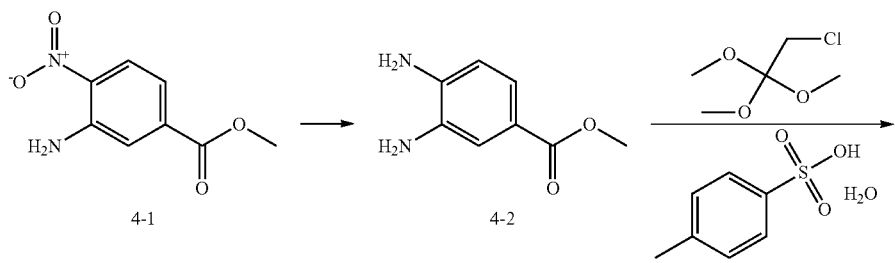

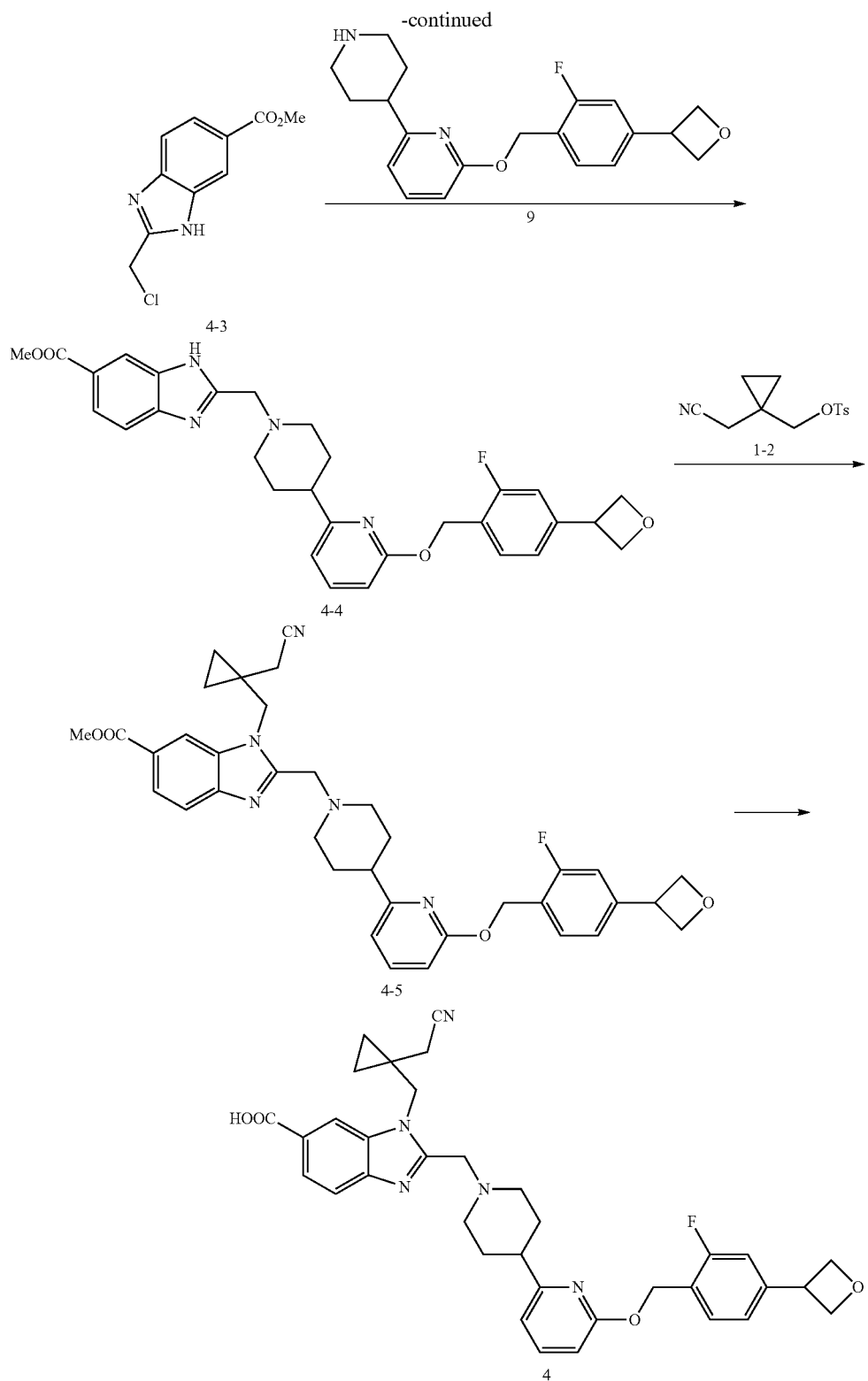

Preparation Method

At 5° C., a solution of p-TsCl (4.94 mmol, 943 mg) in DCM (10 mL) was slowly added to 2-(1-(hydroxymethyl)cyclopropyl)acetonitrile (4.49 mmol, 500 mg) and DABCO (5.84 mmol, 656 mg) in DCM (10 mL), a white precipitate formed after a few minutes. The mixture was stirred for 30 min at room temperature, and diluted with $Et_2O$ (15 mL). The white solid (DABCO-HCl) was filtered off and washed with diethyl ether. The combined organic layers were washed with 0.5% HCl (10 mL), dried ($Na_2SO_4$), and evaporated, and subjected to chromatography on silica using EtOAc:heptane as the eluent to give (1-(cyanomethyl)cyclopropyl)methyl 4-methylbenzenesulfonate. $^1$H NMR (400 MHz, DMSO) δ 7.81 (d, J=8.3 Hz, 2H), 7.49 (d, J=8.2 Hz, 2H), 3.96 (s, 2H), 2.62 (s, 2H), 2.43 (s, 3H), 0.61 (s, 4H).

Compound 4-2: To a solution of 4-1 (900 mg, 4.59 mmol) and NH$_4$Cl (1.96 g, 36.70 mmol) in EtOH, Fe powder (1.03 g, 18.35 mmol) was added to H$_2$O (1:1, 10 mL: 10 mL) at room temperature. The reaction mixture was stirred at 65° C. for 2 h. The reaction mixture was filtered through Celite. The filtrate was extracted with ethyl acetate (50 mL×3). The organic layer was washed with brine (100 mL), and dried over Na$_2$SO$_4$. After filtration, the solvent was concentrated under reduced pressure to give 4-2 (580 mg, crude).

Compound 4-3: To a solution of 4-2 (580 mg, 3.49 mmol) in tetrahydrofuran (10 mL) was added 2-chloro-1,1,1-trimethoxyethane (1.08 g, 6.98 mmol) followed by addition of p-toluenesulfonic acid monohydrate (66 mg, 0.35 mmol). The reaction mixture was heated to 45° C., and stirred for 16 h. H$_2$O (30 mL) was added. The resulting solution was extracted with ethyl acetate (30 mL×3). The combined organic extracts were washed with brine, and dried over anhydrous sodium sulfate. After filtration, the solvent was concentrated under reduced pressure. The residue was purified by flash column chromatography (silica gel, eluted with EA/PE 60-100%) to give 4-3 (420 mg, yield: 41%). $^1$H NMR (400 MHz, DMSO-d6) δ 13.08 (s, 1H), 8.17 (d, J=37.4 Hz, 1H), 7.93-7.53 (m, 2H), 4.97 (s, 2H), 3.87 (s, 3H).

Compound 4-4: To a solution of 4-3 (39 mg, 0.16 mmol) in dioxane (5 mL) and MeCN (3 mL) was added 2-((2-fluoro-4-(oxetan-3-yl)benzyl)oxy)-6-(piperidin-4-yl)pyridine (80 mg, 0.16 mmol) and K$_2$CO$_3$ (47 mg, 0.33 mmol). The mixture was stirred at 65° C. under N$_2$ atmosphere for 16 h. H$_2$O (10 mL) was added. The resulting solution was extracted with ethyl acetate (10 mL×3). The combined organic extracts were washed with brine, and dried over anhydrous sodium sulfate. After filtration, the solvent was concentrated under reduced pressure. The residue was purified by flash column chromatography (silica gel, eluted with 5-10% MeOH/DCM) to give 4-4 (45 mg, yield: 48%). $^1$H NMR (400 MHz, CDCl$_3$) δ 10.47 (s, 1H), 8.26 (s, 1H), 7.89 (dd, J=8.5, 1.4 Hz, 1H), 7.41 (ddd, J=9.7, 7.5, 2.2 Hz, 3H), 7.09-7.03 (m, 2H), 6.64 (d, J=7.2 Hz, 1H), 6.54 (d, J=8.1 Hz, 1H), 5.35 (s, 2H), 5.00 (dd, J=8.3, 6.1 Hz, 2H), 4.65 (t, J=6.3 Hz, 2H), 4.12 (td, J=8.1, 4.1 Hz, 1H), 3.85 (s, 3H), 3.82 (s, 2H), 2.95 (d, J=11.6 Hz, 2H), 2.60-2.54 (m, 1H), 2.31-2.23 (m, 2H), 1.88-1.81 (m, 4H)./LC-MS (ESI) m/z: 531.2 [M+H]$^+$.

Compound 4-5: (1-(cyanomethyl)cyclopropyl)methyl 4-methylbenzenesulfonate (11 mg, 0.04 mmol) and KOH (4 mg, 0.07 mmol) were added to a solution of 4-4 (20 mg, 0.03 mmol) in 5 mL DMF. The reactants were heated to 40-45° C. for 5-6 h with stirring. Water (15 mL) was added. The mixture was extracted with CH$_2$Cl$_2$ (3×10 mL). The organic layer was dried over anhydrous sodium sulfate. The solvent was evaporated in vacuo to give an oil as a crude product which was purified by HPLC (gradient: 10% MeCN/90% H2O, H2O to 100% MeCN) to give 48 mg of compound 4-5. LC-MS (ESI) m/z: 624.4 [M+H]+

Compound 4: A solution of 4-5 (48 mg, 0.07 mmol), LiOH (0.5 mL) in THF (0.5 mL) was stirred at room temperature for 2 h. The solvent was then removed under reduced pressure to give a crude product, which was purified by HPLC (gradient: 10% MeCN/90% H$_2$O, 0.1% NH$_3$·H2O to 100% MeCN) to give 2.15 mg of compound 4. $^1$H NMR (400 MHz, DMSO) δ 12.73 (s, 1H), 8.18 (s, 1H), 7.87 (d, J=8.0 Hz, 1H), 7.70 (d, J=12.0 Hz, 1H), 7.61 (t, J=8.0 Hz, 1H), 7.52 (t, J=6.0 Hz, 1H), 7.26 (d, J=12.0 Hz, 1H), 7.20 (d, J=8.0 Hz, 1H), 6.85 (d, J=8.0 Hz, 1H), 6.65 (d, J=12.0 Hz, 1H), 5.36 (s, 2H), 4.90 (dd, J$_1$=4.0 Hz, J$_2$=8.0 Hz, 2H), 4.58 (t, J=6.0 Hz, 4H), 4.30-4.18 (m, 1H), 3.86 (s, 2H), 2.98 (d, J=8.0 Hz, 3H), 2.69 (s, 2H), 2.61 (s, 1H), 2.21 (t, J=10 Hz, 2H), 1.83-1.68 (m, 4H), 0.73 (m, 4H)./LC-MS (ESI) m/z: 610.4 [M+H]$^+$.

Example 5: 2-((4-(6-((2-fluoro-4-(oxetan-3-yl)ben-zyl)oxy)pyridin-2-yl)piperidin-1-yl)methyl)-1-((1-(fluoromethyl)cyclopropyl)methyl)-1H-benzo[d]imidazole-6-carboxylic acid (compound 5)

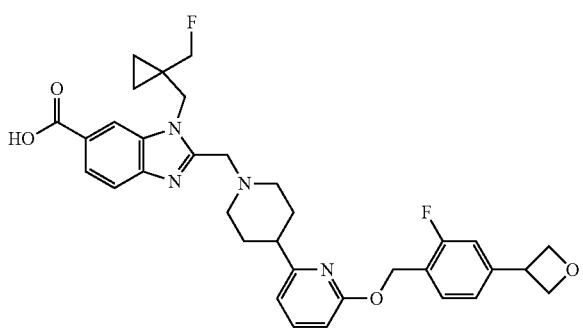 [SMILES: O=C(O)c1ccc2nc(CN3CCC(c4cccc(OCc5ccc(C6COC6)cc5F)n4)CC3)n(CC3(CF)CC3)c2c1]

-continued
Synthetic route
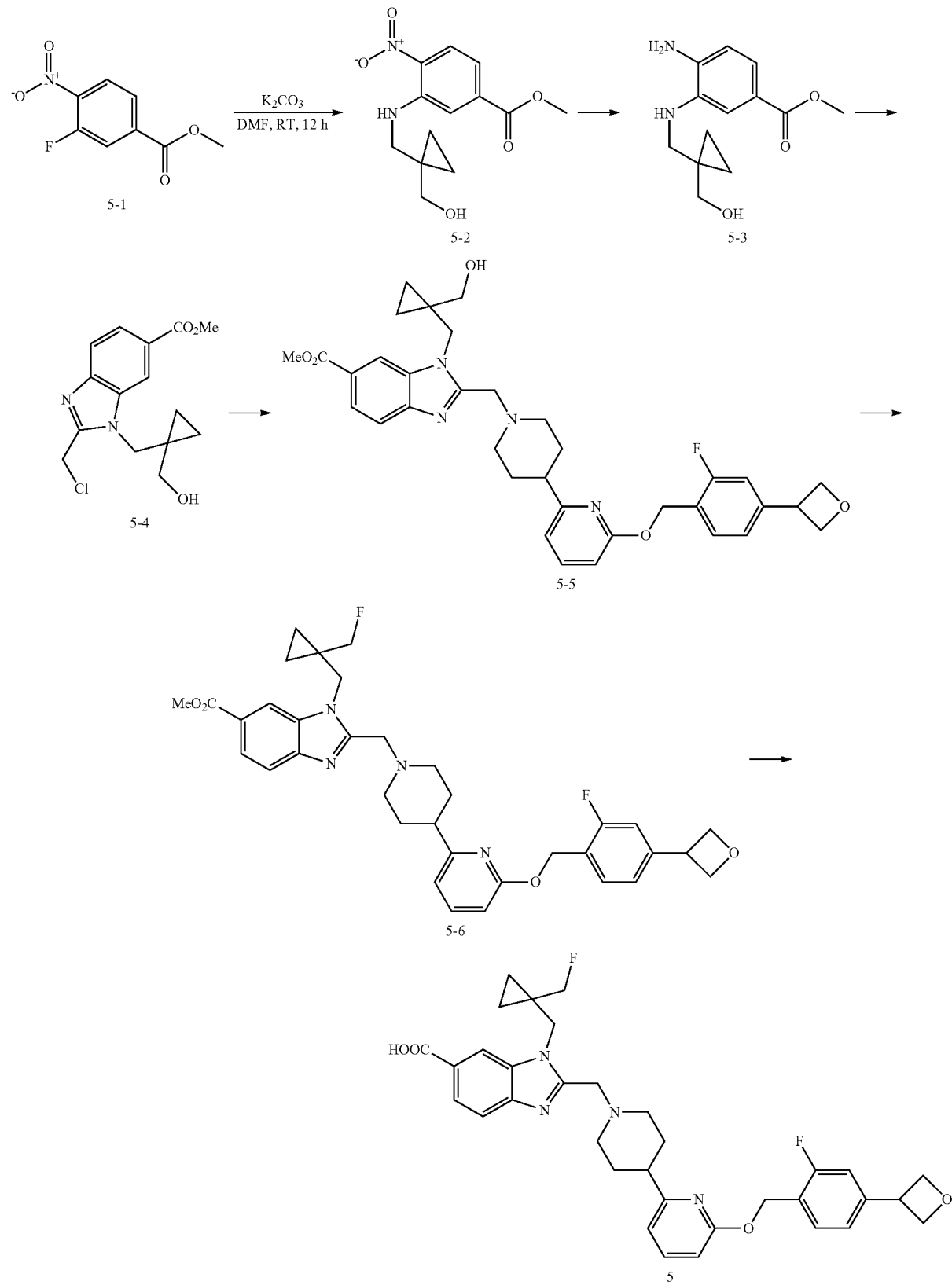

Preparation Method

Compound 5-2: In a glass-lined reactor, potassium carbonate (694 mg, 5.02 mmol) was added to a solution of 5-1 (200 mg, 1.00 mol) in tetrahydrofuran (5 mL), and the mixture was stirred for 10 min. A solution of (1-(aminomethyl)cyclopropyl)methanol (122 mg, 1.2 mmol) in tetrahydrofuran (5 mL) was added. The reaction mixture was stirred at from 20° C. to 30° C. for 12 h. The resulting solution was extracted with ethyl acetate (10 mL×3). The combined organic extracts were washed with brine, dried over anhydrous sodium sulfate, and filtered. The solvent was concentrated under reduced pressure. The residue was purified by flash column chromatography (silica gel, eluted with 20-60% EA in PE) to give 5-2 (238 mg, yield: 84%). $^1$H NMR (400 MHz, DMSO) δ 8.52 (t, J=4.6 Hz, 1H), 8.17 (d, J=8.9 Hz, 1H), 7.52 (d, J=1.6 Hz, 1H), 7.14 (dd, J=8.9, 1.7 Hz, 1H), 4.95 (t, J=5.3 Hz, 1H), 3.88 (s, 3H), 3.37 (dd, J=9.2, 5.1 Hz, 4H), 0.57-0.47 (m, 4H)./LC-MS (ESI) m/z: 281.2 [M+H]+

Compound 5-3: To a solution of 5-2 (238 mg, 0.84 mmol) and NH$_4$Cl (363 mg, 6.79 mmol) in EtOH, Fe powder (190 mg, 3.39 mmol) was added to H$_2$O (1:1, 2 mL/2 mL) at room temperature. The reaction mixture was stirred at 70° C. for 2 h. The reaction mixture was filtered through Celite. The mixture was extracted with ethyl acetate (10 mL×2). The organic layer was washed with brine (10 mL), and dried over Na$_2$SO$_4$. The solvent was evaporated to dryness. The residue yielded 5-3 (210 mg, crude). LC-MS (ESI) m/z: 251.2 [M+H]+.

Compound 5-4: To a solution of 5-3 (3.6 g, 14.38 mmol) in tetrahydrofuran (50 mL) was added 2-chloro-1,1,1-trimethoxyethane (4.45 g, 28.77 mmol) followed by addition of p-toluenesulfonic acid monohydrate (274 mg, 1.44 mmol). The reaction mixture was heated to 45° C. and stirred for 16 h. H$_2$O (100 mL) was added. The resulting solution was extracted with ethyl acetate (50 mL×3). The combined organic extracts were washed with brine, and dried over anhydrous sodium sulfate. After filtration, the solvent was concentrated under reduced pressure. The residue was purified by flash column chromatography (silica gel, eluted with 60-100% EA in PE) to give 5-4 (3.1 g, yield: 81%). $^1$H NMR (400 MHz, DMSO-d6) δ 8.33 (d, J=1.3 Hz, 1H), 7.86 (dd, J=8.5, 1.3 Hz, 1H), 7.74 (d, J=8.5 Hz, 1H), 5.18 (s, 2H), 4.96 (t, J=5.2 Hz, 1H), 4.47 (s, 2H), 3.89 (s, 3H), 3.01 (d, J=5.1 Hz, 2H), 0.67 (t, J=5.1 Hz, 2H), 0.53 (q, J=4.6 Hz, 2H).

Compound 5-5: To a solution of 5-4 (56 mg, 0.18 mmol) in dioxane (6 mL) and MeCN (3 mL) was added 2-((2-fluoro-4-(oxetan-3-yl)benzyl)oxy)-6-(piperidin-4-yl)pyridine (80 mg, 0.18 mmol) and K$_2$CO$_3$ (100 mg, 0.72 mmol). The mixture was stirred at 65° C. under N$_2$ atmosphere for 16 h. H$_2$O (10 mL) was added. The resulting solution was extracted with ethyl acetate (10 mL×3). The combined organic extracts were washed with brine, and dried over anhydrous sodium sulfate. After filtration, the solvent was concentrated under reduced pressure. The residue was purified by flash column chromatography (silica gel, eluted with 5-10% MeOH/DCM) to give 5-5 (70 mg, yield: 63%). $^1$H NMR (400 MHz, DMSO-d6) δ 8.30 (s, 1H), 7.83-7.80 (m, 1H), 7.68 (d, J=8.5 Hz, 1H), 7.61 (t, J=7.8 Hz, 1H), 7.53 (t, J=7.8 Hz, 1H), 7.19-7.25 (m, 2H), 6.85 (d, J=7.4 Hz, 1H), 6.65 (d, J=8.2 Hz, 1H), 5.36 (s, 2H), 5.06 (t, J=5.4 Hz, 1H), 4.90 (dd, J=8.3, 6.0 Hz, 2H), 4.57 (d, J=6.0 Hz, 3H), 4.29-4.19 (m, 1H), 3.92 (s, 2H), 3.88 (s, 3H), 3.04 (d, J=5.4 Hz, 2H), 2.96 (s, 2H), 2.68-2.55 (m, 2H), 2.18-2.26 (m, 2H), 1.83-1.66 (m, 4H), 0.65 (s, 2H), 0.53 (s, 2H).

Compound 5-6: 5-5 (60 mg, 0.09 mmol) was dissolved in 5 mL of DCM, and diethylaminosulfur trifluoride (31 mg, 0.19 mmol) was added. The mixture was reacted overnight at room temperature, cooled in ice bath, added dropwise with 20 mL of saturated sodium bicarbonate solution, and extracted with DCM (20 mL*3). The organic phase was concentrated to dryness with anhydrous sodium sulfate to give a crude product, which was purified by reverse phase to give 62 mg of compound 5-6. LC-MS (ESI) m/z: 617.2 [M+H]+.

Compound 5: A solution of 5-6 (62 mg, 0.1 mmol) and LiOH (0.5 mL) in THF (0.5 mL) was stirred at room temperature for 2 h. The solvent was then removed under reduced pressure to give a crude product, which was purified by HPLC (gradient: 10% MeCN/90% H$_2$O, 0.1% FA to 100% MeCN) to give 4.35 mg of compound 5. $^1$H NMR (400 MHz, DMSO) δ=8.38 (s, 1H), 8.21 (s, 1H), 7.82 (d, J=8.0 Hz, 1H), 7.65-7.57 (m, 2H), 7.52 (t, J=8.0 Hz, 1H), 7.26 (d, J=12.0 Hz, 1H), 7.21 (d, J=8.0 Hz, 1H), 6.85 (d, J=4.0 Hz, 1H), 6.65 (d, J=8.0 Hz, 1H), 5.36 (s, 2H), 4.90 (dd, J=8.0 Hz, 2H), 4.63 (s, 2H), 4.59 (t, J=6.0 Hz, 2H) 4.29-4.19 (m, 2H), 4.12 (s, 1H), 3.84 (s, 2H), 2.93 (d, J=8.0 Hz, 2H), 2.60 (m, 1H), 2.21 (t, J=12.0 Hz, 2H), 1.76 (m, 4H), 0.81-0.70 (m, 4H), (ESI) m/z: 603.3 [M+H]+

Example 6: (S)-1-(oxetan-2-ylmethyl)-2-((4-(6-((5-(oxetan-3-yl)pyridin-2-yl)methoxy)pyridin-2-yl)piperidin-1-yl)methyl)-1H-benzo[d]imidazole-6-carboxylic acid (compound 6)

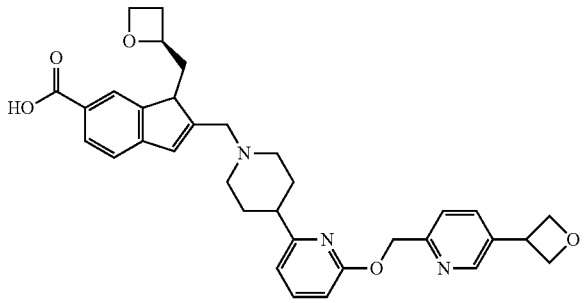 [SMILES: O=C(O)c1ccc2c(c1)C(C[C@@H]1CCO1)C(CN1CCC(c3cccc(OCc4ccc(C5COC5)cn4)n3)CC1)=C2]

-continued
Synthetic route
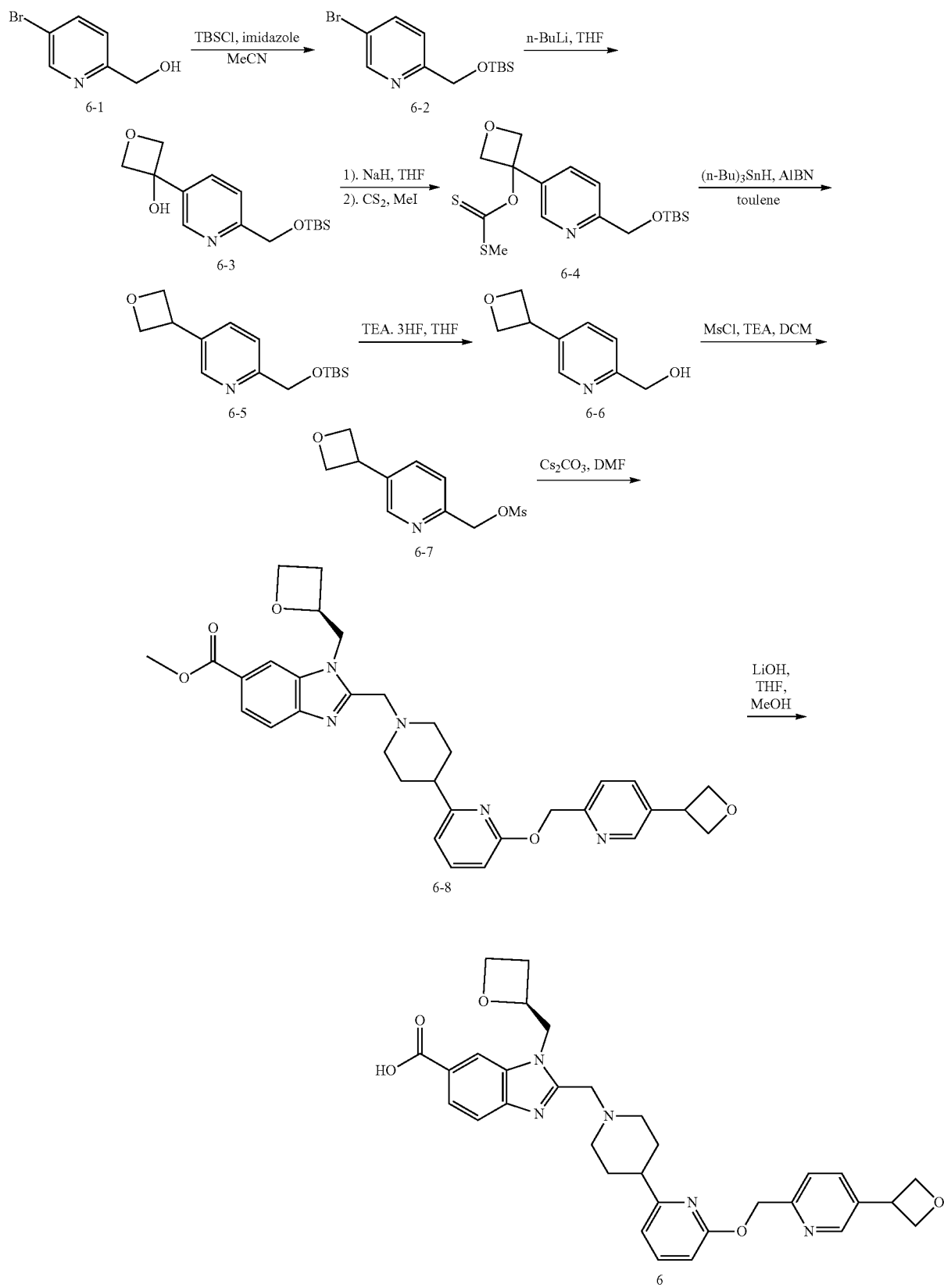

Preparation Method

Compound 6-2: A mixture of 6-1 (20.0 g, 106.38 mmol) and imidazole (10.86 g, 159.57 mmol) was added to MeCN (200 mL) followed by addition of TBSCl (17.64 g, 117.02 mmol). The mixture was stirred at room temperature for 16 h. Upon completion, the mixture was concentrated, and purified by flash chromatography (SiO$_2$, hexane) to give 29 g of product 6-2. $^1$H NMR (400 MHz, DMSO) δ 7.20 (d, J=8.3 Hz, 1H), 7.10-7.05 (m, 2H), 4.55 (s, 2H), 3.73 (s, 3H), 0.83 (s, 9H), 0.00 (s, 6H).

Compound 6-3: To a solution of 6-2 (10.0 g, 33.08 mmol) in anhydrous THF (100 mL) was added N-BuLi (2.5 M in THF, 13.9 mL, 34.73 mmol) at −78° C. under N$_2$. The mixture was stirred at this temperature for 0.5 h, then added with SM2 (2.5 g, 34.73 mmol). The mixture was then stirred at room temperature under N$_2$ atmosphere for 3 h. The reaction solution was quenched with water (50 mL), and extracted with EtOAc (3×100 mL). The combined organic phases were washed with brine (100 mL), dried (Na$_2$SO$_4$), filtered, and concentrated, and subjected to flash chromatography (SiO$_2$, EtOAc-hexane) to give 5.9 g of product 6-3. $^1$H NMR (400 MHz, DMSO) δ 8.65-8.54 (1H, m), 7.89 (1H, dd, J=8.2, 2.4), 7.36 (1H, dd, J=8.1, 0.6), 6.41 (1H, s), 4.72-4.65 (4H, m), 4.61 (2H, d, J=7.0), 0.84-0.81 (9H, m), 0.03--0.03 (6H, m).

Compound 6-4: To a solution of 6-3 (5.9 g, 20 mmol) in anhydrous THF (60 mL) was added NaH (1.6 g, 40 mmol) at 0° C. The mixture was stirred at room temperature for 2 h, and then added with CS$_2$ (1.5 g, 20 mmol) and MeI (2.8 g, 20 mmol) at 0° C. under N$_2$. The mixture was then stirred at 0° C. in N$_2$ for 2 h. The reaction solution was quenched with saturated NH$_4$Cl solution (40 mL), and extracted with EtOAc (3×60 mL). The combined organic phases were washed with brine (60 mL), dried (Na$_2$SO$_4$), filtered, and concentrated, and subjected to flash chromatography (SiO$_2$, EtOAc-hexane) to give 3.3 g of product 6-4. $^1$H NMR (400 MHz, DMSO) δ 8.51 (1H, d, J=2.3), 7.83 (1H, dd, J=8.2, 2.4), 7.39 (1H, d, J=8.2), 5.01 (2H, d, J=8.3), 4.84 (2H, d, J=8.4), 4.66 (2H, s), 2.48 (3H, s), 0.82 (9H, d, J=2.9), -0.00 (6H, d, J=3.1).

Compound 6-5: To a solution of 6-4 (3.0 g, 7.79 mmol) in toluene (100 mL) was added (n-Bu)$_3$SnH (4.53 g, 15.58 mmol) and AIBN (130 mg, 0.78 mmol). The mixture was stirred at 125° C. under N$_2$ atmosphere for 0.5 h. After addition of KF (1.7 G), the mixture was stirred at room temperature for 0.5 h. The reaction solution was concentrated, and subjected to flash chromatographed (SiO$_2$, EtOAc-hexane) to give 1.9 g of product 6-5. $^1$H NMR (400 MHz, DMSO) δ 8.37 (1H, d, J=2.1), 7.84 (1H, dd, J=8.1, 2.3), 7.35 (1H, d, J=8.1), 4.85 (2H, dd, J=8.4, 6.0), 4.65 (2H, s), 4.55-4.49 (2H, m), 4.23-4.14 (1H, m), 0.82 (9H, s), 0.02--0.05 (6H, m)

Compound 6-6: To a stirred solution of 6-5 (600 mg, 2.15 mmol) in THF (10 mL) was added Et$_3$N HF (692 mg, 4.29 mmol). The resulting mixture was stirred at room temperature for 16 h. The solvent was then removed under reduced pressure, and the reaction mixture was concentrated in vacuo to give a residue. The crude product was purified through reverse phase column (gradient: MeCN—H$_2$O) to give 300 mg of product 6-6. $^1$H NMR (400 MHz, DMSO) δ 8.45 (1H, s), 7.91 (1H, dd, J=8.1, 2.1), 7.48 (1H, d, J=8.0), 5.37 (1H, t, J=5.6), 4.95 (2H, dd, J=8.4, 6.0), 4.68-4.59 (2H, m), 4.55 (2H, d, J=5.4), 4.28 (1H, t, J=7.0).

Compound 6-7: To a solution of 6-6 (200 mg, 1.21 mmol) in anhydrous DCM (5 mL) was added MsCl (166 mg, 1.45 mmol) and TEA (123 mg, 12.12 mmol). The reaction mixture was stirred at 0° C. for 1 h, and then quenched with water. After extraction with DCM, the organic layer was washed with brine, dried over anhydrous Na$_2$SO$_4$, and concentrated in vacuo to give 360 mg of crude product 6-7.

Compound 6-8: A mixture of 6-7 (360 mg, 1.48 mmol), (S)-methyl 2-((4-(6-hydroxypyridin-2-yl)piperidin-1-yl)methyl)-1-(oxetan-2-ylmethyl)-1H-benzo[d]imidazole-6-carboxylate (100 mg, 0.21 mmol) and Cs$_2$CO$_3$ (788 mg, 2.96 mmol) in DMF (10 ml) was stirred at 50° C. overnight. The reaction was quenched with H$_2$O (10 ml). After extraction with DCM/MeOH (10 ml×3), the organic layer was washed with brine, dried over anhydrous Na$_2$SO$_4$, and concentrated in vacuo to give a residue. The residue was purified by flash column chromatography (SiO$_2$, EA-PE) to give 130 mg of product 6-8. $^1$H NMR (400 MHz, DMSO) δ 8.52 (1H, d, J=2.2), 8.30 (1H, d, J=1.3), 7.95 (2H, s), 7.90 (1H, dd, J=8.1, 2.3), 7.82 (2H, dd, J=8.5, 1.6), 7.68 (1H, s), 7.46 (1H, d, J=8.1), 6.88 (1H, dd, J=11.7, 7.5), 6.71 (1H, t, J=14.6), 5.42 (2H, s), 5.10 (1H, d, J=6.9), 4.91 (2H, dd, J=8.3, 6.0), 4.78 (2H, d, J=7.2), 4.71-4.64 (1H, m), 4.62-4.55 (2H, m), 4.48 (1H, d, J=4.9), 4.36 (1H, dd, J=5.9, 3.1), 4.27 (1H, s), 3.95 (1H, dd, J=13.5, 9.0), 3.87 (3H, s), 3.78 (1H, t, J=12.7), 3.03-2.95 (1H, m), 2.70-2.65 (1H, m), 2.57 (1H, dd, J=13.9, 8.9), 2.44 (1H, dd, J=13.5, 6.4), 2.27-2.15 (2H, m), 1.78-1.63 (4H, m).

Compound 6: A solution of 6-8 (120 mg, 0.21 mmol), LiOH (1 mL) in THF (1 mL) was stirred at room temperature for 1 h. The solvent was then removed under reduced pressure to give a crude product, which was purified by preparative HPLC to give 43.1 mg of product as compound 6. $^1$H NMR (400 MHz, DMSO) δ (400 MHz, DMSO) 8.52 (1H, d, J=2.2), 8.10 (1H, s), 7.90 (1H, dd, J=8.0, 2.3), 7.76 (1H, d, J=8.4), 7.68-7.62 (1H, m), 7.46 (2H, d, J=8.0), 6.87 (1H, d, J=7.3), 6.72 (1H, d, J=8.1), 5.41 (2H, s), 5.10 (1H, d, J=4.1), 4.91 (2H, dd, J=7.9, 6.1), 4.72 (1H, dd, J=15.1, 6.9), 4.65-4.55 (3H, m), 4.48 (1H, d, J=4.7), 4.37 (1H, dt, J=9.2, 6.0), 4.28 (1H, dd, J=15.2, 6.9), 3.90 (1H, d, J=13.4), 3.73 (1H, d, J=13.3), 2.96 (1H, d, J=11.9), 2.82 (1H, s), 2.67 (1H, s), 2.57 (1H, s), 2.45 (1H, s), 2.16 (2H, dt, J=11.7, 6.7), 1.82-1.58 (4H, m). LC-MS: (ESI) m/z: 570.3 [M+H]$^+$.

Example 7: (S)-2-((2-((2-fluoro-4-(oxetan-3-yl)benzyl)oxy)-5,8,10,11-tetrahydro-oxepino[4,3-b: 6,5-c'] dipyridin-9(7H)-yl)methyl)-1-(oxetan-2-ylmethyl)-1H-benzo[d]imidazole-6-carboxylic acid (compound 7)
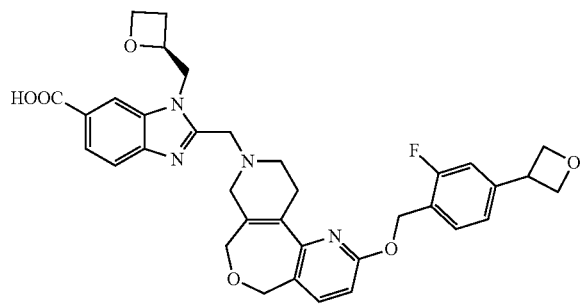 [SMILES: O=C(O)c1ccc2nc(CN3CCC4=C(COCc5ccc(OCc6ccc(C7COC7)cc6F)nc54)C3)n(C[C@@H]3CCO3)c2c1]
Synthetic route
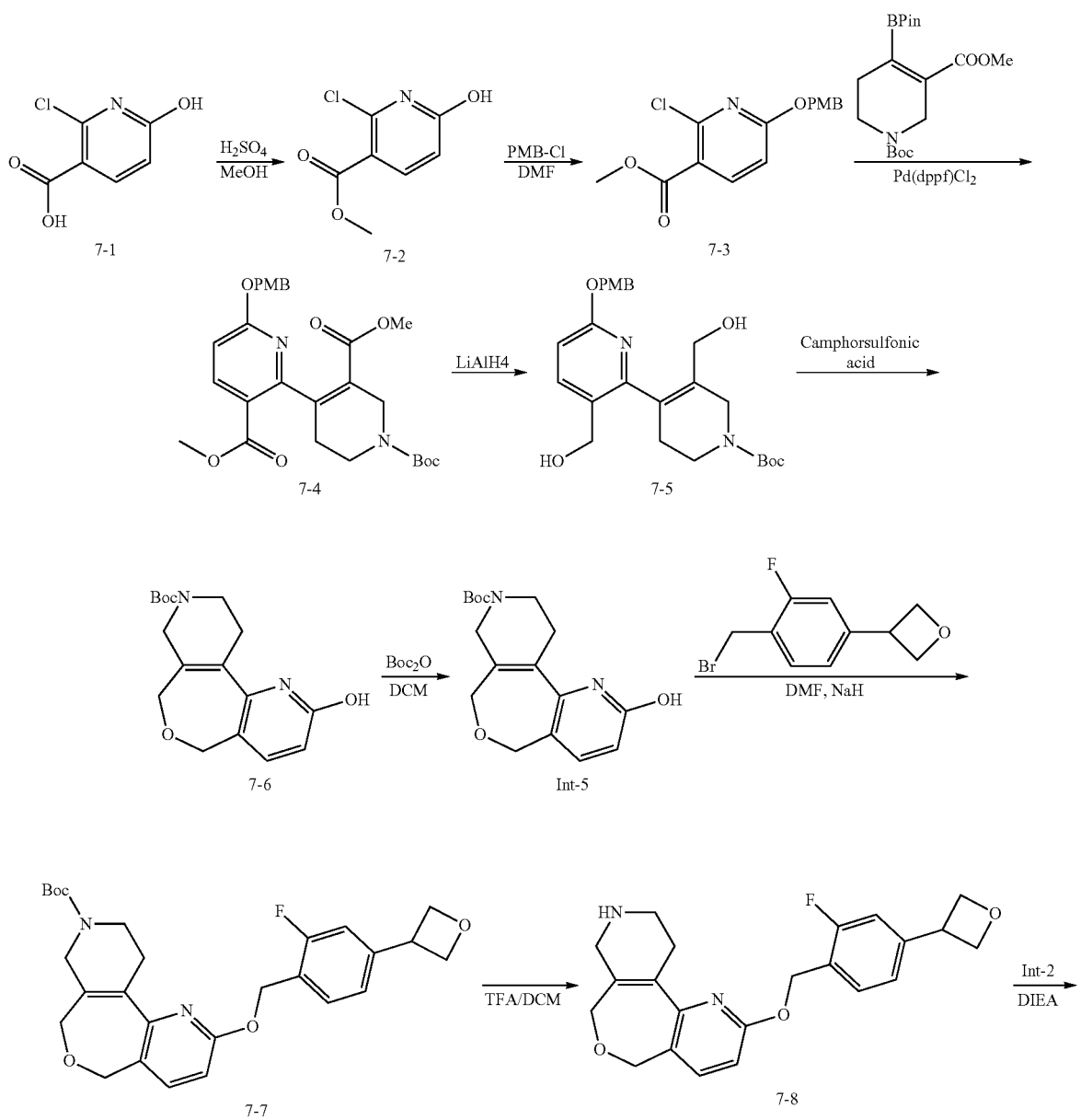

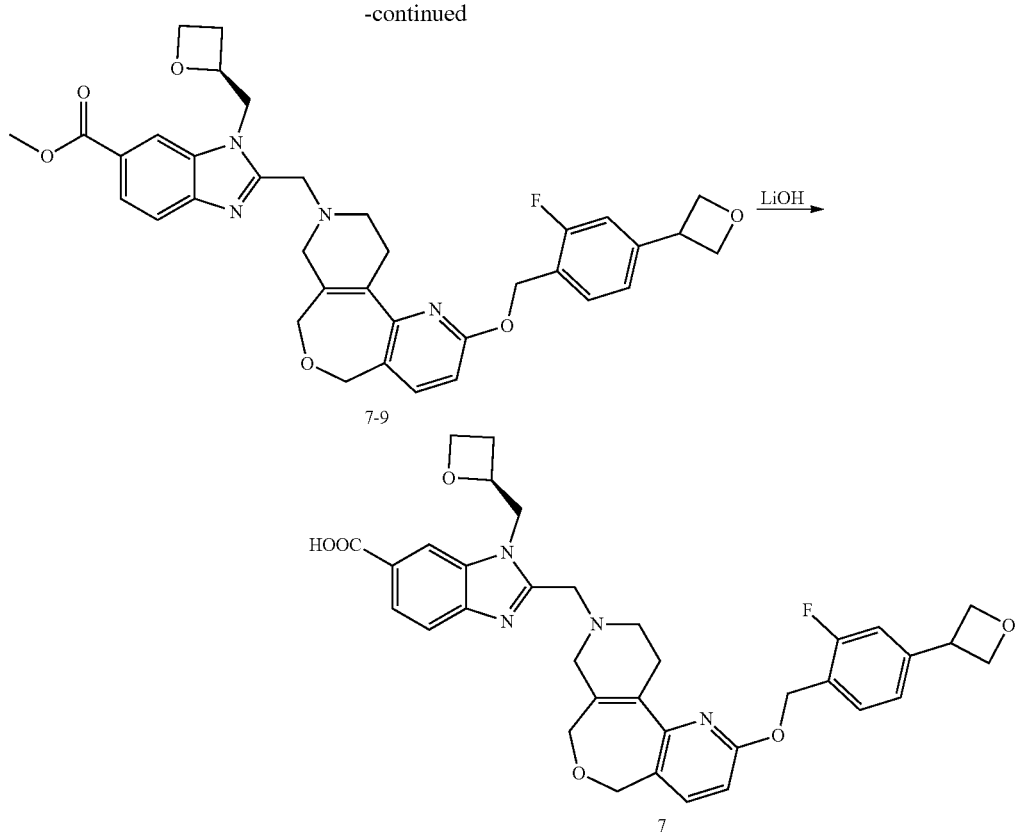

Preparation Method

Compound 7-2: To a mixture of 2-chloro-6-hydroxynicotinic acid 7-1 (5.0 g, 29 mmol) in MeOH (40 mL) was added sulfuric acid (10 mL). The mixture was stirred at 80° C. for 16 h. The reaction was detected by LCMS. The reaction mixture was quenched with ice water, and extracted with EA. The combined organic layers were washed with brine (50 mL), dried over $Na_2SO_4$, and concentrated under reduced pressure to give methyl 2-chloro-6-hydroxynicotinate (7-2) (4.5 g, 83%). LCMS: r.t.=2.1 min, [M+H]$^+$=188, purity: 92%.

Compound 7-3: A reaction mixture of 7-2 (3.4 g, 18.2 mmol), PMB-Cl (3.4 g, 21.2 mmol) and $K_2CO_3$ (3.76 g, 27.3 mmol) in DMF (50 ml) was added. The mixture was stirred at 80° C. with $Ar_2$ for 2 h. The reaction was detected by LCMS. The reaction mixture was quenched by the addition of water. The aqueous phase was extracted with EtOAc (100 ml×3), and washed with brine (50 ml×2). The combined organic layers were dried over $Na_2SO_4$, concentrated, and purified by elution (PE/EA=0-20%) to give methyl 2-chloro-6-((4-methoxybenzyl)oxy)nicotinate (7-3) (2.9 g, 52%). LCMS: r.t.=3.5 min, [M+H]$^+$=308, purity: 95%.

Compound 7-4: A reaction mixture of 7-3 (2.9 g, 9.4 mmol), 4-(4,4,5,5-tetramethyl-1,3,2-dioxaborolan-2-yl)-5,6-dihydropyridine-1,3(2H)-dicarboxylic acid 1-4 methyl ester (4.16 g, 11.3 mmol), $Cs_2CO_3$ (6.16 g, 18.8 mmol) and Pd (dppf) $Cl_2$ (0.69 g, 0.94 mmol) in 1, 4-dioxane (80 ml) was added. The mixture was stirred at 110° C. with $Ar_2$ for 16 h. The reaction was detected by LCMS. The reaction mixture was concentrated, and purified by elution (PE/EA=0-20%) to give 1'-(tert-butyl)$_{3,3}$'-dimethyl-6-((4-methoxybenzyl)oxy)-5',6'-dihydro-[2,4'-bipyridyl]-1',3,3' (2'H)-tricarboxylate (7-4) (2.5 g, 53.2%). LCMS: r.t.=1.37 min, [M+H]$^+$=513, purity: 95%.

Compound 7-5: 7-4 (1.5 g, 2.9 mmol) was dissolved in anhydrous THF (15 mL), and then LiAlH$_4$ (0.222 g, 5.8 mmol) was added in portions at 0° C. After 10 min, the reaction was detected by LCMS. The reaction mixture was quenched with ice water (0.5 ml). The mixture was filtered, and concentrated to give tert-butyl 3,5'-bis(hydroxymethyl)-6-((4-methoxybenzyl)oxy)-3',6'-dihydro-[2,4'-bipyridyl]-1' (2'H)-carboxylate (7-5) (1.2 g, 92%). LCMS: r.t.=1.95 min, [M+H]$^+$=457, purity: 88%.

Compound 7-6: A reaction mixture of 7-5 (1.1 g, 2.4 mmol) and camphorsulfonic acid (3.24 g, 9.6 mmol) in TOL (20 ml) was added. The mixture was heated at 110° C. for 1 h. The reaction was detected by LCMS. The reaction mixture was concentrated, and purified by elution (MeOH/DCM=0-20%) to give 5,7,8,9,10,11-hexahydrooxyepino [4,3-b:6,5-c']bipyridin-2-ol (7-6) (0.4 g, 76%). LCMS: r.t.=1.25 min, [M+H]$^+$=219, purity: 96%.

Preparation of Int-5: A solution of 7-6 (0.35 g, 1.6 mmol), (BOC)$_2$O (0.42 g, 1.9 mmol), and TEA in DCM (15 ml). The mixture was stirred at room temperature for 1 h. The reaction was detected by LCMS. The reaction mixture was concentrated, and purified by elution (MeOH/DCM=0-10%) to give tert-butyl 2-hydroxy-5,8,10,11-tetrahydrooxepino[4,3-b:6,5-c']dipyridine-9(7H)-carboxylate (Int-5) (350 mg, 70%). LCMS: r.t.=2.32 min, [M+H]$^+$=319, purity: 95%. $^1$H NMR (400 MHz, CDCl$_3$) δ 12.63 (s, 1H), 7.43 (d, J=9.2 Hz, 1H), 6.49 (d, J=9.1 Hz, 1H), 4.17 (s, 4H), 3.80 (s, 2H), 3.67 (t, J=5.5 Hz, 2H), 2.72 (s, 2H), 1.51 (s, 9H).

Compound 7-7: Int-5 (0.3 g, 1.2 mmol) was dissolved in anhydrous DMF (5 mL), and then NaH (45 mg, 1.44 mmol)

was added in portions at 0° C. After 5 min, a solution of 4-(bromomethyl)-3-fluorobenzonitrile (0.202 g, 1.2 mm ol) (5 mL DMF) was added to the reaction through a sleeve. After 20 min, the reaction was detected by LC-MS. The reaction mixture was quenched by the addition of water. The aqueous phase was extracted with EtOAc (20 ml×3), and washed with brine (20 ml×2). The combined organic layers were dried over $Na_2SO_4$, concentrated, and purified by elution (PE/EA=0-20%) to give the product 7-7 (0.35 g, 83.3%). LCMS: r.t.=2.21 min, [M+H]$^+$=483.5, purity: 95%.

Compound 7-8: 7-7 (0.35 g, 0.78 mmol) was added to TFA/DCM (20 ml, 3 m), and the mixture was stirred at room temperature for 0.5 h. The reaction of the reaction mixture was complete as detected by LC-MS. The mixture was concentrated to give 7-8 (0.27 g, 98%). LCMS: r.t.=1.21 min, [M+H]$^+$=383.2, purity: 92%.

Compound 7-9: A reaction mixture of 7-8 (0.27 g, 1.1 mmol) and DIEA (0.451 g, 3.5 mmol) in 20 mL $CH_3CN$ was stirred at room temperature for 10 min. Int-2 (206.5 g, 1.0 mmol) was then added. The mixture was heated at 65° C. for 15 h. The reaction was detected by LC-MS. The reaction mixture was concentrated, and purified by elution (MeOH/DCM=0-8%) to give the product 7-9 (250 mg, 59%). LCMS: r.t.=2.51 min, [M+H]$^+$=641.3, purity: 95%.

Compound 7: 7-9 (0.25 g, 0.41 mmol) was dissolved in THF (4 mL), and then aqueous lithium hydroxide (4 mL) was added. The mixture was stirred at room temperature for 8 h. The reaction was detected by LC-MS. The reaction mixture was concentrated, and purified by preparative HPLC ($NH_3 \cdot H_2O$) to give compound 7 (0.13 g, 53%). LCMS: r.t.=1.225 min, [M+H]$^+$=627.0, purity: 96%. $^1$H NMR (400 MHz, MeOD) $^1$H NMR (400 MHz, MeOD) δ 8.18 (s, 1H), 7.95 (dd, J=8.4, 1.4 Hz, 1H), 7.59 (dd, J=8.4, 4.1 Hz, 2H), 7.49 (t, J=7.9 Hz, 1H), 7.20-7.13 (m, 2H), 6.69 (d, J=8.2 Hz, 1H), 5.45 (s, 2H), 5.32-5.22 (m, 1H), 5.05 (dd, J=8.3, 6.0 Hz, 2H), 4.90-4.84 (m, 2H), 4.74-4.67 (m, 3H), 4.61 (dd, J=13.8, 7.8 Hz, 1H), 4.46 (dt, J=9.1, 6.0 Hz, 1H), 4.34 (s, 2H), 4.30-4.20 (m, 1H), 4.20-4.02 (m, 2H), 3.86 (s, 2H), 3.24 (t, J=10.7 Hz, 2H), 2.87-2.68 (m, 5H), 2.59-2.46 (m, 1H).

Example 8: 1-((1-(cyanomethyl)cyclopropyl)methyl)-2-(2-fluoro-4-(6-((2-fluoro-4-(oxetan-3-yl)benzyl)oxy)pyridin-2-yl)benzyl)-1H-benzo[d]imidazole-6-carboxylic acid (compound 8)

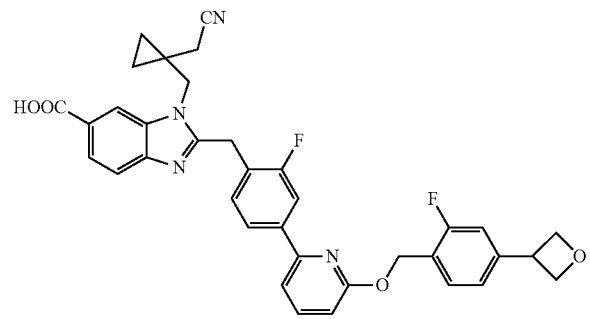 [SMILES: N#CCC1(Cn2c(Cc3ccc(-c4cccc(OCc5ccc(C6COC6)cc5F)n4)cc3F)nc3ccc(C(=O)O)cc32)CC1]

Synthetic route

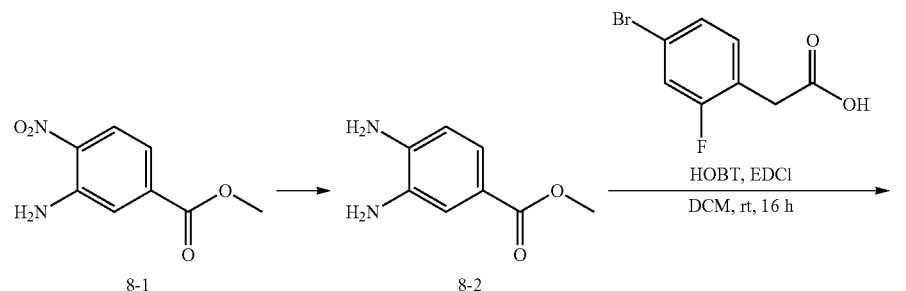

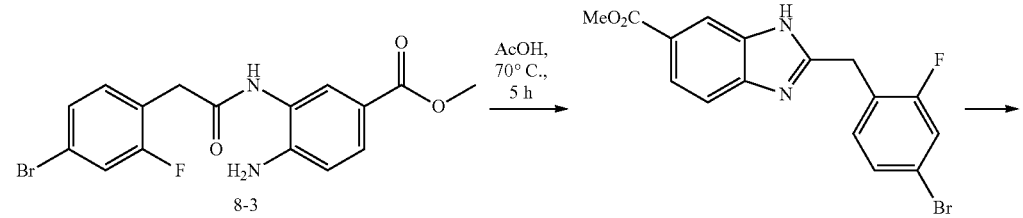

-continued
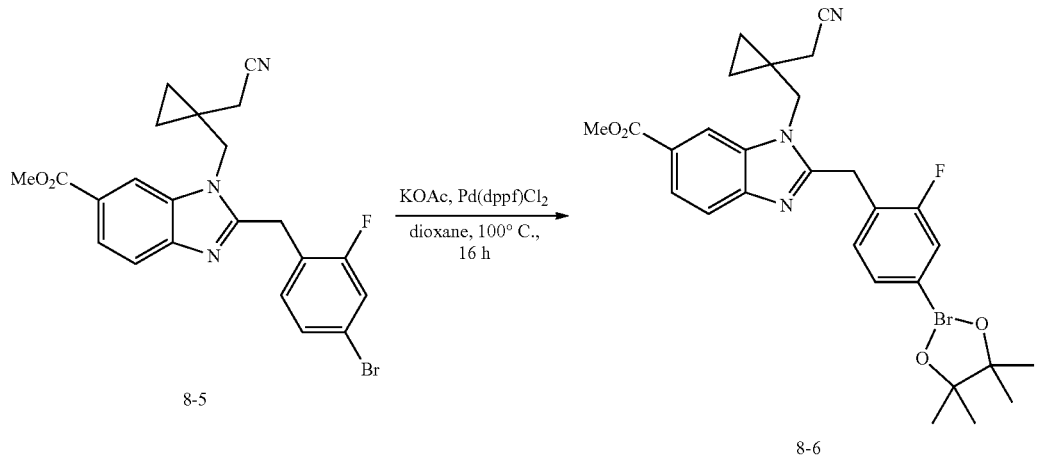
8-5
8-6
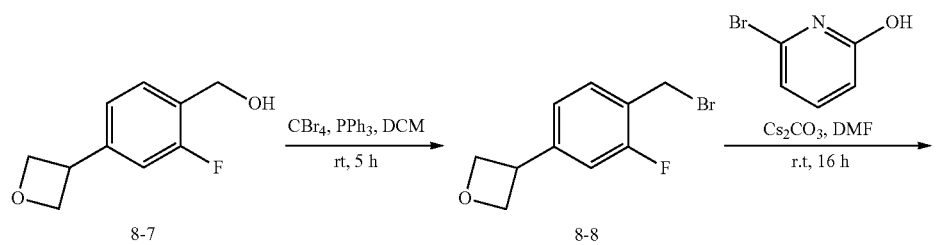
8-7
8-8
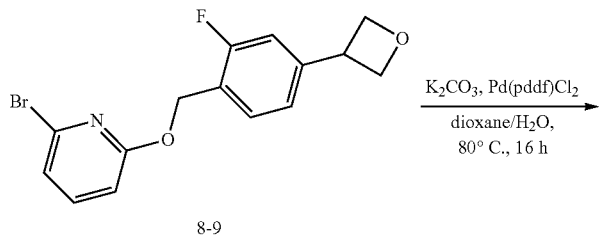
8-9
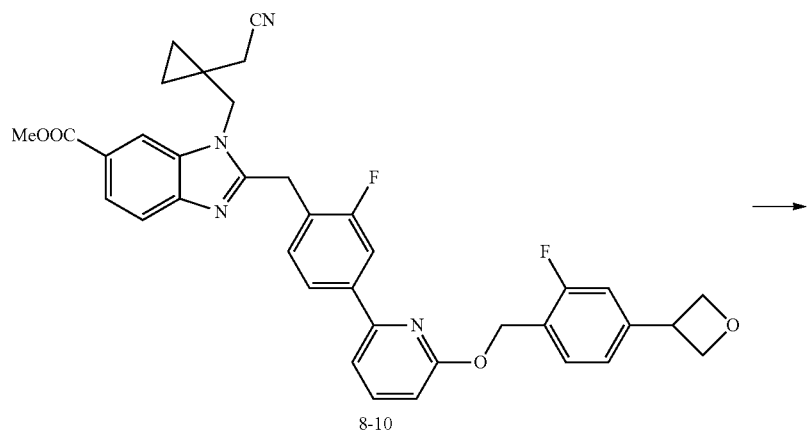
8-10

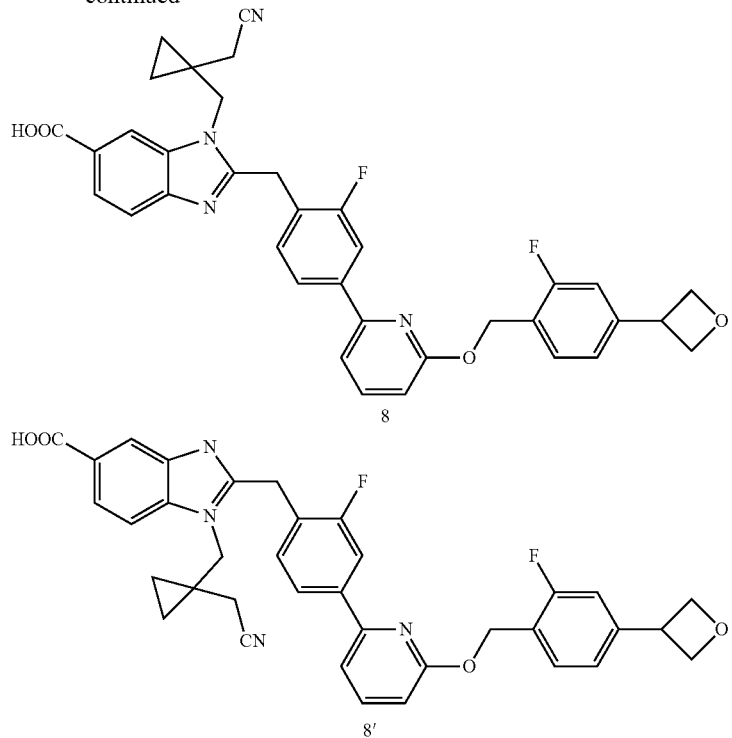

Preparation Method

Compound 8-2: To a solution of 8-1 (3 g, 15.29 mmol) and NH₄Cl (6.5 g, 122.35 mmol) in EtOH, Fe powder (3.4 g, 61.17 mmol) was added to H$_2$O (1:1, 30 mL: 30 mL) at room temperature. The reaction mixture was stirred at 65° C. for 2 h. The reaction mixture was filtered through Celite. The filtrate was extracted with ethyl acetate (50 mL). The organic layer was washed with brine (100 mL), and dried over Na$_2$SO$_4$. After filtration, the solvent was concentrated under reduced pressure to give product 18-2 (2.3 g, crude). $^1$H NMR (400 MHz, DMSO) δ 7.81 (d, J=8.3 Hz, 2H), 7.49 (d, J=8.2 Hz, 2H), 3.96 (s, 2H), 2.62 (s, 2H), 2.43 (s, 3H), 0.61 (s, 4H).

Compound 8-3: To a solution of 2-(4-bromo-2-fluorophenyl)acetic acid (3.5 g, 15.22 mmol) in DCM (40 mL) was added HOBT (2.1 g, 15.22 mmol) and EDCI (3.2 g, 16.61 mmol) at room temperature. The mixture was stirred at room temperature for 30 min. Then a solution of 8-2 (2.3 g, 13.84 mmol) in DCM (20 mL) was added. The reaction mixture was stirred at room temperature for 16 h. The reaction mixture was extracted with DCM, and concentrated. The crude product was filtered 3 to 5 times with DCM. The filtrate was dried to give product 8-3 (3.9 g, crude). $^1$H NMR (400 MHz, DMSO) δ 9.38 (s, 1H), 7.81 (d, J=1.9 Hz, 1H), 7.53 (dd, J=8.7, 1.8 Hz, 2H), 7.39 (d, J=6.5 Hz, 2H), 6.73 (d, J=8.5 Hz, 1H), 5.79 (s, 2H), 3.74 (d, J=4.5 Hz, 5H).

Compound 8-4: A solution of 8-3 (3.9 g, 381.20 mmol) in AcOH (80 mL) was heated to 70° C. and stirred for 16 h. The resulting solution was extracted with ethyl acetate (100 mL) and NaHCO$_3$ (equivalent). The combined organic extracts were washed with brine, and dried over anhydrous sodium sulfate. After filtration, the solvent was concentrated under reduced pressure. The residue was reacted with MeOH: MeCN (20:1) to give product 8-4 (2 g). $^1$H NMR (400 MHz, DMSO) δ 12.69 (s, 1H), 8.25-7.94 (m, 1H), 7.78 (d, J=10.7 Hz, 1H), 7.63-7.52 (m, 2H), 7.45-7.34 (m, 2H), 4.28 (d, J=19.6 Hz, 2H), 3.84 (d, J=9.7 Hz, 3H).

Compound 8-5: LiHMDS (2.75 ml, 2.75 mmol) was added to a mixture of 8-4 (500 mg, 1.37 mmol) in THF (5 ml) at 0° C. and stirred for 1 h. Then, 2-(1-ethylcyclopropyl) acetonitrile (401 mg, 2.75 mmol) was added to the mixture, and stirred at 60° C. overnight. Afterwards, the reaction was quenched with saturated NH$_4$C$_1$. The aqueous layer was extracted with EtOAc, and dried over Na$_2$SO$_4$. The combined organic layers were concentrated. The residue was purified by SGC (EA/PE=0-50%) to give product 8-5 (100 mg).

Compound 8-6: A solution of 8-5 (100 mg, 0.22 mmol) and 2,4,4,5,5-pentamethyl-1,3,2-dioxaborolane (83 mg, 0.32 mmol) was dissolved in dioxane (4 mL). KOAc (65 mg, 0.65 mmol) was then added. Under nitrogen atmosphere, PdCl$_2$(dppf)/DCM (32 mg, 0.04 mmol) was added. The resulting mixture was stirred at 100° C. overnight. The mixture was quenched under reduced pressure, and then extracted with EA. The organic phase was washed twice with brine, dried over Na$_2$SO$_4$, evaporated in vacuo to remove the solvent, and purified by flash column chromatography (silica gel, eluted with PE/EA=50%-80%) to give product 8-6 (80 mg).

Compound 8-8: A solution of CBr$_4$ (4.0 g, 12.0 mmol) and 8-7 (2.0 g, 10.9 mmol) in DCM (20 mL) was added. The mixture was stirred at 0° C. under N$_2$ for 10 min, and then added with PPh$_3$ (3.16 g, 12.0 mmol) at 0° C. The mixture was stirred at room temperature under N$_2$ atmosphere for 5 h. H$_2$O (10 mL) was added. The reaction solution was extracted with DCM (3 mL) at room temperature with stirring. The combined organic phases were washed with brine (10 mL), dried (Na$_2$SO$_4$), filtered, and concentrated, and purified by flash chromatography (SiO$_2$, EtOAc-hexane) to give product 8-8 (941 mg).

Compound 8-9: A mixture of 8-8 (891 mg, 3.63 mmol), 6-bromopyridin-2-ol (632 mg, 3.63 mmol), and $Cs_2CO_3$ (1.3 g, 3.99 mmol) in DMF (10 ml) was stirred at room temperature overnight. The reaction was quenched with $H_2O$ (10 ml). After extraction with EA (10 ml×3), the organic layer was washed with brine, dried over anhydrous $Na_2SO_4$, and concentrated in vacuo to give a residue. The residue was purified by flash column chromatography (silica gel, 0-50%=EA/PE solution) to give product 8-9 (1.06 g). $^1$H NMR (400 MHz, DMSO) δ 7.72-7.65 (m, 1H), 7.55 (t, J=7.8 Hz, 1H), 7.31 (dd, J=11.3, 1.3 Hz, 1H), 7.26 (dd, J=7.6, 2.7 Hz, 2H), 6.92 (d, J=8.1 Hz, 1H), 5.34 (s, 2H), 4.93 (dd, J=8.3, 6.0 Hz, 2H), 4.61 (t, J=6.3 Hz, 2H), 4.36-4.23 (m, 1H).

Compounds 8-10: Solutions of 8-6 (80 mg, 0.15 mmol) and 8-9 (49 mg, 0.14 mmol) were dissolved in dioxane (4 mL) and $H_2O$ (1 mL). Then $K_2CO_3$ (40 mg, 0.28 mmol) was added. Under nitrogen atmosphere, $PdCl_2$(dppf)/DCM (11 mg, 0.014 mmol) was added. The resulting mixture was stirred at 80° C. overnight. The mixture was quenched under reduced pressure, and then extracted with EA. The organic phase was washed twice with brine, dried over $Na_2SO_4$, evaporated in vacuo to remove the solvent, and purified by flash column chromatography (silica gel, PE/EA=50%-80%) to give product 8-10 (80 mg).

Compound 8: A solution of 8-10 (80 mg, 0.12 mmol), LiOH (0.5 mL) in THF (0.5 mL) was stirred at room temperature for 2 h. The solvent was then removed under reduced pressure to give a crude product. The crude product was purified by HPLC (gradient: 10% MeCN/90% $H_2O$, 0.1% $NH_3H_2O$ to 100% MeCN) to give product compound 8 (5.01 mg) and compound 8' (12.78 mg).

Compound 8: $^1$H NMR (400 MHz, DMSO) δ 8.24 (s, 1H), 7.96-7.89 (m, 2H), 7.82 (dd, $J_1$=10 Hz, $J_2$=18 Hz, 2H), 7.64 (d, J=8.0 Hz, 1H), 7.57 (t, J=8.0 Hz, 2H), 7.47 (t, J=8.0 Hz, 1H), 7.30 (d, J=12.0 Hz, 1H), 7.25 (d, J=12.0 Hz, 1H), 6.87 (d, J=8.0 Hz, 1H), 5.52 (s, 2H), 4.91 (dd, $J_1$=4.0 Hz, $J_2$=8.0 Hz, 2H), 4.60 (t, J=6.0 Hz, 2H), 4.54 (s, 2H), 4.43 (s, 2H), 4.31-4.22 (m, 1H), 2.66 (s, 2H), 0.70 (s, 4H).

Compound 8': $^1$H NMR (400 MHz, DMSO) δ 8.10 (s, 1H), 7.96-7.89 (m, 2H), 7.84 (dd, $J_1$=8 Hz, $J_2$=16 Hz, 2H), 7.70 (d, J=8.0 Hz, 1H), 7.65 (d, J=4.0 Hz, 1H), 7.57 (t, J=8.0 Hz, 1H), 7.46 (t, J=8.0 Hz, 1H), 7.30 (d, J=12.0 Hz, 1H), 7.25 (d, J=8.0 Hz, 1H), 6.87 (d, J=8.0 Hz, 1H), 5.53 (s, 2H), 4.91 (dd, $J_1$=4.0 Hz, $J_2$=8.0 Hz, 2H), 4.60 (t, J=6.0 Hz, 2H), 4.49 (s, 2H), 4.43 (s, 2H), 4.30-4.23 (m, 1H), 2.65 (s, 2H), 0.70 (d, J=12.0 Hz, 4H).

Example 9: 2-((4-(6-((2-fluoro-4-(oxetan-3-yl)benzyl)oxy)pyridin-2-yl)piperidin-1-yl)methyl)-1-((1-fluorocyclobutyl)methyl)-1H-benzo[d]imidazole-6-carboxylic acid (compound 9)

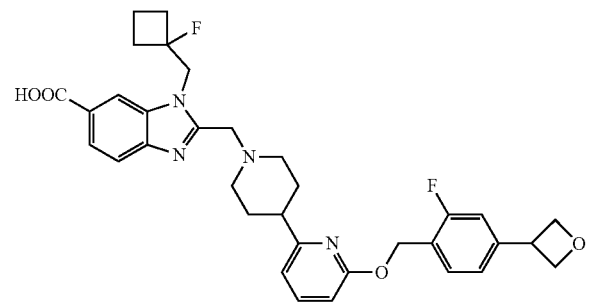 [SMILES: O=C(O)c1ccc2nc(CN3CCC(c4cccc(OCc5ccc(C6COC6)cc5F)n4)CC3)n(CC3(F)CCC3)c2c1]

Synthetic route

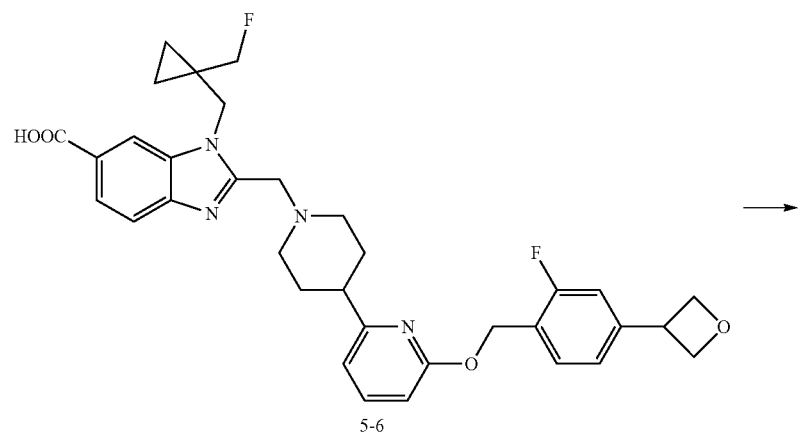

5-6

-continued

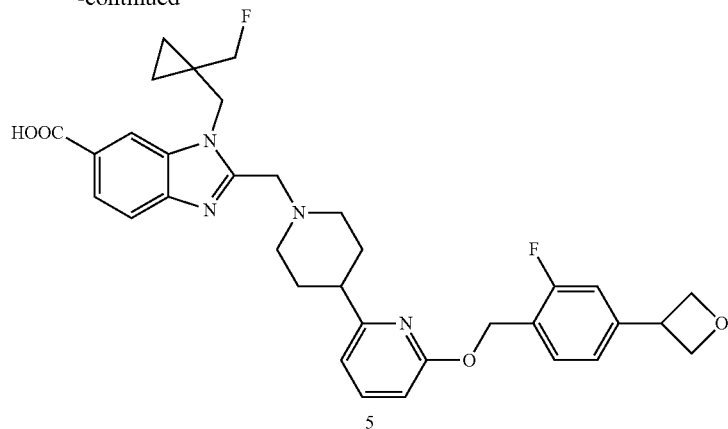

5

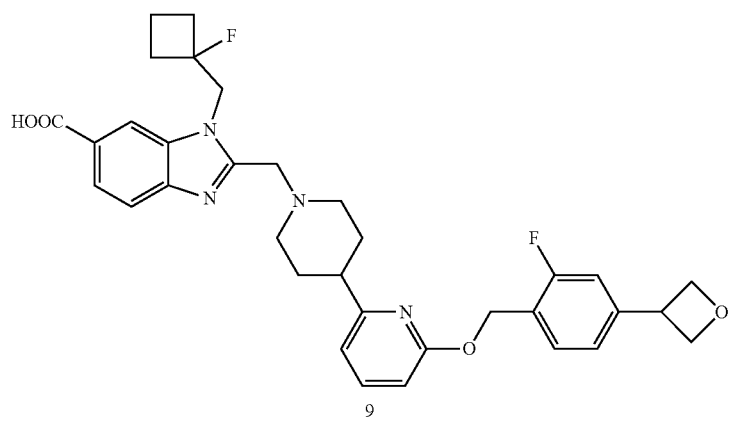

9

Preparation Method

Compound 9: A solution of 5-6 (62 mg of mixture, 0.1 mmol) and LiOH (0.5 mL) in THF (0.5 mL) was stirred at room temperature for 2 h. The solvent was then removed under reduced pressure to give a crude product. The crude product was purified by HPLC (gradient: 10% MeCN/90% H$_2$O, 0.1% FA to 100% MeCN) to give compound 5 (4.35 mg) and compound 9 (4.09 mg). $^1$H NMR (400 MHz, DMSO) δ 8.41 (s, 1H), 8.24 (s, 1H), 7.83 (d, J=8.2 Hz, 1H), 7.65-7.55 (m, 2H), 7.52 (t, J=7.8 Hz, 1H), 7.27 (d, J=11.2 Hz, 1H), 7.21 (d, J=7.7 Hz, 1H), 6.85 (d, J=7.3 Hz, 1H), 6.65 (d, J=8.2 Hz, 1H), 5.37 (s, 2H), 4.94-4.80 (m, 4H), 4.58 (t, J=6.3 Hz, 2H), 4.31-4.19 (m, 1H), 3.85 (s, 2H), 2.96 (d, J=11.0 Hz, 2H), 2.61 (s, 1H), 2.24 (dd, J=23.4, 12.2 Hz, 6H), 1.77 (dd, J=29.8, 9.5 Hz, 6H).

Example 10: 2-(2-fluoro-4-(6-((2-fluoro-4-(oxetan-3-yl)benzyl)oxy)pyridin-2-yl)benzyl)-1-((1-(fluoromethyl)cyclopropyl)methyl)-1H-benzo[d]imidazole-6-carboxylic acid (compound 10)

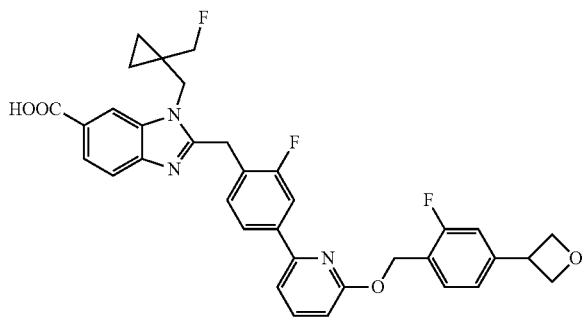 [SMILES: O=C(O)c1ccc2nc(Cc3ccc(-c4cccc(OCc5ccc(C6COC6)cc5F)n4)cc3F)n(CC3(CF)CC3)c2c1]

-continued
Synthetic route
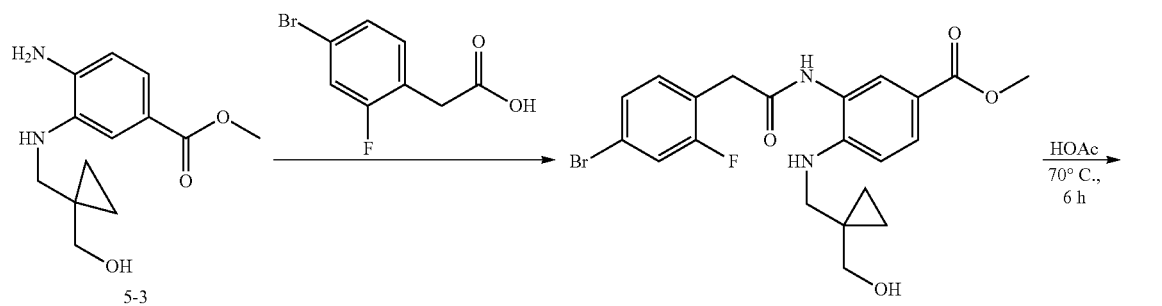
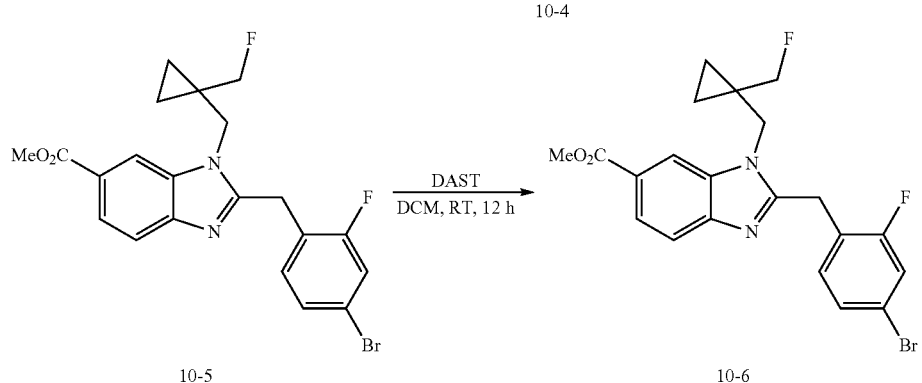
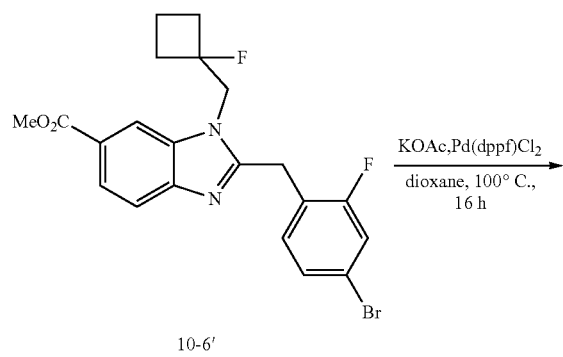
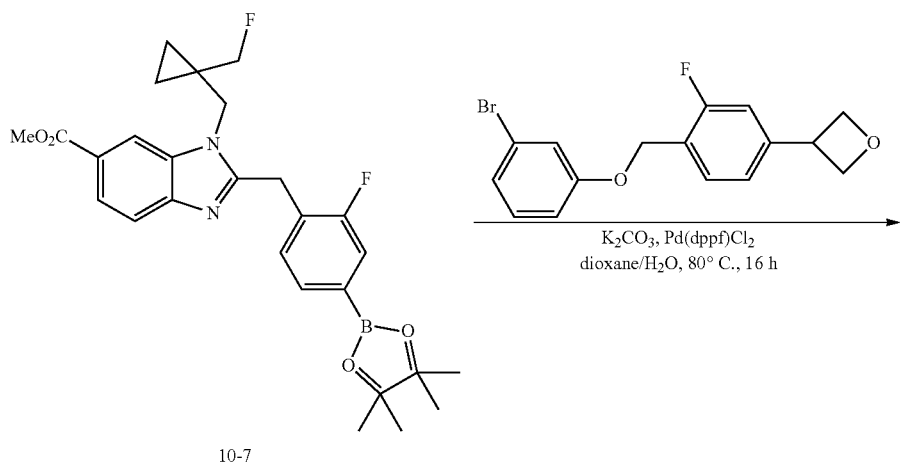

-continued

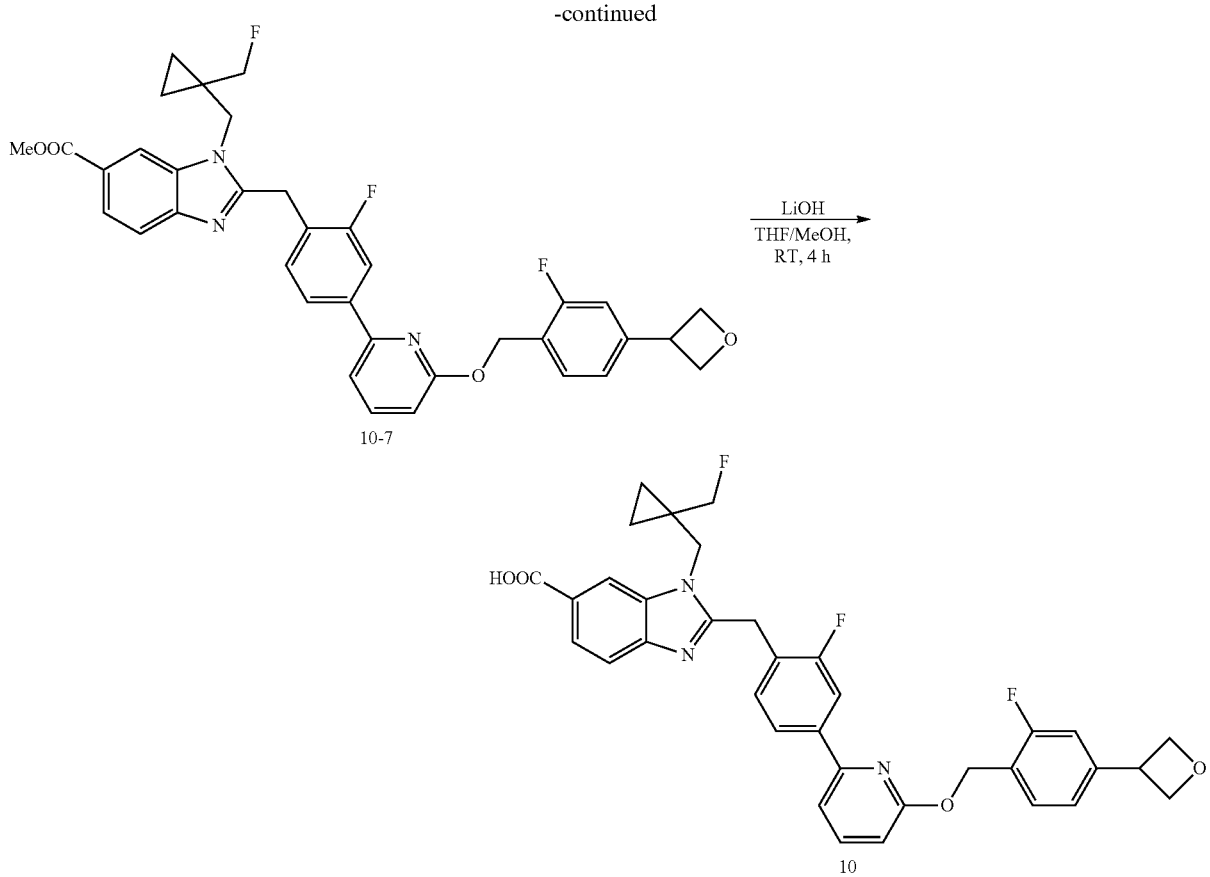

Preparation Method

Compound 10-4: To a solution of 2-(4-bromo-2-fluorophenyl)acetic acid (1.02 g, 4.39 mmol) in anhydrous DCM (10 mL) was added EDCI (919 mg, 4.79 mmol), and HOBt (593 mg, 4.39 mmol). After addition of 5-3 (1.0 g, 3.99 mmol), the reaction mixture was stirred at room temperature for 0.5 h. The reaction mixture was stirred at room temperature for 16 h. After partitioning the reaction mixture between water (10 ml) and DCM (10 ml), the organic phase was washed with brine, and dried over anhydrous sodium sulfate. After filtration, the solvent was concentrated under reduced pressure. The residue was purified by flash column chromatography (silica gel, 0-50% PE/EA) to give product 10-4 (992 mg).

Compound 10-5: A solution of 10-4 (992 mg, 2.13 mmol) in HOAc (20 ml) was stirred at 70° C. for 6 h. Then the reaction was quenched with saturated $Na_2HCO_3$. The aqueous layer was extracted with EtOAc, and dried over $Na_2SO_4$. The combined organic layers were concentrated. The residue was purified by SGC (EA/PE=0-50%) to give product 1-5 (620 mg). $^1$H NMR (400 MHz, DMSO) δ 8.27 (s, 1H), 7.78 (dd, J=8.5, 1.3 Hz, 1H), 7.62-7.52 (m, 2H), 7.40 (dd, J=8.2, 1.7 Hz, 1H), 7.30 (t, J=8.1 Hz, 1H), 4.89 (t, J=5.2 Hz, 1H), 4.43 (d, J=2.3 Hz, 4H), 3.87 (s, 3H), 3.10 (d, J=5.2 Hz, 2H), 0.66-0.46 (m, 4H).

Compound 10-6: 10-5 (670 mg, 1.49 mmol) was dissolved in 30 mL of DCM, and diethylaminosulfur trifluoride (0.2 mL, 1.49 mmol) was added. The mixture was reacted at 0° C. for 1 h, cooled in ice bath, added dropwise with 20 mL of saturated sodium bicarbonate solution, and extracted with DCM (20 mL*3). The organic phase was extracted with anhydrous sodium sulfate, and concentrated to dryness to give a crude product. The residue was purified by SGC (EA/PE=0-30%) to give product 1-06 (189 mg). $^1$H NMR (400 MHz, DMSO) δ 8.24 (s, 1H), 7.79 (dd, J=8.5, 1.4 Hz, 1H), 7.64-7.53 (m, 2H), 7.41 (dd, J=8.2, 1.8 Hz, 1H), 7.32 (t, J=8.1 Hz, 1H), 4.51 (s, 2H), 4.35 (s, 2H), 4.20 (s, 1H), 4.08 (s, 1H), 3.88 (s, 3H), 0.79 (d, J=4.8 Hz, 2H), 0.70 (s, 2H).

Compound 10-7: A solution of 10-6 (80 mg, 0.17 mmol) and 2,4,4,5,5-pentamethyl-1,3,2-dioxaborolane (68 mg, 0.26 mmol) was dissolved in dioxane (4 mL). KOAc (52 mg, 0.53 mmol) was then added. Under nitrogen atmosphere, $PdCl_2$(dppf)/DCM (26 mg, 0.03 mmol) was added. The resulting mixture was stirred at 100° C. overnight. The mixture was quenched under reduced pressure, and then extracted with EA. The organic phase was washed twice with brine, dried over $Na_2SO_4$, evaporated in vacuo to remove the solvent, and purified by flash column chromatography (silica gel, PE/EA=50%-80%) to give product 10-7 (50 mg).

Compound 10-8: Solutions of 10-7 (50 mg, 0.1 mmol) and 8-9 (31 mg, 0.09 mmol) were dissolved in dioxane (4 mL) and $H_2O$ (1 mL). Then $K_2CO_3$ (28 mg, 0.2 mmol) was added. Under nitrogen atmosphere, $PdCl_2$(dppf)/DCM (8 mg, 0.01 mmol) was added. The resulting mixture was stirred at 80° C. overnight. The mixture was quenched under reduced pressure, and then extracted with EA. The organic phase was washed twice with brine, dried over $Na_2SO_4$, evaporated in vacuo to remove the solvent, and purified by flash column chromatography (silica gel, PE/EA=50%-80%) to give product 10-8 (40 mg). $^1$H NMR (400 MHz, DMSO) δ 8.26 (s, 1H), 7.96-7.88 (m, 2H), 7.86-7.78 (m, 2H), 7.60 (dt, J=15.7, 7.4 Hz, 3H), 7.45 (t, J=8.1 Hz, 1H), 7.31 (d, J=11.3 Hz, 1H), 7.25 (d, J=7.9 Hz, 1H), 6.87 (d, J=8.2 Hz, 1H), 5.53 (s, 2H), 4.92 (dd, J=8.3, 6.0 Hz, 2H), 4.60 (t, J=6.3 Hz, 2H), 4.54 (s, 2H), 4.43 (s, 2H), 4.28 (dd, J=15.4, 7.7 Hz, 1H), 4.23 (s, 1H), 4.11 (s, 1H), 3.89 (s, 3H), 0.85-0.79 (m, 2H), 0.72 (s, 2H).

Compound 10: A solution of 10-8 (40 mg, 0.06 mmol) and LiOH (0.5 mL) in THF (0.5 mL) was stirred at room temperature for 2 h. The solvent was then removed under reduced pressure to give a crude product. The crude product was purified by HPLC (gradient: 10% MeCN/90% H₂O, 0.1% NH₃H₂O to 100% MeCN) to give product compound 10 (7.2 mg). ¹H NMR (400 MHz, DMSO) δ 8.13 (s, 1H), 7.93-7.89 (m, 2H), 7.86-7.75 (m, 2H), 7.63 (d, J=8.0 Hz, 1H), 7.57 (t, J=8.0 Hz, 1H), 7.47-7.39 (m, 2H), 7.30 (d, J=12.0 Hz, 1H), 7.25 (d, J=8.0 Hz, 1H), 6.86 (d, J=8.0 Hz, 1H), 5.52 (s, 2H), 4.91 (dd, J₁=4.0 Hz, J₂=8.0 Hz, 2H), 4.60 (t, J=6.0 Hz, 2H), 4.47 (s, 2H), 4.38 (s, 2H), 4.31-4.22 (m, 2H), 4.13 (s, 1H), 0.78-0.69 (m, 4H).

Example 11: (S)-2-(2-fluoro-4-(6-((2-fluoro-4-(oxetan-3-yl)benzyl)oxy)pyridin-2-yl)benzyl)-1-(oxetan-2-ylmethyl)-1H-benzo[d]imidazole-6-carboxylic acid (compound 11)

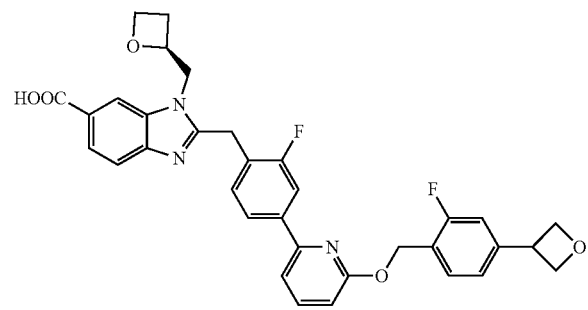 [SMILES: O=C(O)c1ccc2nc(Cc3ccc(-c4cccc(OCc5ccc(C6COC6)cc5F)n4)cc3F)n(C[C@@H]3CCO3)c2c1]

Synthetic route

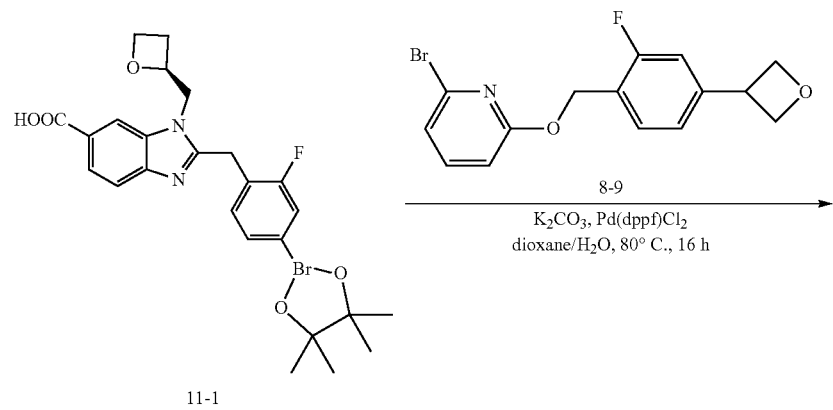

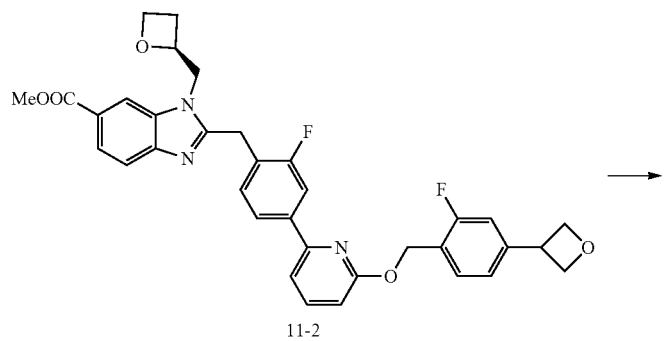

-continued

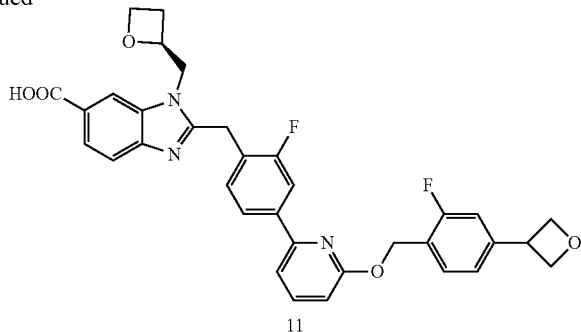

11

Preparation Method

Compound 11-2: A solution of (S)-2-(2-fluoro-4-(4,4,5,5-tetramethyl-1,3,2-dioxaborolan-2-yl)benzyl)-1-(oxetan-2-ylmethyl)-1H-benzo[d]imidazole-6-carboxylic acid (100 mg, 0.21 mmol) and 8-9 (66 mg, 0.19 mmol) was dissolved in dioxane (8 mL) and H$_2$O (2 mL). Then K$_2$CO$_3$ (54 mg, 0.39 mmol) was added. Under nitrogen atmosphere, PdCl$_2$(dppf)/DCM (14 mg, 0.019 mmol) was added. The resulting mixture was stirred at 80° C. overnight. The mixture was quenched under reduced pressure, and then extracted with EA. The organic phase was washed twice with brine, dried over Na$_2$SO$_4$, evaporated in vacuo to remove the solvent, and purified by flash column chromatography (silica gel, 80%-100% PE/EA) to give product 11-2 (31 mg).

Compound 11: A solution of 11-2 (31 mg, 0.05 mmol) and 1 N LiOH (0.5 mL) in THF (0.5 mL) was stirred at room temperature for 2 h. The solvent was then removed under reduced pressure to give a crude product. The crude product was purified by HPLC (gradient: 10% MeCN/90% H$_2$O, 0.1% NH$_3$H$_2$O to 100% MeCN) to give 9.35 mg of product, compound 11. $^1$H NMR (400 MHz, DMSO) δ 8.03 (s, 1H), 7.91 (t, J=8.0 Hz, 2H), 7.87-7.75 (m, 2H), 7.63 (d, J=8.0 Hz, 1H), 7.58 (t, J=8.0 Hz, 1H), 7.44-7.22 (m, 4H), 6.86 (d, J=8.0 Hz, 1H), 5.53 (s, 2H), 5.06 (s, 1H), 4.96-4.88 (m, 2H), 4.60 (dd, J=6.0 Hz, J$_2$=14.0 Hz, 3H), 4.48 (d, J=16.0 Hz, 3H), 4.42-4.34 (m, 2H), 4.31-4.24 (m, 1H), 2.69 (m, 1H), 2.40 (m, 1H).

Example 12 2-(((7aR,11aR)-2-((2-fluoro-4-(oxetan-3-yl)benzyl)oxy)-7a,8,11,11a-tetrahydrooxepino[4,3-b:6,5-c']dipyridin-9(5H,7H,10H)-yl)methyl)-1-((S)-oxetan-2-ylmethyl)-1H-benzo[d]imidazole-6-carboxylic acid and 2-(((7aS,11aS)-2-((2-fluoro-4-(oxetan-3-yl)benzyl)oxy)-7a,8,11,11a-tetrahydrooxepino[4,3-b:6,5-c']dipyridin-9(5H,7H,10H)-yl)methyl)-1-((S)-oxetan-2-ylmethyl)-1H-benzo[d]imidazole-6-carboxylic acid

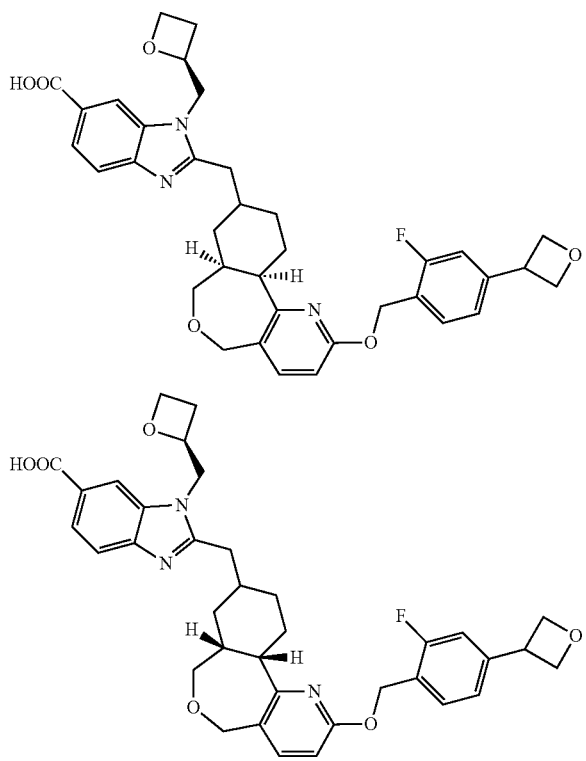

-continued
Synthetic route
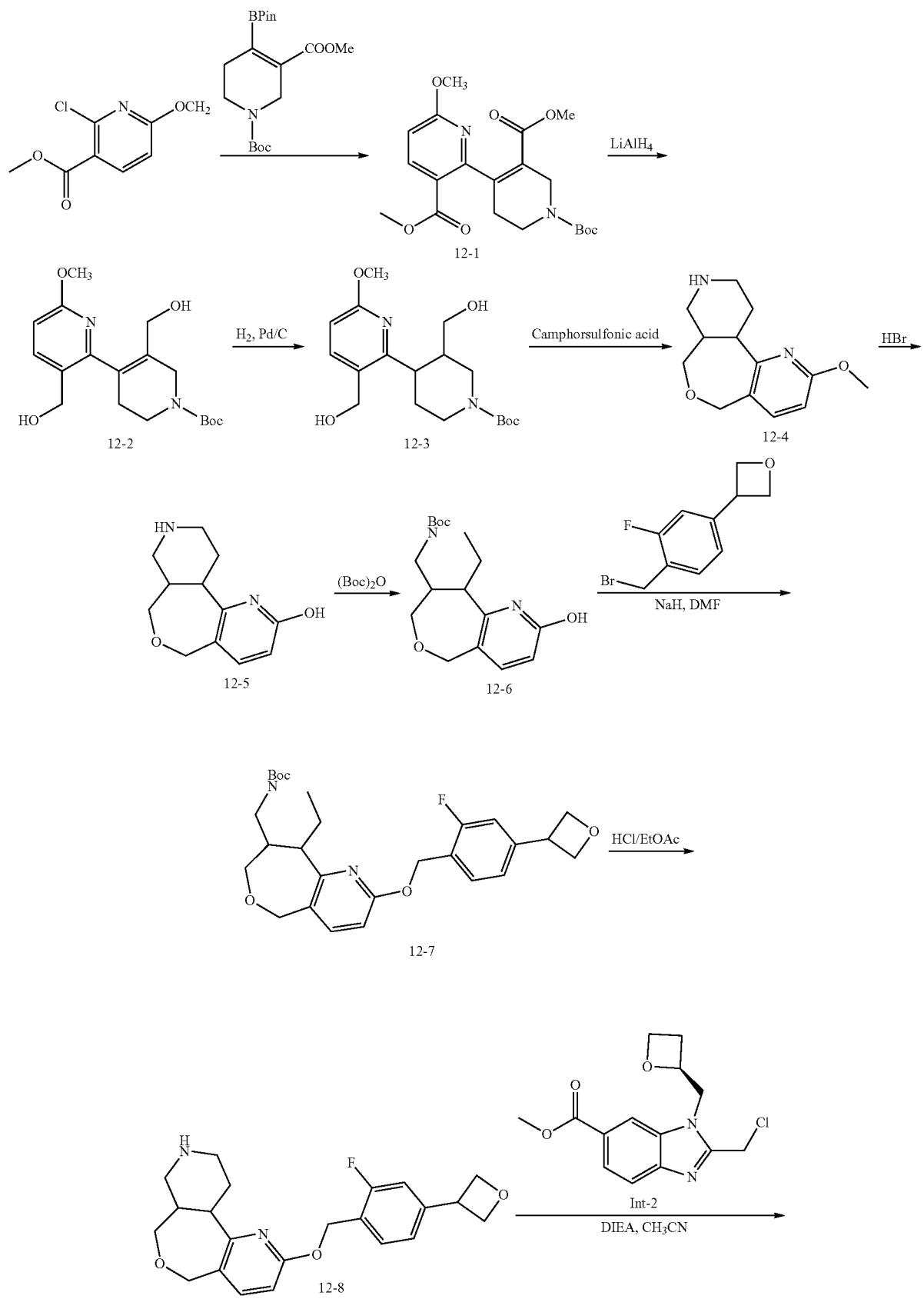

-continued
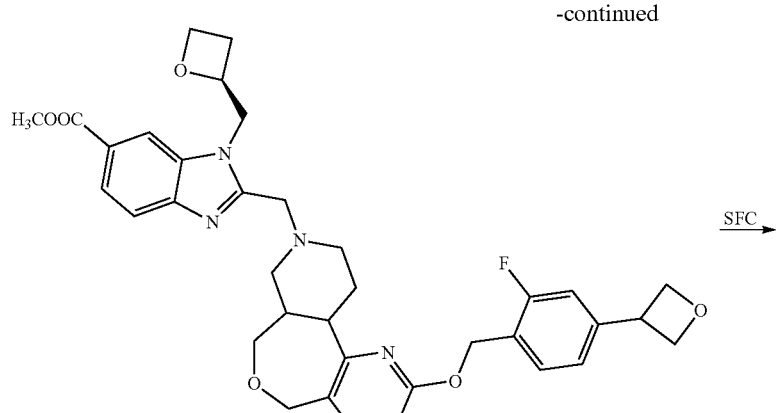
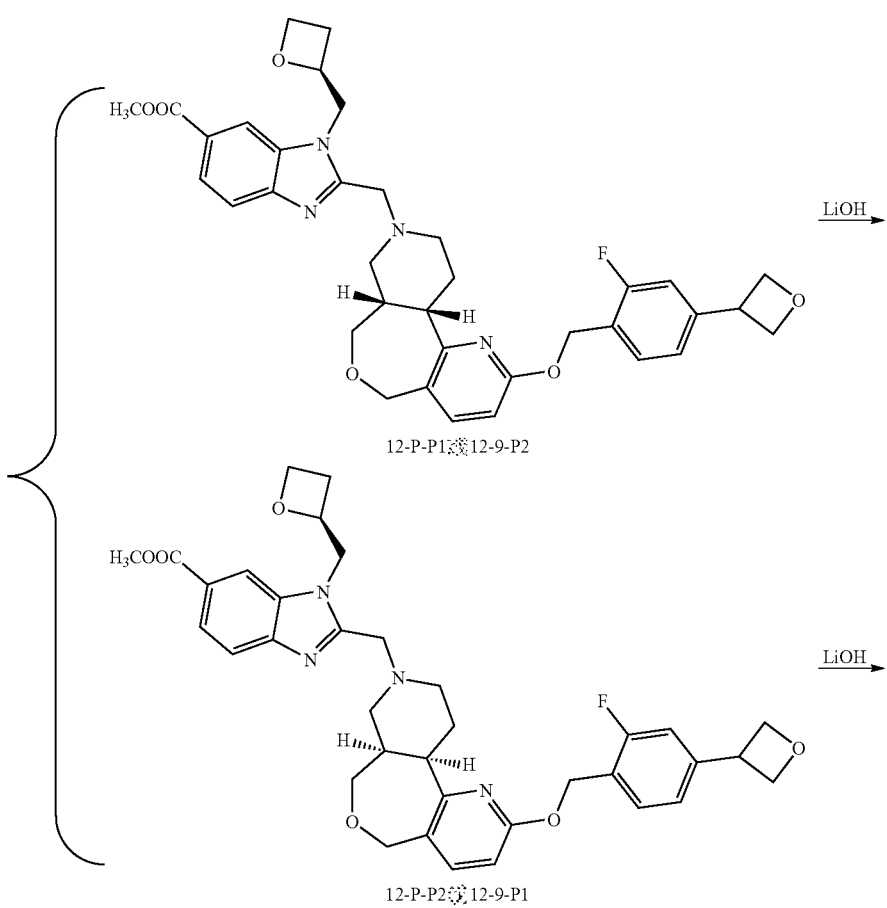

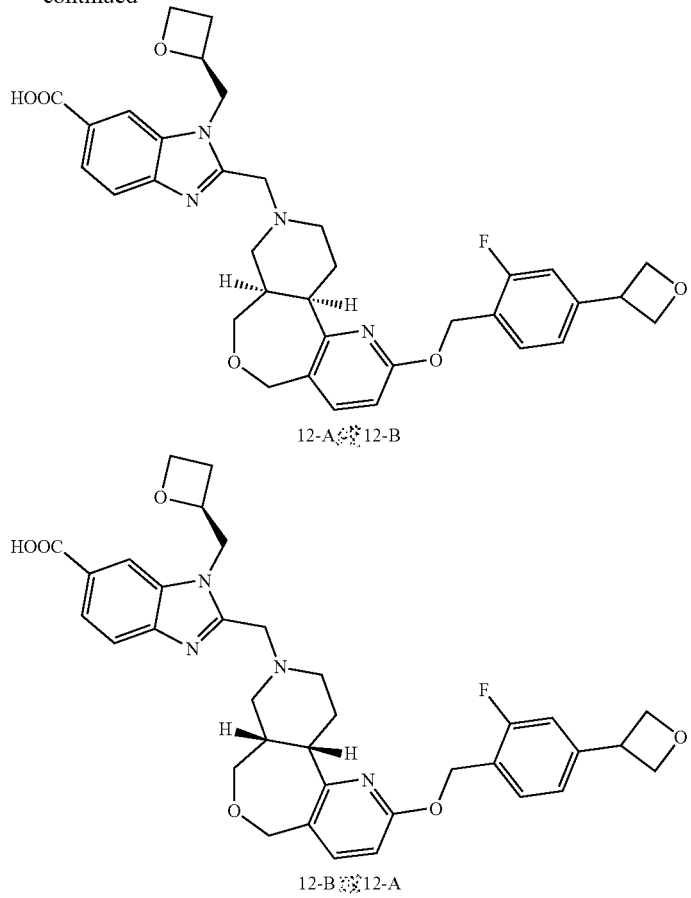 [SMILES: O=C(O)c1ccc2nc(CN3CC[C@H]4c5nc(OCc6ccc(C7COC7)cc6F)ccc5COC[C@H]4C3)n(C[C@@H]3CCO3)c2c1 ; O=C(O)c1ccc2nc(CN3CC[C@@H]4c5nc(OCc6ccc(C7COC7)cc6F)ccc5COC[C@@H]4C3)n(C[C@@H]3CCO3)c2c1]

12-A∷12-B

12-B∷12-A

Preparation Method

Compound 12-1: To a solution of methyl 2-chloro-6-methoxynicotinate (2 g, 10 mmol, 1.0 eq) in dioxane (50 mL) were added 1-(tert-butyl) 3-methyl-4-(4,4,5,5-tetramethyl-1,3,2-dioxaborolan-2-yl)-5,6-dihydropyridine-1,3 (2H)-dicarboxylate (3.67 g, 10 mmol, 1.0 eq), K$_2$CO$_3$ (2.76 g, 20 mmol, 2.0 eq) and Pd (dppf) Cl$_2$ (731 mg, 1 mmol, 0.1 eq). The mixture was stirred at 90° C. under N$_2$ atmosphere for 16 h. The reaction was detected by LCMS. The mixture was concentrated directly to give a residue. The residue was purified by silica gel column chromatography eluted with (EA/PE=0-30%) to give 1'-(t-butyl) 3,3'-dimethyl-6-methoxy-5',6'-dihydro-[2,4'-bipyridine]-1',3,3'(2'H)-tricarboxylate 12-1 (1.1 g, 27.1% yield). LCMS: r.t.=2.025 min, [M+H]$^+$=407, purity: 92%.

Compound 12-2: To a solution of 12-1 (0.83 g, 2 mmol, 1.0 eq) in THF (50 mL) at 0° C. was added LiAlH$_4$ (152 mg, 4 mmol, 2.0 eq), and then the mixture was stirred at 20° C. for 10 min. The reaction was detected by LCMS. H$_2$O (0.2 mL), 15% NaOH solution (0.2 mL), and EtOAc (50 mL) were slowly added to the mixture. The organic layer was washed with brine, dried over Na$_2$SO$_4$, and concentrated to give product 12-2 (630 mg, 90% yield). LCMS: r.t.=1.57 min, [M+H]$^+$=351.0, purity: 90%.

Compound 12-3: A solution of 12-2 (300 mg, 0.286 mmol, 1.0 eq) and Pd/C (100 mg) in THF (15 mL) was stirred at 20° C. under H$_2$ (15 psi) for 14 h. The reaction was detected by LCMS. The resulting mixture was filtered. The filter cake was washed with THF (3×20 mL). The filtrate was concentrated directly to give a residue which was purified by column chromatography on silica gel, eluted with (PE/EA=0-50%) to give product 12-3 (118 mg, 40% yield). LCMS: r.t.=1.60 min, [M+H]$^+$=353.2, purity: 95.9%.

Compound 12-4: To a solution of 12-3 (1.2 g, 3.4 mmol, 1.0 eq) in toluene (80 mL) was added camphorsulfonic acid (3.95 g, 17 mmol, 5.0 eq). The mixture was stirred at 110° C. for 2 h. The reaction was detected by LCMS. The reaction mixture was concentrated directly to give a residue which was purified by silica gel column chromatography, eluted with (MeOH/DCM=0-10%) to give product 12-4 (700 mg, 87.9% yield). LCMS: r.t.=1.528 min, [M+H]$^+$=235.2, purity: 86.9%.

Compound 12-5: A solution of 12-4 (0.35 g, 1.5 mmol, 1.0 eq) in HBr (10 mL) was stirred at 120° C. for 6 h. The reaction was detected by LCMS. The reaction mixture was adjusted to PH=7 with NaOH (1 N), and extracted with DCM (20 mL×3). The combined organic layers were dried over Na$_2$SO$_4$, filtered, and concentrated to give product 12-5 (200 mg, 60.6% yield). LCMS: r.t.=0.385 min, [M+H]$^+$=221.1, purity: 87.18%.

Compound 12-6: To a solution of 12-5 (200 mg, 0.91 mmol, 1.0 eq) in DCM (10 mL) were added TEA (184.2 mg, 1.82 mmol, 2.0 eq) and Boc$_2$O (238 mg, 1.1 mmol, 1.2 eq). The mixture was stirred at 25° C. for 2 h. The reaction was detected by LCMS. The reaction mixture was concentrated directly to give a residue which was purified by silica gel column chromatography, eluted with (MeOH/DCM=0-10%) to give product 12-6 (190 mg, 65.5% yield). LCMS: r.t.=1.35 min, [M+H]$^+$=343, purity: 93.8%.

Compound 12-7: To 12-6 (190 mg, 594 mmol) in 10 mL DMF were added 3-(4-(bromomethyl)-3-fluorophenyl)oxetane (150 mg, 0.594 mmol) and NaH (35.6 mg, 0.89 mmol) over 0.5 h with stirring at 25° C. under $N_2$. The reaction was detected by LCMS. The reaction mixture was poured into water (30 mL), extracted with DCM (20 mL×3), washed with brine and dried, and concentrated to give a crude product, which was further purified by elution (PE/EtOAc=0-47%) to give 12-7 (260 mg, 70% yield). LCMS: r.t.=2.32 min, [M+H]$^+$=485, purity: 99.7%.

Compound 12-8: A solution of 12-7 (260 mg, 0.57 mmol) in 6 mL HCl/EA was stirred at room temperature for 30 min. The reaction was detected by LCMS. The reaction mixture was concentrated to give ae crude product 12-8 (200 mg). The crude product was used directly in the next step without purification. LCMS: r.t.=0.92 min, [M+H]$^+$=385, purity: 98%.

Compound 12-9: To 12-8 (200 mg, 0.57 mmol) was added DIEA (736.7 mg, 0.57 mmol). Then, Int-2 (166.6 mg, 5.7 mmol) was added to the reaction mixture at 60° C. over 16 h. The reaction was detected by LCMS. The reaction mixture was concentrated to a crude product, which was further purified by elution (PE/EtOAc=0-5%) to give 12-9 (180 mg, yield: 50.3%). LCMS: r.t.=1.053 min, [M+H]$^+$=643, purity: 98.5%.

Compound 12-9-P1 and compound 12-9-P2: A sample of 12-9 (180 mg, 0.27 mmol) was further purified by the "SFC method" to give 12-9-P1 (60 mg, SFC r.t=2.176 mins, yield: 67%) and 12-9-P2 (60 mg, SFC r.t=2.68 mins, yield: 67%).

Compound 12-A: To a solution of 12-9-P1 (60 mg, 0.09 mmol) in THF/$H_2O$ (5 mL) was added LiOH (22 mg, 0.92 mmol) with stirring at room temperature for 16 h. The reaction was detected by LCMS. The reaction mixture was concentrated to a crude product, which was further purified by preparative HPLC to give compound 12-A (32.15 mg, yield: 71.2%). LCMS: r.t.=1.197 min, [M+H]$^+$=629, purity: 100%. $^1$H NMR (400 MHz, MeOD) δ 8.16 (s, 1H), 7.94 (dd, J=8.4, 1.4 Hz, 1H), 7.57 (d, J=8.4 Hz, 1H), 7.50 (t, J=7.8 Hz, 1H), 7.39 (d, J=8.3 Hz, 1H), 7.23-7.16 (m, 2H), 6.58 (d, J=8.2 Hz, 1H), 5.45-5.36 (m, 2H), 5.27 (qd, J=7.1, 3.0 Hz, 1H), 5.06 (dd, J=8.3, 6.1 Hz, 2H), 4.77-4.59 (m, 8H), 4.44-4.22 (m, 3H), 3.99-3.82 (m, 3H), 3.25 (d, J=9.4 Hz, 1H), 2.96 (s, 1H), 2.83-2.74 (m, 1H), 2.65-2.29 (m, 6H).

Compound 12-B: To a solution of 12-9-P2 (60 mg, 0.09 mmol) in THF/$H_2O$ (5 mL) was added LiOH (22 mg, 0.9 mmol), and the mixture was stirred at room temperature for 16 h. The reaction was detected by LCMS. The reaction mixture was concentrated to a crude product, which was further purified by preparative HPLC to give 12-B (38.5 mg, yield: 72.3%). LCMS: r.t.=1.213 min, [M+H]$^+$=629, purity: 100%. $^1$H NMR (400 MHz, MeOD) δ 8.17 (s, 1H), 7.93 (dd, J=8.4, 1.3 Hz, 1H), 7.56 (d, J=8.4 Hz, 1H), 7.50 (t, J=7.9 Hz, 1H), 7.39 (d, J=8.3 Hz, 1H), 7.23-7.16 (m, 2H), 6.59 (d, J=8.2 Hz, 1H), 5.41 (q, J=12.6 Hz, 2H), 5.25 (dt, J=7.2, 4.8 Hz, 1H), 5.06 (dd, J=8.2, 6.2 Hz, 2H), 4.73-4.62 (m, 9H), 4.49 (dt, J=9.1, 6.0 Hz, 1H), 4.32-4.22 (m, 1H), 4.10-3.90 (m, 2H), 3.76 (d, J=13.4 Hz, 1H), 3.25 (s, 1H), 2.94-2.77 (m, 2H), 2.71-2.27 (m, 6H).

Example 13: (S)-1-(oxetan-2-ylmethyl)-2-((4-(6-((1-(oxetan-3-yl)piperidin-4-yl)methoxy)pyridin-2-yl)piperidin-1-yl)methyl)-1H-benzo[d]imidazole-6-carboxylic acid (compound 13)

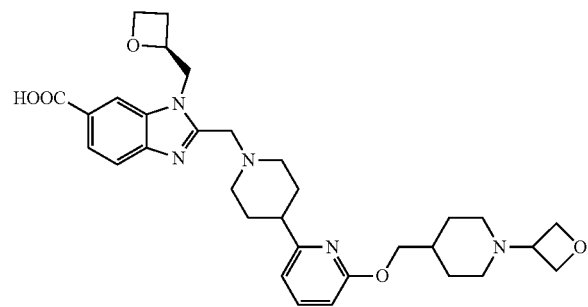 [SMILES: O=C(O)c1ccc2nc(CN3CCC(c4cccc(OCC5CCN(C6COC6)CC5)n4)CC3)n(C[C@@H]3CCO3)c2c1]

Synthetic route

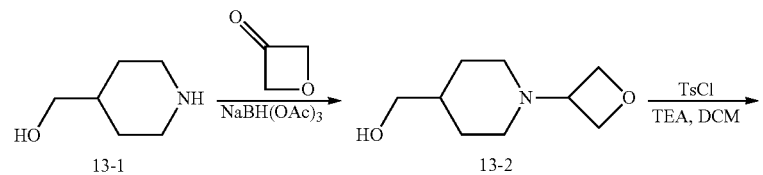

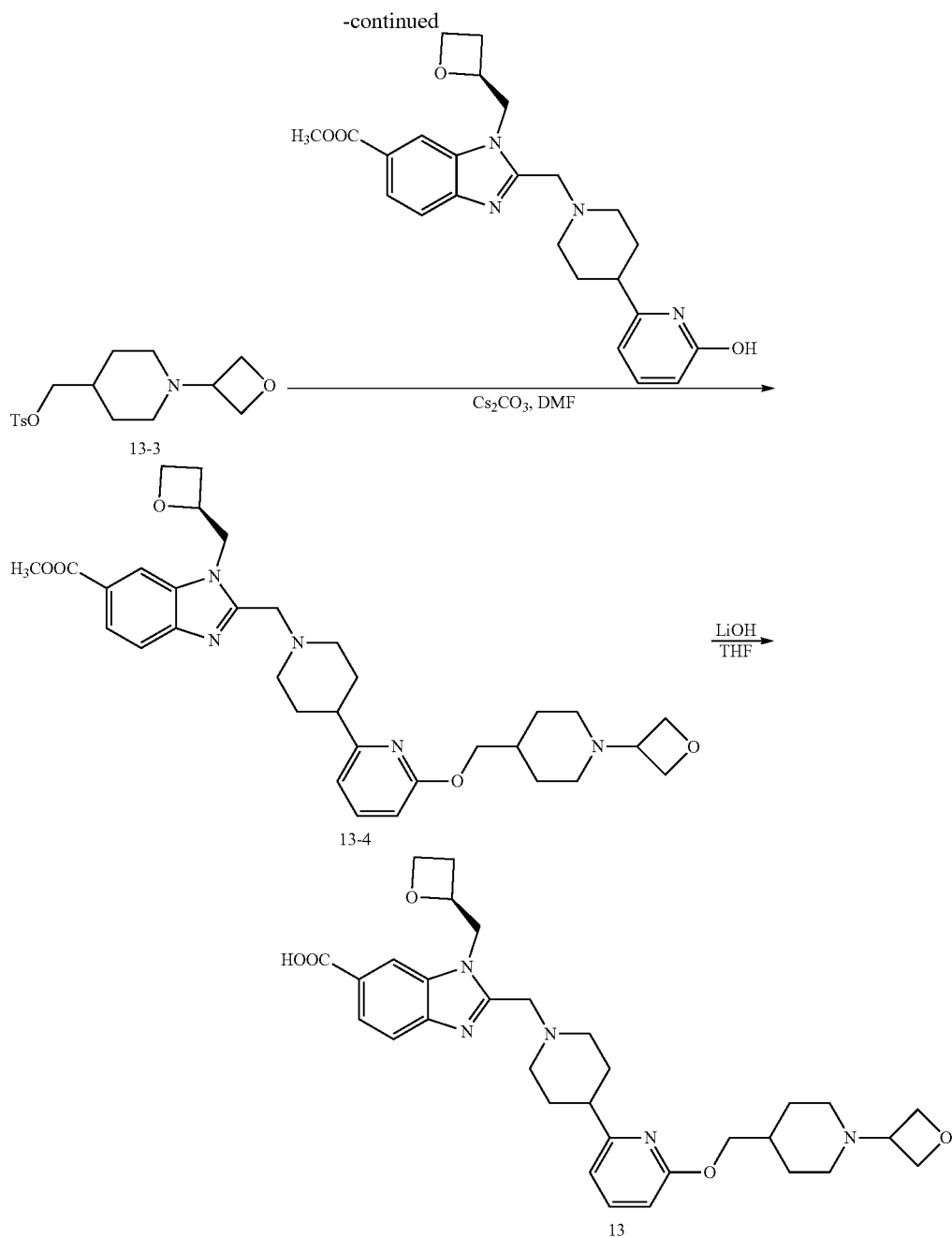

Preparation Method

Compound 13-2: To a mixture of 13-1 (1.0 g, 8.7 mmol) in DCE (10 mL) were added NaBH (OAc)$_3$ (1.84 g, 8.7 mmol) and oxetane-3-one (0.63 g, 8.7 mmol). The mixture was stirred at 30° C. for 16 h. The reaction was detected by LCMS. The reaction mixture was quenched with ice water. The mixture was extracted with EA. The combined organic layers (50 mL) were washed with brine, dried over Na$_2$SO$_4$, and concentrated under reduced pressure to give 13-2 (1.48 g, 99.0%). LCMS: r.t.=2.1 min, [M+H]$^+$=172, purity: 92%.

Compound 13-3: A mixture of 13-2 (1 g, 5.84 mmol), TsCl (1.11 g, 5.84 mmol) and TEA (1.18 g, 11.68 mmol) in DMF (50 ml) was stirred at 20° C. for 2 h. The reaction was detected by LC-MS. The reaction mixture was quenched by the addition of water. The aqueous phase was extracted with EtOAc (100 ml×3), and washed with brine (50 ml×2). The combined organic layers were dried over Na$_2$SO$_4$, concentrated, and purified by elution (PE/EA=0-20%) to give 13-3 (1.1 g, 62%). LCMS: r.t.=3.5 min, [M+H]$^+$=326, purity: 94%.

Compound 13-4: A reaction mixture of 13-3 (1 g, 3.1 mmol), methyl (S)-2-((4-(6-hydroxypyridin-2-yl) piperidin-1-yl)methyl)-1-(oxetan-2-ylmethyl)-1H-benzo[d]imidazole-6-carboxylate (1.34 g, 3.07 mmol) and Cs$_2$CO$_3$ (2 g, 6.15 mmol) in DMF (20 ml) was added. The mixture was stirred with Ar$_2$ at 20° C. for 16 h. The reaction was detected by LC-MS. The mixture was concentrated, and purified by elution (PE/EA=0-20%) to give 13-4 (0.9 g, 33.2%). LCMS: r.t.=1.37 min, [M+H]$^+$=590.7, purity: 96%.

Compound 13: Compound 13-4 (0.25 g, 0.41 mmol) was dissolved in THF (4 mL) followed by addition of aqueous lithium hydroxide (4 mL). The mixture was stirred at room temperature for 8 h. The reaction was detected by LC-MS. The mixture was concentrated, and purified by preparative HPLC (NH$_3$·H$_2$O) to give compound 13 (0.13 g, 53%). LCMS: r.t.=1.225 min, [M+H]$^+$=576.3, purity: 96%. $^1$H NMR (400 MHz, MeOD) δ8.19 (s, 1H), 7.94 (dd, J=8.4, 1.3 Hz, 1H), 7.61-7.48 (m, 2H), 6.78 (d, J=7.3 Hz, 1H), 6.54 (d, J=8.2 Hz, 1H), 5.28 (dt, J=7.0, 4.3 Hz, 1H), 4.90 (d, J=7.1 Hz, 1H), 4.66 (ddt, J=16.2, 12.6, 4.6 Hz, 6H), 4.48 (dt, J=9.1, 6.0 Hz, 1H), 4.16 (d, J=5.9 Hz, 2H), 4.01 (d, J=13.6 Hz, 1H), 3.90 (d, J=13.6 Hz, 1H), 3.49 (dd, J=13.0, 6.5 Hz, 1H), 3.05 (d, J=11.2 Hz, 1H), 2.96 (d, J=11.4 Hz, 1H), 2.80 (dd, J=14.7, 6.6 Hz, 3H), 2.68-2.49 (m, 2H), 2.29 (ddd, J=21.6, 14.9, 9.8 Hz, 2H), 1.93-1.79 (m, 9H), 1.48-1.36 (m, 2H).

Example 14: (S)-2-((4-(6-((2-fluoro-4-(3-hydroxyoxetan-3-yl)benzyl)oxy)pyridin-2-yl)piperidin-1-yl)methyl)-1-(oxetan-2-ylmethyl)-1H-benzo[d]imidazole-6-carboxylic acid (Compound 14)

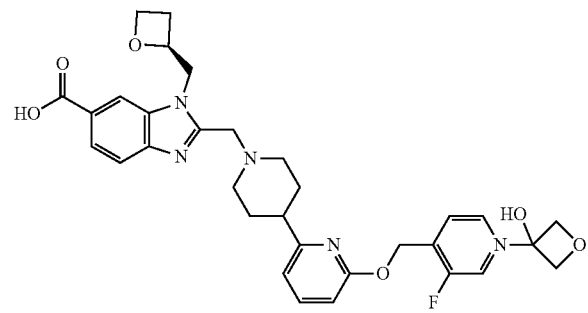

Synthetic route

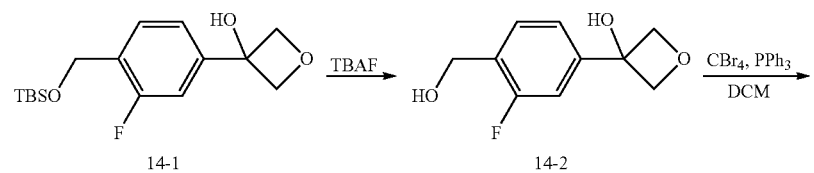

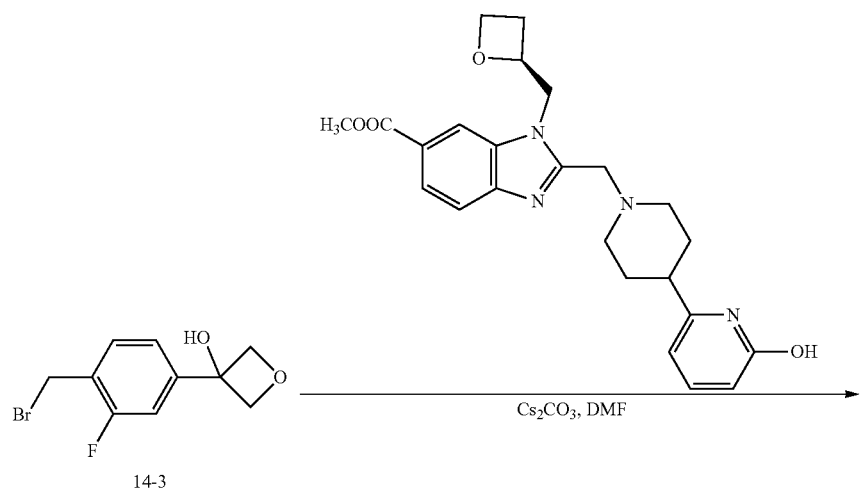

-continued

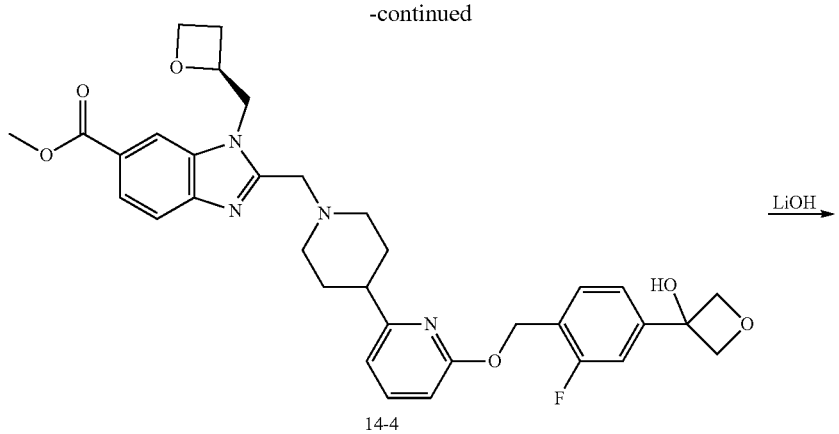

14-4

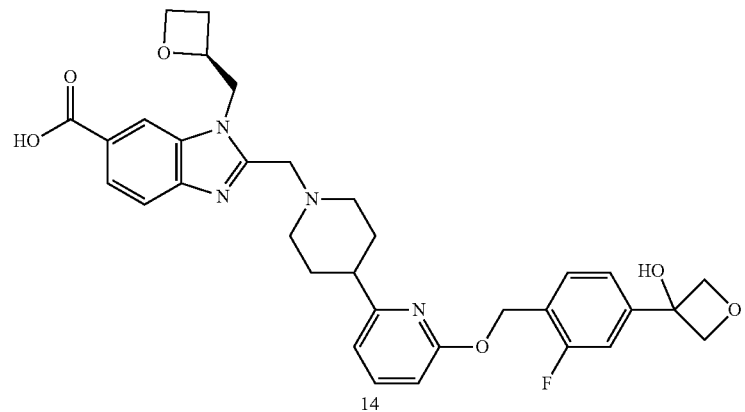

14

Preparation Method

Compound 14-2: To a solution of 3-(4-(((tert-butyldimethylsilyl)oxy)methyl)-3-fluorophenyl)oxetane-3-ol (2 g, 6.4 m mol, 1.0 eq) in THF (20 mL) was added TBAF (6.4 mL, 6.4 m mol, 1.0 eq). The mixture was stirred at room temperature for 30 min. The reaction was detected by TLC. The residue was washed with 20 mL of brine, dried over Na$_2$SO$_4$, and concentrated under pressure. The residue was eluted with PE/EtOAc (2:1) to give product 14-2 (1.2 g, 60% yield). $^1$H NMR (400 MHz, CDCl$_3$) δ 11.12-10.98 (m, 1H), 7.48 (t, J=7.7 Hz, 1H), 7.43 (d, J=1.3 Hz, 1H), 7.33 (d, J=11.3 Hz, 1H), 4.90 (d, J=7.0 Hz, 2H), 4.85 (d, J=7.0 Hz, 2H), 4.78 (s, 2H).

Compound 14-3: To a solution of 14-2 (1 g, 5.1 mmol, 1.0 eq) in DCM (10 mL) was added PPh$_3$ (1.338 g, 5.1 mol, 1.0 eq), cooled at −30° C., and then CBr$_4$ (1.691 g, 5.1 mmol, 1.0 Eq) was added. The mixture was reacted for 4 h. The reaction was detected by TLC, and NMR showed that the starting material reacted to form the product. The mixture was extracted with water and DCM, dried over Na$_2$SO$_4$, and subjected to silica gel column chromatography (EA/PE=0-10%) to give product 14-3 (0.5 g, 50% yield). $^1$H NMR (400 MHz, CDCl$_3$) δ 7.44 (p, J=8.0 Hz, 2H), 7.37 (d, J=11.3 Hz, 1H), 4.91 (d, J=7.3 Hz, 2H), 4.85 (d, J=7.4 Hz, 2H), 4.53 (s, 2H).

Compound 14-4: To a solution of 14-3 (250 mg, 0.905 mmol, 1.0 eq) in DMF (10 mL) were added methyl (S)-2-((4-(6-hydroxypyridin-2-yl)piperidin-1-yl)methyl)-1-(oxetan-2-ylmethyl)-1H-benzo[d]imidazole-6-carboxylate (434 mg, 0.9955 mmol, 1.1 eq) and Cs$_2$CO$_3$ (590 mg, 2 mmol, 2 eq), and the reaction was subjected to nitrogen replacement at room temperature for 16 h. The reaction was detected by TLC, and NMR showed that the starting material reacted to form the product. Purification by silica gel column chromatography (EA/PE=0-20%) gives product 14-4 (0.2 g, 33% yield). $^1$H NMR (400 MHz, CDCl$_3$) δ 8.17 (s, 1H), 7.97 (dd, J=8.5, 1.4 Hz, 1H), 7.77 (d, J=8.5 Hz, 1H), 7.49 (dd, J=15.6, 7.9 Hz, 2H), 7.44-7.36 (m, 2H), 6.73 (d, J=7.3 Hz, 1H), 6.64 (d, J=8.1 Hz, 1H), 5.48 (s, 2H), 4.93 (dd, J=6.9, 2.1 Hz, 2H), 4.82 (d, J=7.1 Hz, 2H), 4.66 (ddd, J=21.7, 14.6, 5.5 Hz, 2H), 4.42 (dt, J=9.2, 6.0 Hz, 1H), 4.12 (q, J=7.2 Hz, 2H), 3.95 (s, 3H), 3.82 (s, 2H), 2.96 (s, 1H), 2.88 (s, 1H), 2.52-2.40 (m, 1H), 2.29 (s, 2H), 2.04 (s, 2H), 1.26 (t, J=7.1 Hz, 4H).

Compound 14: A solution of 14-4 (0.1 g, 0.016 mmol, 1 eq) in LiOH (5 mL) was reacted at room temperature for 3 h. The reaction was detected by TLC. The reaction product was concentrated to a crude product which was purified by pre-HPLC to give the product compound 14 (50 mg, 40% yield). $^1$H NMR (400 MHz, MeOD) δ 8.20 (s, 1H), 7.94 (d, J=8.4 Hz, 1H), 7.61-7.50 (m, 3H), 7.45 (d, J=8.0 Hz, 1H), 7.37 (d, J=11.6 Hz, 1H), 6.81 (d, J=7.4 Hz, 1H), 6.62 (d, J=8.2 Hz, 1H), 5.45 (s, 2H), 5.29 (d, J=4.7 Hz, 1H), 4.91 (dd, J=15.3, 7.0 Hz, 1H), 4.85 (s, 2H), 4.78-4.69 (m, 3H), 4.62 (dd, J=13.8, 7.7 Hz, 1H), 4.48 (dt, J=9.0, 6.0 Hz, 1H), 3.95 (dd, J=44.4, 13.6 Hz, 2H), 3.04 (d, J=10.8 Hz, 1H), 2.94 (d, J=11.0 Hz, 1H), 2.87-2.74 (m, 1H), 2.69-2.48 (m, 2H), 2.28 (ddd, J=21.3, 12.5, 9.2 Hz, 2H), 2.01-1.73 (m, 4H).

Example 15: (S)-2-((4-(6-((2-fluoro-4-(3-fluoroxetan-3-yl)benzyl)oxy)pyridin-2-yl)piperidin-1-yl)methyl)-1-(oxetan-2-ylmethyl)-1H-benzo[d]imidazole-6-carboxylic acid (compound 15)
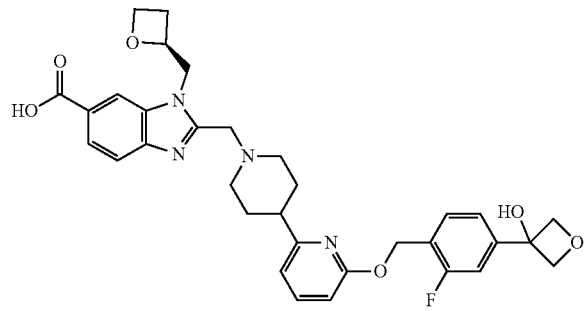 [SMILES: O=C(O)c1ccc2nc(CN3CCC(c4cccc(OCc5ccc(C6(O)COC6)cc5F)n4)CC3)n(C[C@@H]3CCO3)c2c1]
Synthetic route
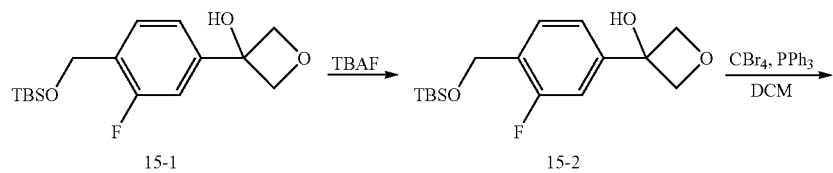
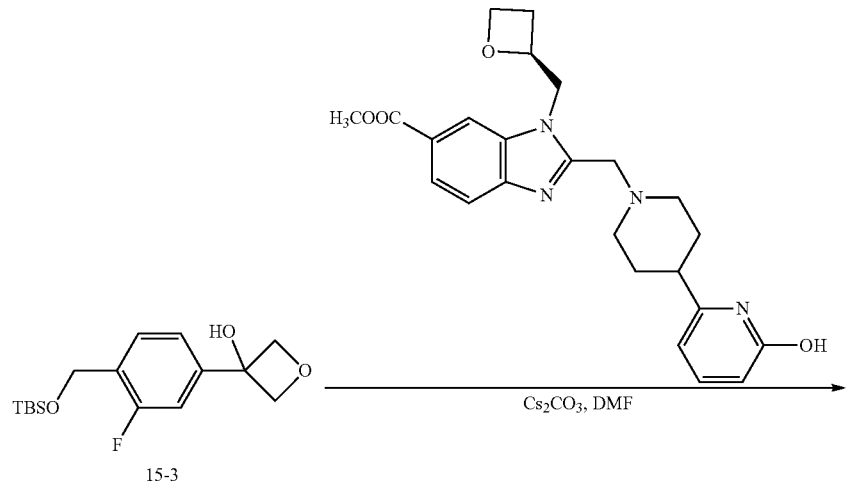
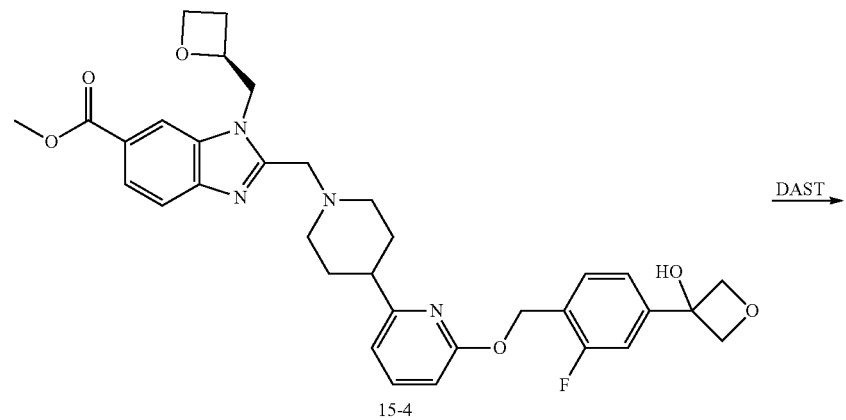

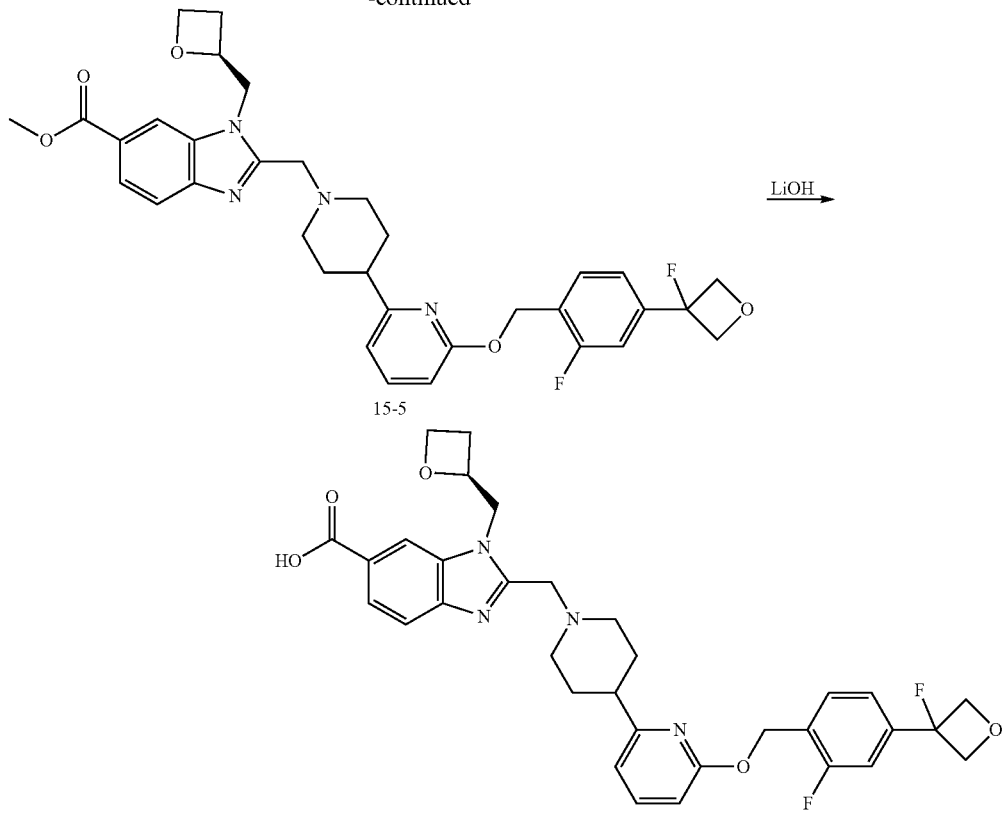

Compound 15-2: To a solution of 3-(4-(((tert-butyldimethylsilyl)oxy)methyl)-3-fluorophenyl) oxetane-3-ol (2 g, 6.4 m mol, 1.0 eq) in THF (20 mL) was added TBAF (6.4 mL, 6.4 m mol, 1.0 eq). The mixture was stirred at room temperature for 30 min. The reaction was detected by TLC. The residue was washed with 20 mL of brine, dried over Na$_2$SO$_4$, and concentrated under pressure. The residue was eluted with PE/EtOAc (2:1) to give 15-2 (1.2 g, 60% yield). $^1$H NMR (400 MHz, CDCl$_3$) δ 11.12-10.98 (m, 1H), 7.48 (t, J=7.7 Hz, 1H), 7.43 (d, J=1.3 Hz, 1H), 7.33 (d, J=11.3 Hz, 1H), 4.90 (d, J=7.0 Hz, 2H), 4.85 (d, J=7.0 Hz, 2H), 4.78 (s, 2H).

Compound 15-3: To a solution of 15-2 (1 g, 5.1 mmol, 1.0 eq) in DCM (10 mL) was added PPh$_3$ (1.338 g, 5.1 m mol, 1.0 eq), cooled at −30° C., and then CBr$_4$ (1.691 g, 5.1 mmol, 1.0 eq) was added. The mixture was reacted for 4 h. The reaction was detected by TLC, and NMR showed that the starting material reacted to form the product. The mixture was extracted with water and DCM, dried over Na$_2$SO$_4$, and subjected to silica gel column chromatography (EA/PE=0-10%) to give product 15-3 (0.5 g, 50% yield). $^1$H NMR (400 MHz, CDCl$_3$) δ 7.44 (p, J=8.0 Hz, 2H), 7.37 (d, J=11.3 Hz, 1H), 4.91 (d, J=7.3 Hz, 2H), 4.85 (d, J=7.4 Hz, 2H), 4.53 (s, 2H).

Compound 15-4: To a solution of 15-3 (250 mg, 0.905 mmol, 1.0 eq) in DMF (10 mL) were added methyl (S)-2-((4-(6-hydroxypyridin-2-yl)piperidin-1-yl)methyl)-1-(oxetan-2-ylmethyl)-1H-benzo[d]imidazole-6-carboxylate (434 mg, 0.9955 mmol, 1.1 eq) and Cs$_2$CO$_3$ (590 mg, 2 mmol, 2 eq), and the reaction was subjected to nitrogen replacement at room temperature for 16 h. The reaction was detected by TLC, and NMR showed that the starting material reacted to form the product. Purification by silica gel column chromatography (EA/PE=0-20%) gives the product 15-4 (0.2 g, 33% yield). $^1$H NMR (400 MHz, CDCl$_3$) δ 8.17 (s, 1H), 7.97 (dd, J=8.5, 1.4 Hz, 1H), 7.77 (d, J=8.5 Hz, 1H), 7.49 (dd, J=15.6, 7.9 Hz, 2H), 7.44-7.36 (m, 2H), 6.73 (d, J=7.3 Hz, 1H), 6.64 (d, J=8.1 Hz, 1H), 5.48 (s, 2H), 4.93 (dd, J=6.9, 2.1 Hz, 2H), 4.82 (d, J=7.1 Hz, 2H), 4.66 (ddd, J=21.7, 14.6, 5.5 Hz, 2H), 4.42 (dt, J=9.2, 6.0 Hz, 1H), 4.12 (q, J=7.2 Hz, 2H), 3.95 (s, 3H), 3.82 (s, 2H), 2.96 (s, 1H), 2.88 (s, 1H), 2.52-2.40 (m, 1H), 2.29 (s, 2H), 2.04 (s, 2H), 1.26 (t, J=7.1 Hz, 4H).

Compound 15-5: DAST (0.52 mg, 0.324 mmol, 2 eq) was slowly added to a solution of 15-4 (100 mg, 0.162 mmol, 1.0 eq) in DCM (3 ml) by nitrogen replacement and cooled to 0° C. After the addition, the reaction was carried out at room temperature for 2 h. The reaction was detected by TLC and LCMS to give product 15-5. LCMS: r.t.=1.324 min, [M+H]$^+$=619.2, purity: 57%.

Compound 15: A solution of 15-5 (0.1 g, 0.016 mmol, 1 eq) in LiOH (5 mL) was reacted at room temperature for 3 h. The reaction was detected by TLC. The reaction product was concentrated to a crude product, which was purified by pre-HPLC to give compound 15 (23.7 mg, 40% yield). $^1$H NMR (400 MHz, CD$_3$OD_SPE) δ 8.30 (s, 1H), 7.96 (d, J=7.6 Hz, 1H), 7.68-7.53 (m, 3H), 7.33 (dd, J=23.4, 9.4 Hz, 2H), 6.81 (d, J=7.1 Hz, 1H), 6.63 (d, J=8.2 Hz, 1H), 5.46 (s, 2H), 5.27 (d, J=6.6 Hz, 1H), 4.99 (dd, J=21.1, 8.0 Hz, 3H), 4.82-4.68 (m, 3H), 4.66-4.57 (m, 1H), 4.46 (d, J=8.1 Hz, 1H), 4.01 (dd, J=45.2, 13.7 Hz, 2H), 3.04 (dd, J=43.8, 10.7 Hz, 2H), 2.79 (s, 1H), 2.65 (s, 1H), 2.54 (d, J=8.6 Hz, 1H), 2.37 (d, J=9.1 Hz, 2H), 1.86 (d, J=10.2 Hz, 4H).

Example 16: (S)-1-(oxetan-2-ylmethyl)-2-((4-(6-((4-(oxetan-3-yl)-2-(2,2,2-trifluoroethoxy)benzyl) oxy) pyridin-2-yl)piperidin-1-yl)methyl)-1H-benzo[d] imidazole-6-carboxylic acid (compound 16)
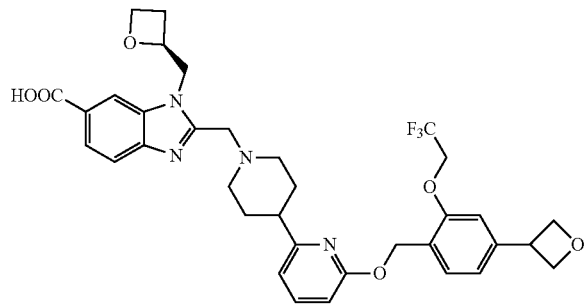 [SMILES: O=C(O)c1ccc2nc(CN3CCC(c4cccc(OCc5ccc(C6COC6)cc5OCC(F)(F)F)n4)CC3)n(C[C@@H]3CCO3)c2c1]
Synthetic route
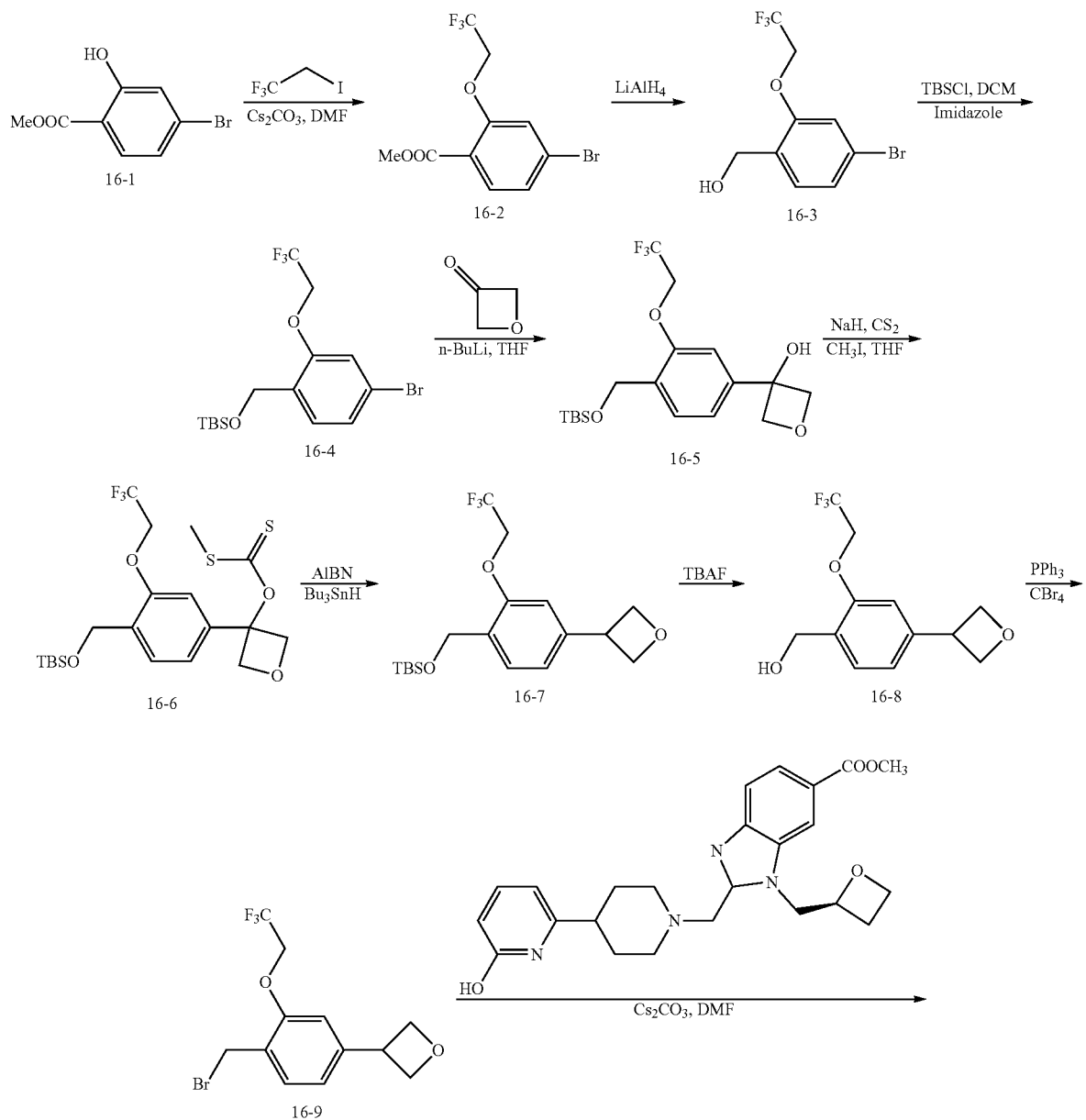

-continued

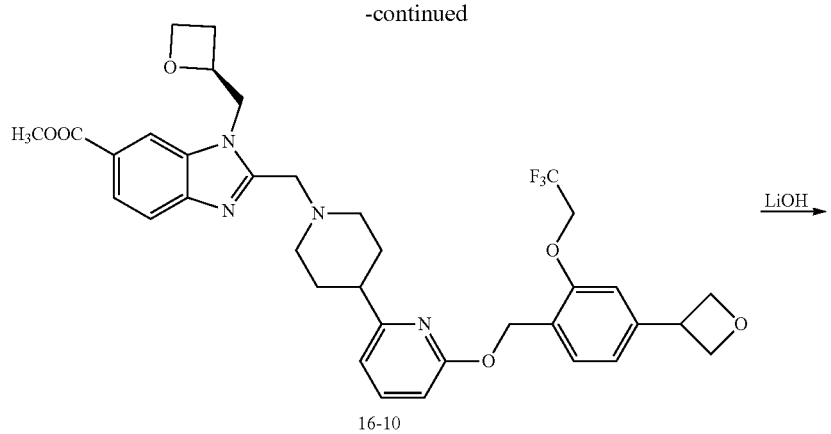

16-10

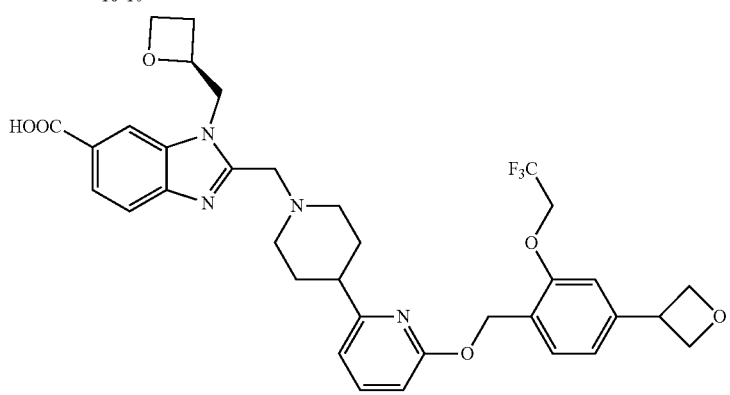

16

Preparation Method

Compound 16-2: To a stirred solution of methyl 4-bromo-2-hydroxybenzoate 16-1 (10 g, 43.5 mmol, 1.00 eq) in DMF (100 mL) was added $Cs_2CO_3$ (28 g, 87.0 mmol, 2.00 eq) in portions. To the above mixture, 1,1,1-trifluoro-2-iodoethane (9.1 g, 43.5 mmol, 1.00 eq) was added at room temperature over 16 h. The reaction was detected by TLC. The mixture was diluted with $H_2O$ (300 mL), and extracted with EtOAc (100 mL×3). The combined organic layers were washed with brine (200 mL), dried over $Na_2SO_4$, and concentrated under reduced pressure to give a residue which was purified by silica gel column chromatography, eluted with PE/EtOAc (3:1) to give product 16-2 (8.0 g, 46% yield). LCMS: r.t.=2.031 min, $[M+1]^+$=312.9, purity: 89.7%.

Compound 16-3: To a solution of 16-2 (8 g, 25.6 mmol, 1.0 eq) in THF (50 mL) was added $LiAlH_4$ (487 mg, 12.8 mmol, 2.0 eq) at 0° C., and then the mixture was stirred at 20° C. for 10 min. The reaction was detected by LCMS. $H_2O$ (0.2 mL), 15% NaOH solution (0.2 mL) and EtOAc (50 mL) were slowly added to the mixture. The organic layer was washed with brine, dried over $Na_2SO_4$, and concentrated to give product 16-3 (7 g, 90% yield).

Compound 16-4: To a solution of 16-3 (7 g, 24.6 mmol, 1 eq) in DCM (70 mL) were added TBSCl (4.5 g, 29.52 mmol, 1.2 eq) and imidazole (2.5 g, 36.9 mmol, 1.5 eq) at 25° C. over 16 h. The reaction was detected by TLC. The mixture was diluted with $H_2O$ (100 mL), and extracted with DCM (100 mL×3). The combined organic layers were dried over $Na_2SO_4$, filtered, and concentrated to give a residue which was purified by column chromatography on silica gel, eluted with (EA/PE=0-30%) to give product 16-4 (8.6 g, 72.7% yield). LCMS: r.t.=1.932 min, $[M+1]^+$=400.0, purity: 91.3%.

Compound 16-5: To a solution of 16-4 (4.5 g, 14.6 mmol, 1.0 eq) in THF (50 mL), n-BuLi (7.6 mL, 19.0 mmol, 1.3 eq) was added slowly at a temperature not higher than −70° C. under nitrogen with stirring over 0.5 h. $C_3H_4O_2$ (1.6 g, 21.9 mmol, 1.5 eq) was then slowly added to the reaction mixture with stirring over 2 h at a temperature not higher than −65° C. The reaction was detected by TLC. The mixture was slowly added to $H_2O$ (10 mL) and EtOAc (10 mL), and purified by silica gel column chromatography eluted with (PE/EA=0-50%) to give product 16-5 (1.8 g, 40% yield). LCMS: r.t.=1.734 min, $[M+1]^+$=393.1, purity: 93.5%.

Compound 16-6: To a solution of 16-5 (1.8 g, 4.6 mmol, 1.0 eq) in THF (20 mL), NaH (276 mg, 6.9 mmol, 1.5 eq) was added slowly at a temperature not higher than 10° C. under nitrogen with stirring over 1 h, then $CS_2$ (0.3 mL, 4.6 mmol, 1.0 eq) and $CH_3I$ (0.3 mL, 4.6 mmol, 1.0 eq) were slowly added to the reaction mixture at a temperature not higher than 0° C. with stirring over 0.5 h. The reaction was detected by LCMS. The mixture was slowly added to $H_2O$ (20 mL) and EtOAc (20 mL). The organic layer was washed with brine, dried over $Na_2SO_4$, and concentrated to afford product 16-6 (1.2 g, 70% yield). LCMS: r.t.=1.357 min, $[M+H]^+$=483.1, purity: 80%.

Compound 16-7: To a solution of 16-6 (1.2 g, 2.5 mmol, 1.0 eq) in toluene (15 mL) were added $(n-Bu)_3SnH$ (1.4 mL, 5.0 mmol, 2 eq) and AIBN (40.9 mg, 0.25 mmol, 0.1 eq) under nitrogen with stirring over 0.5 h. The reaction was detected by LCMS. The crude product was purified by silica gel column chromatography eluted with (EA/PE=0-50%) to give product 16-7 (754 mg, 70% yield). LCMS: r.t.=1.579 min, [M+H]⁺=377.2, purity: 93%.

Compound 16-8: To a solution of 16-7 (754 mg, 2.0 mmol, 1.0 eq) in THF (10 mL) was added TBAF (2.0 mL, 2.0 mmol, 1.0 eq) with stirring over 0.5 h. The reaction was detected by TLC. The reaction mixture was directly concentrated to give a residue which was purified by column chromatography on silica gel eluted with (PE/EA=0-50%) to give product 16-8 (481 mg, 80% yield). LCMS: r.t.=1.157 min, [M+H]⁺=263.3, purity: 89.5%.

Compound 16-9: To a solution of 16-8 (380 mg, 1.45 mmol, 1.0 eq) in DCM (10 mL) was added CBr₄ (482 mg, 1.45 mmol, 1.0 eq), and the system was allowed to cooled to 0 to 5° C. in an ice bath. PPh₃ (380 mg, 1.45 mmol, 1.0 eq) was then slowly added to the reaction mixture at a temperature no higher than 5° C. with stirring over 0.5 h. The reaction was detected by TLC. The mixture was diluted with H₂O (20 mL), and extracted with EtOAc (10 mL×3). The combined organic layers were dried over Na₂SO₄, filtered, and concentrated to give a residue which was purified by silica gel column chromatography eluted with (EtOAc/petroleum ether=0-30%) to give product 16-9 (90 mg, 78% yield). LCMS: r.t.=1.462 min, [M+H]⁺=323.4, purity: 89.5%.

Compound 16-10: To a stirred solution of 16-9 (100 mg, 0.31 mmol, 1.00 eq) in DMF (3 mL) was added Cs₂CO₃ (202 mg, 0.62 mmol, 2.00 eq) in portions. To the above mixture was added methyl (S)-2-((4-(6-hydroxypyridin-2-yl)piperidin-1-yl)methyl)-1-(oxetan-2-ylmethyl)-1H-benzo[d]imidazole-6-carboxylate (135 mg, 0.31 mmol, 1.00 eq) at room temperature over 16 h. The reaction was detected by TLC. The mixture was diluted with H₂O (300 mL), and extracted with EtOAc (100 mL×3). The combined organic layers were washed with brine (200 mL), dried over Na₂SO₄, and concentrated under reduced pressure to give a residue which was purified by column chromatography on silica gel eluted with PE/EtOAc (3:1) to give product 16-(120 g, 80% yield). LCMS: r.t.=1.754 min, [M+H]⁺=681.0, purity: 96.3%.

Compound 16: To a solution of 16-10 (120 mg, 0.18 mmol, 1.0 eq) in THF/H₂O (5 mL), stirred at room temperature for 16 h, LiOH (43.2 mg, 1.8 mmol, 10 eq) was added. The reaction detected by LCMS. The reaction mixture was concentrated to a crude product, which was further purified by preparative HPLC To give (S)-1-(oxetan-2-ylmethyl)-2-((4-(6-((4-(oxetan-3-yl)-2-(2,2,2-trifluoroethoxy)benzyl)oxy)pyridin-2-yl) piperidin-1-yl)methyl)-1H-benzo[d]imidazole-6-carboxylic acid as compound 16 (34.5 mg, yield: 63.2%). LCMS: r.t.=1.297 min, [M+H]⁺=667.4, purity: 100%. ¹HNMR (400 MHz, MeOD) δ 8.21 (s, 1H), 7.94 (dd, J=8.4, 1.1 Hz, 1H), 7.61-7.53 (m, 2H), 7.44 (d, J=7.7 Hz, 1H), 7.12-7.06 (m, 2H), 6.80 (d, J=7.4 Hz, 1H), 6.60 (d, J=8.2 Hz, 1H), 5.42 (s, 2H), 5.27 (d, J=4.3 Hz, 1H), 5.05 (dd, J=8.3, 6.0 Hz, 2H), 4.90 (d, J=7.1 Hz, 1H), 4.73 (dd, J=13.6, 7.0 Hz, 3H), 4.66-4.57 (m, 3H), 4.45 (dt, J=9.1, 5.9 Hz, 1H), 4.31-4.20 (m, 1H), 3.96 (dd, J=43.2, 13.7 Hz, 2H), 3.00 (dd, J=38.7, 11.4 Hz, 2H), 2.82-2.73 (m, 1H), 2.69-2.59 (m, 1H), 2.57-2.48 (m, 1H), 2.37-2.23 (m, 2H), 1.88 (dt, J=9.9, 6.8 Hz, 4H).

Example 17 2-((2-((2-chloro-4-(oxetan-3-yl)benzyl)oxy)-7a,8,11,11a-tetrahydrooxepino[4,3-b: 6,5-c'] dipyridin-9(5H,7H,10H)-yl)methyl)-1-((S)-oxetan-2-ylmethyl)-1H-benzo[d]imidazole-6-carboxylic acid (Compound 17)

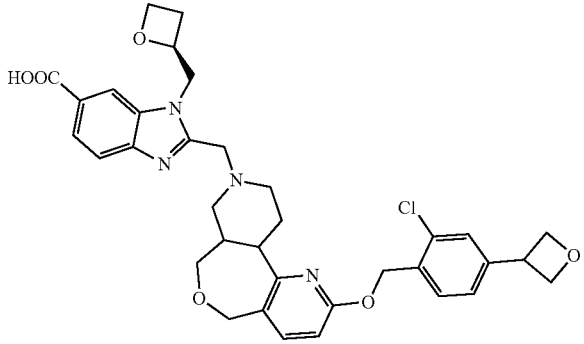 [SMILES: O=C(O)c1ccc2nc(CN3CCC4c5nc(OCc6ccc(C7COC7)cc6Cl)ccc5COCC4C3)n(C[C@@H]3CCO3)c2c1]

Synthetic route

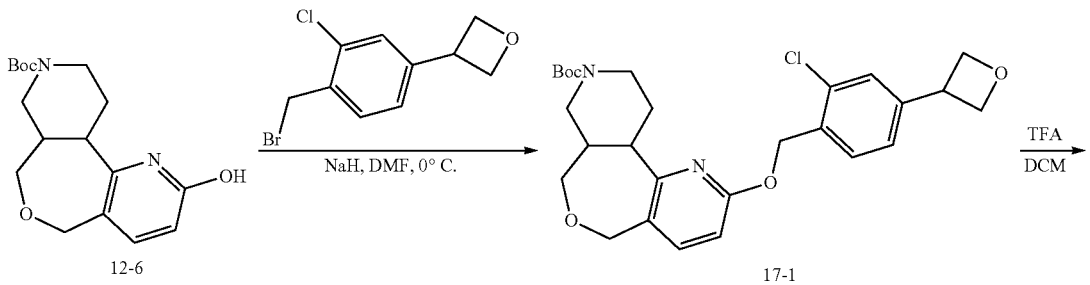

-continued
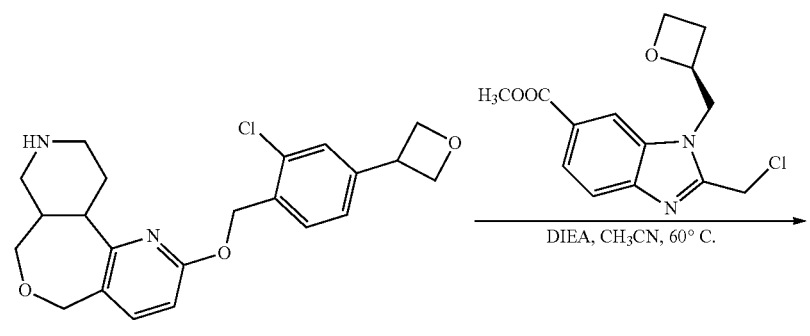
17-2
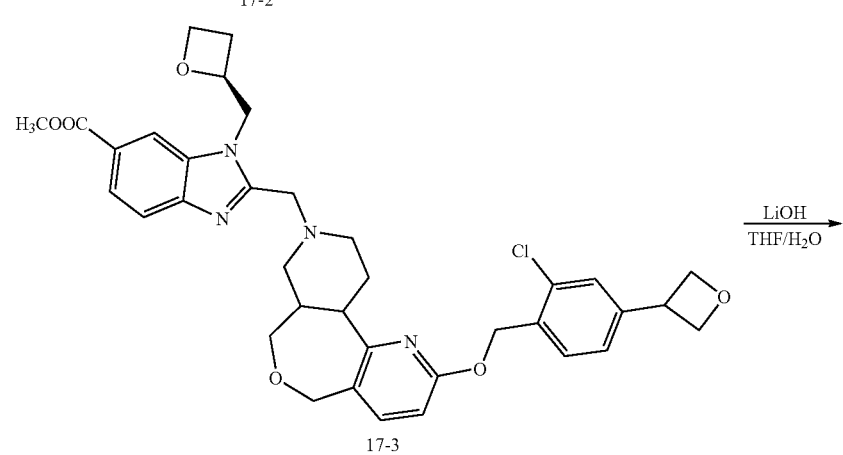
17-3
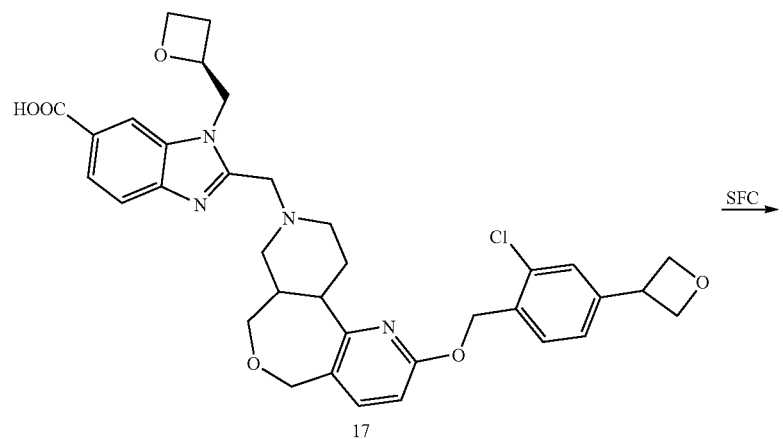
17
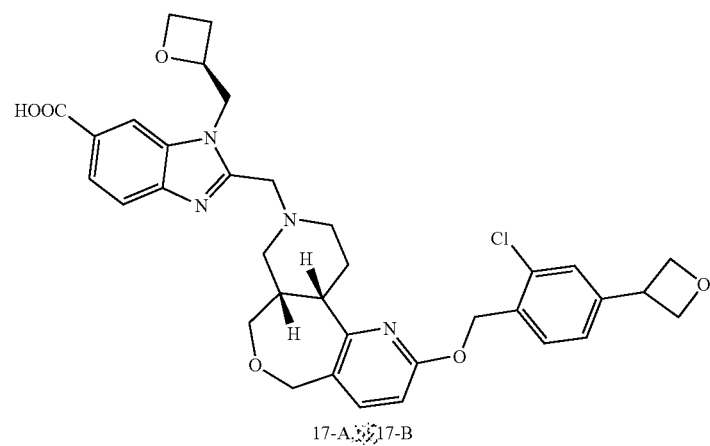
17-A & 17-B

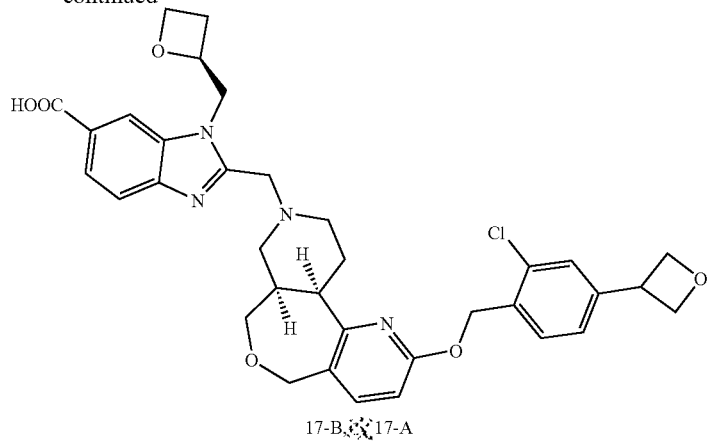

17-B, 17-A

Preparation Method

Compound 17-1: To a solution of 12-6 (120 mg, 0.375 mmol, 1.0 eq) in DMF (3 mL) was added NaH (22 mg, 0.56 mmol, 1.5 eq) at 0° C. After reaction for 15 min, the reaction system was added dropwise to a solution of 3-(4-(bromomethyl)-3-chlorophenyl)oxetane (97.5 mg, 0.375 mmol, 1.0 eq) in DMF. The ice bath was then removed. The reaction was detected by LCMS. The crude product was fractionated by column chromatography to give product 17-1. LCMS: r.t.=2.34 min, [M+H]$^+$=501, purity: 86%.

Compound 17-2: TFA (1 mL) in this system was added to a solution of 17-1 (380 mg, 0.76 mmol, 1.0 eq) in DCM (20 mL). The reaction was carried out at room temperature for 30 min. The reaction was detected by LCMS to give product 17-2. LCMS: r.t.=1.337 min, [M+H]$^+$=659, purity: 95%.

Compound 17-3: To a solution of 17-2 (304 mg, 0.76 mmol, 1.0 eq) in CH3CN (15 mL) was added DIEA (982.2 mg, 7.6 mmol, 10 eq). The mixture was reacted for 5 min. Int-2 (202 mg, 0.68 mmol, 0.9 eq) was added to the solution in the system. The mixture was stirred at 600° C. overnight. The reaction was detected by LCMS. The crude product was isolated by column chromatography to give product 17-3. LCMS: r.t.=1.337 min, [M+H]$^+$=659, purity: 78%.

Compound 17: To a solution of 17-3 (680 mg, 1.03 mmol, 1.0 eq) in THF (20 ml) was added a solution of LiOH (247.2 mg, 5.2 mmol, 10 eq) in water (3 ml). The reaction was detected by LCMS to give the product compound 17. LCMS: r.t.=1.26 min, [M+H]$^+$=645, purity: 77%.

Compounds 17-A and 17-B: A sample of compound 17 (390 mg, 0.606 mmol) was further purified by the "SFC method", to give compound 17-A (65 mg, SFC r.t=2.178 mins, yield: 56%) and compound 17-B (57 mg, SFC r.t=3.179 mins, yield: 44%).

$^1$H NMR (400 MHz, MeOD) δ 8.16 (s, 1H), 7.84 (dd, J=8.4, 1.4 Hz, 1H), 7.57 (d, J=8.4 Hz, 1H), 7.50 (t, J=7.8 Hz, 1H), 7.39 (d, J=8.3 Hz, 1H), 7.23-7.16 (m, 2H), 6.58 (d, J=8.2 Hz, 1H), 5.45-5.36 (m, 2H), 5.27 (qd, J=7.1, 3.0 Hz, 1H), 5.06 (dd, J=8.3, 6.1 Hz, 2H), 4.77-4.59 (m, 8H), 4.44-4.22 (m, 3H), 3.99-3.82 (m, 3H), 3.25 (d, J=9.4 Hz, 1H), 2.96 (s, 1H), 2.83-2.74 (m, 1H), 2.67-2.29 (m, 6H).

$^1$H NMR (400 MHz, MeOD) δ 8.17 (s, 1H), 7.93 (dd, J=8.4, 1.3 Hz, 1H), 7.56 (d, J=8.4 Hz, 1H), 7.49 (t, J=7.9 Hz, 1H), 7.39 (d, J=8.3 Hz, 1H), 7.22-7.16 (m, 2H), 6.59 (d, J=8.2 Hz, 1H), 5.41 (q, J=12.6 Hz, 2H), 5.25 (dt, J=7.2, 4.8 Hz, 1H), 5.06 (dd, J=8.2, 6.2 Hz, 2H), 4.73-4.62 (m, 9H), 4.49 (dt, J=9.1, 6.0 Hz, 1H), 4.32-4.22 (m, 1H), 4.10-3.90 (m, 2H), 3.76 (d, J=13.4 Hz, 1H), 3.25 (s, 1H), 2.94-2.77 (m, 2H), 2.70-2.27 (m, 6H).

Example 18: (S)-2-((4-(6-((2-(difluoromethyl)-4-(oxetan-3-yl)benzyl)oxy)pyridin-2-yl)piperidin-1-yl)methyl)-1-(oxetan-2-ylmethyl)-1H-benzo[d]imidazole-6-carboxylic acid (compound 18)

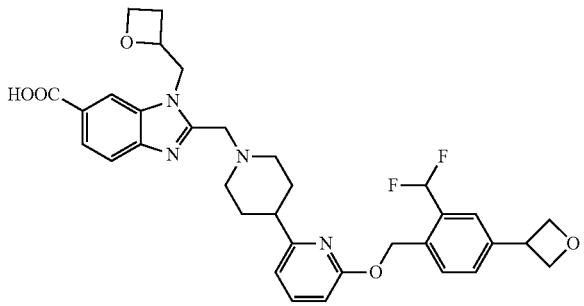 [SMILES: O=C(O)c1ccc2nc(CN3CCC(c4cccc(OCc5ccc(C6COC6)cc5C(F)F)n4)CC3)n(CC3CCO3)c2c1]

-continued
Synthetic route
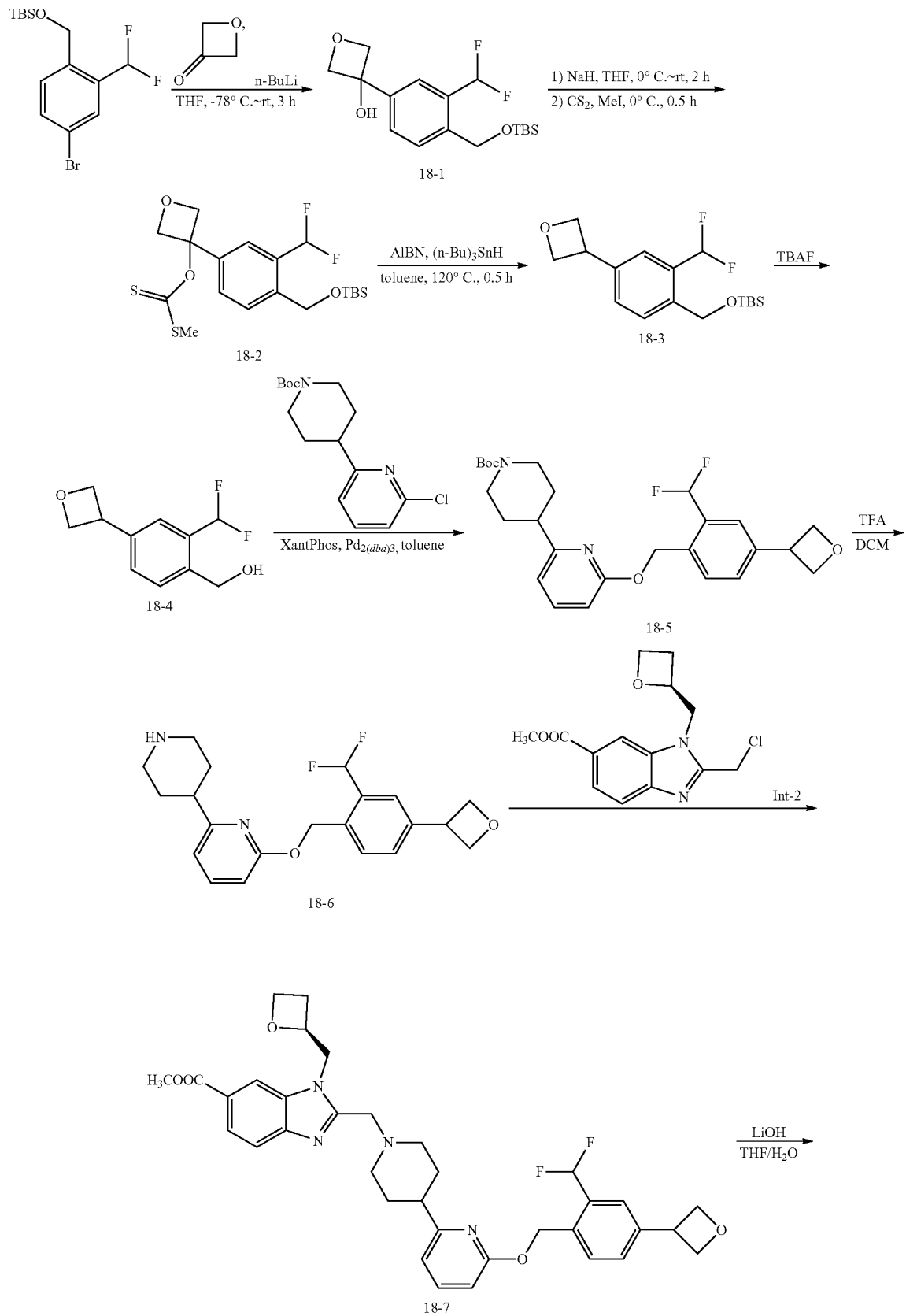

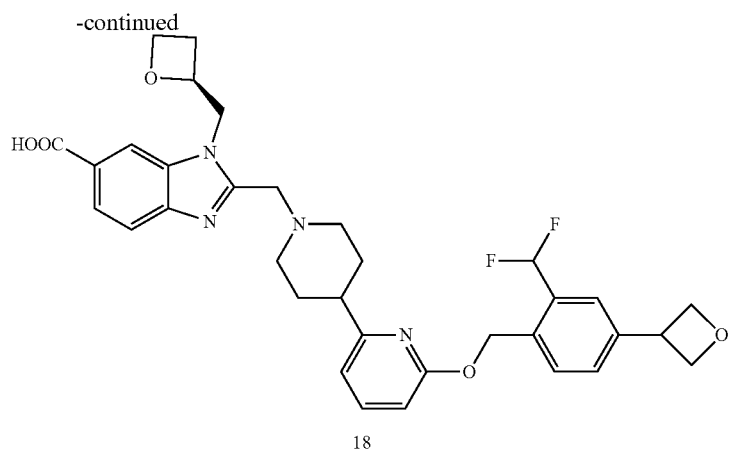

18

Preparation Method

Compound 18-1: To a solution of ((4-bromo-2-(difluoromethyl)benzyl)oxy)(tert-butyl)dimethylsilane (500 mg, 1.4 mmol, 1.0 eq) in THF (5 mL) was slowly added n-BuLi (1 mL, 1.6 mmol, 1.3 eq) at a temperature not higher than −70° C. under nitrogen with stirring over 0.5 h. Then $C_3H_4O_2$ was slowly added to the reaction mixture with stirring at a temperature not higher than −65° C. over 2 h. The reaction was detected by TLC. The mixture was slowly added with $H_2O$ (10 mL) and EtOAc (10 mL), and purified by silica gel column chromatography eluted with (EA/PE=0-50%) to give product 18-1 (130 mg, 80% yield). LCMS: r.t.=2.049 min, [M+H]$^+$=345.1, purity: 86%.

Compound 18-2: To a solution of 18-1 (260 mg, 0.76 mmol, 1.0 eq) in THF (5 mL) was added slowly NaH (60 mg, 1.5 mmol, 2 eq) at a temperature not higher than 10° C. under nitrogen with stirring over 1 h. Then, $CS_2$ (0.05 mL, 0.76 mmol, 1 eq) and $CH_3I$ (0.05 mL, 0.76 mmol, 1 eq) were slowly added to the reaction mixture at a temperature not higher than 0° C. with stirring over 0.5 h. The reaction was detected by LCMS. The mixture was slowly added to $H_2O$ (20 mL) and EtOAc (20 mL). The organic layer was washed with brine, dried over $Na_2SO_4$, and concentrated to give the product 18-2 (150 mg, 70% yield). LCMS: r.t.=1.572 min, [M+H]$^+$=435.0, purity: 90%.

Compound 18-3: To a solution of 18-2 (252 mg, 0.63 mmol, 1.0 eq) in toluene (7 mL) were added (n-Bu)$_3$SnH (0.34 mL, 1.26 mmol, 2 eq) and AIBN (10.3 mg, 0.063 mmol, 0.1 eq) under nitrogen with stirring over 0.5 h. The reaction was detected by LCMS. The crude product was purified by silica gel column chromatography eluted with (EA/PE=0-50%) to give 18-3 (136 mg, 90% yield). LCMS: r.t.=1.472 min, [M+H]$^+$=329.1, purity: 96%.

Compound 18-4: To a solution of 18-3 (700 mg, 2.13 mmol, 1.0 eq) in THF (4 mL) was added TBAF (2.13 mL, 2.13 mmol, 1.0 eq) and stirred for 0.5 h. The reaction was detected by TLC. The reaction mixture was directly concentrated to give a residue which was purified by column chromatography on silica gel eluted with (PE/EA=0-50%) to give the product 18-4 (500 mg, 90% yield). LCMS: r.t.=1.132 min, [M+H]$^+$=215.1, purity: 86.9%.

Compound 18-5: 18-5 (509 mg, 1.72 mmol, 1.0 eq), $Cs_2CO_3$ (1.12 g, 3.44 mmol, 2.0 eq), xantphos (199 mg, 0.344 mmol, 0.2 eq), and Pd (dba)$_3$ (157 mg, 0.172 mmol, 0.1 eq) were stirred at 100° C. for 4 h. The reaction was detected by LCMS. The toluene in the mixture was dried. The resulting mixture was dissolved in dichloromethane. The combined organic layers were concentrated to give a residue which was purified by column chromatography on silica gel eluted with (PE/EA=0-20%) to give the product 18-5 (650 mg, 80% yield). LCMS: r.t.=1.937 min, [M+H]$^+$=475.2, purity: 87.18%.

Compound 18-6: To a solution of 18-5 (300 mg, 0.63 mmol) in 6 mL of DCM was added TFA (1 mL) and stirred at room temperature for 30 min. The reaction was detected by LCMS. The reaction mixture was concentrated to give the crude product 18-6 (200 mg). The crude product was used directly in the next step without purification. LCMS: r.t.=1.371 min, [M+H]$^+$=375.1, purity: 93.8%.

Compound 18-7: To a solution of 18-6 (200 mg, 0.54 mmol, 1.0 eq) in 15 mL MeCN (10 mL) was added DIEA (696.6 mg, 5.4 mmol, 10 eq) and stirred at room temperature under nitrogen for 10 min. Then, Int-2 (159 mg, 0.54 mmol, 1.0 eq) was added to the reaction mixture at 60° C. over 16 h. The reaction was detected by LCMS. The reaction mixture was concentrated to a crude product, which was further purified by elution (PE/EtOAc=0-5%) to give the product 18-7 (100 mg, yield: 50.3%). LCMS: r.t.=1.013 min, [M+H]$^+$=633.4, purity: 99.7%.

Compound 18: To a solution of 18-7 (100 mg, 0.16 mmol, 1.0 eq) in THF/$H_2O$ (5 mL) was added LiOH (38 mg, 1.6 mmol, 10 eq) with stirring at room temperature for 16 h. The reaction was detected by LCMS. The reaction mixture was concentrated to a crude product, which was further purified by preparative HPLC to give compound 18 (40.86 mg, yield: 63.2%). LCMS: r.t.=1.239 min, [M+H]$^+$=619.2, purity: 97.4%. $^1$HNMR(400 MHz, CD$_3$OD_SPE) δ 8.14 (d, J=139.3 Hz, 2H), 7.69-7.50 (m, 5H), 7.13 (t, J=55.2 Hz, 1H), 6.80 (s, 1H), 6.63 (d, J=8.3 Hz, 1H), 5.53 (s, 2H), 5.27 (s, 1H), 5.06 (dd, J=8.0, 6.3 Hz, 2H), 4.85 (s, 1H), 4.71 (dd, J=17.0, 10.8 Hz, 3H), 4.60 (s, 1H), 4.45 (s, 1H), 4.32-4.25 (m, 1H), 4.01 (d, J=29.4 Hz, 2H), 3.09 (s, 1H), 2.99 (s, 1H), 2.79 (s, 1H), 2.65 (s, 1H), 2.52 (s, 1H), 2.36 (s, 2H), 1.85 (s, 4H).

Example 20: 2-[(4-{6-[(4-cyano-2-fluorophenyl)methoxy]pyridin-2-yl}piperidin-1-yl)methyl]-1-{[(2S)-oxetan-2-yl]methyl}-1H-1, 3-benzodiazole-6-carboxylic acid (compound 20)

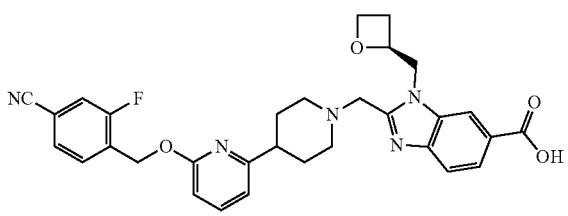 [SMILES: N#Cc1ccc(COc2cccc(C3CCN(Cc4nc5ccc(C(=O)O)cc5n4C[C@@H]4CCO4)CC3)n2)c(F)c1]

Compound 20, i.e., PF06882961, was prepared according to the preparation method described in WO2018109607A1.

Biological Assays
Experimental Example 1 - GLP-1R agonistic activity assay
(1) Test instruments and reagents

| Instruments/reagents | Supplier | Model |
| --- | --- | --- |
| cAMP-GS DYNAMIC kit | CisBio | 62AM4PEC |
| DMEM | CellMax | CGN101.5 |
| FBS | Gemini | 900-108 |
| 1% Pen-3trep | Sangom biotech | E607011-0100 |
| IBMX | Meilunbio | MB5226 |
| 384 well plate | Corning | 3824 |
| Incubator | Thermo | 3111 |
| Microscope | Jiangnan | XD-202 |
| Cell counter | Counter Star | Star IC1000 |
| Plate reader | Tecan | Tecan Spark |

(2) GLP-1R Kit

GLP-1R-mediated agonist activity was determined by cell-based assays using a homogeneous time-resolved fluorescence (i.e., HTRF)-based cAMP detection kit, which measures the level of cAMP in cells. The method was a competitive immunoassay. It enabled direct pharmacological characterization of compounds acting on Gs-coupled receptors in adherent or suspending cells.

The standard curve of native cAMP or unlabeled cAMP produced by cells competed with d2-labeled cAMP red receptors to bind monoclonal anti-cAMP Eu3+ cryptate donors, and the specific signal was inversely proportional to the concentration of cAMP in standard or tested samples.

Human GLP-1R encoding sequence (NCBI reference sequence NP_002053.3) was subcloned into pEGFP-N1 (tsingke), and the cell line stably expressing the receptor was isolated. The expression density of GLP-1R was confirmed by the expression of GFP observed under a fluorescence microscope.

(3) GLP-1R-GFP-293A Cell Culture

293A GFP-GLP-1R cells were incubated in DMEM growth medium, 10% heat-inactivated fetal bovine serum (GEMINI Cat #900-108), 1% Pen-3Trep (Sangom Biotech Cat #E607011-0100)] in a moist incubator with 5% $CO_2$ at 37° C.

(4) cAMP Level Test Method

The tested compounds (in DMSO) at different concentrations were 1:5 diluted in distilled water in a stimulating buffer, followed by addition of 500 μm 3-isobutyl-1-methylxanthine (IBMX; Meilunbiocat #MB5226) to obtain a working solution of 2x compound, and then 5 μL of the compound was added to a white 384-well assay plate (Corning 3824) using a multi-channel pipette. The final DMSO concentration in the buffer mixture was determined to be 1‰.

Cells were collected from a T25 tissue culture flask and centrifuged at room temperature at 1000 rpm for 5 minutes. The cell precipitates were then re-suspended in 1 mL of the stimulating buffer. 20 μL sample of cell suspension was counted on a counter STAR IC 1000 to determine the cell viability and the cell count per mL. The remaining cell suspension was then regulated with the stimulating buffer to deliver 2000 living cells per well using a multi-channel pipette. 5 μL of the cell suspension was added to each well of the plate which already contained the compound. The plate was sealed and incubated at 37° C. with 5% $CO_2$ for 30 minutes.

After 30 minutes of incubation, 5 μL of d2-labeled cAMP and 5 μL of anti-cAMP cryptate (both 1:20 diluted in the cell lysis buffer) were added to each well of the plate. The plate was then incubated at room temperature for 60 minutes, and the changes of HTRF signal were read with Tecan Spark reader: absorbance values at 340 nm (excitation)/at 615 nm and 665 nm (emission). Raw data were converted into nM cAMP by interpolation from the cAMP standard curve, and the effect in percentage was determined relative to the saturated concentration of the complete agonist GLP-17~37 (400 nM) contained in each plate. Determination of EC50 was performed based on the agonist dose-response curve, which was analyzed using a four-parameter logical dose-response equation with a curve fitting program.

This test proved that the compound of the present disclosure activated GLP-1R signaling through the cAMP pathway, thus acting as a GLP-1R agonist. The test data presented the results in the form of a geometric mean (EC50) based on the number of repetition times.

Experimental results:

| Compound No. | $EC_{50}$ (nM) |
| --- | --- |
| 1 | 0.03 |
| 2 | 0.07 |
| 3 | 0.03 |
| 4 | 0.08 |
| 5 | 0.003 |
| 6 | 0.7 |
| 7 | 0.1 |
| 8 | 0.02 |
| 9 | 0.39 |
| 10 | 0.03 |
| 11 | 0.011 |
| 12-B | 0.1 |
| 15 | 0.08 |
| 17-B | 0.14 |
| 18 | 0.85 |

Experiment Example 2—Test for Inhibition of hERG Potassium Channels

1. Experimental materials: stable cell line HEK-hERG, strain: HEK 293, source: Academy of Military Medical Sciences;

| Instrument | Model | Supplier |
| --- | --- | --- |
| Manual patch clamp system | EPC 10 USB PatchMaster software | HEKA Elektronik |
| Rapid perfusion system | ALA-VM8 | ALA Scientific Ins. |

-continued

| 1. Experimental materials: stable cell line HEK-hERG, strain: HEK 293, source: Academy of Military Medical Sciences; | | |
|---|---|---|
| Instrument | Model | Supplier |
| Micro manipulator | MPC200 | Sutter Instrument Co. |
| Inverted microscope | TI-FL | Nikon |
| Microelectrode puller | PC-10 | NARISHIGE |
| Vibration isolation table | 637512M | TMC |
| Peristaltic pump | LEAD15-24 | Longer pump |

2. Electrophysiological Solution

Extracellular fluid (mM): N-2-hydroxyethylpiperazine-N'-2-ethanesulfonic acid (HEPES) 10, NaCl 145, KCl 4, CaCl$_2$ 2, MgCl$_2$ 1, Glucose 10, a pH adjusted to 7.3-7.4 with sodium hydroxide; an osmotic pressure adjusted to 290-310 mOsm; stored at 4° C. after filtration.

Pippette solution (mM): KCl 120, KOH 31.25, CaCl$_2$ 5.374, MgCl$_2$ 1.75, ethylene glycol-bis(D-aminoethyl ether)-N,N,N',N'-tetraacetic acid (EGTA) 10, HEPES 10, Na$_2$-ATP 4, a pH adjusted to 7.2-7.3 with potassium hydroxide; an osmotic pressure adjusted to 290-310 mOsm; packed after filtration and stored at −20° C.

3. Positive Control Compound

Positive control: Amitriptyline hydrochloride or Terfenadine

Source: Sigma-Aldrich

4. Preparation of the Dosed Formulations

Preparation of the solvent control: a certain volume of DMSO was added to the extracellular fluid to the same content of DMSO as in the final test solution (if the test solution contained a different content of DMSO, the maximum DMSO content shall prevail), so as to eliminate the interference of DMSO on the own current of cells.

Preparation of test samples: the above 10 mM mother liquor was prepared into a DMSO stock solution with a desired concentration (generally 1000/3 times of the actual dosing concentration), which was finally diluted with the extracellular fluid to the desired dosing concentration for the experiment.

Preparation of the positive control solution: a proper amount of the positive control compound was weighed and placed in a suitable container, followed by addition of a certain volume of DMSO, and extensive stirring or shaking to dissolve all positive control compound to prepare a 10 mM stock solution, which was then proportionally prepared into a stock solution with a desired concentration. The resulting solution was finally diluted with the extracellular fluid to a desired dosing concentration for the experiment.

Before using the solution with the working concentration, whether precipitation occurred was checked. If precipitation occurred, the stock solution was diluted to raise the final concentration of DMSO in the extracellular fluid, but the final concentration of DMSO in the extracellular fluid should not exceed 0.5%. Continuous perfusion from low concentration to high concentration was adopted in the experiment. After the experiment was complete, the remaining dosing solutions of the test sample and the positive control were treated as waste liquids.

5. Experimental Protocol

Preparation of Cells

After the passage and culture of HEK-293-hERG cells to a proper state, the cells were washed with PBS (or DPBS), digested and separated with Tryple solution, and then resuspended in the medium and stored in a centrifuge tube. After centrifugation, the supernatant was discarded, and the cells were resuspended in the extracellular fluid for later use and stored at 2-8° C. Before patch clamp recording, the cells were dropped into a culture dish to ensure that the cells had a certain density and were isolated from one another.

| Concentration settings: | |
|---|---|
| Tested sample/positive control sample | Concentration (μM) |
| The compounds of the present disclosure | 1-10 |
| Amitriptyline hydrochloride or Terfenadine | 1 |

Electrophysiological Test

A whole-cell patch clamp technique was used to record hERG current. The cell suspension was added to a small petri dish and placed on an inverted microscope stage. After adherence, the cells were perfused with the extracellular fluid at a recommended flow rate of 1-2 mL/min. The glass microelectrode was made by two-step pulling using a microelectrode puller, and had a resistance of 2 to 5 MΩ in water after filled with the electrode interior liquid.

After the whole-cell recording mode was set up, the clamping potential was maintained at −80 mV. The depolarization voltage was applied to +60 mV for 850 ms, and then repolarized to −50 mV for 1275 ms to induce hERG tail current. Such a set of pulse programming was repeated every 15 seconds throughout the experiment.

After the current was stable, a dosing mode was applied using extracellular continuous perfusion from low to high concentrations. Starting from a low concentration, perfusion continued until the efficacy was stable, then perfusion at a next concentration was performed. In this experiment, the blocking effect of the test sample and the positive control on hERG tail current was tested (N≥2); and the actual concentration could be adjusted according to the actual solubility and effect, which was not regarded as deviation from the protocol.

Stable efficacy was defined as follows: it was considered as stable that the change of the current value in the last five stimulations during the dosing at each concentration was less than 10% of the average value (when the current was greater than or equal to 200 pA) or less than 30% of the average value (when the current was less than 200 pA); if unstable, data for the concentration would not be adopted.

6. Data Analysis

In data processing, when determining the blocking effect on hERG, the peak value and baseline of tail current were calibrated. The inhibition rate (IR) of tail current was used to represent the effects of the compounds at different concentrations. An SD≤15 of the % IR for all cells at various concentrations was considered an acceptable standard (except for abnormal data).

IR=100%×(the peak value of the tail current before dosing−the peak value of the tail current after dosing)/the peak value of the tail current before dosing.

| 7. Experimental results: | | |
|---|---|---|
| Compound No. | hERG (IR) | hERG IC50 (uM) |
| 1 | 3.75% (1 μM) 40.7 (10 μM) | 15.9 |
| 20 | / | 5.8 |

8. Experimental Conclusion: Compound 1 Did not Exhibit hERG Inhibitory Activity, and had Excellent Safety.

Experiment Example 3—Metabolic Stability in (Human) Liver Microsomes

1. Experimental design: test concentration: 1 μM; control compound: testosterone; culture conditions: cultured at 37° C. for 0, 5, 15, 30, 45 minutes; method of determination: LC-MS/MS; calculation method: $T_{1/2}=0.693/K$ (K is the rate constant of the ln [concentration] vs. incubation time profile), $Cl_{int}=(0.693/T_{1/2})\times(1/(\text{microsomal protein concentration }(0.5 \text{ mg/mL})))\times\text{scaling factor}$.

The scaling factors for predicting the intrinsic clearance in human microsomes are provided in the following table:

| Species | Microsome protein /g liver | Liver weight/kg body weight | Scaling factor | Hepatic blood flow (mL/min/kg) |
|---|---|---|---|---|
| Mouse | 45 | 87.5 | 3937.5 | 90 |
| Rat | 44.8 | 40 | 1792 | 55.2 |
| Monkey | 45 | 32.5 | 1462.5 | 44 |
| Human | 48.8 | 25.7 | 1254.2 | 20.7 |

Scaling factor = (microsome protein/g liver) × (liver weight/kg body weight)

2. Experimental method: 1. preheating 0.1 M K-buffer, 5 nM $MgCl_2$, pH=7.4; 2. test solutions of test compound and reference compound, 500 μM additive solution: 5 μL of 10 mM stock solution was added to 95 μL can; 1.5 μM additive solution of microsome (0.75 Mg/mL): 1.5 μL of 500 μM additive solution and 18.75 μL of 20 Mg/mL liver microsome were added to 479.75 μL of K/Mg buffer; 3. 3×NADPH stock solution (6 mM, 5 mg/mL) was prepared by dissolving NADPH in the buffer solution; 4. 30 μL of 1.5 μM additive solution containing 0.75 mg/mL microsomal solution was distributed to the plates designated for different time points (0, 5, 15, 30, 45 minutes); 5. at 0 min, 150 μL of ACN containing IS was added to the wells of the plate, followed by addition of 15 μL of NADPH stock solution (6 mM, step 3); 6. all other plates were pre-incubated at 37° C. for 5 minutes; 7. adding 15 μL of NADPH stock solution to the plate to start the reaction and timing; 8. 150 μL of ACN containing IS was added to the wells of the corresponding plates to stop the reaction at 5 min, 15 min, 30 min and 45 min, respectively; 9. after quenching, the plates were shaken on a shaker for 10 minutes (600 rpm/min) and then centrifuged at 6000 rpm for 15 minutes; 10. 80 μL of supernatant was transferred from each well to a 96-well sample plate containing 140 μL water for LC/MS analysis.

3. Analysis Method

Detection method: LC-MS/MS-11 (8050), internal standard: tolbutamide; MS conditions: positive ion ESI for testosterone and test compound, and negative ion ESI for tolbutamide; Mobile phases: mobile phase A is 0.1% FA in water, and mobile phase B is 0.1% FA in ACN; Column and specification: ACQUITY UPLC HSS T3 1.8 um 2.1*50 mm.

| LC conditions: | | | |
|---|---|---|---|
| Testosterone 0.60 mL/min | | Test compound 0.60 mL/min | |
| Time | Pump B | Time | Pump B |
| 0.01 | 10 | 0.01 | 10 |
| 0.5 | 90 | 0.3 | 95 |
| 1.5 | 90 | 1 | 95 |
| 1.51 | 10 | 1.01 | 10 |
| 1.8 | Stop | 1.5 | Stop |

4. Experimental results (human microsomes):

| Compound No. | LMS($t_{1/2}$ min) |
|---|---|
| 1 | 130.39 |
| 2 | 123.34 |
| 3 | 153.67 |
| 6 | 43.0 |
| 7 | 104.37 |
| 11 | 63.21 |
| 12-B | 71.90 |
| 20 | 112.0 |

5. Experimental conclusion: Compounds 1-3, 7, 11 and 12-B exhibited good stability in liver microsomes.

Experiment Example 4—Caco-2 Cell Transport Experiment

1. Experimental Materials

Caco-2 cells, 77th passage; HBSS, Lot: G210713; ACN+ IS (tolbutamide 200 ng/mL);

2. Cell Culture:

Caco-2 was inoculated on polyethylene (PET) in a 96-well Falcon plate at $2\times10^5$ cells/cm² until a confluent cell monolayer was formed on day 21-28. The culture medium was changed every 3-4 days.

3. Experimental Protocol:

The test compound was diluted to a concentration of 10 uM with a transport buffer of 10 mM stock solution (HBSS without BSA) and applied to the apical side or the basolateral side of the cell monolayer. Incubation was carried out at 37° C., 5% $CO_2$, and 95% relative humidity for 120 minutes, and the permeability of the test compound from the A to B direction or the B to A direction was determined in duplicate. The efflux ratio of each compound was determined. Test and reference compounds were quantitated by LC-MS/MS analysis based on the analyte/IS peak area ratio.

4. Experiment Determination:

The apparent permeability coefficient Papp (cm/s) was calculated by the following equation:

$$Papp=(dCr/dt)\times Vr/(A\times C0),$$

wherein dCr/dt was the cumulative concentration of the compound in the recipient chamber, which was a function of time (S); Vr was the volume of the solution in the recipient chamber (the apical side: 0.1 mL, the basal side: 0.25 mL), A was the surface area for transport, i.e., 0.0804 cm² which was the area of the monolayer, and C0 is the initial concentration in the donor chamber;

The efflux ratio was calculated by the following formula:

$$\text{Efflux Ratio}=Papp(BA)/Papp(AB);$$

The % Recovery was calculated by the following equation:

% Recovery=100×[(Vr×Cr)+(Vd×Cd)]/(Vd×C0)

% Total recovery=100×[(Vr×Cr)+(Vd×Cd)+(Vc×Cc)]/(Vd×C0), wherein Vd was the volume in the donor chamber (the apical side: 0.1 mL, the basal side: 0.25 mL), Cd and Cr were the final concentrations of transported compound in the donor and recipient chambers, respectively, Cc was the concentration of compound in the cell lysate solution, and Vc was the volume of the inserted well (0.1 mL in this experiment).

5. Lc/Ms Condition:

Detection method: LC-MS/MS-20(TQ-6500+) & LC-MS/MS-11(8050); internal standard: tolbutamide; MS conditions: positive ion ESI for atenolol, propranolol and test compound, negative ion ESI for digoxin; Mobile phase: mobile phase A is 0.1% FA in water, mobile phase B is 0.1% FA in ACN; Column and specification: ACQUITY UPLC HSS T3 1.8 um 2.1*50 mm.

| LC conditions: | | | | | | | |
|---|---|---|---|---|---|---|---|
| Atenolol 0.60 mL/min | | Propranolol 0.50 mL/min | | Digoxin 0.60 mL/min | | Test compound 0.60 mL/min | |
| Time | Pump B | Time | Pump B | Time | Pump B | Time | Pump B |
| 0.01 | 0 | 0.01 | 15 | 0.01 | 10 | 0.01 | 10 |
| 0.4 | 0 | 0.5 | 90 | 0.3 | 95 | 0.3 | 195 |
| 0.6 | 95 | 1.1 | 90 | 1 | 95 | 1 | 95 |
| 1.5 | 95 | 1.11 | 15 | 1.01 | 10 | 1.01 | 10 |
| 1.51 | 0 | 1.5 | Stop | 1.2 | Stop | 1.5 | Stop |
| 1.8 | Stop | | | | | | |

| 6. Experimental results: | |
|---|---|
| Compound No. | A-B/B-A/Efflux ratio |
| 1 | 3.14/16.51/5.26 |

7. Experimental Conclusion:

The compounds of the invention were well absorbed in the intestinal tract.

Experimental Example 5: Toxicological Experiment in Mice

Experimental objective: To evaluate the toxicity and toxicokinetics of compound 1 and compound 20 (control compound) in ICR mice after repeated oral gavage for 14 days.

Experimental method: 212 ICR mice (SPF grade), half male and half female. Animals in groups 1-5 were used for toxicity study, with 10 male and 10 female animals in each group; and animals in groups 6-9 were used for toxicokinetic study, with 14 male and 14 female animals in each group (2 of them were spare animals). Groups 1 to 5 were vehicle control (0 mg/kg), compound 1 at doses of 50, 100 and 200 mg/kg, and control compound at 200 mg/kg, respectively; groups 6 to 9 had the same dose design as groups 2 to 5. Animals in Groups 1-9 were administered orally once a day for 14 consecutive days.

Experimental observation: In the toxicity study, 2 (2/10) male animals in the group of compound 20 at 200 mg/kg were found dead on Day 5 and Day 12, respectively. In the toxicokinetic study, one (1/14) female in the group of compound 1 at 200 mg/kg was found dead on Day 3, and four (4/14) males in the group of compound 20 at 200 mg/kg were found dead on Day 11, Day 3, Day 3 and Day 4, respectively. The remaining animals survived to the end of the experiment. In the toxicity study, the animals in the group of compound 1 at 100 mg/kg occasionally showed abnormal gait, decreased activity, piloerection and traumatic abnormalities which were presumed to be mechanical injuries and were not related to the test compound 1; other abnormalities were not related to the test article because they had no dose-effect relationship and the symptoms could be recovered. In the toxicity and toxicokinetic studies, decreased activity, piloerection, cold skin when touched, arched-back posture and prone position were frequently observed in animals in the group of compound 20 at 200 mg/kg. Biochemical analysis of serum showed no significant toxicological changes associated with compound 1 compared to vehicle control. The increase in TBIL in the group of compound at 200 mg/kg was considered to be related to compound 20.

Experimental results: $AUC_{(0-t)}$, the systemic exposure of compound 1 at 200 mg/kg in plasma of male animals on Day 14, $AUC_{(0-t)}$ and $C_{max}$ were 218148.74 h*ng/mL, 199768.76 h*ng/mL, and 81039.97 ng/mL, respectively; and $AUC_{(0-t)}$, the systemic exposure of compound 1 at 200 mg/kg in plasma of female animals on Day 14, $AUC_{(0-t)}$ and $C_{max}$ were 291010.82 h*ng/mL, 270696.18 h*ng/mL, and 117480.84 ng/mL, respectively. At the same time, $AUC_{(0-t)}$, the systemic exposure of compound 20 at 200 mg/kg in plasma of male animals on Day 14, $AUC_{(0-\infty)}$ and $C_{max}$ were 387293.58 h*ng/mL, 253720.92 h*ng/mL, and 91002.30 ng/mL, respectively; and $AUC_{(0-t)}$, the systemic exposure of compound 20 at 200 mg/kg in plasma of female animals on Day 14, $AUC_{(0-\infty)}$ and $C_{max}$ were 338426.01 h*ng/mL, 331124.48 h*ng/mL, and 104210.33 ng/mL.

Experimental conclusion: Compound 1 and compound 20 were administered to ICR mice by gavage once a day for 14 consecutive days, and the results showed that the non-toxic response dose level of compound 1 was 200 mg/kg, and that of compound 20 was less than 200 mg/kg. That is, compound 1 had no significant toxicological effects on experimental animals at this studied dose, and had a higher level of safe dose (the maximum tolerable dose was higher). Compound 1 is safer than compound 20.

Experiment 6: Pharmacokinetic Experiment in Cynomolgus Monkeys

Experimental objective: To evaluate the pharmacokinetic profile of compound 1 and compare it with compound 20 (control compound).

Experimental method: 6 male Non-juvenile cynomolgus monkeys, 4~5 kg, were purchased from Huazheng Experimental Animal Center. Group IV was administered intravenously at a dose of 2 mg/kg (5 mL/kg) (n=3), and the group PO was administered orally at a dose of 20 mg/kg (10 mL/kg) (n=3). Approximately 500 μL blood was collected from cephalic vein and saphenous vein at each experimental time point, and centrifuged at 2,000 g for 5 min (4° C.) within 15 min after sampling for subsequent analysis.

Experimental results:
Individual and Mean Plasma Concentration-Time Data After Intravenous Injection of Compound 1 (2 mg/kg) in Male Cynomolgus Monkeys

| PK indicators | Unit | #1 | #2 | #3 | Mean | SD | CV (%) |
|---|---|---|---|---|---|---|---|
| CL | L/hr/kg | 0.131 | 0.229 | 0.262 | 0.207 | 0.0681 | 32.8 |
| $V_{ss}$ | L/kg | 0.0508 | 0.0564 | 0.0635 | 0.0569 | 0.00637 | 11.2 |
| *$T_{1/2}$ | hr | 1.23 | 1.46 | 1.50 | 1.39 | 0.145 | 10.4 |
| $AUC_{last}$ | hr * ng/ml | 15215 | 8739 | 7607 | 10520 | 4105 | 39.0 |
| $AUC_{INF}$ | hr * ng/ml | 15231 | 8749 | 7622 | 10534 | 4106 | 39.0 |
| $MRT_{INF}$ | hr | 0.387 | 0.247 | 0.242 | 0.292 | 0.0822 | 28.2 |
| Rsq_adjusted | NA | 0.929 | 0.972 | 0.787 | NA | NA | NA |
| Regression Points | hr | 2~8 | 2~8 | 1~8 | NA | NA | NA |
| $AUC_{last}$ | hr * μM | 26.0 | 14.9 | 13.0 | 17.9 | 7.00 | 39.0 |
| $AUC_{INF}$ | hr * μM | 26.0 | 14.9 | 13.0 | 18.0 | 7.00 | 39.0 |
| CL | mL/min/kg | 2.19 | 3.81 | 4.37 | 3.46 | 1.13 | 32.8 |

Note:
NA means not assayed.

Individual and Mean Plasma Concentration-Time Data After Intravenous Injection of Compound 20 (2 mg/kg) in Male Cynomolgus Monkeys

| PK indicators | Unit | #1 | #2 | #3 | Mean | SD | CV (%) |
|---|---|---|---|---|---|---|---|
| CL | L/hr/kg | 0.871 | 0.382 | 0.758 | 0.670 | 0.256 | 38.2 |
| $V_{ss}$ | L/kg | 0.148 | 0.126 | 0.235 | 0.170 | 0.0577 | 34.0 |
| $T_{1/2}$ | hr | 0.524 | 1.22 | 1.88 | 1.21 | 0.680 | 56.3 |
| $AUC_{last}$ | hr * ng/mL | 2294 | 5226 | 2631 | 3383 | 1604 | 47.4 |
| $AUC_{INF}$ | hr * ng/ml | 2296 | 5231 | 2639 | 3389 | 1604 | 47.3 |
| $MRT_{INF}$ | hr | 0.170 | 0.330 | 0.311 | 0.270 | 0.0869 | 32.2 |
| Rsq_adjusted | NA | 0.854 | 0.935 | 0.934 | NA | NA | NA |
| Regression Points | hr | 0.5~4 | 2~8 | 2~8 | NA | NA | NA |
| $AUC_{last}$ | hr * μM | 4.13 | 9.41 | 4.73 | 6.09 | 2.89 | 47.4 |
| $AUC_{INF}$ | hr * μM | 4.13 | 9.41 | 4.75 | 6.10 | 2.89 | 47.3 |
| CL | mL/min/kg | 14.5 | 6.37 | 12.6 | 11.2 | 4.26 | 38.2 |

Note:
NA means not assayed.

Individual and Mean Plasma Concentration-Time Data After Oral Administration of Compound 1 (20 mg/kg) to Male Cynomolgus Monkeys

| PK indicators | Unit | #4 | #5 | #6 | Mean | SD | CV (%) |
|---|---|---|---|---|---|---|---|
| $T_{max}$ | hr | 2.00 | 2.00 | 1.00 | 1.67 | 0.577 | 34.6 |
| $C_{max}$ | ng/ml | 12500 | 2270 | 23200 | 12657 | 10466 | 82.7 |
| *$T_{1/2}$ | hr | 3.03 | 10.4 | 2.52 | 5.32 | 4.42 | 83.0 |
| $AUC_{last}$ | hr * ng/ml | 42563 | 17014 | 44038 | 34538 | 15194 | 44.0 |
| $AUC_{INF}$ | hr * ng/mL | 42676 | 21853 | 44083 | 36204 | 12448 | 34.4 |
| $MRT_{INF}$ | hr | 3.15 | 14.5 | 2.47 | 6.71 | 6.77 | 101 |
| Rsq_adjusted | NA | 0.563 | 0.315 | 0.690 | NA | NA | NA |
| Regression Points | hr | 4~24 | 4~24 | 2~24 | NA | NA | NA |
| F | % | 40.5 | 16.2 | 41.8 | 32.8 | 14.5 | 44.0 |
| $AUC_{last}$ | hr * μM | 72.6 | 29.0 | 75.1 | 58.9 | 25.9 | 44.0 |
| $AUC_{INF}$ | hr * μM | 72.8 | 37.3 | 75.2 | 61.8 | 21.2 | 34.4 |
| $C_{max}$ | μM | 21.3 | 3.87 | 39.6 | 21.6 | 17.9 | 82.7 |

Note:
NA means not assayed.

Individual and Mean Plasma Concentration-Time Data Following Oral Administration of Compound 20 (20 mg/kg) to Male Cynomolgus Monkeys

| PK indicators | Unit | #4 | #5 | #6 | Mean | SD | CV (%) |
|---|---|---|---|---|---|---|---|
| $T_{max}$ | hr | 4.00 | 4.00 | 2.00 | 3.33 | 1.15 | 34.6 |
| $C_{max}$ | ng/mL | 151 | 140 | 199 | 163 | 31.4 | 19.2 |
| *$T_{1/2}$ | hr | 6.31 | 5.15 | 9.57 | 7.01 | 2.29 | 32.7 |
| $AUC_{last}$ | hr * ng/ml | 950 | 1071 | 1279 | 1100 | 166 | 15.1 |
| $AUC_{INF}$ | hr * ng/ml | 1056 | 1127 | 1769 | 1317 | 393 | 29.8 |
| $MRT_{INF}$ | hr | 9.70 | 7.46 | 16.9 | 11.3 | 4.91 | 43.3 |
| Rsq_adjusted | NA | 0.616 | 0.881 | 0.942 | NA | NA | NA |

-continued

| Individual and Mean Plasma Concentration-Time Data Following Oral Administration of Compound 20 (20 mg/kg) to Male Cynomolgus Monkeys | | | | | | | |
|---|---|---|---|---|---|---|---|
| PK indicators | Unit | #4 | #5 | #6 | Mean | SD | CV (%) |
| Regression Points | hr | 4~24 | 4~24 | 2~24 | NA | NA | NA |
| F | % | 3.11 | 3.33 | 3.78 | 3.41 | 0.340 | 10.0 |
| $AUC_{last}$ | hr * μM | 1.71 | 1.93 | 2.30 | 1.98 | 0.299 | 15.1 |
| $AUC_{INF}$ | hr * μM | 1.90 | 2.03 | 3.18 | 2.37 | 0.707 | 29.8 |
| $C_{max}$ | μM | 0.272 | 0.252 | 0.358 | 0.294 | 0.0565 | 19.2 |

Note:
NA means not assayed.

Experimental conclusion: Compound 1 has good plasma binding rate and high oral bioavailability with an average oral $C_{max}$=12,657 ng/mL, an average $AUC_{last}$=34,538, and an average F=32.8%. The pharmacokinetic profile of compound 1 orally administered is significantly better than that of the control compound 20.

Various modifications of the invention in addition to those described herein, in light of the foregoing description, are also intended to fall within the scope of the appended claims. Each reference cited in this application, including all patents, patent applications, journal articles, books, and any other publications, is incorporated herein by reference in its entirety.

What is claimed is:

1. A compound having a structure of Formula II-4:

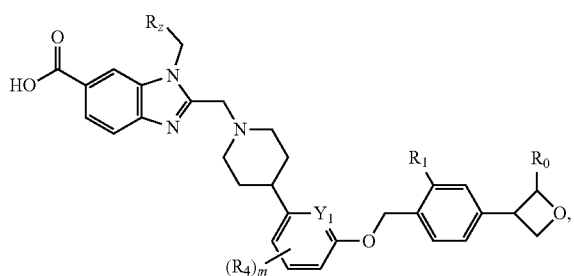

(II-4)

or a pharmaceutically acceptable salt or stereoisomer thereof,
wherein:
$Y_1$ is N;

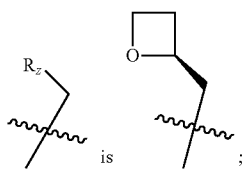

m is 0;
$R_4$ is hydrogen;
$R_1$ is selected from halogen; and
$R_0$ is hydrogen.

2. The compound according to claim 1, wherein $R_1$ is selected from F, and Cl.

3. The compound according to claim 1, which is:

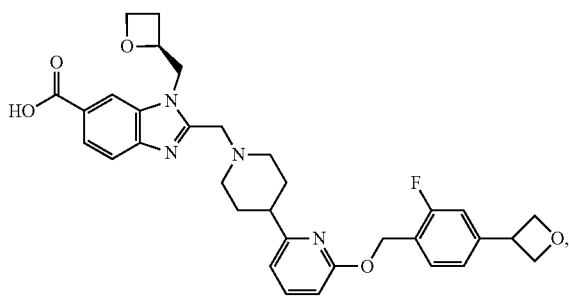 [SMILES: O=C(O)c1ccc2nc(CN3CCC(c4cccc(OCc5ccc(C6COC6)cc5F)n4)CC3)n(C[C@@H]3CCO3)c2c1]

or a pharmaceutically acceptable salt or stereoisomer thereof.

4. A pharmaceutical composition comprising the compound according to claim 1, or a pharmaceutically acceptable salt or stereoisomer thereof, and a pharmaceutically acceptable carrier, excipient or diluent.

5. A method for treating a GLP-1 receptor mediated or related disease or disorder in a subject, wherein said disease or disorder is selected from a group consisting of diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia comprising administering to the subject a therapeutically effective amount of the compound according to claim 1, or a pharmaceutically acceptable salt or stereoisomer thereof.

6. The compound according to claim 1, which is:

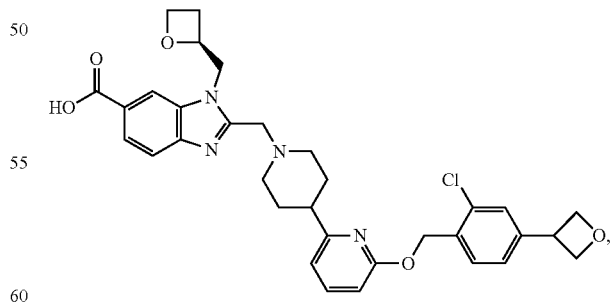

or a pharmaceutically acceptable salt or stereoisomer thereof.

7. A pharmaceutical composition comprising the compound according to claim 2, or a pharmaceutically acceptable salt or stereoisomer thereof, and a pharmaceutically acceptable carrier, excipient or diluent.

8. A method for treating a GLP-1 receptor mediated or related disease or disorder in a subject, wherein said disease or disorder is selected from a group consisting of diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia, comprising administering to the subject a therapeutically effective amount of the compound according to claim 2, or a pharmaceutically acceptable salt or stereoisomer thereof.

9. A pharmaceutical composition comprising the compound according to claim 3, or a pharmaceutically acceptable salt or stereoisomer thereof, and a pharmaceutically acceptable carrier, excipient or diluent.

10. A method for treating a GLP-1 receptor mediated or related disease or disorder in a subject, wherein said disease or disorder is selected from a group consisting of diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia, comprising administering to the subject a therapeutically effective amount of the compound according to claim 3, or a pharmaceutically acceptable salt or stereoisomer thereof.

11. A pharmaceutical composition comprising the compound according to claim 6, or a pharmaceutically acceptable salt or stereoisomer thereof, and a pharmaceutically acceptable carrier, excipient or diluent.

12. A method for treating a GLP-1 receptor mediated or related disease or disorder in a subject, wherein said disease or disorder is selected from a group consisting of diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia, comprising administering to the subject a therapeutically effective amount of the compound according to claim 6, or a pharmaceutically acceptable salt or stereoisomer thereof.

\* \* \* \* \*